(12) United States Patent
Kiani et al.

(10) Patent No.: US 12,128,213 B2
(45) Date of Patent: Oct. 29, 2024

(54) METHOD OF OPERATING REDUNDANT STAGGERED DISEASE MANAGEMENT SYSTEMS

(71) Applicant: Willow Laboratories, Inc., Irvine, CA (US)

(72) Inventors: Massi Joe E. Kiani, Laguna Niguel, CA (US); Venkatramanan Krishnamani, Irvine, CA (US); Hung The Vo, Fountain Valley, CA (US); Sai Kong Frank Lee, Irvine, CA (US); Kevin Hughes Pauley, Lake Forest, CA (US); Cristiano Dalvi, Lake Forest, CA (US); Jeroen Poeze, Rancho Santa Margarita, CA (US); Jesse Chen, Foothill Ranch, CA (US); Gregory A. Olsen, Lake Forest, CA (US); Derek Treese, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 307 days.

(21) Appl. No.: 17/161,528

(22) Filed: Jan. 28, 2021

(65) Prior Publication Data
US 2021/0236729 A1     Aug. 5, 2021

Related U.S. Application Data

(60) Provisional application No. 63/044,831, filed on Jun. 26, 2020, provisional application No. 63/015,272, (Continued)

(51) Int. Cl.
*A61M 5/172*     (2006.01)
*A61K 38/28*     (2006.01)

(52) U.S. Cl.
CPC .......... *A61M 5/1723* (2013.01); *A61K 38/28* (2013.01); *A61M 2205/18* (2013.01); *A61M 2230/201* (2013.01)

(58) Field of Classification Search
CPC ............ A61M 5/1723; A61M 2205/18; A61M 2230/201; A61K 38/28
See application file for complete search history.

(56) References Cited

U.S. PATENT DOCUMENTS

| 4,960,128 A | 10/1990 | Gordon et al. |
| 4,964,408 A | 10/1990 | Hink et al. |

(Continued)

FOREIGN PATENT DOCUMENTS

| EP | 0 351 891 | 9/1993 |
| EP | 1 957 135 | 5/2015 |

(Continued)

OTHER PUBLICATIONS

US 2024/0016391 A1, 01/2024, Lapotko et al. (withdrawn)
(Continued)

*Primary Examiner* — Kevin S Orwig
*Assistant Examiner* — John Michael Cronin
(74) *Attorney, Agent, or Firm* — Knobbe, Martens, Olson & Bear, LLP

(57) ABSTRACT

A system which provides closed loop insulin administration is disclosed. The system includes redundant glucose sensors which may be interleaved in order to provide monitoring when one of the glucose sensors is in a settling period. The system may include a disease management unit which includes both a glucose sensor and an insulin pump. A closed loop disease management system which bases insulin administration on accurate glucose measurements may improve a patient's quality of life.

9 Claims, 167 Drawing Sheets

Related U.S. Application Data filed on Apr. 24, 2020, provisional application No. 62/978,480, filed on Feb. 19, 2020, provisional application No. 62/968,107, filed on Jan. 30, 2020.

(56) References Cited

U.S. PATENT DOCUMENTS

| | | |
|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,911,716 A | 6/1999 | Rake et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |

(56) References Cited

U.S. PATENT DOCUMENTS

| | | |
|---|---|---|
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,811,246 B2 | 10/2010 | Koops |
| RE41,912 E | 11/2010 | Parker |
| 7,875,004 B2 | 1/2011 | Yodfat et al. |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,267,921 B2 | 9/2012 | Yodfat et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,486,005 B2 | 7/2013 | Yodfat et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,696,570 B2 | 4/2014 | Yodfat et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,924 B2 | 7/2014 | Kanderian, Jr. et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,894,632 B2 | 11/2014 | Yodfat et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,072,476 B2 | 7/2015 | Shah et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,179,870 B2 | 11/2015 | Shah et al. |
| 9,192,329 B2 | 11/2015 | Al-Ali |
| 9,192,351 B1 | 11/2015 | Telfort et al. |
| 9,192,713 B2 | 11/2015 | Yodfat et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,259,175 B2 | 2/2016 | Stafford |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,603,558 B2 * | 3/2017 | Burnett ............ A61M 5/14276 |
| 9,615,779 B2 | 4/2017 | Pryor et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,693,722 B2 | 7/2017 | Shah et al. |
| 9,697,928 B2 | 7/2017 | Al-Ali et al. |

(56) References Cited

U.S. PATENT DOCUMENTS

| | | |
|---|---|---|
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| 10,137,242 B2 | 11/2018 | Neta et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,251,605 B2 | 4/2019 | Liu et al. |
| 10,265,464 B2 | 4/2019 | Yodfat et al. |
| 10,279,247 B2 | 5/2019 | Kiani |
| 10,292,664 B2 | 5/2019 | Al-Ali |
| 10,293,101 B2 * | 5/2019 | Brewer ............ A61M 5/142 |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| 10,660,201 B2 | 5/2020 | Frick et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |

(56) References Cited

U.S. PATENT DOCUMENTS

| | | |
|---|---|---|
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 11,951,186 B2 | 4/2024 | Krishnamani et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0216100 A1 | 8/2009 | Ebner et al. |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0174239 A1 | 7/2010 | Yodfat et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040163 A1 | 2/2011 | Telson et al. |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041343 A1 | 2/2013 | Toumazou et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0005633 A1 | 1/2014 | Finan |
| 2014/0081202 A1 | 3/2014 | Tsoukalis |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0243634 A1 | 8/2014 | Huang et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2017/0281864 A1* | 10/2017 | Searle ................ G16H 40/63 |
| 2017/0311891 A1 | 11/2017 | Kiani et al. |
| 2018/0103874 A1 | 4/2018 | Lee et al. |
| 2018/0207356 A1 | 7/2018 | Joseph et al. |
| 2018/0228416 A1 | 8/2018 | Frick |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2019/0015023 A1 | 1/2019 | Monfre |
| 2019/0076068 A1* | 3/2019 | Yang ................ G01N 27/4163 |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374713 A1 | 12/2019 | Kiani et al. |
| 2020/0060869 A1 | 2/2020 | Telfort et al. |
| 2020/0093989 A1 | 3/2020 | Koops et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |

(56) References Cited

U.S. PATENT DOCUMENTS

| | | |
|---|---|---|
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |

FOREIGN PATENT DOCUMENTS

| | | |
|---|---|---|
| EP | 3 329 847 | 6/2018 |
| NL | 2019661 | 4/2019 |
| WO | WO 2011/162843 | 12/2011 |
| WO | WO 2017/198116 | 11/2017 |
| WO | WO 2019/083354 | 5/2019 |
| WO | WO 2021/155048 | 8/2021 |

OTHER PUBLICATIONS

"24-Bit Capacitance to Digital Converter with Temperature Sensor", Analog Devices, AD7745/AD7746, 2005, https://www.analog.com/media/en/technical-documentation/data-sheets/AD7745_7746.pdf, pp. 28.

Donnelly et al., "Hydrogel-Forming Microneedles Prepared from 'Super Swelling' Polymers Combined with Lyophilised Wafers for Transdermal Drug Delivery", PLOS One, Oct. 2014, vol. 9, No. 10, e111547, pp. 12.

Ghoreishizadeh et al., "Study of Electrochemical Impedance of a Continuous Glucose Monitoring Sensor and its Correlation With Sensor Performance", IEEE Sensors Letters, 2018, pp. 4.

Pauliukaite et al., "Electrochemical impedance studies of chitosan-modified electrodes for application in electrochemical sensors and biosensors", Electrochimica Acta, vol. 55, 2010, pp. 6239-6247.

International Search Report and Written Opinion received in PCT Application No. PCT/US2021/015559, dated Jul. 27, 2021 in 18 pages.

\* cited by examiner

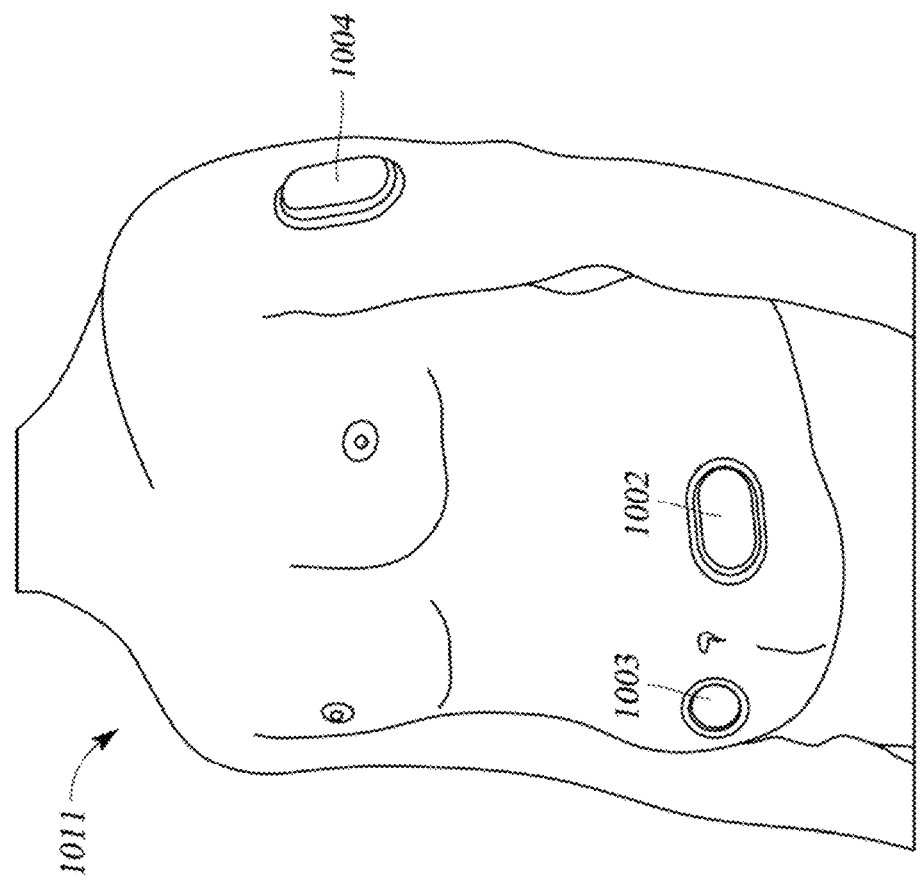
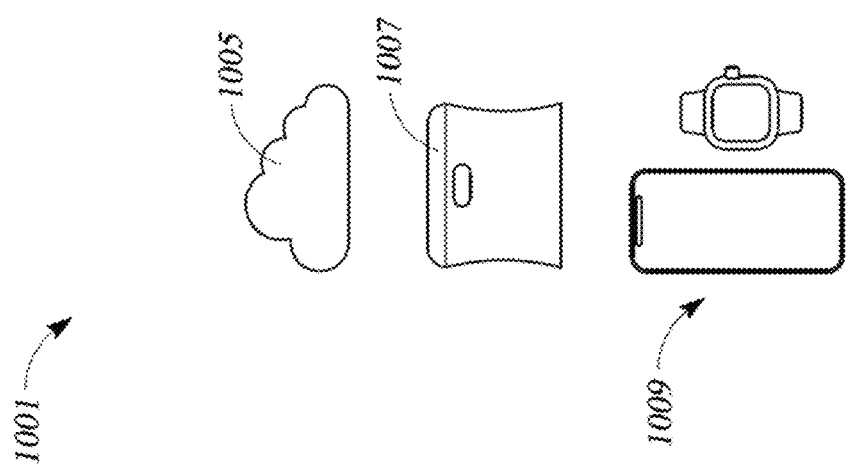
FIG. 1B

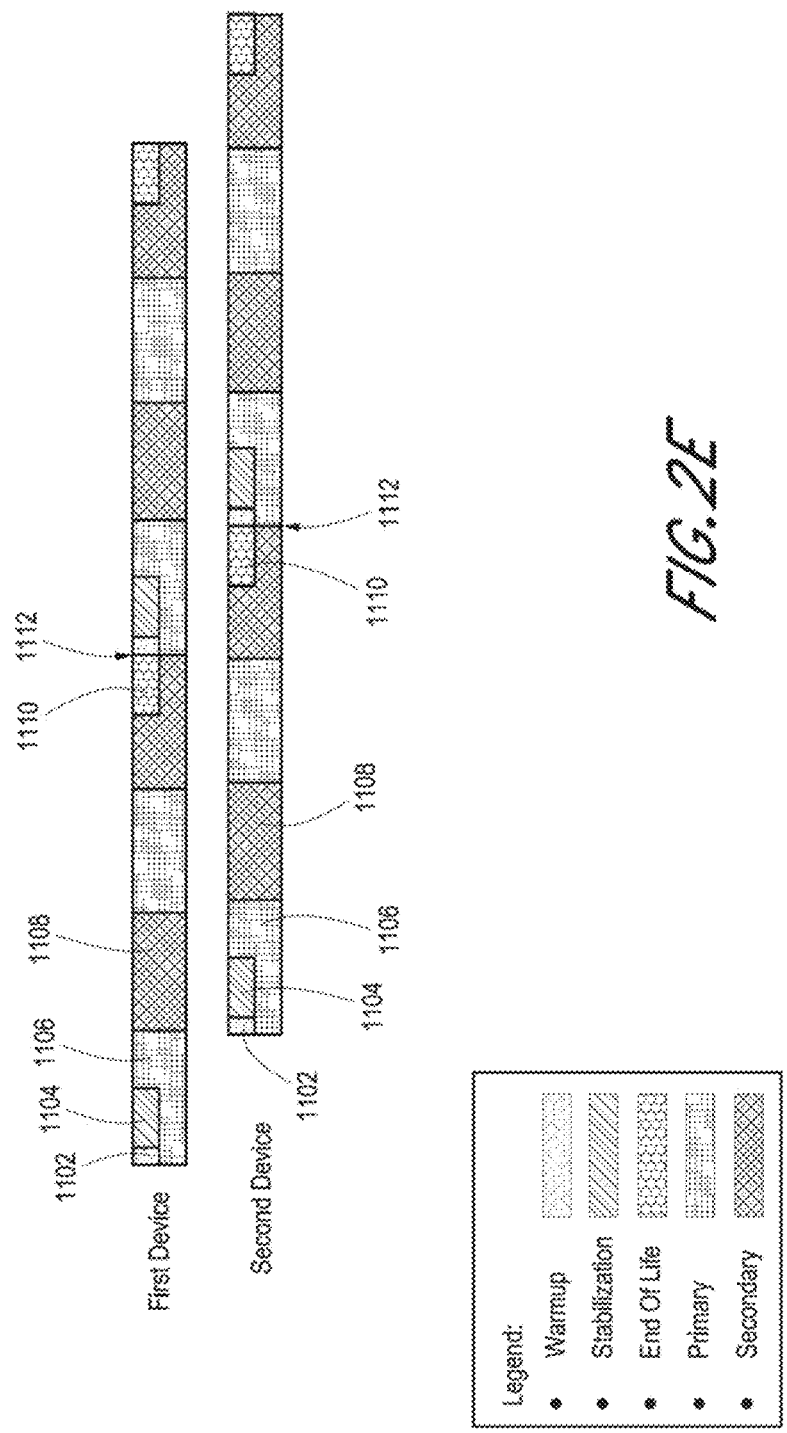

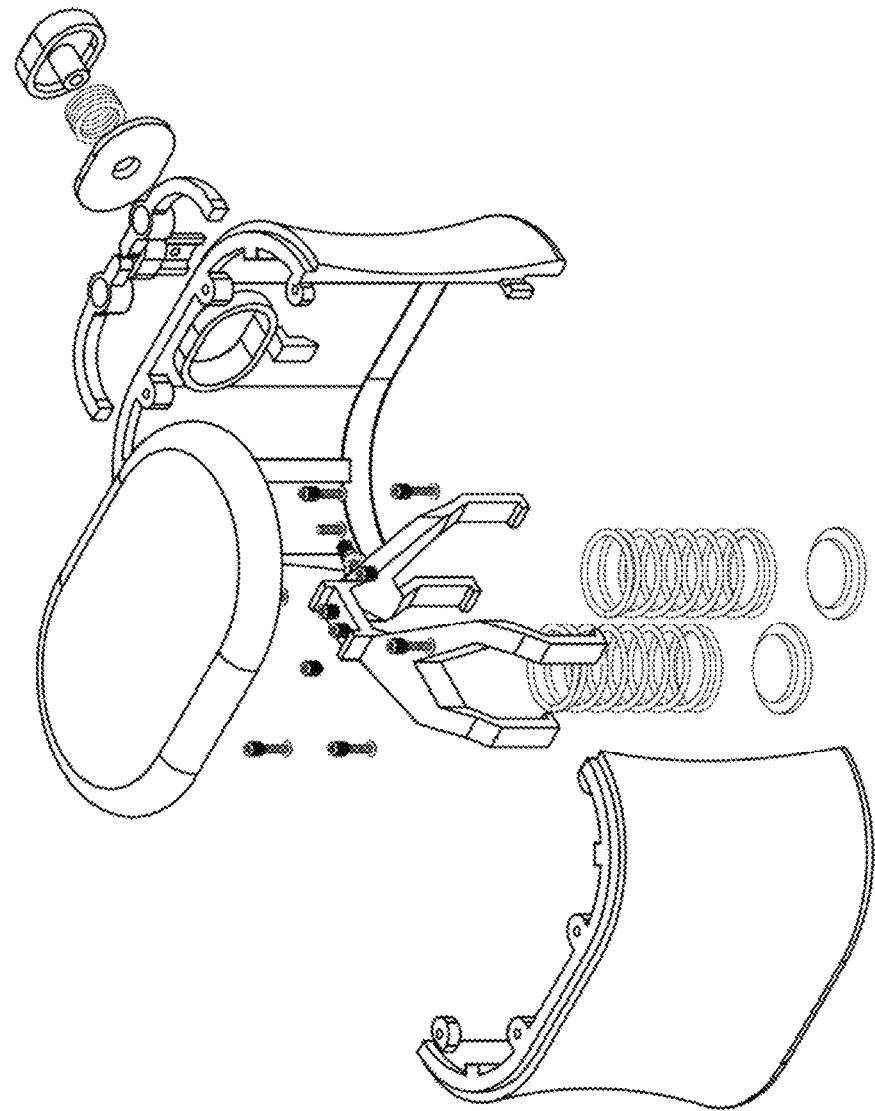
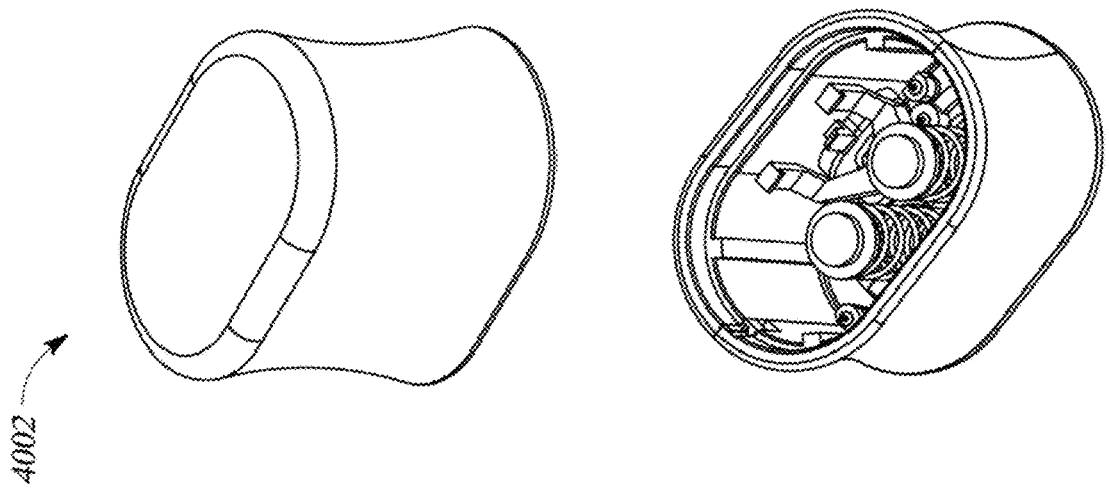
FIG. 21

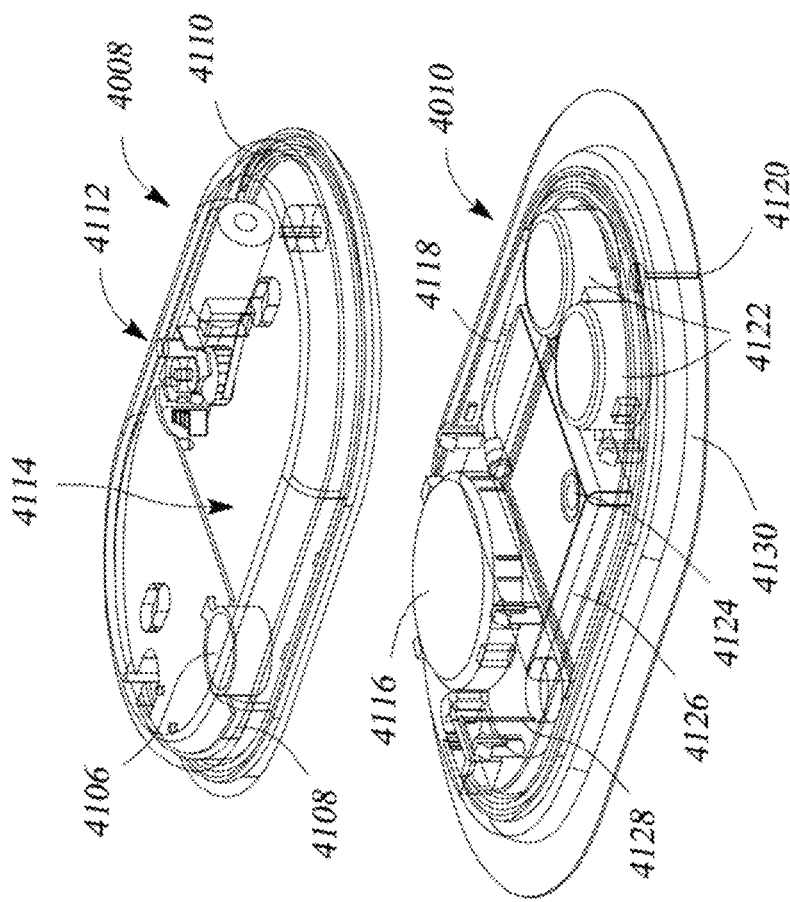
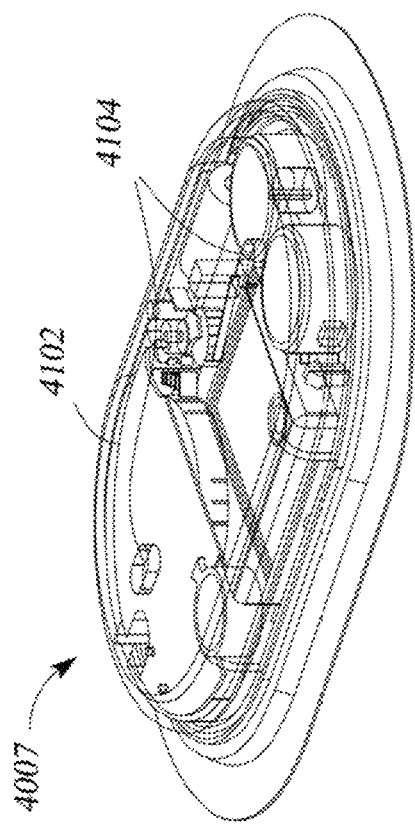
FIG. 2K

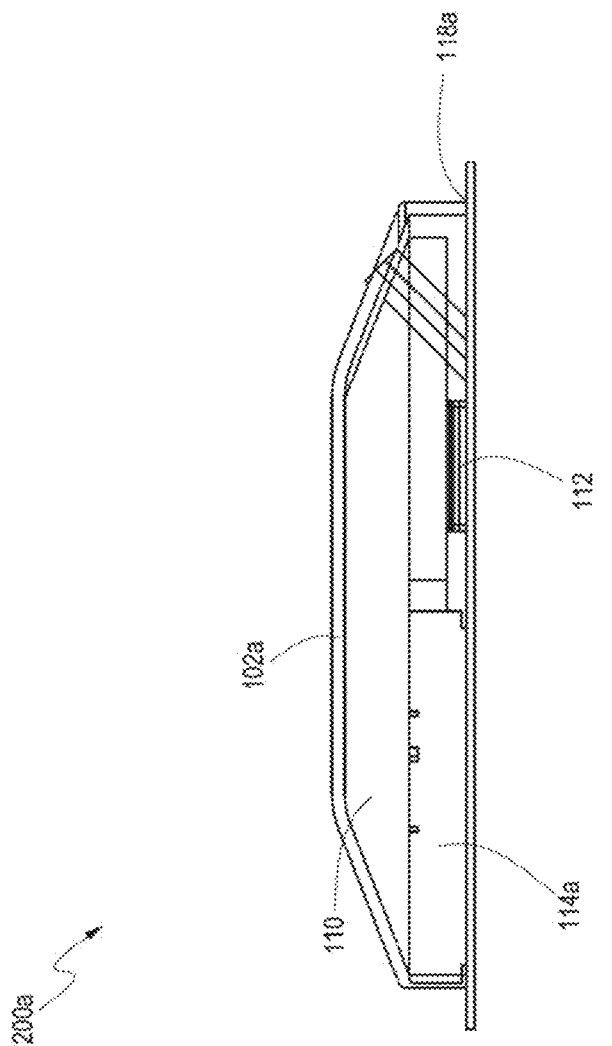

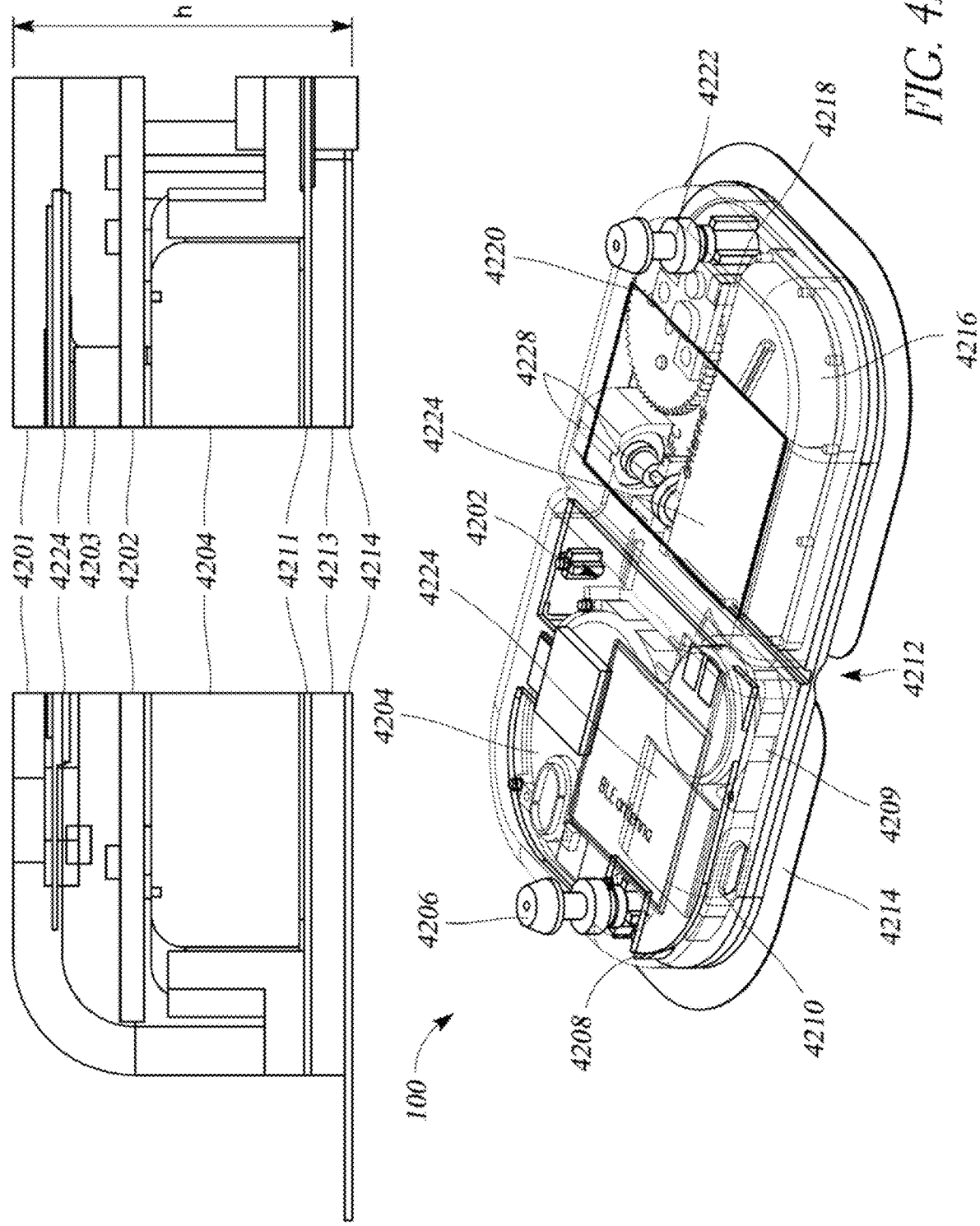

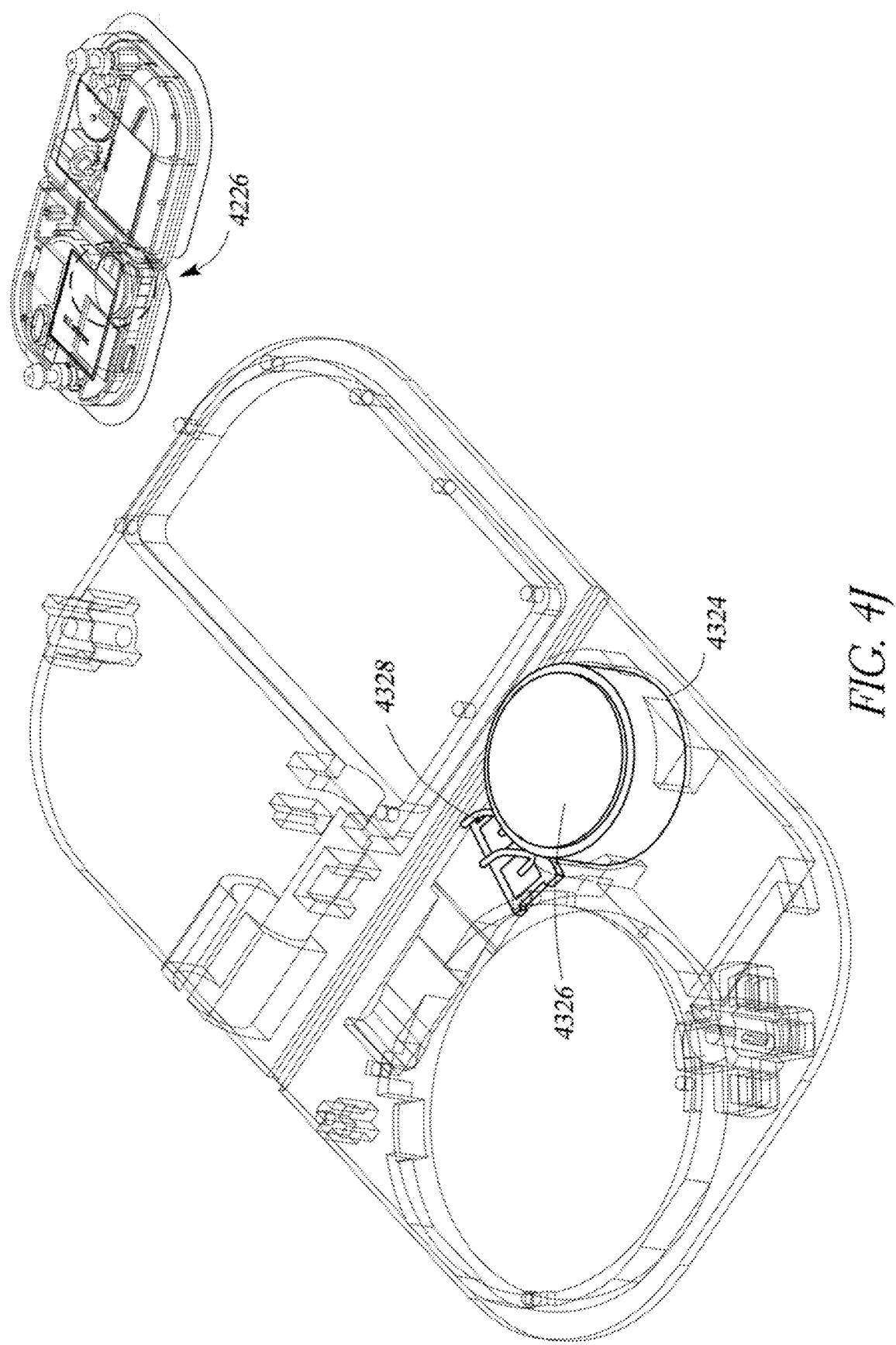

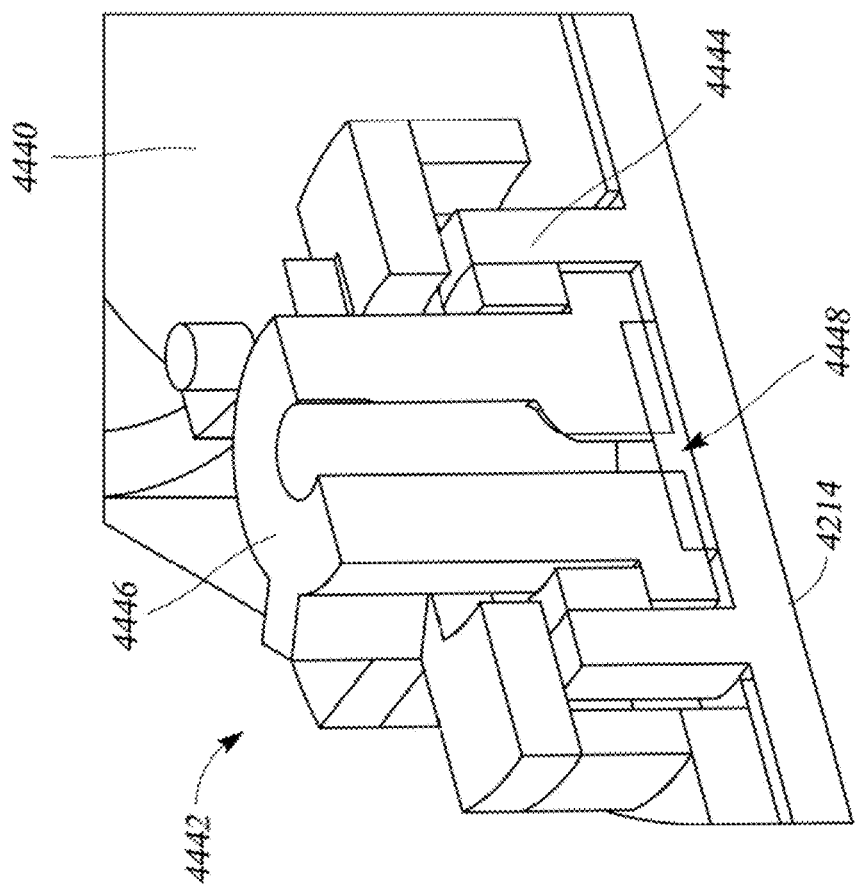
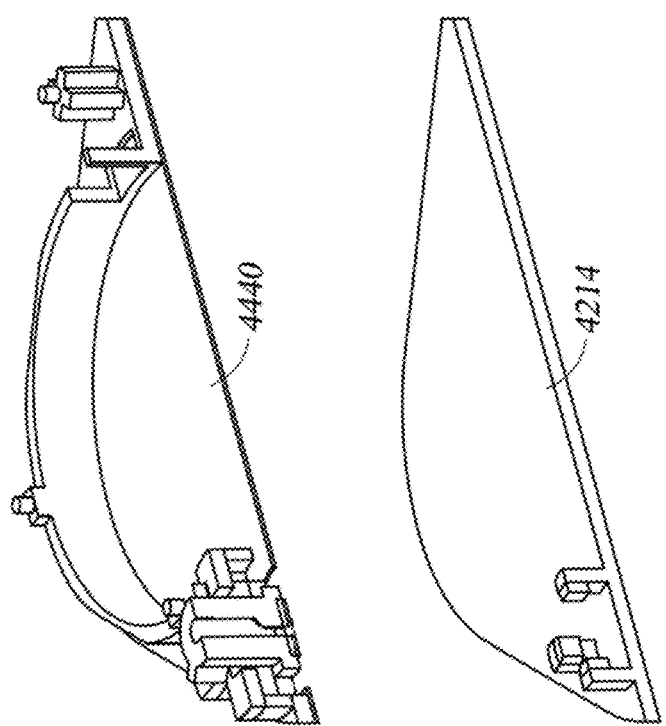
FIG. 4M

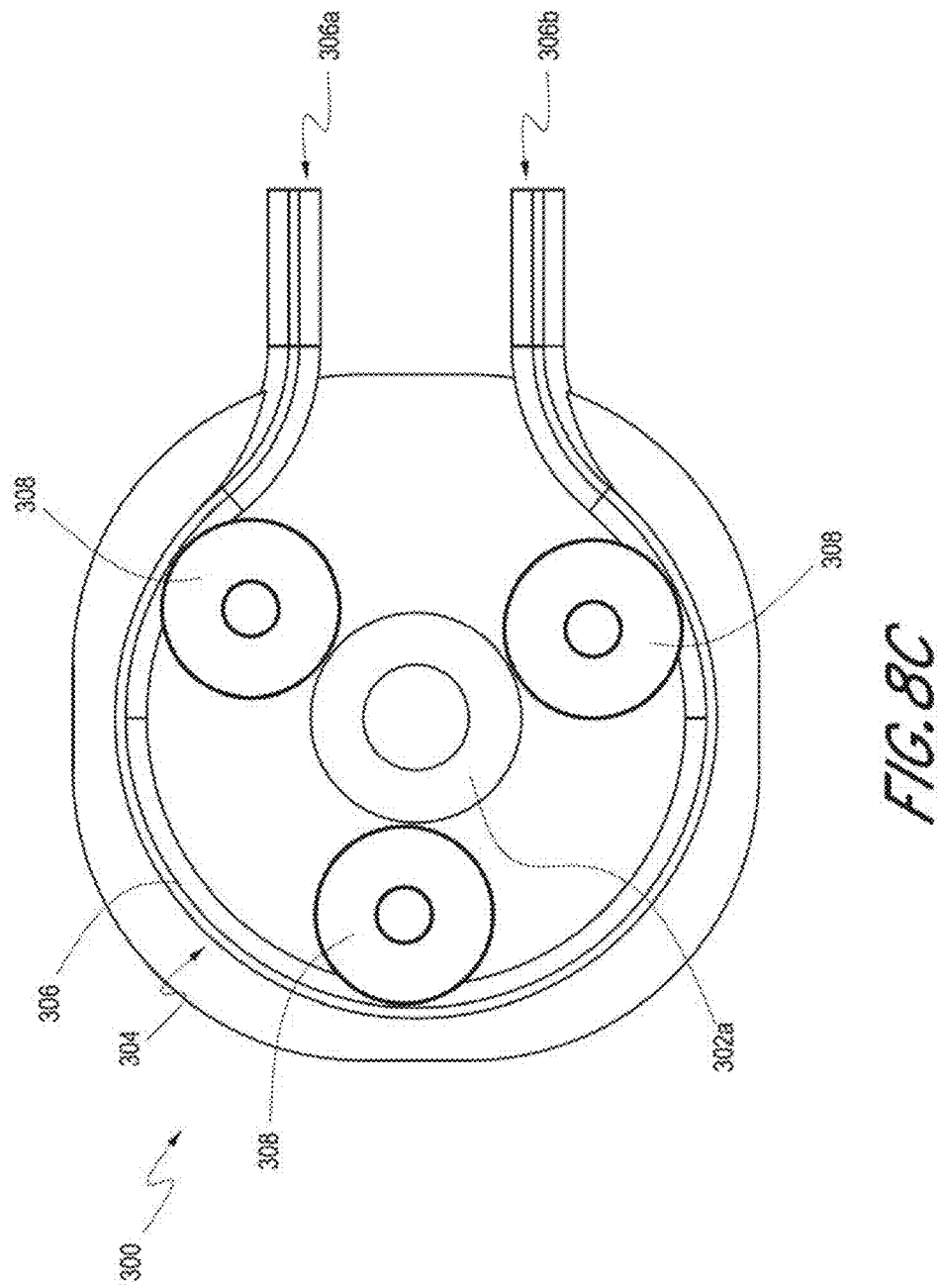

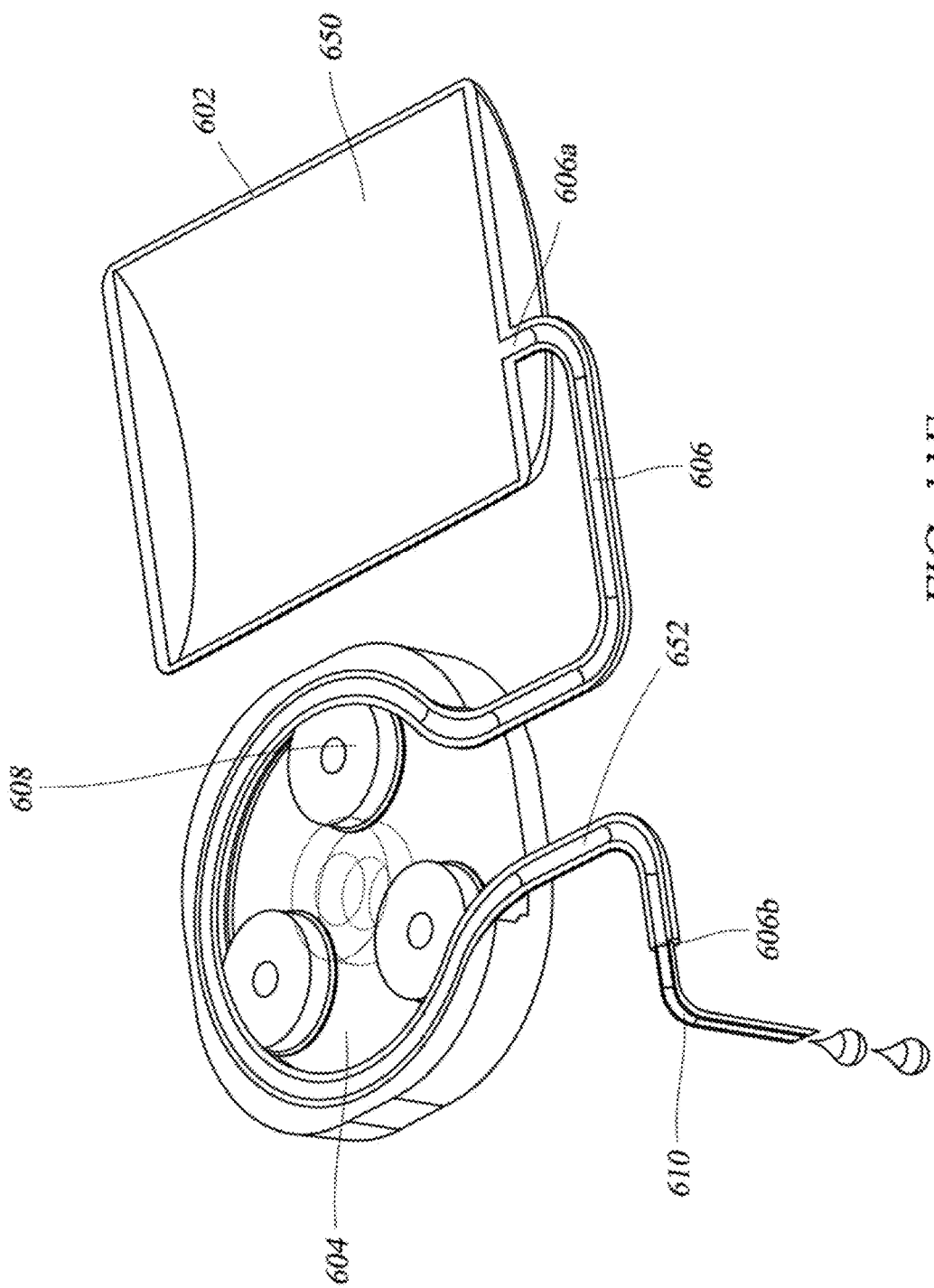

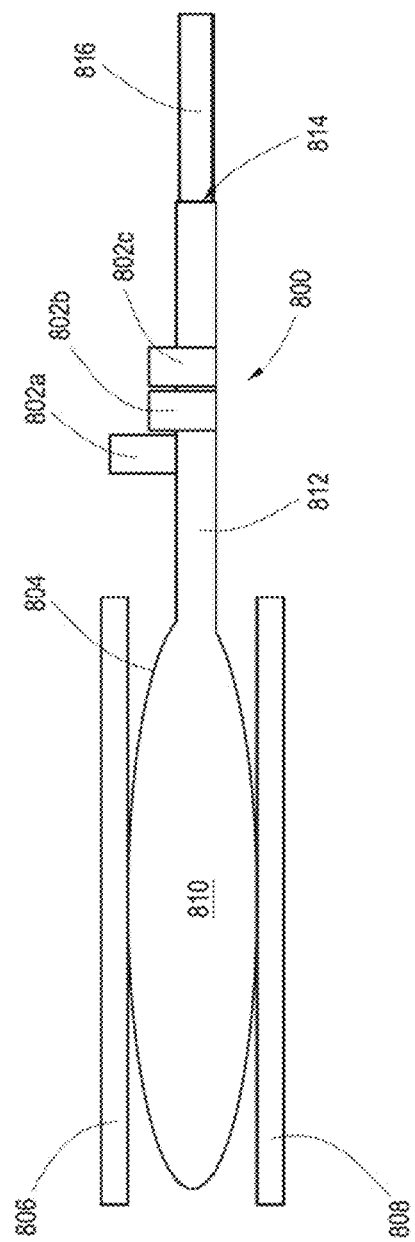

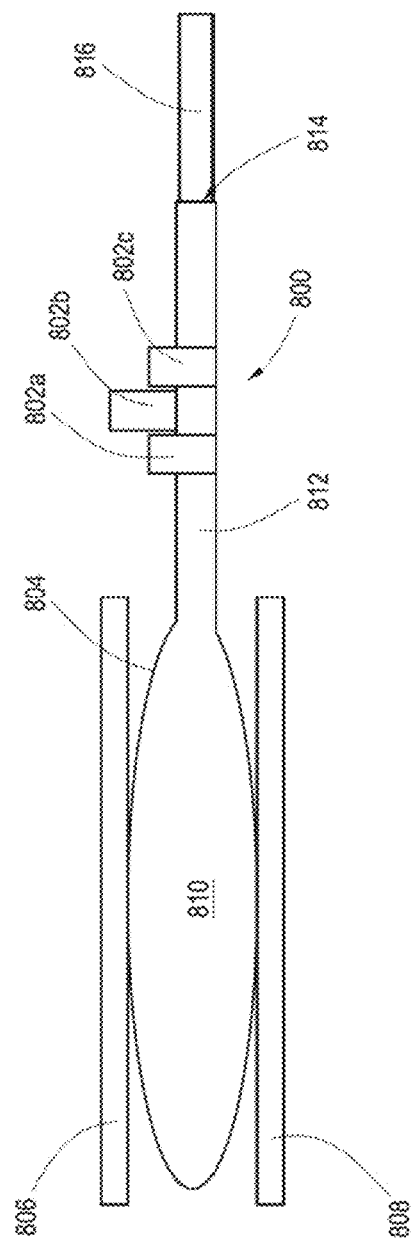

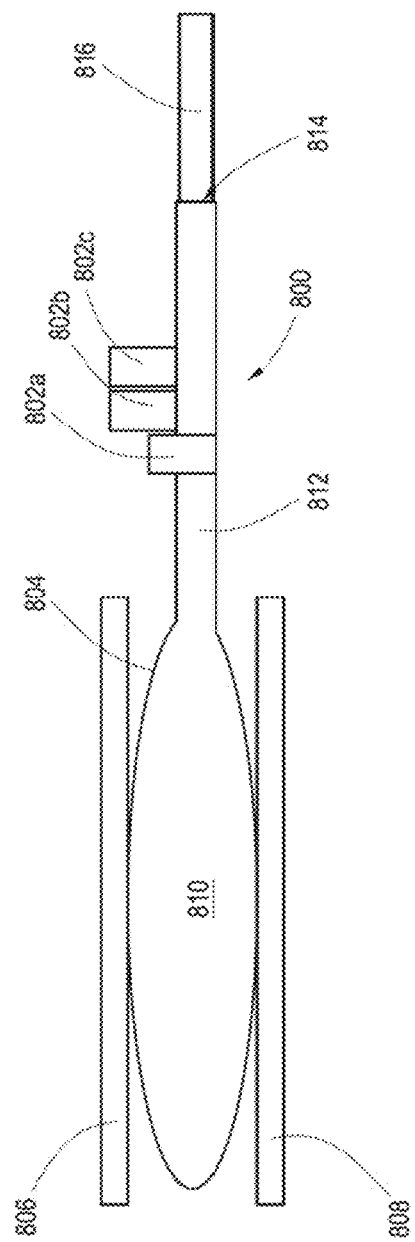

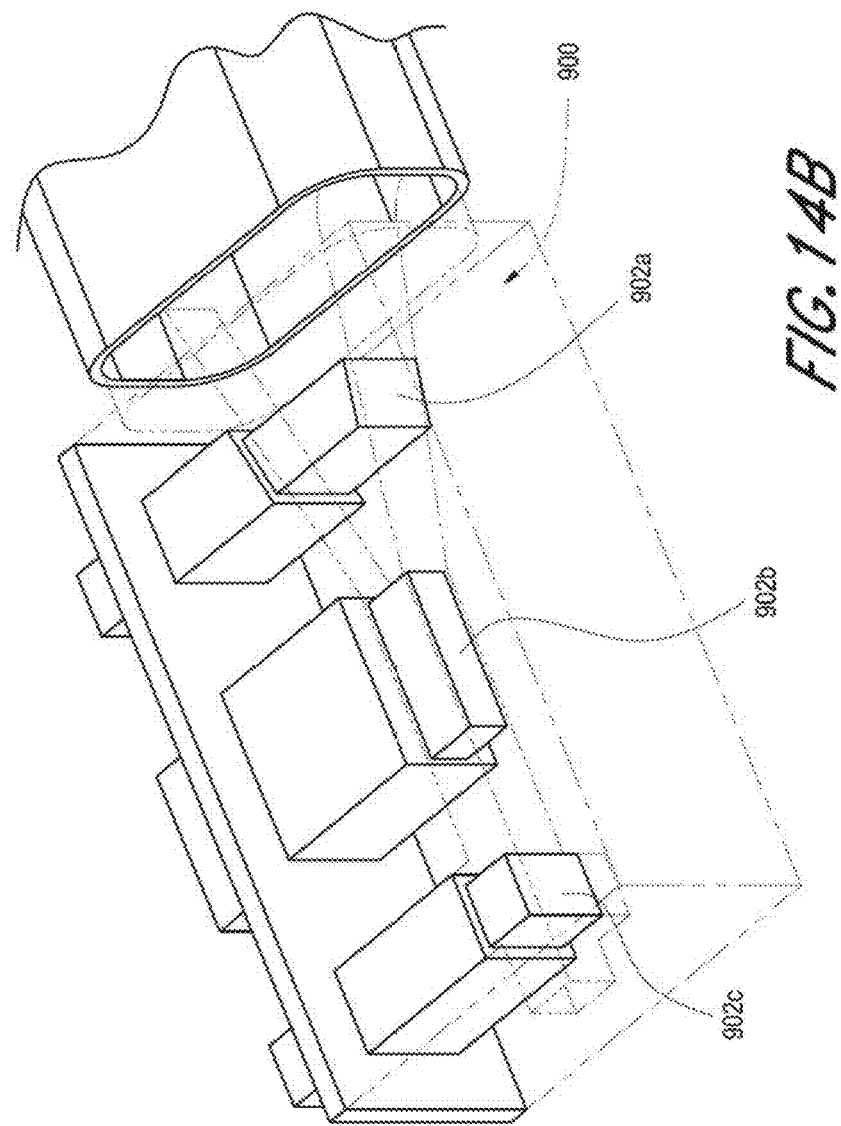

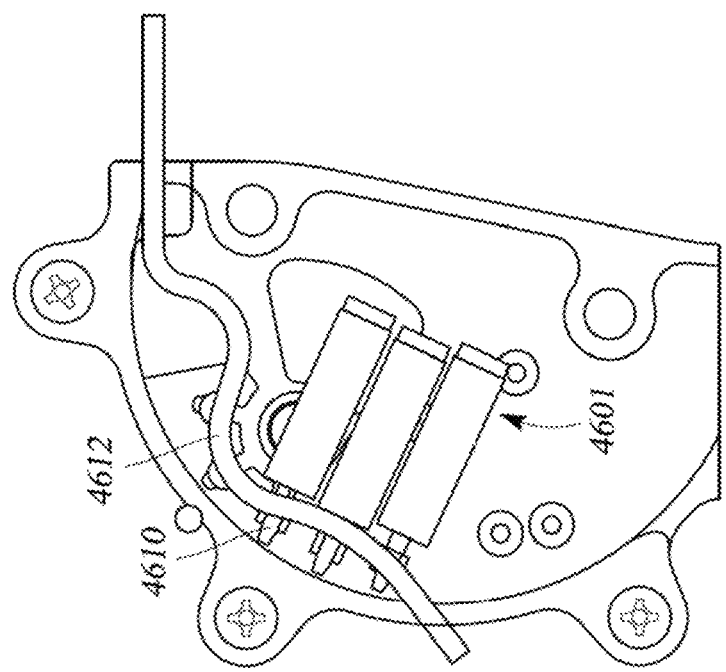
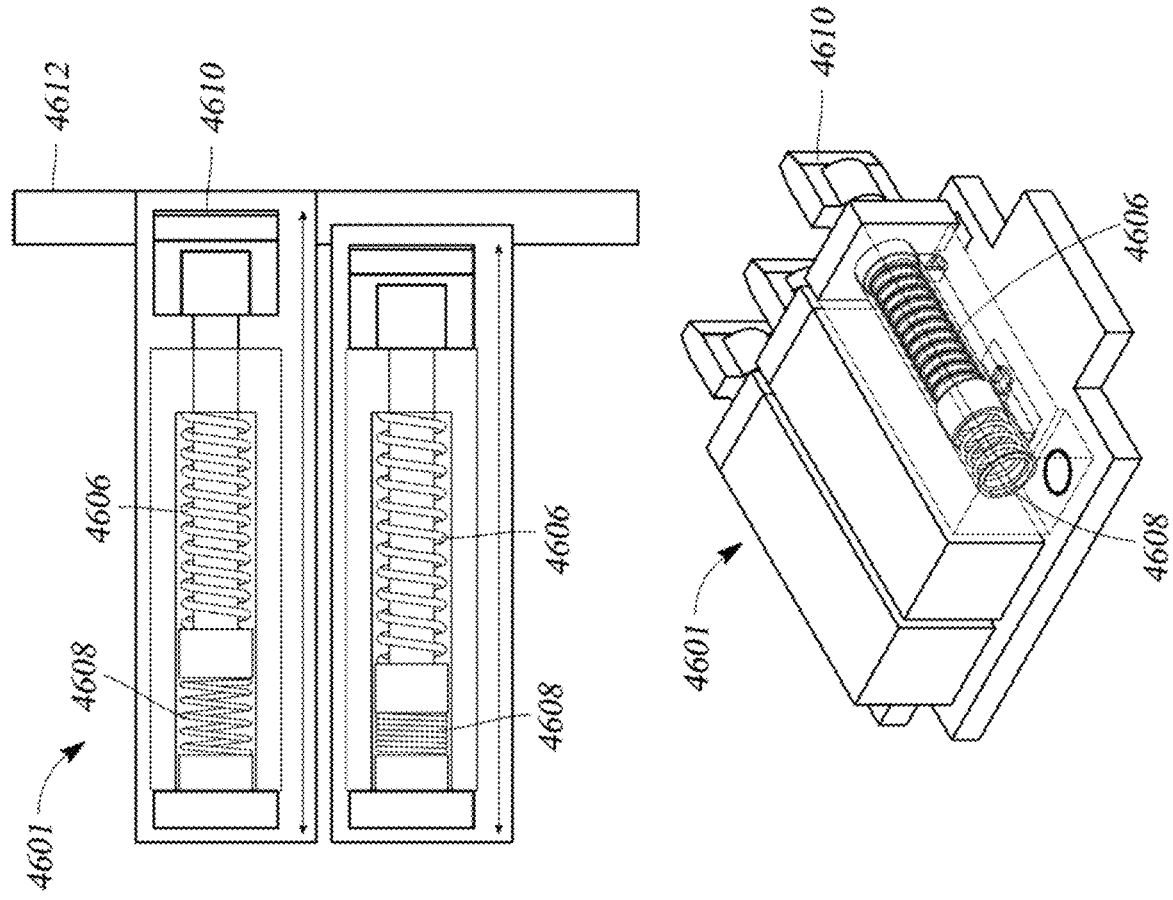
FIG. 14N

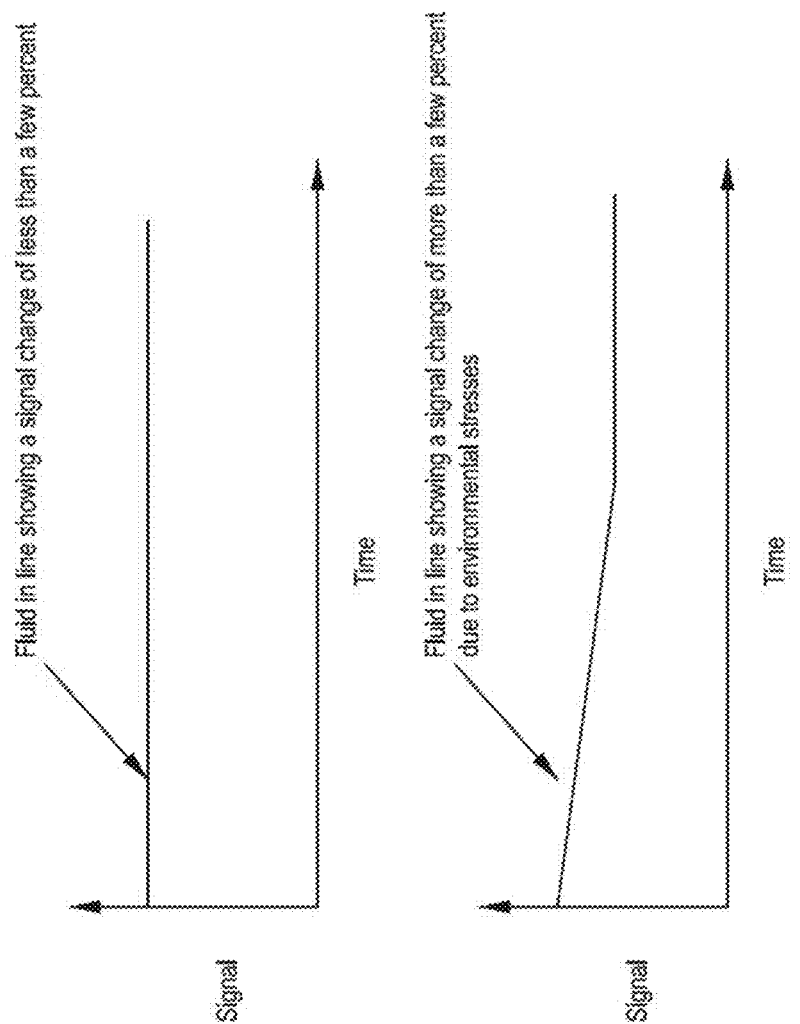

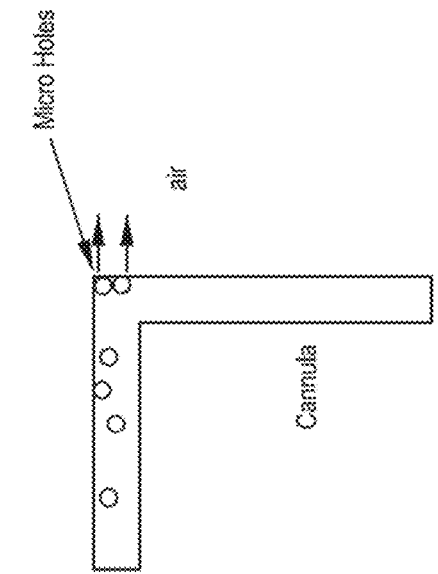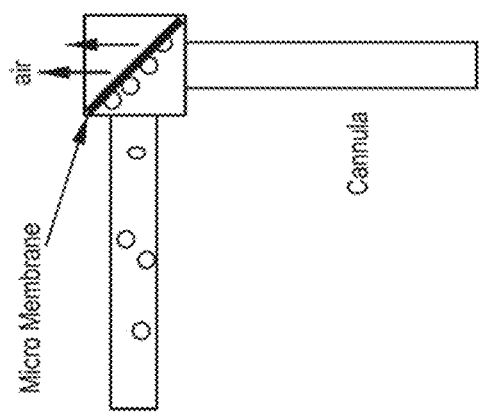
FIG. 17

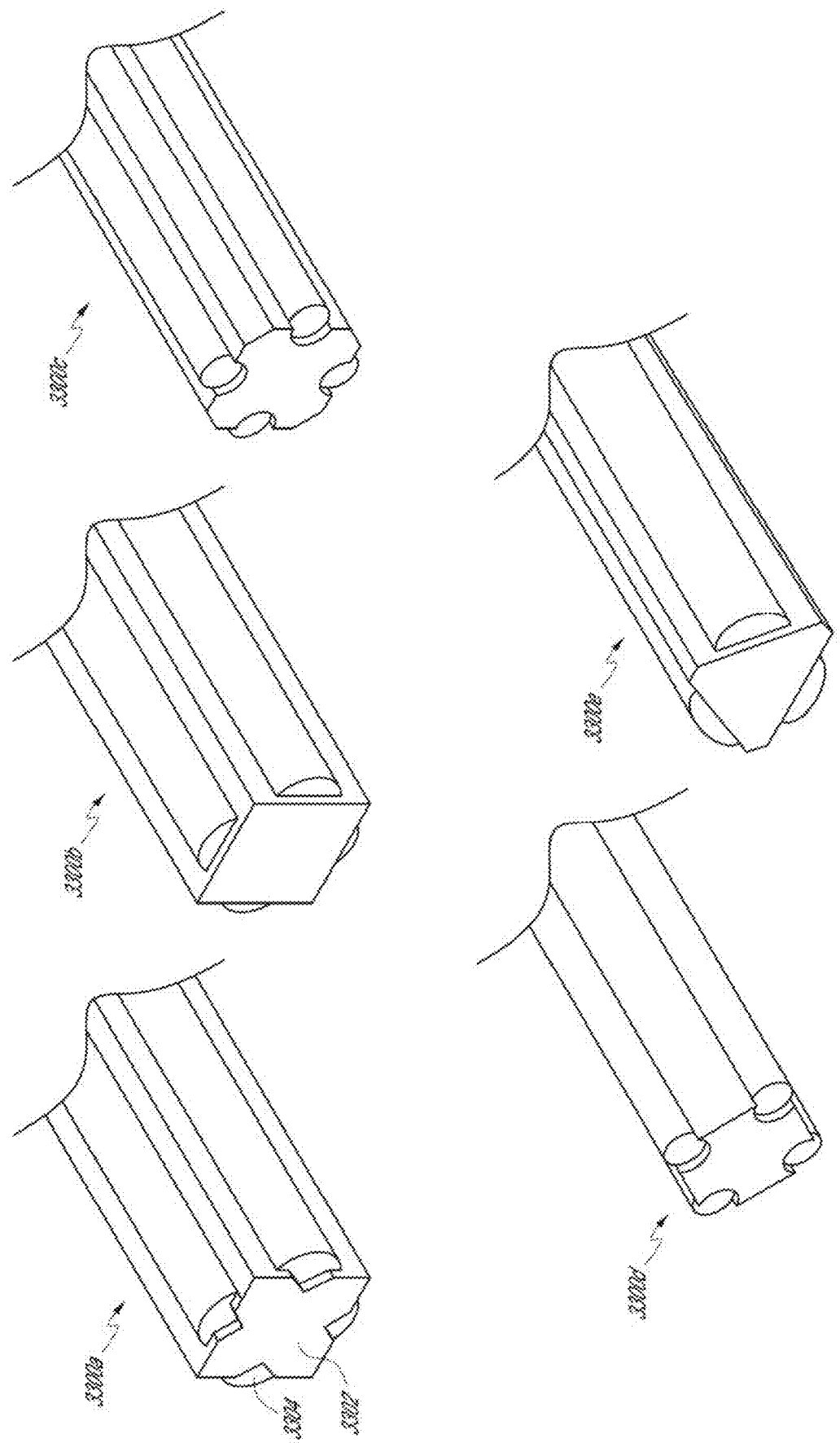

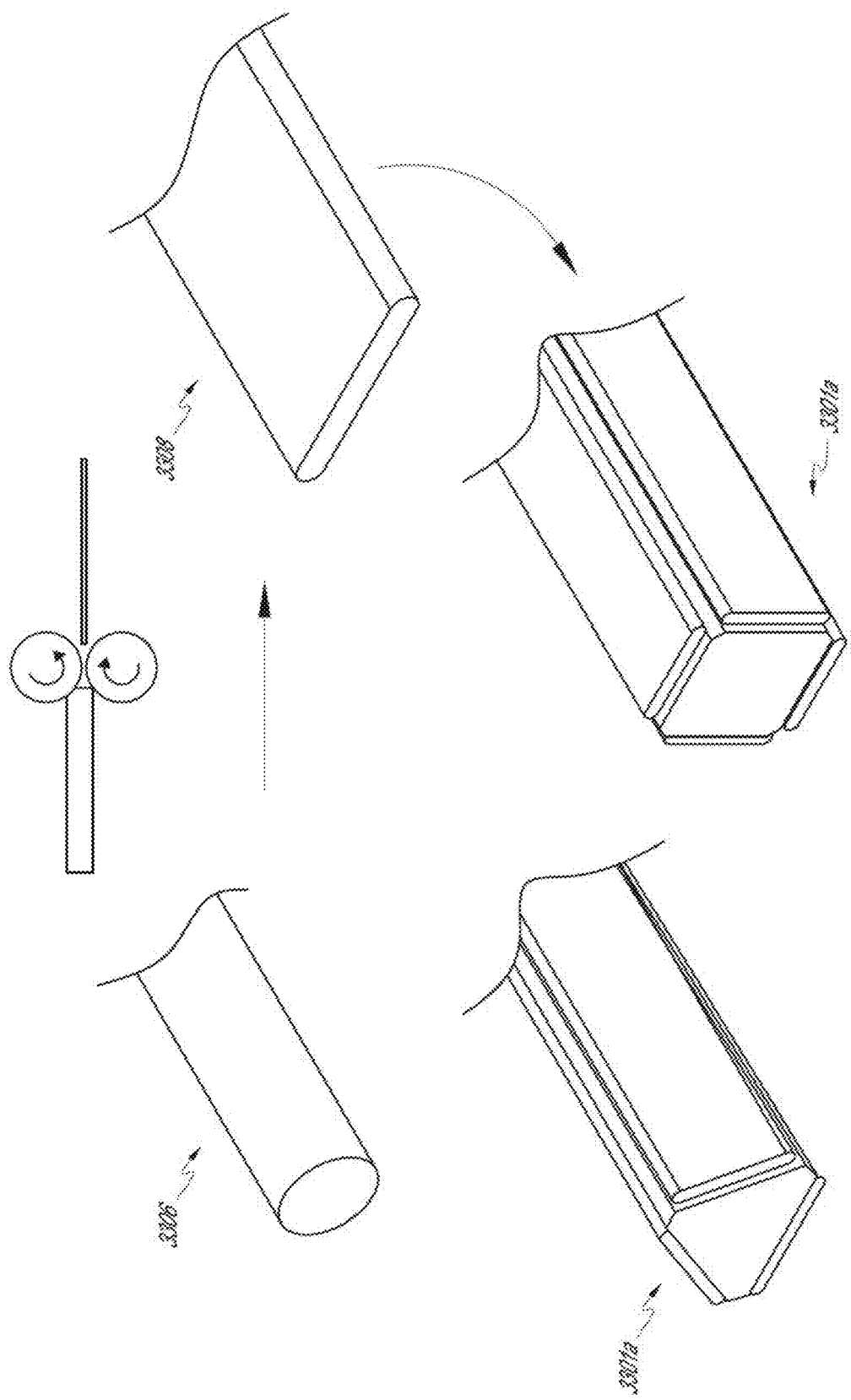

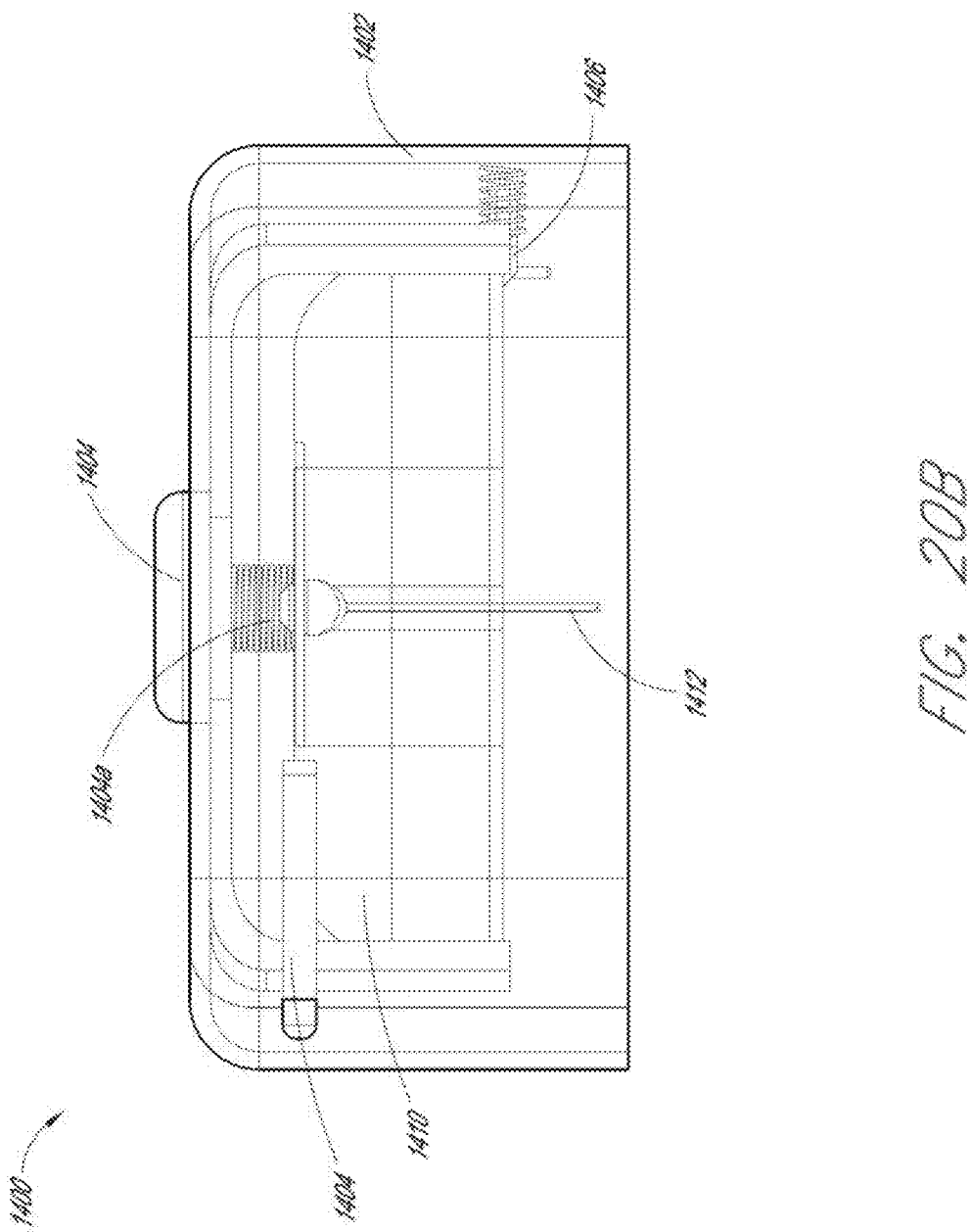

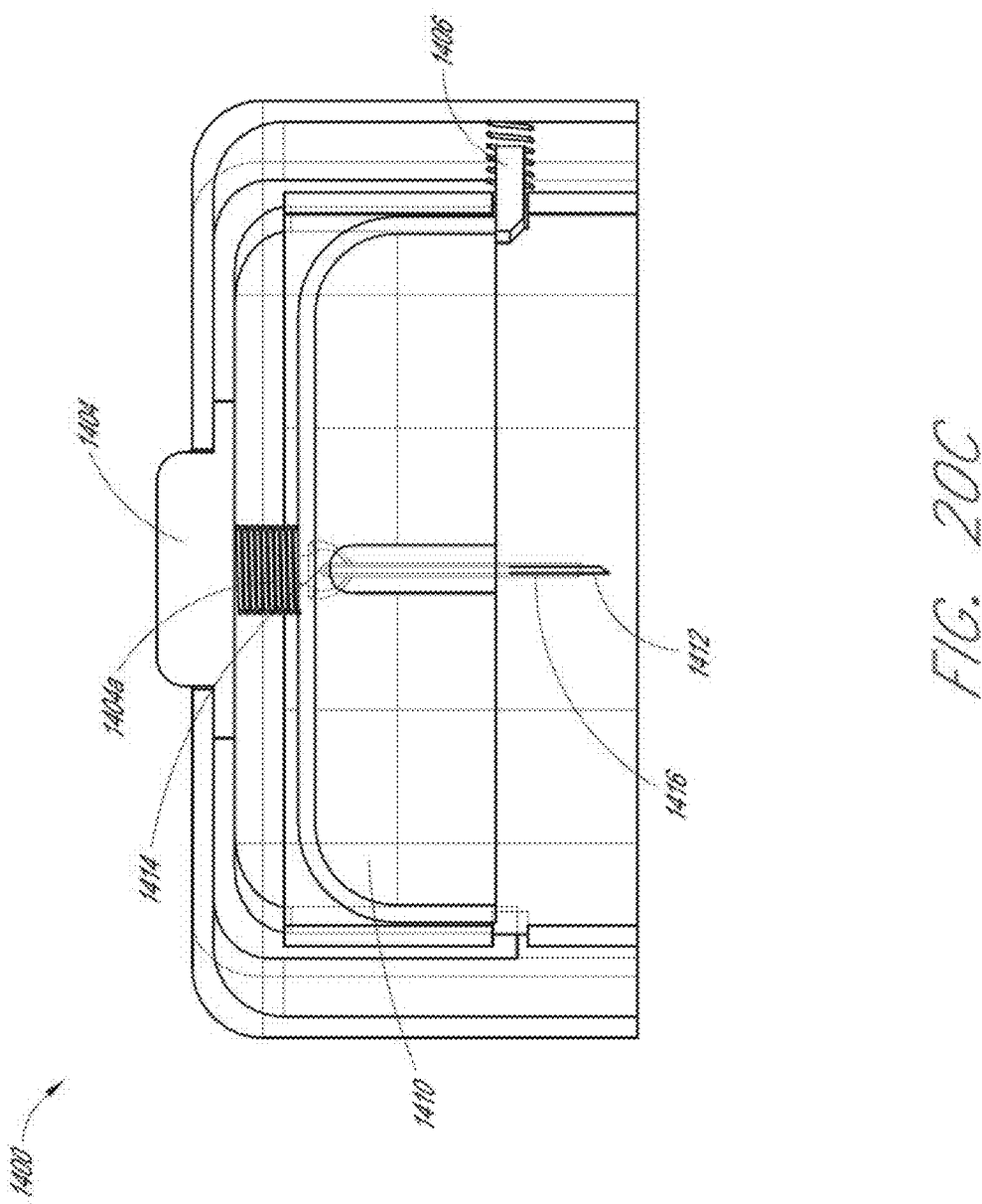

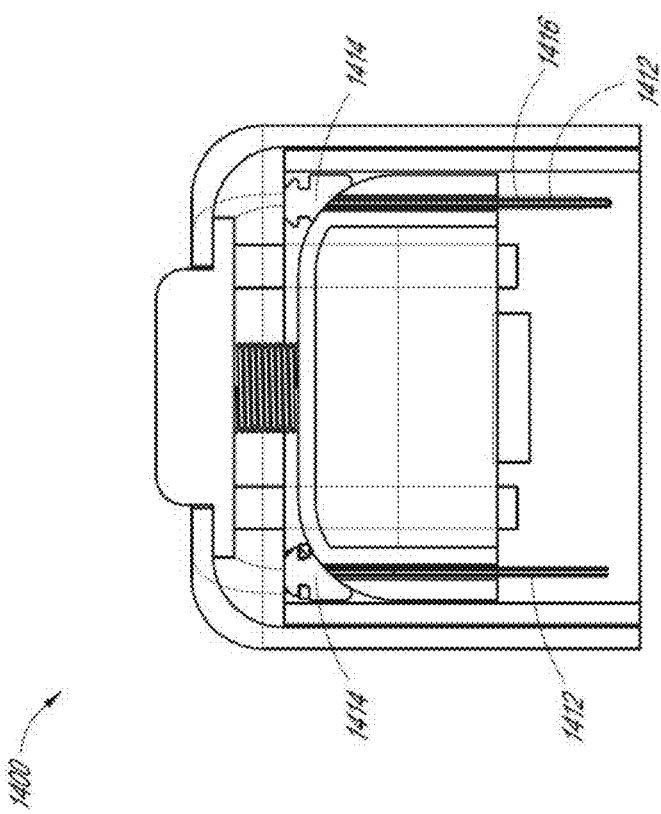

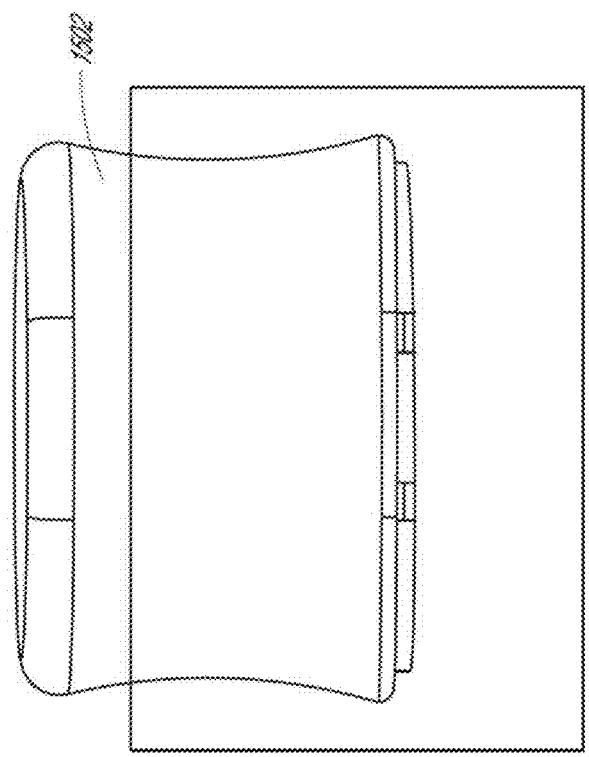
FIG. 21A

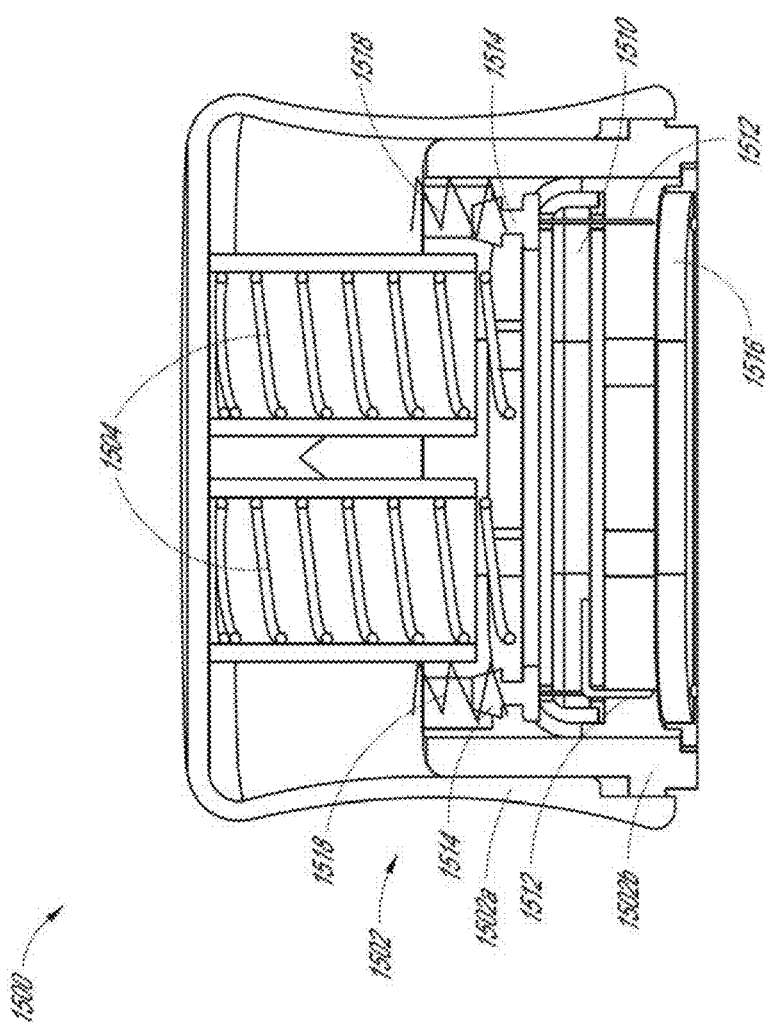

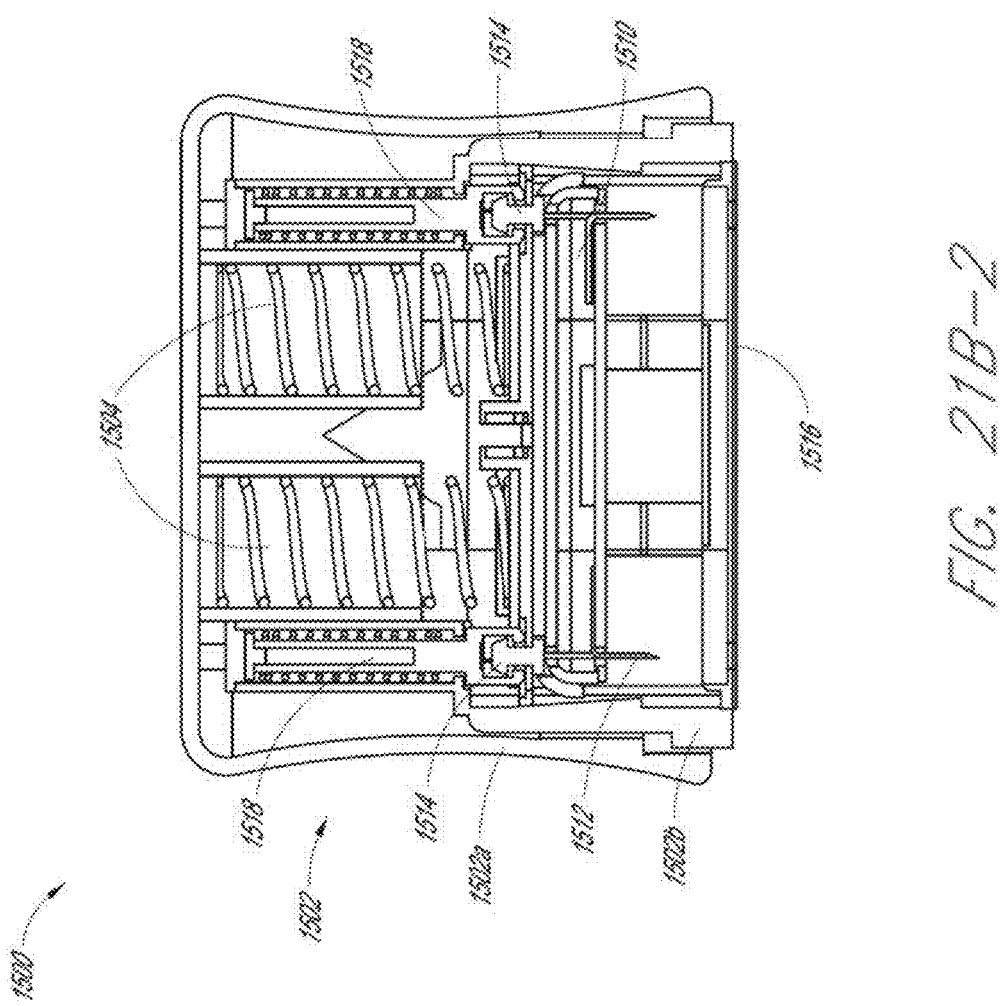

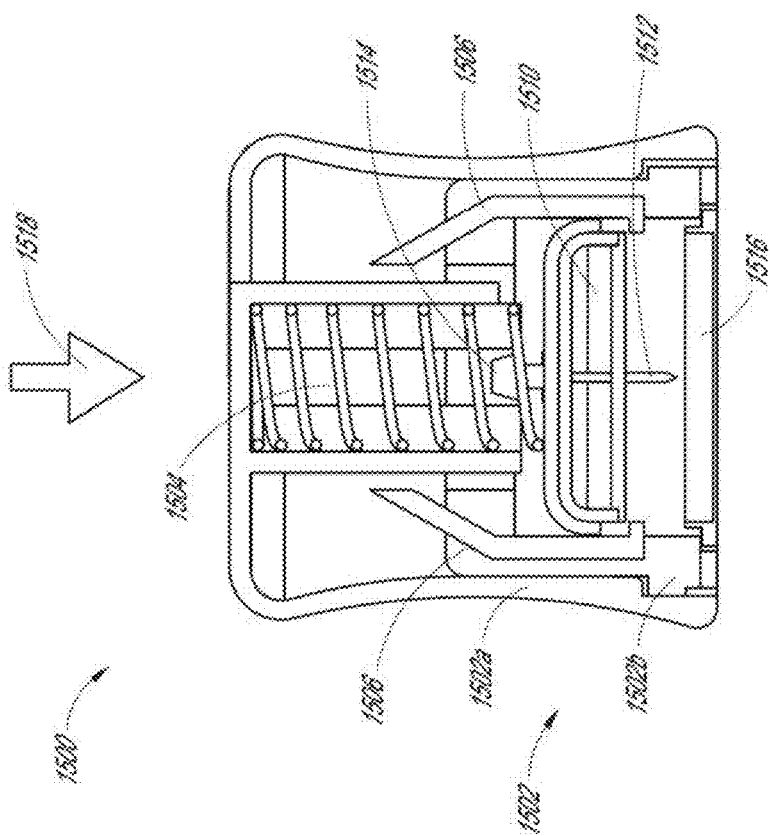

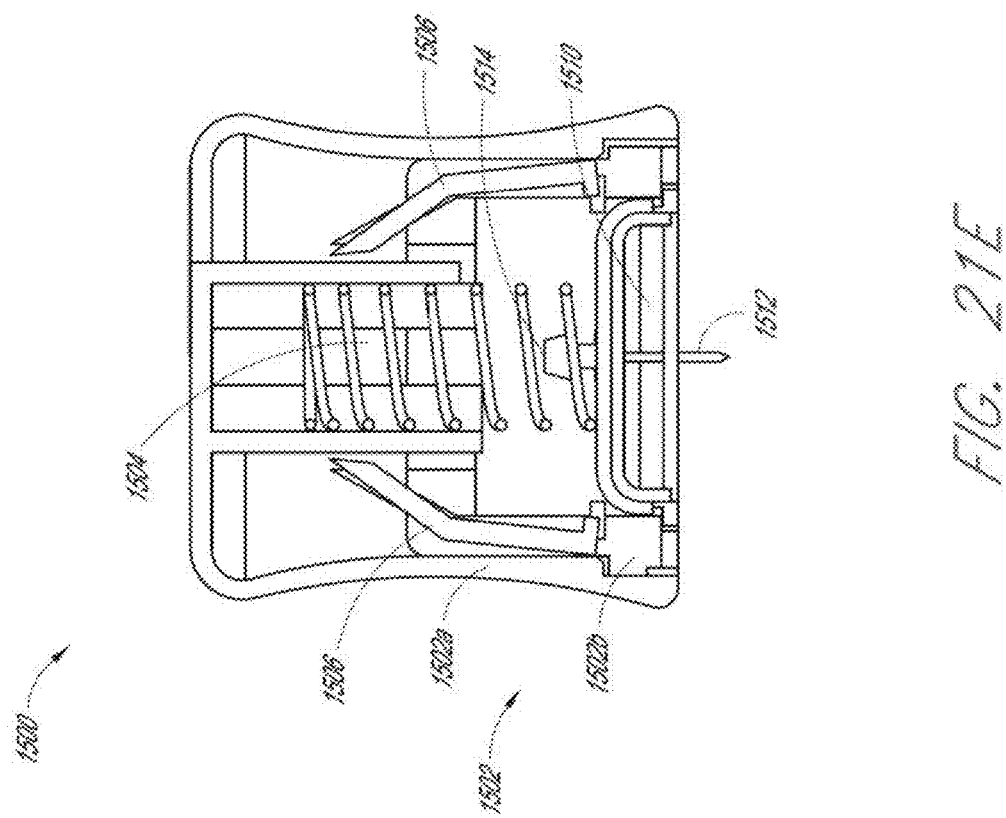

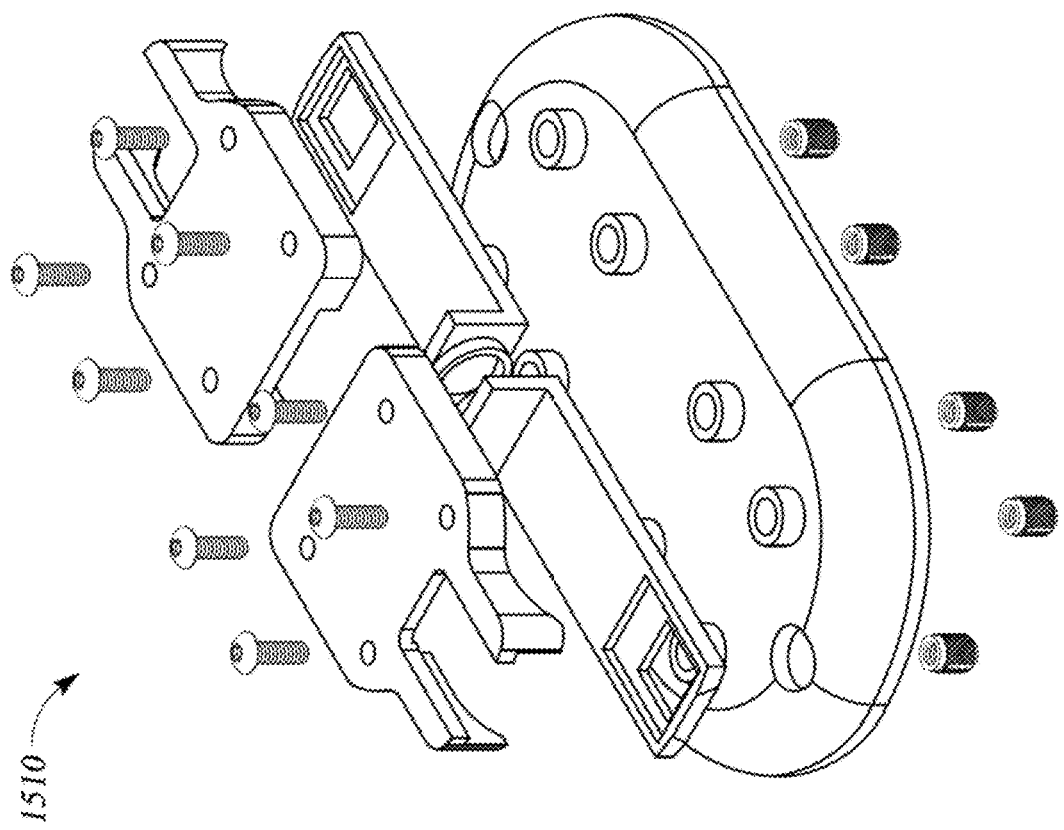

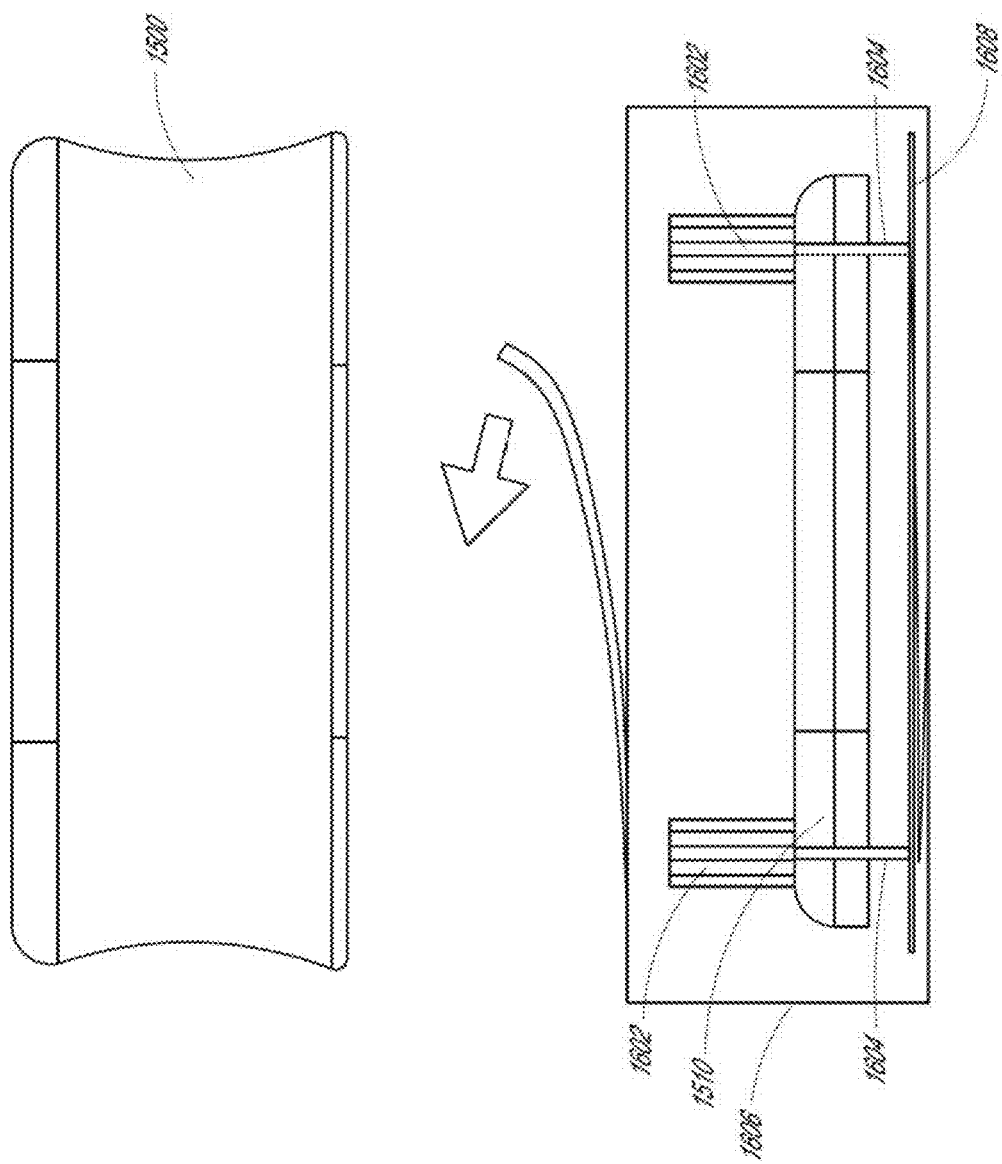

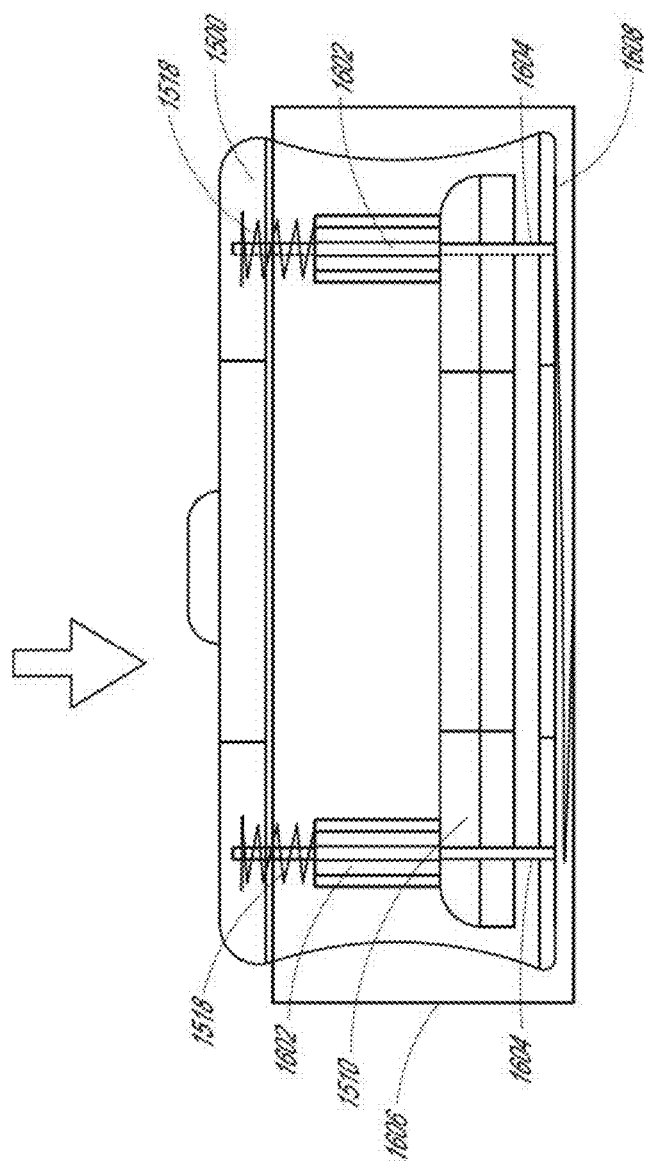

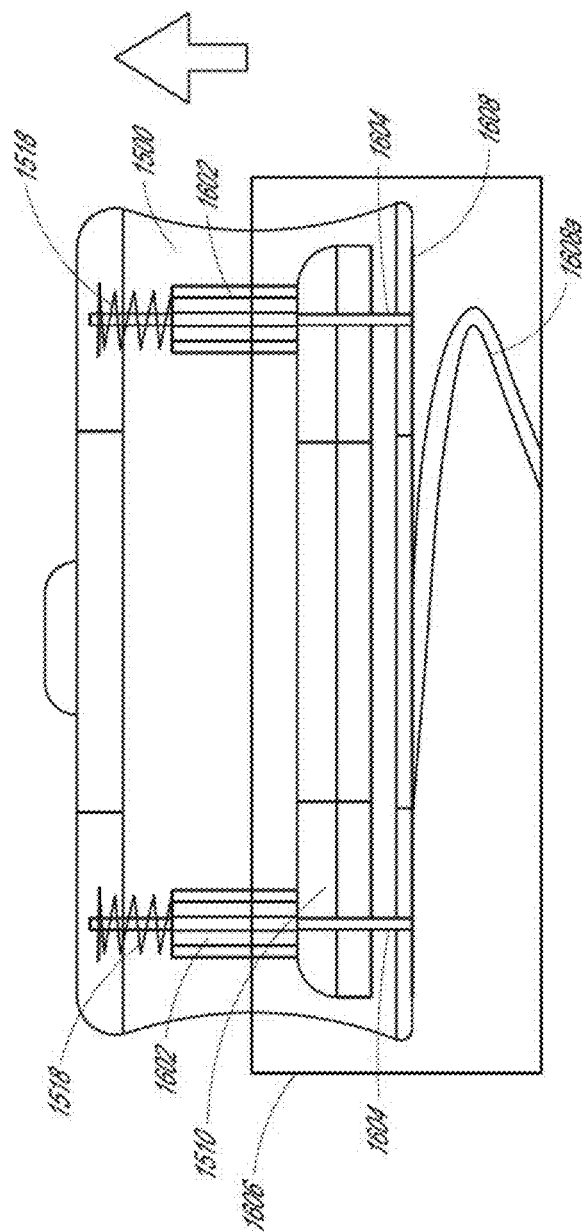

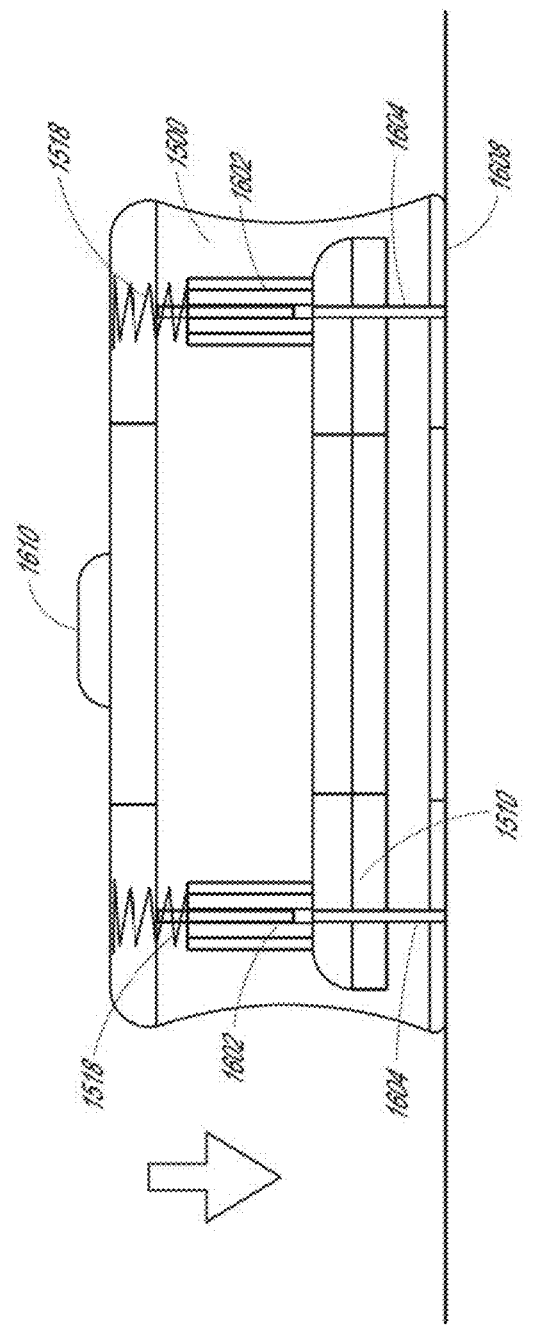

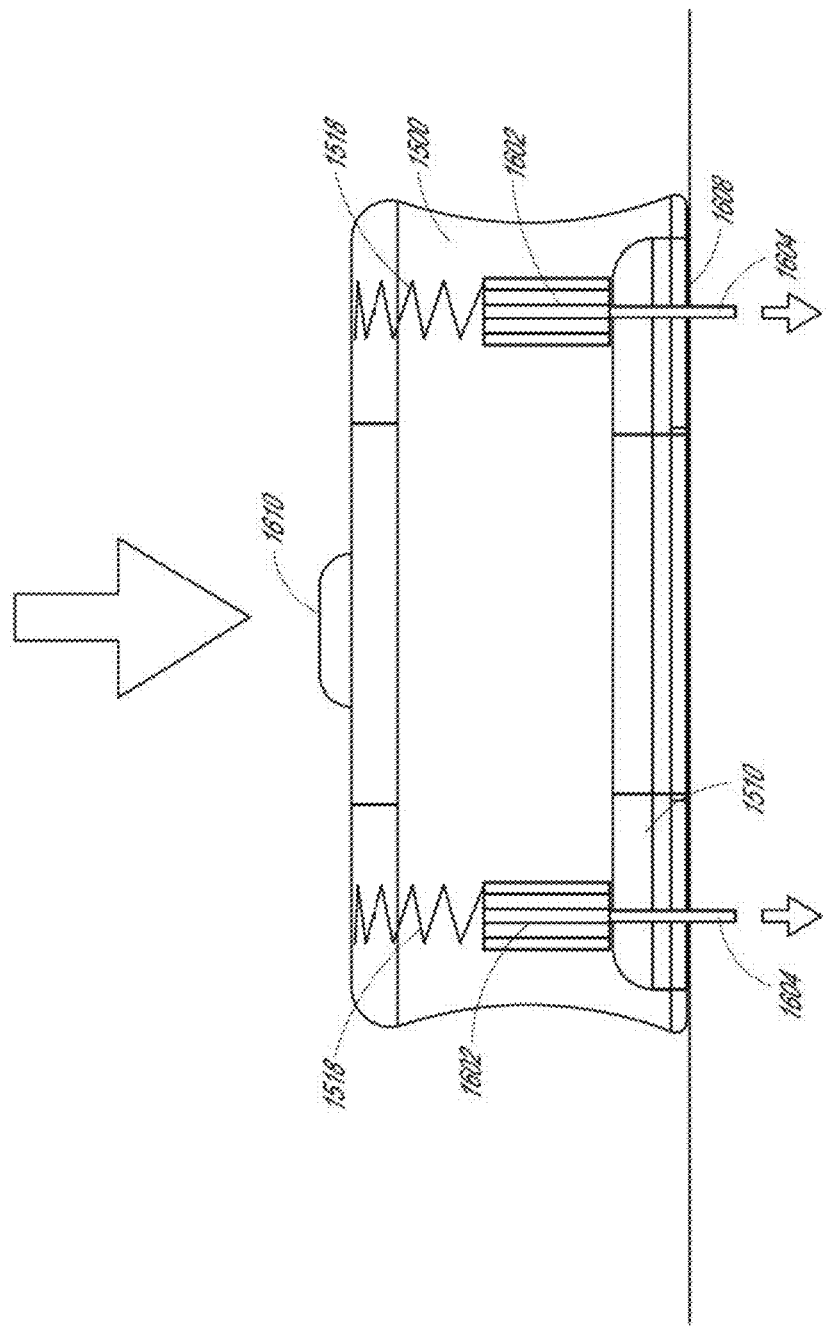

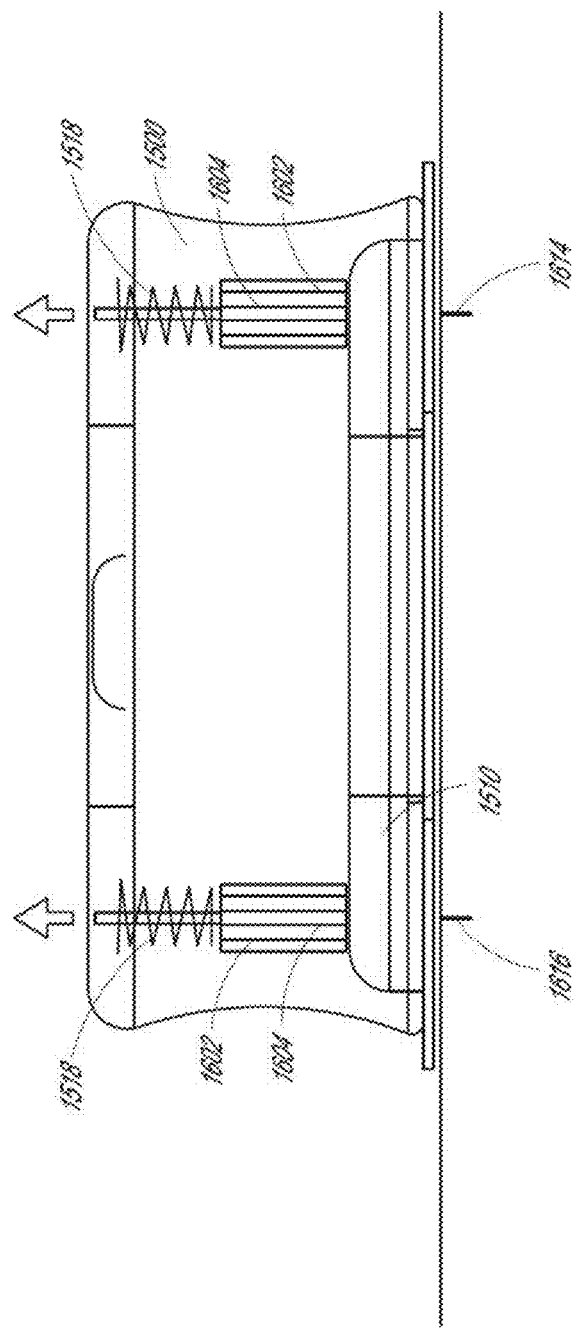

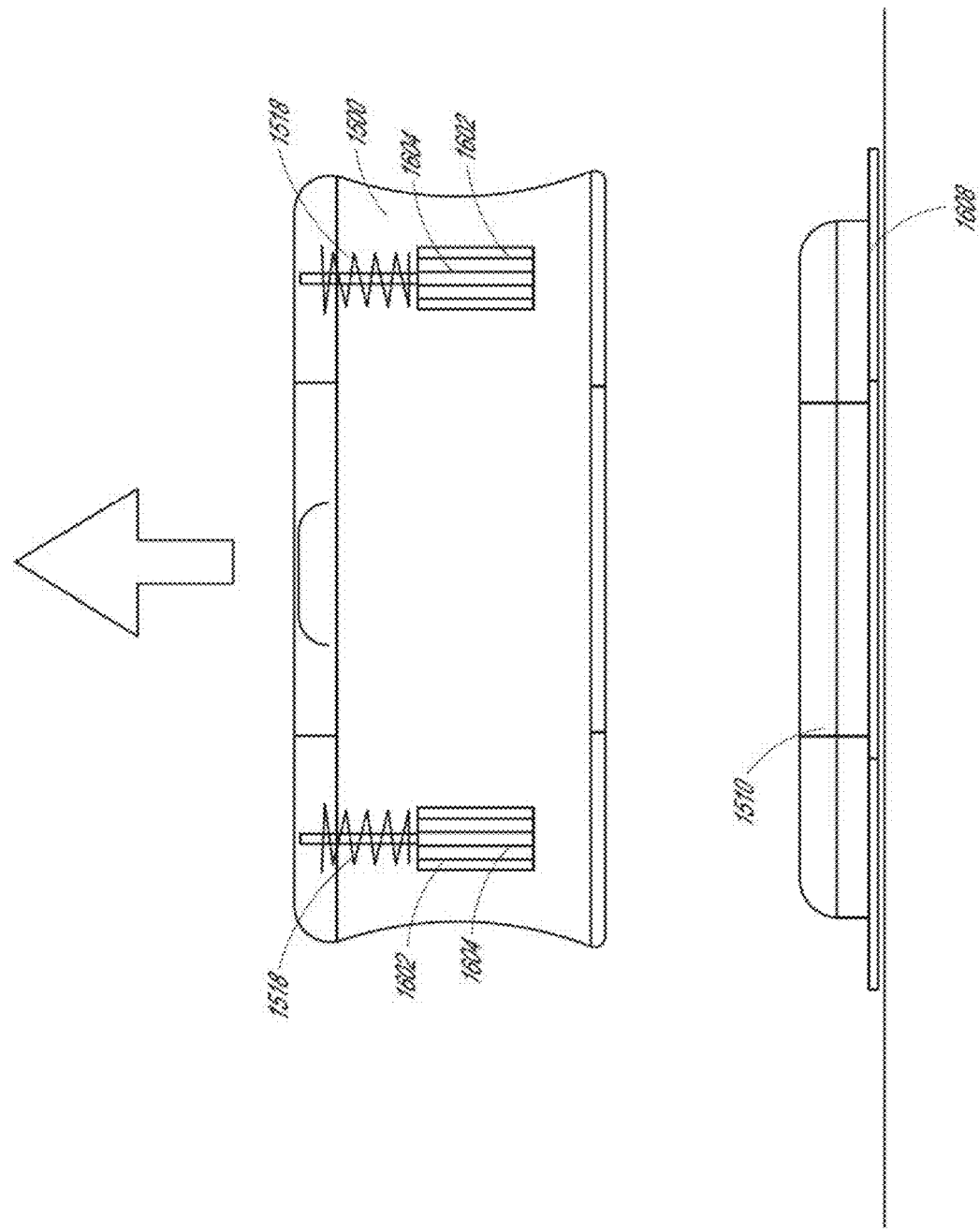

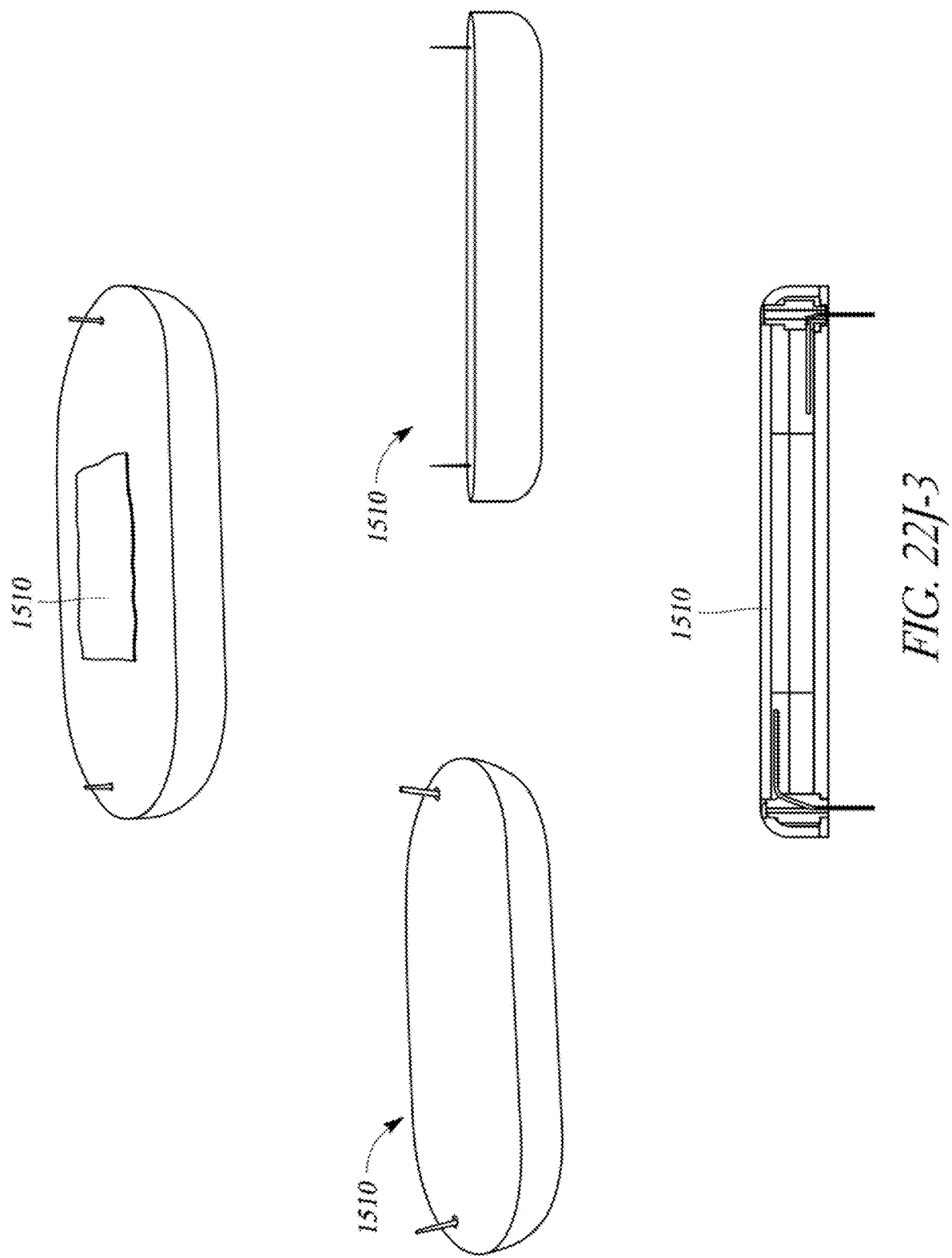

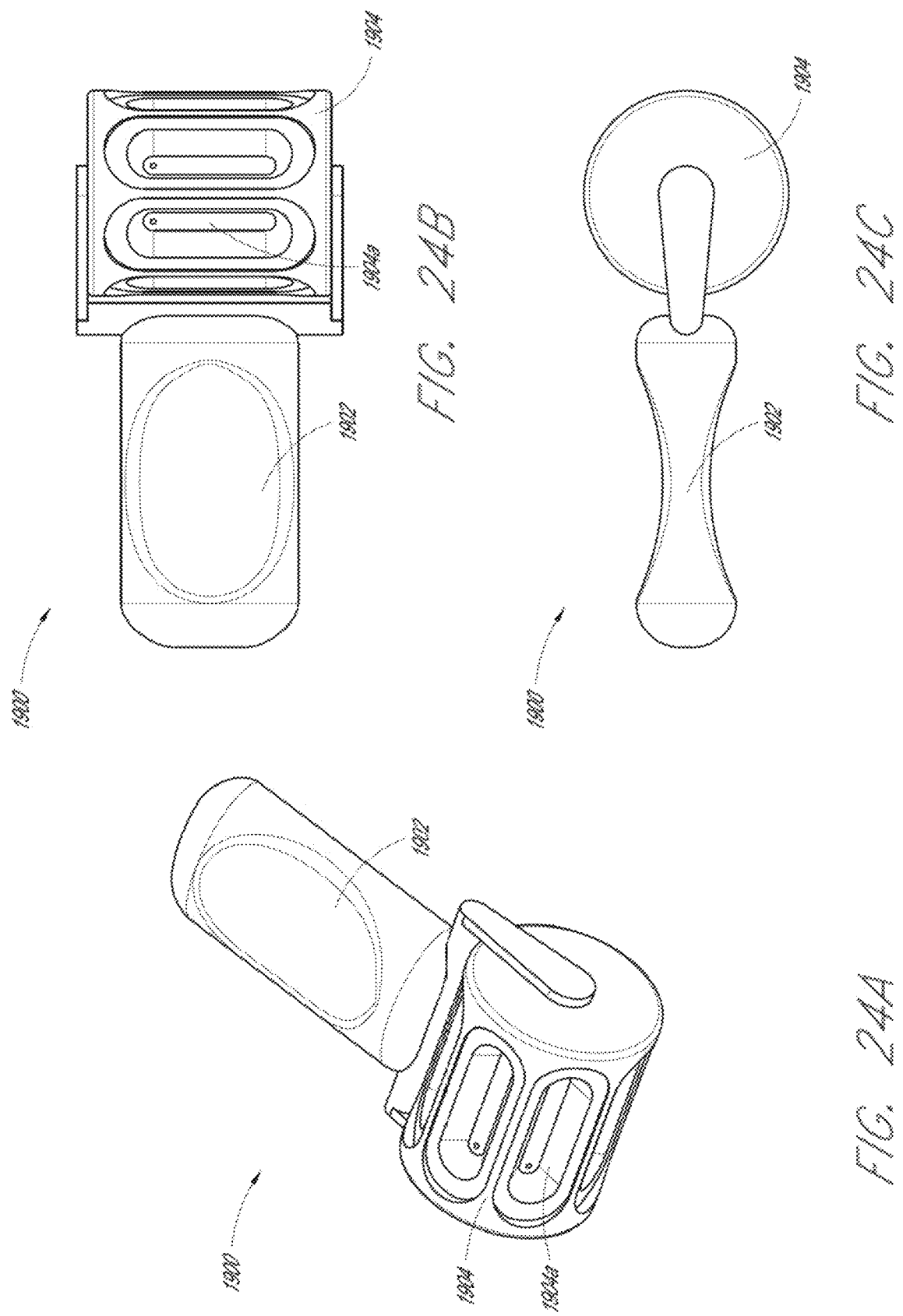

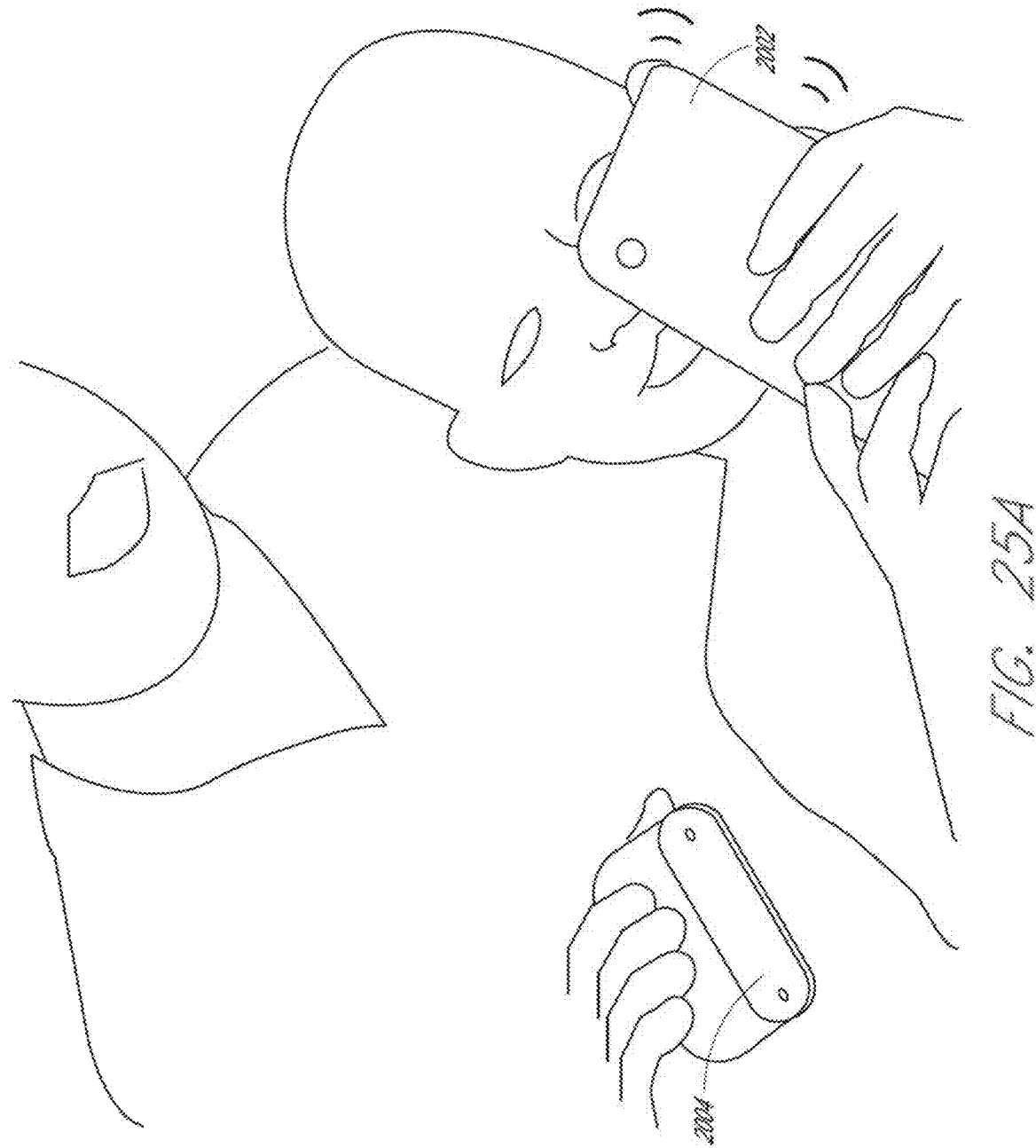

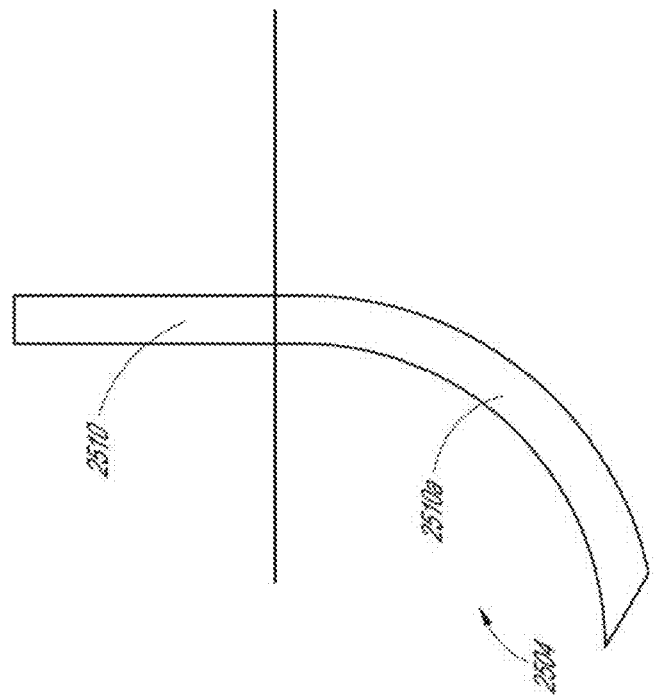
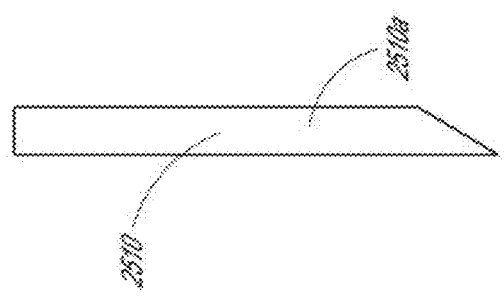
FIG. 27D-2
FIG. 27D-1

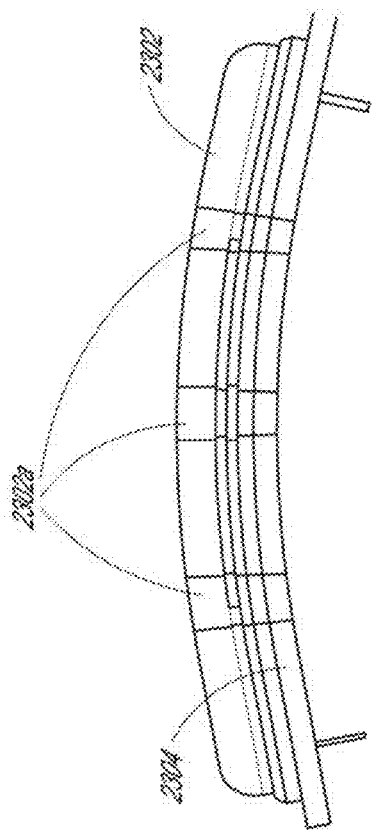
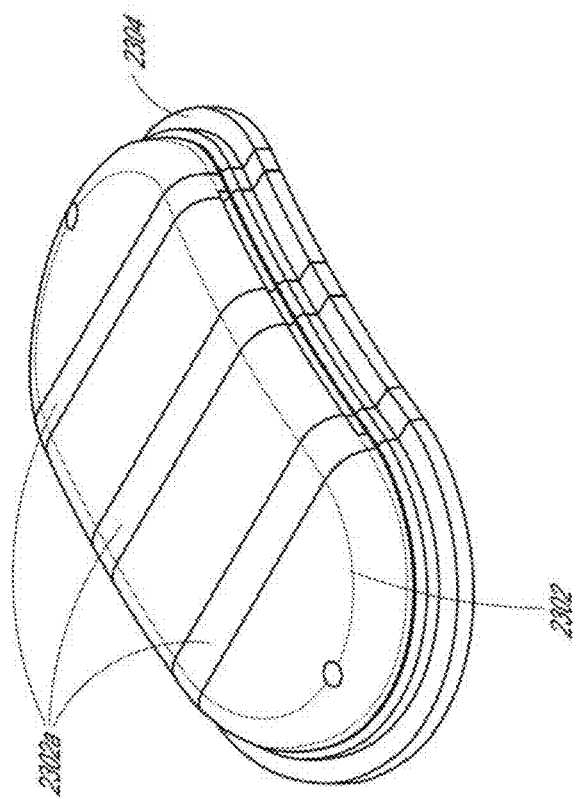
FIG. 30B
FIG. 30A

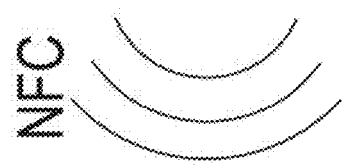
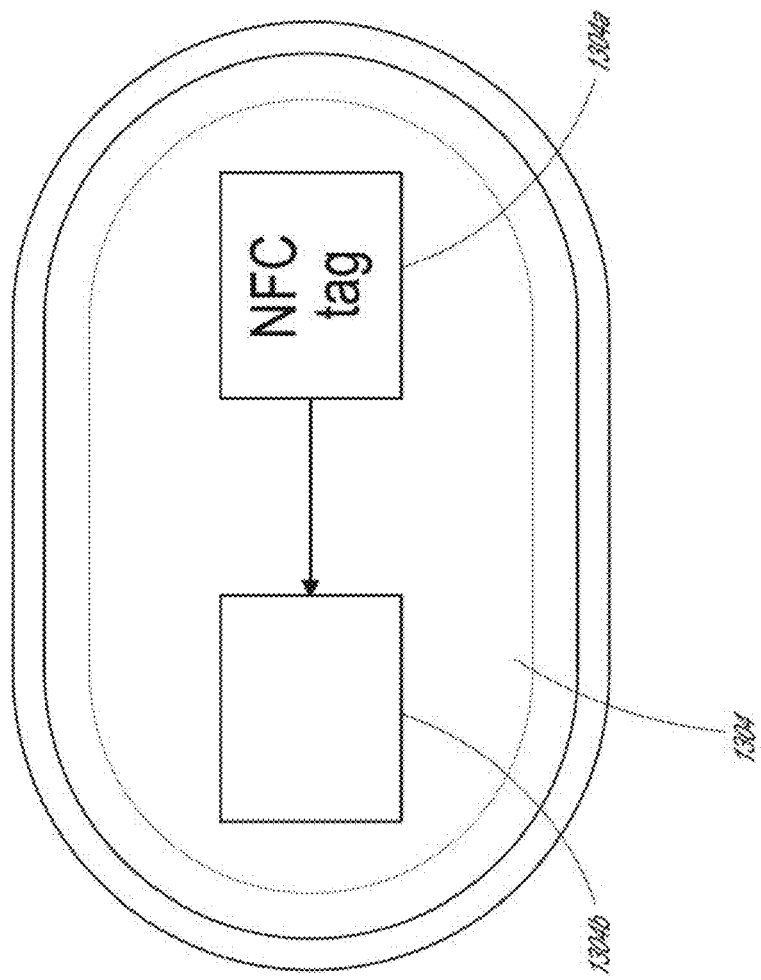
FIG. 32A

METHOD OF OPERATING REDUNDANT STAGGERED DISEASE MANAGEMENT SYSTEMS

CROSS REFERENCE TO RELATED APPLICATIONS

This application claims the benefit of priority under 35 U.S.C. § 119(e) to U.S. Provisional Application No. 62/968,107, filed on Jan. 30, 2020, entitled "CLOSED LOOP INSULIN DELIVERY SYSTEM," U.S. Provisional Application No. 62/978,480, filed Feb. 19, 2020, entitled "REDUNDANT STAGGERED GLUCOSE SENSOR DISEASE MANAGEMENT SYSTEM," U.S. Provisional Application No. 63/015,272, filed on Apr. 24, 2020, entitled "REDUNDANT STAGGERED GLUCOSE SENSOR DISEASE MANAGEMENT SYSTEM," and U.S. Provisional Application No. 63/044,831, filed on Jun. 26, 2020, entitled "REDUNDANT STAGGERED GLUCOSE SENSOR DISEASE MANAGEMENT SYSTEM" the disclosures of each of which are hereby incorporated by reference herein in their entirety.

FIELD OF THE DISCLOSURE

The general field of this disclosure is glucose sensing and disease management systems.

BACKGROUND

Diabetes is a chronic disease that impacts many individuals, both adults and children. The management of diabetes may include the measurement of glucose within the interstitial space including blood and/or interstitial fluid of a patient and administration of insulin to the patient. A closed loop insulin administration system includes both a sensor to take glucose measurements from the interstitial space including blood and/or interstitial fluid of the patient and an insulin administration device which administers insulin to the patient based on the glucose measurements. Closed loop insulin administration systems allow individuals impacted by diabetes to go about daily life with much less worry about their insulin or glucose levels which can vastly improve a diabetic's quality of life.

SUMMARY

The present disclosure provides redundant staggered glucose sensors and disease management system. The system includes a system which includes a glucose sensor and insulin pump to administer insulin to a patient based on glucose measurements from the glucose sensor. The system further includes another system with a separate glucose sensor. The separate glucose sensor provides redundancy for the system to ensure continuous monitoring when one of the glucose sensors is in a warmup period, a stabilization period, or an end of life period.

In some configurations, a disease management system can include a first disease management system and a second disease management system. The first disease management system can include a first glucose sensor and a first insulin pump. The second disease management system can include a second glucose sensor and a second insulin pump. In some configurations, the first disease management system and second disease management system can be configured to simultaneously attach to a patient and communicate with each other. In some configurations, the first glucose sensor can be in a settling period, the second glucose sensor is configured to provide patient glucose information to at least one of the first disease management system or the second disease management system.

In some configurations, the settling period can include a warmup period and/or a stabilization period.

In some configurations, the at least one of the first disease management system or the second disease management system can be configured to calculate a proper dosage of insulin based on patient glucose information from at least one of the first glucose sensor or the second glucose sensor. In some configurations, calculating the proper dosage of insulin can be further based on patient entered data. The patient entered data can include age, height, weight, and/or sex. In some configurations, calculating the proper dosage of insulin is further based on a customized glucose metabolization rating for the patient. The customized glucose metabolization rating can be based on the patient's weight, age, digestion rate, and/or insulin sensitivity.

In some configurations, the first disease management system or the second disease management system can be configured to communicate with a user device, such as a mobile phone, smart phone, tablet, computer, smart watch, other wearable device, or any other electronic user device. In some configurations, the first disease management system or the second disease management system can be configured to communicate with user device through Bluetooth and/or RF signal.

In some configurations, at least one of the first disease management system or the second disease management system can be configured to communicate with the user device. The user device can be configured to communicate with the smartwatch.

In some configurations, a first disease management system can further include a first insulin storage container fluidly connected to the first insulin pump. The first insulin pump can be fluidly connected to a needle which is capable of being inserted into a cannula that is implanted into a patient. The insulin storage container can include a flexible insulin pouch and the first disease management system can further include a spring that can be configured to apply pressure to the flexible insulin pouch. The flexible insulin pouch can be prefilled with insulin.

In some configurations, a first insulin pump can include a valve that is controlled in order administer a specific dosage of insulin to the patient. The valve can include 3 or more piezoelectric crystal valves. The valve can include 3 or more voice coil valves. The valve can include 3 or more piezoelectric stack valves. The first insulin pump can further include a filter connected between the valve and the needle. The valve can include a beginning valve, an end valve, and one or more intermediate valves located between the beginning valve and the end valve, the intermediate valves individually controllable in order to administer the specific dosage of insulin.

In some configurations, the first insulin pump can include a peristaltic pump. The peristaltic pump can include a circular gear; a circular portion attached to the circular gear such that when the circular gear rotates the circular portion can rotate at the same rotational speed, the circular portion located below the circular gear; two or more rollers located radially outward from the circular portion and in physical contact with the circular portion such that the roller can rotate as the circular portion rotates; a casing which wraps around the circumference of the rollers and the circular portion such that the casing and the rollers cooperate to form a circular channel, wherein the rollers are located at an inside portion of the circular channel and the casing is located on the outside of the circular channel; and a tubing located within the circular channel such that the tubing physically contacts both the casing and the rollers, wherein when the circular gear is rotated, the circular portion drives the two or more rollers which apply pressure to the tubing such that liquid within the tubing is driven from an inlet of the tubing to an outlet of the tubing.

In some configurations, a peristaltic pump can be a ratcheting peristaltic pump comprising a ratcheting driving mechanism in physical contact with the circular gear, wherein the ratcheting driving mechanism is capable of ratcheting teeth within the circular gear at one tooth at a time. The peristaltic pump can include: a circular gear with a circular hollow center; two or more rollers located within the circular hollow center and in physical contact with an inner wall of the circular gear such that the rollers rotate when the circular gear rotates; a stationary inner portion which is fixed, the stationary inner portion and the roller cooperate to form a circular channel, wherein the rollers are located at an outside portion of the circular channel and the stationary inner portion is located at the inner portion of the channel; and a tubing located within the circular channel such that the tubing physical contacts both the stationary inner portion and the rollers, wherein when the circular gear is rotated, the two or more rollers rotate which applies pressure to the tubing such that liquid within the tubing is driven from an inlet of the tubing to an outlet of the tubing. The peristaltic pump can include a ratcheting peristaltic pump can include a ratcheting driving mechanism in physical contact with the circular gear, wherein the ratcheting driving mechanism is capable of ratcheting teeth within the circular gear at one tooth at a time.

In some configurations, the first disease management system can include a case; a computing device capable of controlling the first insulin pump and receiving measurements from the first glucose sensor; a battery configured to power the first glucose sensor, the first insulin pump; the computing device; and an antenna connected to the computing device. The computer device can be configured to broadcast information through the antenna. The computing device, battery, first glucose sensor and the first insulin pump can be housed within the case. The antenna can be located outside or inside of the case. The case can include one or more needle insertion holes capable of having a needle inserted. The first disease management system can be mounted to a patient through an adhesive which connects to the case. The first disease management system can further include at least one of a light source, a photodiode, a vibration device, a tissue impedance measurement device, an insulin cannula impedance measurement device, an accelerometer, or a gyroscope. The first disease management system can further include one or more flexion points which may allow the first disease management system to flex. The one or more flexion points can include two flexion points.

In some configurations, the first disease management system can include: a first case housing the first insulin pump, a first computing device, an antenna, and a first battery; and a second case housing the first glucose sensor, a second computing device, an antenna, and a second battery. At least one of the first case or the second case further can house at least one of a light source, a photodiode, a vibration device, an accelerometer, or a gyroscope.

In some configurations, a peristaltic pump can include: a circular gear; a circular portion attached to the circular gear such that when the circular gear rotates the circular portion can rotate at the same rotational speed, the circular portion located below the circular gear; two or more rollers located radially outward from the circular portion and in physical contact with the circular portion such that the roller can rotate as the circular portion rotates; a casing which can wrap around the circumference of the rollers and the circular portion such as to cooperate to form a circular channel, wherein the rollers are located at an inside portion of the circular channel and the casing is located on the outside of the circular channel; and a tubing located within the circular channel such that the tubing physically contacts both the casing and the rollers, wherein when the circular gear is rotated, the circular portion can drive the two or more rollers which apply pressure to the tubing such that liquid within the tubing is driven from an inlet of the tubing to an outlet of the tubing.

In some configurations, a peristaltic pump can include: a circular gear with a circular hollow center; two or more rollers located within the circular hollow center and in physical contact with an inner wall of the circular gear such that the rollers can rotate when the circular gear rotates; a stationary inner portion which can be fixed, the stationary inner portion and the roller can cooperate to form a circular channel, wherein the roller can be located at an outside portion of the circular channel and the stationary inner portion can be located at the inner portion of the channel; and a tubing located within the circular channel such that the tubing physical can contact both the stationary inner portion and the rollers, wherein when the circular gear is rotated, the two or more rollers rotate which can apply pressure to the tubing such that liquid within the tubing is driven from an inlet of the tubing to an outlet of the tubing.

In some configurations, a ratcheting peristaltic pump can include: a peristaltic pump, such as described above; a ratcheting driving mechanism in physical contact with the circular gear, wherein the ratcheting driving mechanism can be capable of ratcheting teeth within the circular gear at one tooth at a time. The ratcheting driving mechanism can include a solenoid, muscle wire, a ratchet motor, and/or a direct current motor.

In some configurations, a method of priming a peristaltic pump can include: providing a peristaltic pump; connecting the inlet of the tubing an insulin source; running the peristaltic pump to pump insulin from the insulin source from the inlet to the outlet until insulin exits the outlet; connecting the outlet of the tubing to a buffered solution source; running the peristaltic pump to pump buffered solution from the buffered solution source until the buffered solution enters all of the tubing contacting each of the rollers.

In some configurations, a primed peristaltic pump can include: a peristaltic pump such as described above, wherein the input of the tubing is connected to an insulin source, wherein the portion of the tubing from the closest roller to the input of the tubing all the way to the output of the tubing is filled with a buffered solution, and wherein the portion of the tubing starting where the buffered solution is located all the way to the input of the tubing connected to the insulin source is filled with insulin.

In some configurations, a method of using a primed peristaltic pump can include: providing the primed peristaltic pump; connecting the outlet of the tubing to a patient; monitoring the patient's glucose level; determining the patient's glucose level is at a safe range to accept a small dosage of insulin; operating the primed peristaltic pump until all of the buffered solution has exited the tubing; and verifying that the patient's glucose level has not changed.

In some configurations, a method of operating redundant glucose sensors can include: operating a first glucose sensor on a patient; operating a second glucose sensor on the patient; wherein at least one of the first glucose sensor or second glucose sensor is not in a warmup period, a stabilization period, or an end of life period; operating an insulin pump based on the measurements of the first glucose sensor or second glucose sensor not operating during a warmup period, a stabilization period, or an end of life period. The first glucose sensor or the second glucose sensor and the insulin pump can be housed in one unit. The insulin pump and at least one of the first glucose sensor or second glucose sensor operating during a warmup period, a stabilization period, or an end of life period can be housed in one unit. The first glucose sensor or second glucose sensor not operating during a warmup period, a stabilization period, or an end of life period and another insulin pump can be housed in another unit. The insulin pump can be based on the measurements of the first glucose sensor or second glucose sensor not operating during a warmup period when the insulin pump is not operating. The one unit can include a first insulin source storing insulin and the another unit can include a second insulin source storing insulin, and wherein the insulin pump and another insulin pump deliver insulin from the first insulin source and the second insulin source such that the insulin in the first insulin source and the second insulin source is emptied before the insulin in the first insulin source and the second insulin source expires.

In some configurations, a method can further include notifying the patient when it is time to replace the one unit or the other unit. Notifying the patient can include sending a message through the patient's user device or enabling the one unit or the other unit to vibrate.

In some configurations, the first glucose sensor, the second glucose sensor, and the insulin pump can all be housed in separate units. The first glucose sensor or the second glucose sensor and the insulin pump can be housed in one unit. The first glucose sensor or the second glucose sensor and another insulin pump can be housed in one unit, and wherein the insulin pump can be housed in another system.

In some configurations, a method can include replacing the first glucose sensor or the second glucose sensor with a third glucose sensor when the not replaced first glucose sensor or second glucose sensor is not operating in a warmup period, a stabilization period, or an end of life period, wherein the not replaced first glucose sensor or second glucose sensor will not be operating in an end of life period when the third glucose sensor is running in a warmup period or a stabilization period.

In some configurations, a method of using an applicator for applying a disease management system, the method can include: providing the disease management system within packaging; opening the top of the packaging to expose the top of the disease management system, wherein the disease management system is preloaded with needles, the needles including tips which face towards the bottom of the packaging; grasping the disease management system within the applicator; positioning the applicator with the disease management system on a patient; launching the disease management system onto the patient such that the needles puncture the patient's skin, wherein the applicator comprises a retracting mechanism which retracts the needles after they puncture the patient's skin; and ejecting the used needles from the applicator such that the applicator is ready to apply another disease management system. The needles can be housed within guidance tubes before launching the insulin dosage unit onto the patient. When in the packaging, the disease management system can be preloaded with lancet backings, wherein when the needles are retracted, the needles can retract into the lancet backings, and wherein ejecting the used needles can include ejecting the used needles within the lancet backings. A method can include removing the applicator after launching the disease management system onto the patient, wherein removing the applicator can include leaving the applicator on the patient while removing the needles within the lancet backings.

In some configurations, a disease management system can include: a case; a glucose sensor; an insulin storage chamber; an insulin pump in fluid connection with the insulin storage chamber; a battery; a computing device configured to receive measurements from the glucose sensor and control the insulin pump provide dosages of insulin to a patient based on measurements from the glucose sensor; and an antenna connected to the computing device, wherein the computing device can be further configured to send measurements from the glucose sensor to other disease management units, a smart device, and/or a smartwatch through the antenna, receive glucose measurements from other disease management units, a smart device, and/or a smartwatch, and send dosage instructions through the antenna to other disease management units, and wherein the case houses the glucose sensor, the insulin storage chamber, the insulin pump, the battery, and the computer device.

In some configurations, a disease management system can include a near field communication (NFC) device including a unique ID tag associated with the disease management system, wherein a user device is capable of causing the NFC device to send the unique ID tag to the user device which allows the user device to identify the disease management unit and pair with the disease management system. The NFC device can be configured to communicate with the user device to trigger the disease management system to manually administer a dosage of insulin to the patient. The NFC device can be configured to communicate with a wearable NFC device to trigger the disease management system to manually administer a dosage of insulin to the patient. The wearable NFC device can include a safety mechanism to prevent the wearable NFC device from triggering the disease management system from manually administering a dosage of insulin to the patient unless the safety mechanism is enabled. The safety mechanism can include a switch, toggle, button, and/or knob. The wearable NFC device can be mounted on a bracelet, watch, necklace, or belt. The NFC device can be configured to differentiate between different wearable NFC devices such that one of the wearable NFC devices communicates with the NFC device to trigger the disease management system to manually administer a different dosage of insulin to the patient than another of the wearable NFC devices. The computing device can be configured to block a manual administration of a dosage from the wearable NFC device at least during a portion of the time.

In some configurations, a case can include a manual dosage mechanism which is capable of triggering the disease management system to manually administer a dosage of insulin to the patient. The case can be segmented such that the portion of the case with the manual dosage mechanism is removable and replaceable. The computing device can be configured to communicate with an additional manual dosage device which can be configured to be physically connected with the case, the additional manual dosage device can be configured to trigger the disease management system to manually administer a dosage of insulin to the patient. The antenna can be embedded within the case or on the outside of the case.

In some configurations, a disease management system can include: a first disease management system and a second disease management system. The first disease management system can include: a first glucose sensor; a first insulin pump; a first computing device can be configured to receive measurements from the first glucose sensor and control the first insulin pump provide dosages of insulin to a patient based on measurements from the first glucose sensor; a first antenna connected to the first computing device; a first near field communication (NFC) device can include a first unique ID tag associated with the first disease management unit, wherein a user device is capable of causing the first NFC device to send the first unique ID tag to the user device which allows the user device to identify the disease management unit and pair with the disease management unit. A second disease management system can include: a second glucose sensor; a second insulin pump; a second computing device configured to receive measurements from the second glucose sensor and control the second insulin pump provide dosages of insulin to a patient based on measurements from the second glucose sensor; a second antenna connected to the second computing device; a second near field communication (NFC) device can include a second unique ID tag associated with the second disease management unit, wherein the user device is capable of causing the second NFC device to send the second unique ID tag to the user device which allows the user device to identify the second disease management unit, and wherein the first disease management system can be configured to pair to the second disease management system through request of the user device. The second disease management system can be configured to pair with the user device. The user device can include a smartphone, tablet, wearable device, or other electronic device. In some examples, the other electronic device can include an emergency glucagon device.

In some configurations, a flexible disease management system can include: a glucose sensor; a computer device; an antenna, wherein the computing device can be configured to transmit glucose data received from the glucose sensor through the antenna; a flexible battery configured to power the computer device and the glucose sensor; and a flexible bandage configured to adhere the flexible battery, computer device, and the glucose sensor to the patient.

In some configurations, an applicator for a disease management system can include: a cylindrical applicator wheel capable of storing one or more patient treatment units; a handle attached to the applicator wheel at the center of two opposing sides of the applicator wheel, wherein the applicator wheel can be configured to physically contact a patient and roll on a patient and, when rolling, apply at least one of the one or more patient treatment units to a patient. The one or more disease management systems can include one or more glucose sensor units, one or more insulin pump systems, and/or one or more combined glucose sensor and insulin pump units.

In some configurations, a method of distracting a patient during application of a disease management system can include: providing the disease management system for application to the patient, wherein the disease management system comprises one or more needles; applying the disease management system to the patient; and using a distraction device to distract the patient during application of the disease management system to the patient, wherein the distraction device interacts with the disease management system such that the distraction device times a distracting event with application of the disease management system. The distraction device can include a user device or another disease management system including a vibration device. The distraction device can include a user device which allows a patient to play a game, watch a movie, or read a story before and during application of the disease management system, and wherein the distracting event comprises the climax of the game, movie, or story. The distraction device can include another disease management system including the vibration device, and wherein the distracting event comprises vibration of the vibration device just before and during application of the disease management system. The method can include operating a vibration device within the patient treatment unit after application of the disease management system to the patient. The disease management system can include an indicator which can indicate when a distracting event is occurring in order to indicate that the timing is optimal to apply the disease management system to the patient. An indicator can include a light emitter or a vibrating module. In some configurations this event sequence and timing can be an API that allows other 3rd parties to develop games around the event process and timing to have new distraction games created.

In some configurations, a needle for implanting a glucose sensor or cannula can include a top portion and a bottom portion, wherein the bottom portion is rigid at some times and flexible at some times. The bottom portion can include a material which is flexible when exposed to water and rigid when not exposed to water. The bottom portion can include hydrogel or collagen. The bottom portion can include an inner layer and an outer layer, wherein the inner layer and outer layer can be made out of different materials. One of the inner layer or the outer layer can include hydrogel or collagen and the other of the inner layer or the outer layer can include metal or plastic. The bottom portion can be rigid when not exposed to ultra-violet light and flexible when exposed to ultra-violet light. The bottom portion can include a bioresorbable material. The needle can be a hollow needle. The needle can be a solid needle.

BRIEF DESCRIPTION OF THE DRAWINGS

FIG. 1B illustrates an example disease management environment that may include a disease management system.

FIGS. 2A-2E illustrate various interleaved device replacement schedules.

FIGS. 2H-2K illustrate aspects of an example disease management system that can be reused, refurbished, or disposed of after use.

FIG. 4C is a cross sectional view of the insulin pump system of FIGS. 4A and 4B.

FIG. 4D-2 illustrates an example layout of components of a disease management system.

FIGS. 4E-1 and 4E-2 illustrate various example implementations of a disease management system having flexible and rigid portions.

FIG. 4G-1 illustrates an example medication pouch or bladder.

FIG. 4G-2 illustrates an example seal of a pouch, such as illustrated in FIG. 4G-1.

FIG. 4G-3 illustrates an example pressure release valve for a pouch, such as illustrated in FIG. 4G-1.

FIG. 4J illustrates an example vibration motor mount for an implementation of a disease management system.

FIG. 4M illustrates an example adhesive plate locking mechanism for an implementation of a disease management system.

FIG. 5B-1 is a perspective schematic view of an exemplary implementation of a disease management system.

FIG. 5B-2 is a schematic view of an exemplary implementation of a circuit board which may be used in a disease management system.

FIG. 5B-3 is a perspective schematic view of an implementation of an insulin cannula as implemented within the disease management system.

FIG. 8C illustrates a cross-sectional view of the peristaltic pump.

FIGS. 11E and 11F illustrate various views of the process of FIG. 12 for using a primed peristaltic pump.

FIGS. 13A-13G illustrate various operational views of a valve style insulin pump.

FIGS. 14A and 14B illustrate perspective views of an implementation of a valve style insulin pump.

FIG. 14J-1 illustrates perspective views of another example pump of a disease management system.

FIGS. 14J-2 and 14J-3 illustrates perspective views of a first implementation of the example pump of FIG. 14G-1.

FIG. 14K-1 illustrates example plungers of an example pump of a disease management system.

FIG. 14K-2 illustrates example plunger positions and orientation in an example pump of a disease management system.

FIG. 14K-3 illustrates example priming of an example pump of a disease management system.

FIG. 14N illustrates another example muscle wire pump of a disease management system.

FIG. 14O illustrates perspective views of an example muscle wire pump of a disease management system.

FIGS. 15A-15D illustrate aspects of an example air bubble detection systems that may be part of an insulin pump.

FIG. 17 illustrates an example air bubble removal system that may be part of an insulin pump.

FIGS. 19A-19D depict example iterations of a disease management system configured to perform electrochemical measurements.

FIGS. 20B-20d illustrate various cross sectional views of the applicator of FIG. 20A.

FIG. 21A illustrates a perspective view of an applicator for applying a disease management system to a patient.

FIGS. 21B-1 to 21F-2 illustrate various cross sectional views at various stages of use of the applicator of FIG. 25A.

FIGS. 21F-3-21F-21 illustrate various views of disease management system components including an applicator.

FIGS. 22A-22I illustrates various views of an implementation of the applicator of FIGS. 22A-22F applying a disease management system to a patient.

FIGS. 22J-1-22J-2 illustrates an implementation of a disease management system integrated with needles.

FIGS. 22J-3 illustrates an implementation of a disease management system that may be applied by an applicator.

FIGS. 24A-24D illustrate various perspective views of an applicator for applying disease management systems to a patient.

FIGS. 25A and 25B illustrate views of various steps in a method of distracting a patient during application of a disease management system.

FIGS. 27A-1 and 27A-2 illustrate an exemplary implementation of a solid needle.

FIGS. 27B-1 and 27B-2 illustrate an exemplary implementation of a solid needle.

FIG. 27B-3 illustrates an exemplary implementation of a multi-layer solid needle.

FIGS. 27C-1 and 27C-2 illustrate an exemplary implementation of a hollow needle.

FIGS. 27D-1 and 27D-2 illustrate an exemplary implementation of a hollow needle.

FIGS. 27E-1 and 27E-2 illustrate an exemplary implementation of a hollow needle.

FIG. 30A is a perspective view of an exemplary implementation of a disease management system.

FIGS. 30B and 30C are side views of the disease management system of FIG. 30A.

FIG. 32A illustrates a system for connecting a user device with a disease management system.

DETAILED DESCRIPTION

Figure 1A:
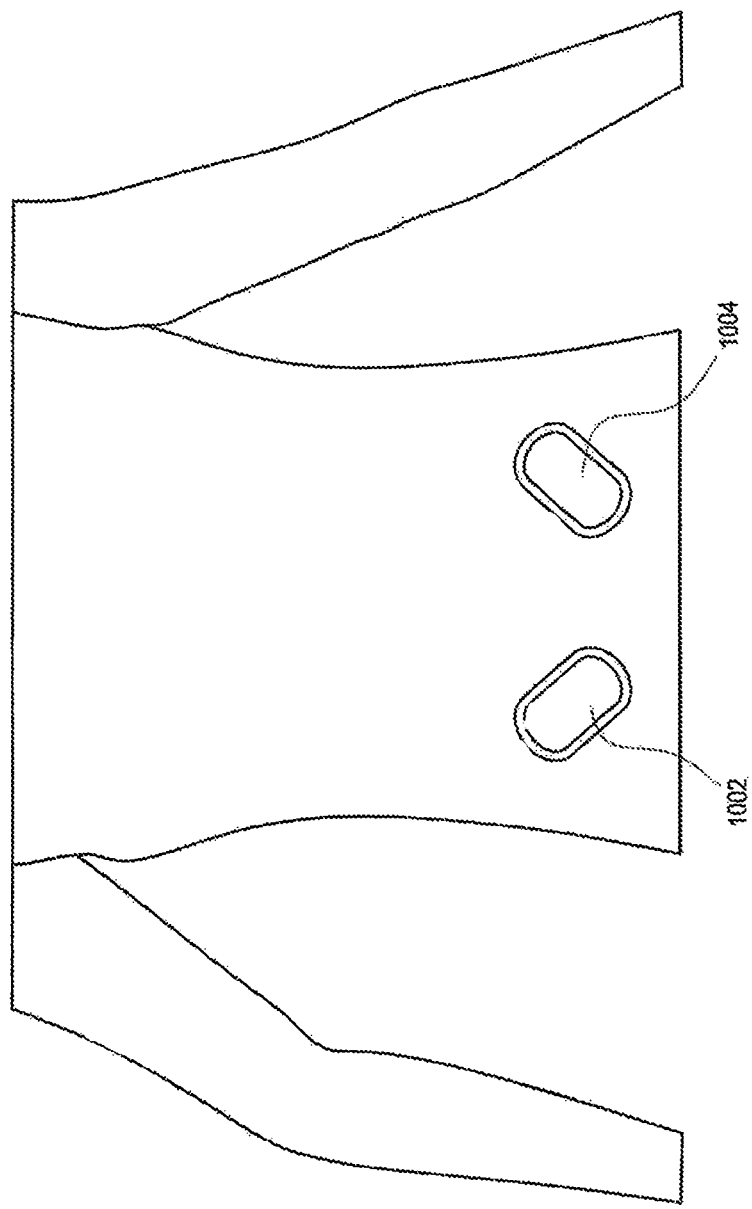
FIG. 1A illustrates a view of interleaved operation of disease management systems on a patient.

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

Systems and methods described herein may be applicable to diabetic disease management or other patient condition that may be treated with an implant or other minimally or non-invasive device configured to monitor a patient state and deliver medication on an ongoing or temporary basis. While reference may be made to a specific disease, such as diabetes, systems and methods described herein may be applicable to other diseases and conditions.

While in some examples, systems and methods described herein may reference monitoring or sensing of a specific parameter or blood analyte, such as glucose, other physiological conditions, physiological states, physiological parameters, physiological markers, blood analytes, the like or a combination thereof may be monitored or determined in addition or in the alternative to glucose. Similarly, while in some examples, reference may be made to a specific type of sensor, such as a glucose sensor, other analyte sensors may additionally or alternatively be used. For example, a glucose sensor may be configured to additionally measure other analytes. Additionally or alternatively, while reference may be made to specific types of invasive or non-invasive sensors, such as an invasive glucose sensor, any type of invasive or non-invasive sensor may be used, such as a non-invasive analyte sensor.

Additionally or alternatively, while in some examples, systems and methods described herein may reference specific medication, such as insulin or glucagon, to be delivered to the patient, other medications, fluids, or treatments may be administered in addition or in the alternative to medications such as insulin or glucagon. Similarly, while in some examples, reference may be made a specific type of pump or other component associated with a medication or fluid, such as an insulin pump, the components described herein may be used with any fluid or medication.

Additionally, while reference may be made to the use of a certain number or type of device, any combination and number of devices may be used, such as one, two, three, four or more redundant or different devices. In some examples, a single device may be used to manage aspects of a patient's health, such as a combined medication pump and analyte sensor. In some examples, redundant devices may be used to manage aspects of a patient's health, such as two combined medication pump and analyte sensor devices. In some examples, different devices may be used and in communication to manage different aspects of a patient's health or different aspects of disease management, such as a separate medication pump and analyte sensor.

It has been discovered that when first beginning operation, glucose sensors have a settling period which may include a warmup period where the glucose sensors do not give off measurements and a stabilization period where the glucose sensors produce measurements but these measurements are inaccurate. The warmup period may typically last for one to two hours and the stabilization period may typically last for up to 24 hours. Further, during the end of the glucose sensors' operational life, there is another period where the glucose sensors produce measurements but these measurements are often inaccurate. This period is often referred to as the end of life period and typically covers the last few days of the sensor's operational life. During the settling period and the end of life period, it is advantageous to supplement the glucose measurements with other more accurate readings.

Disclosed is a disease management system including a first disease management system including a first glucose sensor and a first insulin pump and a second disease management system including a second glucose sensor and a second insulin pump. The first disease management system and the second disease management system are configured to simultaneously attach to a patient and communicate with each other. While the first glucose sensor is in a settling period, the second glucose sensor is configured to provide blood glucose information about the patient to the first glucose sensor. Thus, while the first glucose sensor is giving no measurements or inaccurate measurements, the second glucose sensor may be used to provide accurate glucose measurements to increase the likelihood of accurate administration of insulin.

The present disclosure also describes an integrated system that incorporates the dosage system and glucose sensor into one unit. Various components of the unit are described in detail such as various insulin pumps and applicators that may be used to apply the unit to a patient.

In some examples, systems and methods described herein can include at least one disease management system, such as an insulin pump, CGM, combined insulin pump and CGM or applicator for applying a device to a patient or user.

A disease management system can have form factor parameters that improve upon current CGM and/or insulin pump system such as having a smaller, thinner, or more body conforming form. More body conforming can include a form factor, such as a belt, bandage, soft silicone, or similar form. In some examples, a smaller form factor may include smaller form as compared to current insulin pumps (for example, X mm×Y mm×5-10 mm).

In some examples, a disease management system may have an appealing visual appearance. The appearance of the device may be intuitive to its function.

A disease management system may have intuitive and easy placement such that a user may be able to intuitively perform the procedure after initial use or uses. A disease management system may have intuitive and easy removal such that a user may be able to intuitively perform the procedure after initial use or uses.

A device may be resistant to electrical, moisture, temperature, or other operating conditions. For example, a device may be configured to operate throughout and after defibrillation. In another example, a device may be configured operate without insulin in 50-113° F. (10-45° C.) and humidity of 10-95% between ground level and 12,000 feet of elevation. In another example, a device may be configured to operate with insulin in 50-98.6° F. (10-37° C.) and humidity of 10-95% between ground level and 12,000 feet of elevation. In another example, a device may be configured to operate in 7-130° F. (10-48° C.) with heat resistant genetically engineered proteins. In another example, device may be configured to operate after prolonged storage in a variety of conditions, such as up to 6 months in 35.6-77 (2-25° C.) and humidity of 10-95% between ground level and 12,000 feet of elevation. A device may be configured to operate in the presence of MRI. A device may be configured to operate through and not alarm metal detectors. A device may be configured to operate while submersed under water. For example, a device may be able to be submersed and functioning but not necessarily communicating with a mobile device while connected to the body in 1.5 meters (5 feet) of water for 60 minutes (IPX8). In another example, a device may be able to be submersed and functioning but not necessarily communicating with a mobile device while connected to the body in 7.6 meters (25 feet) of water for 60 minutes. A device may be configured to be dust resistant. For example, a device may be configured to have IP5X dust protection.

A device may be configured to be placed on a plurality of tissue sites, such as an arm, abdomen, lower back, upper buttocks, thigh or other site.

A device may be configured to stay on a tissue site for an extended period, such as for 3 days, 6 days, or 12 days. For example, a device may be configured to operate in an interleaved configuration, with a life of 3 days for an insulin pump component(s) and 6 days for a CGM component(s). In another example, a device may be configured to stay on the body for 12 days in an interleaved configuration, with a life of 6 days for an insulin pump component(s) and 12 days for a CGM component(s).

One or more interleaved disease management systems may be configured to use up to the entire amount of insulin in an insulin pump. Advantageously, the full use of insulin may prevent insulin extraction by a user. In some examples, as an interleaved device approaches end of insulin (for example, approximately 3 days), the treatment system may prompt the user to add a new interleaved device prior to the end of insulin. For example, a system may alert a user before insulin runs out with up to 6 hours, 12 hours, or other amount of time.

In some examples, one or more disease management systems may be preloaded with insulin and stored in refrigerated state (12 months) before use. A device may be able to withstand shipping in 36-77° F. (2-25° C.). A device may be able to withstand shipping in 20-120° F. (−6-48° C.) with heat resistant genetically engineered proteins and/or additional testing. Prior to usage, a device may be configured to have reduced air bubble formation as the insulin warms to room temperature. In some examples, a device may be shipped in sterile packaging until ready to be used by the patient.

In some examples, a device may be configured to use one or more separate applicators to facilitate insertion of a CGM sensor and insulin cannula. In some examples, one or more applicators and/or other disease management systems may utilize pain reduction or distraction systems and methods to reduce anticipatory, actual, or residual pain, such as haptic distraction on a device not being inserted to prevent anticipation pain.

In some examples, one or more disease management systems may not have any visible or external tubes.

In some examples, a treatment system may include one or more visual, audible, or haptic indicators configured to notify a user of one or more device and/or biological states associated with managing insulin and/or glucose. The one or more indicators may be generated, displayed, or otherwise indicated on a mobile device paired with a disease management system, an application, or on a disease management system. The one or more indicators may indicate a status such as working, expired, will expire in 12 hours, or next one to be replaced. In some examples, a device may display an intuitive status of, for example: overall system function (by, for example, Green, yellow, or red color coded indicators), good to go, warnings (such as low battery or insulin supply), or errors. This intuitive display include interfaces beyond visual such as but not limited to feedback such as audible or tactile patterns.

In some examples, a device can include multiple insertion sites, such as an insertion site for a CGM and an insertion site for insulin administration.

A device can be configured to avoid injecting a venous air bubble of lethal dosage, such as greater than 12 ml.

A device may be configured to use U-200 insulin (or equivalents) to decrease an insulin reservoir size by half as compared to other disease management systems.

A device may include a continuous glucose monitor (CGM), continuous analyte monitor (CAM), or insulin assay on the tip of the insulin cannula.

A device or applicator may be configured to prime insulin for administration.

In some examples, a device may have physically separated components. For example, a device may have an insulin cannula and a continuous analyte monitor electrode (s) (CAM or CGM) separated at tip to tip by, for example, at least 50 mm.

In some examples, a device may include a continuous analyte monitor (CAM). A CAM may be configured to measure analytes including but not limited to chylomicrons, triglycerides, and cholesterol.

A device may be sterile to 1E-6 SAL. A device may be manufacturable without a clean room.

A device may include a glucose accuracy of less than or equal to and including 8% mean absolute relative difference (MARD) or more. A device may not require SMBG bias measurements to reach 8% MARD.

A device may have an insulin dosing accuracy such that a device may pump all discrete insulin volume to within 5% for U-100 or 2.5% if U-200 maximum error.

In some examples, a disease management system may be configured to have a minimum insulin dosage of 0.175 uL for U-200 insulin.

In some examples, a disease management system may include multiple electrodes. In some examples, an electrode may have a diameter of less than or equal to approximately 300 um.

A pump of a disease management system may be configured to emit low noise levels. For example, a pump may be quiet enough to allow discrete usage of an insulin pump.

A cannula and electrode may be configured to resist breaking by in-body or extraction forces.

An insulin cannula may have an outer diameter of up to and including 600 um or more. A cannula or electrode may be longer than 4 mm stratum corneum surface to deepest point in tissue. A cannula or electrode of a length up to and including 13 mm or more from a stratum corneum surface to deepest point.

A device may include a buffer to prevent over insertion by children between 7-12 years of age. For example, a device may have a 1 mm buffer added to an adhesive to make the insertions penetrate no deeper than 3 mm. In another example, pre-teens and adults 13 and older may have no additional thickness added to the adhesive to make the insertions penetrate no deeper than 4 mm.

In some examples, a device may include an adhesive. An adhesive may be configured to not create a rash. An adhesive may retain contact to a tissue site for a period of time up to and including 6 days. An adhesive may contain an anesthetic around the insertion site location that may last long enough to address movement paint, such as for a few hours.

A device may be configured to detect if it is on body or off body. Advantageously, this may help prevent titration while in unusual circumstances (for example, even in situations where a device is removed from the body such that an active sensor is removed and then placed in sugar water bath while a device is still in applicator).

A device may be configured to observe one or more biometric parameters, such as a user's pulse rate or a user's SpO2. In some configurations, a device may be configured to detect compression, such as by a force sensor.

A device may have a ratcheted peristaltic or piezo or solenoid pump mechanism. A device may include an insulin pouch. The insulin pouch, pathway, and cannula may be configured to not facilitate crystallization, aggregation, leeching (of insulin or preservatives), denaturing, adsorption, or bubble formation. A device may be configured to utilize multiple brands of pre-filled insulin.

In some examples, a treatment system can include a starter or CGM only device that does not contain an insulin cannula, pump or insulin reservoir. A starter or CGM only device may be configured to connect to one or more companion applications via SDK to communicate blood glucose values.

A disease management system that includes both a CGM and insulin pump may be configured to connect to one or more companion applications via SDK to give blood communicate blood glucose values. In some examples, a device may be configured to receive recommended or directly dose cloud-based control algorithm insulin doses. In some examples, a device may be configured to run a simple algorithm that gives recommendations to the user in the app of insulin bolus values. In some examples, a device may be configured to control basal insulin and set points even without a connected companion application or cloud service.

A device may be configured to include arsenic-free glass, Mercury-free, Brominated flame retardant-free, PVC-free, Beryllium-free or other recycled or compostable materials.

A device may be able to apply a bolus of insulin without other instruments. This should be possible either manually or in an automatic method. For example, in emergency situation the device may have a physical method that allows an insulin bolus to be administered. In some examples, a physical bolus administration may have a maximum amount it can administer in a single time period. A device may prevent manual boluses when a user is in a hypoglycemic or tending towards a hypoglycemic state.

In some examples, an interleaved device(s) may be configured to dynamically or statically synchronize states. For example, one or more interleaved devices may be configured to minimally or less frequently synchronize all states at a time of new device setups and device stabilizations, but synchronize more frequently to improve confidence of control system. A device may be able to sample a measurement as frequently as once per minute.

In some examples, a device or companion application or connected cloud storage may be configured to store multiple days of data, such on treatment decisions and observations. For example, a device may have 6 days of secure data storage and be able to track all treatment decisions and observations (for example, manual overrides, user states, controller decisions). Stored results may be retained after device expiry. In some examples, a device or companion application or connected cloud storage may store secure personalized configuration(s). Data may be stored in a secure way to prevent unauthorized access.

A disease management system may include a real time clock, accelerometer and Bluetooth or similar communication capability. A connection between a disease management system and a mobile device may include a secure communication protocol, such as encryption, and reliability. A device may utilize an NFC connection in order to deliver a life critical function, such as remote insulin bolus or change a critical insulin parameter from a user device, such as a phone, tablet, computer or other user electronic device. A device may ignore related bolus requests when a user is not in need of insulin. In some examples, a device may ignore NFC related bolus requests when a pattern is detected that suggests a replay attack (superfluous requests).

A disease management system may include one or more sensors. For example, a treatment system may include an electrode temperature sensor to help facilitate compensation for electrical/enzymatic drift or disturbance. A disease management system may be configured to have an insulin temperature sensor to detect insulin spoilage or degradation due to body or ambient temperature. An insulin reservoir may be temperature controlled away from body temperature to extend its useful life and improve its activity. Advantageously, this may help allow longer interleaved cycles such as 7 to 14 days. A disease management system may have an environmental temperature sensor. A disease management system may have a 3 axis accelerometer to detect and classify types of exercise. The disease management system can also be used for body orientation (such as for an emergency glucagon system) if given two known states and insulin absorption rate of the location. A disease management system may have a 3 axis gyroscope to detect fine movements for improved exercise classification. A disease management system may have a communication system, such as Bluetooth, for communication with a user device and reduced power consumption. A disease management system may have a Near Field Communication (NFC) tag to interface with an NFC reader on a user device for easy setup of Bluetooth pairing and opening or downloading an application. A disease management system may have automated or manual retraction of a cannula. The retraction may help facilitate wound healing, such as on day 3. A disease management system may be powered by external or integrated batteries (for example, a CR2032 3V). A disease management system may have haptic and/or audible feedback components. A disease management system may have an SOC and memory. A disease management system may have an actuator and drive circuitry for insulin delivery. A disease management system may have a frontend for continuous analyte monitor (CAM) or continuous glucose monitor (CGM). A disease management system may have LEDs, detectors, and frontend for diffuse reflectance SpO2 sensor. A disease management system may have LEDs, detectors, and frontend for a diffuse reflectance pulse rate sensor. Respiration rate may also be measured by a treatment system sensor.

A. EXAMPLE REDUNDANT DISEASE MANAGEMENT SYSTEMS

Closed loop systems are inherently high risk due to their use and treatment with a biologic and performing life-sustaining functions to persons with Type 1 diabetes. The need for redundancy to ensure error free and accurate glucose titration is paramount. CGM devices often have periods of no measurements when first applied to a user's body called "warm-up time". This period can typically last 1-2 hours. CGM devices also have periods of inaccuracy after the warm-up time called "Stabilization time". This period can last up to 24 hours. Devices also have "end of life" issues such as sensitivity decrease and noise increase. Sensitivity decreases by use over time and environmental stimuli. Tracking this is a non-linear process and uncertain, therefore decreases in sensor sensitivity is a key source of error for devices on market today.

Having a combined CGM (or CAM)/insulin pump device can greatly reduce overall cost for users. By using an interleaved configuration the percentage time in a reliable closed loop can be increased because the user will virtually never be out of closed loop during a warmup time or any other uncertain period. Current modern CGM's also allow the user to titrate during stabilization and end-of-life periods and frequently have false-alarms the night of insertion. By interleaving devices, this situation may be greatly alleviated. Having interleaved devices also enables complete emptying of insulin reservoirs. This addresses a major concern of persons with Type 1 which is insulin waste.

In systems and methods described herein, two devices may be used to provide redundant measurements. In contrast, in traditional systems, while some users may be used to two devices in a closed loop CGM system, each of the devices in a traditional system may serve a different function (for example, one device for a CGM and one device for an insulin pump) and thus do not provide redundancy.

During the first ever insertion of a device, the user may begin with either a secondary or a primary device. In some embodiments, both devices may contain both an insulin pump and a CGM. A secondary device may be a device which has emptied or expired its insulin supply and only has a CGM remaining.

In such a case where a secondary device is used first, the initial secondary device may contain a dummy or empty insulin pouch when a disposable lot of devices are shipped out together. This care of providing a dummy insulin device enables a user to immediately begin closed loop use with redundant coverage.

In some examples, it may take roughly 1 month to fully use 10 devices. However, other use rates are also possible. For a new user, a starter pack may be provided that has a dummy device (with no insulin) and a number of primary devices (for example, 9 devices in order to last a user a 1 month interval in the case of a 10 device a month use rate) that are ready to start in a primary configuration. In addition, or in the alternative to a starter pack, a set of primary devices could be provided (also referred to as a refill-lot). Should a user start with a refill-lot and not a starter pack lot, two insulin containing devices could be placed on the body but the closed loop system may only use a single insulin containing device and the other may not be used by the closed loop system.

A mobile device as well as the two applied devices can communicate wirelessly via Bluetooth or another communication method, such as RF. The devices may communicate data associated with the device operation or status, such as current insulin reservoir statuses, the mode each device is operating in (primary or secondary), CGM values, embedded device model states, user calibrations or settings or configurations, personalization variables, battery states, error states, user activity states, orientations, the like or a combination thereof.

Advantageously, the use of overlapping devices may provide a consistently reliable CGM value with few exceptions (such as during first time warmup or stabilization periods). This consistency may allow for avoidance of non-measurement periods or moments in time where closed loop would otherwise be unavailable due to follow-up devices placement in warmup time. Stabilization period measurements can also be dynamically averaged with stable measurements from a secondary device, or they can be altogether probed off. End of sensor life measurements can also be dynamically averaged with stable measurements from a primary device, or they can be altogether probed off. End of life measurements being validated by primary devices are particularly helpful to improve sensor predictions in ultra-long life CGMs that may wish to stabilize measurements with an interleaved configuration. For example, interleaved devices may improve sensor predictions on 6-day life devices that can be extended to 7, 10, 12, 14, or longer day lifetimes of modern CGMs.

Additionally, systems and methods described herein may stabilize insulin and lipohyperatrophy could be reduced by switching devices to longer periods than CGMs at current technological standards. Additionally, systems and methods described herein may enable fewer insertions and much longer wear time, resulting in better user experience and potentially better compliance.

Interleaved devices can occur at any suitable area of the body, including but not limited to: stomach, butt, chest, back of arms, side of arms, lower back, legs, the like or combination thereof.

FIG. 1A illustrates a disease management system that may include one or more redundant disease management systems that may include standalone or combined glucose sensor and/or disease management systems. The disease management system may include a first disease management system 1002 and a second disease management system 1004. The first disease management system 1002 and the disease management system 1004 may be, for example, the disease management system 100 of FIGS. 4A and 4B or the sensor system 200B and the insulin pump system 200A of FIGS. 5A and 5B, as described below or any other example disease management system described herein. Further, both the first disease management system 1002 and the second disease management system 1004 may each be duplicate disease management systems including an insulin pump and glucose monitor in a single device (for example, the first disease management system 1002 is a disease management system and the second disease management system 1004 is another disease management system). In another example, the first disease management system 1002 can be a disease management system and the second disease management system 1004 can be a glucose monitor. In another example, the first disease management 1002 can be a disease management system including an insulin pump and glucose monitor and the second disease management system can include an emergency glucagon device. Advantageously, redundant management devices may facilitate reduce or eliminate warmup times, improve stabilization of disease management, and reduce or eliminate end of life errors for disease management systems.

While FIG. 1A illustrates the first disease management system 1002 and the second disease management system 1004 attached on different sides of a patient's abdomen, it is understood that the first disease management system 1002 and the second disease management system 1004 may be attached on the same side of a patient's body. Further, it is understood that the disease management systems 1002, 1004 may be attached to other body parts such as the arms, legs, buttocks, abdomen, torso, or back.

FIG. 1B illustrates an example disease management environment 1001. For example, as illustrated, a first disease management system 1002 and a second disease management system 1004 may be attached to a patient's body. In addition, or in the alternative, to one or both of the first disease management system 1002 and second disease management system 1004, a disease management environment 1001 can include a glucagon administration system 1003. In some examples, the glucagon administration system 1003 can communicate directly or indirectly with one or more of the disease management systems to administer glucagon at appropriate times to help manage a patient's glucose.

As illustrated in FIG. 1B, one or more of the disease management systems or glucagon administration system may be configured to communicate with at least one of a cloud based hardware processor (or the cloud) 1005 and at least one user device 1009. In some examples, a user device 1009 can include, but is not limited to, a smart watch, a smart phone, a dedicated wrist band, such as described herein, or other computing device.

In some examples, a disease management environment may include an applicator 1007 configured to facilitate application or removal of at least one of a disease management system and glucagon administration system. In some examples, the applicator 1007 may be reusable. In some examples, an applicator 1007 may include an applicator such as described with reference to FIGS. 20A-22I.

Figure 1C:
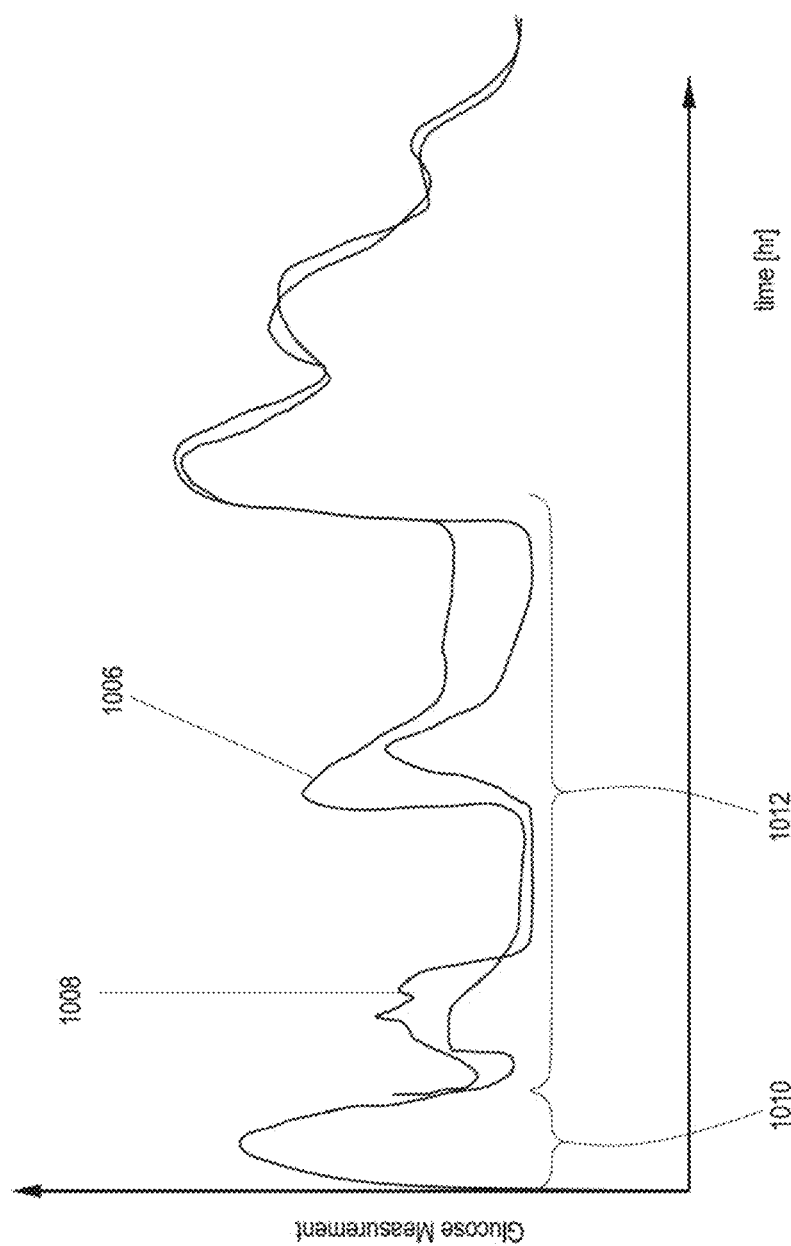
FIG. 1C illustrates a graph comparing an ideal glucose measurement with a glucose measurement of an exemplary glucose sensor from beginning of operation.

FIG. 1C is a graph illustrating an ideal glucose measurement 1006 vs a glucose measurement 1008 of an exemplary glucose sensor when just beginning operation. The ideal glucose measurement is in blue whereas the glucose measurement from an exemplary glucose sensor is in green. Glucose sensors may have periods where no measurement occurs which is referred to as a warmup period 1010. This period can last from one to two hours, they may, however, be longer or shorter depending on the glucose sensor. After the warmup period, there may also be periods of inaccuracy referred to as a stabilization period 1012 where the glucose sensor may output measurements, however these measurements are not always accurate. The stabilization period 1012 may last for up to 24 hours depending on the glucose sensor used. As is seen, during warmup 1010 there is no measurement from the glucose sensor and during stabilization the glucose measurement 1008 does not match with the ideal glucose measurement 1006. Further, glucose sensors also exhibit end of life sensitivity decreases and noise increases which is referred to as an end of life period. The end of life period may be around 10 days depending on the glucose sensor.

Thus, there exists circumstances where a sensor may be operating on a patient during the warmup period 1010, the stabilization period 1012, and the end of life period where there will be no measurement or inaccurate measurement. For example, when a disease management system combining an insulin pump and a glucose sensor, such as the disease management system described herein in FIG. 2F or FIGS. 3A and 3B or Figs., are first applied to a patient, the glucose sensor will go through a warmup period and a stabilization period. Further, the administration system may have a glucose sensor in its end of life period while the administration system may still be able to pump fresh insulin into the patient. Disease management systems may also have a certain insulin storage capacity and insulin within the disease management system may have a certain shelf life which may be affected by the date the insulin is first administered to the patient. When insulin is exposed to higher temperatures (for example, about 37° C. or above) in situations such as being in close proximity to the body or high ambient temperatures, insulin effectiveness may degrade, which may reduce the insulin's shelf life. Additionally, other potential adverse effects of extended use of a disease management system, such as a disease management system, outside of its recommended shelf life include skin irritation, scar tissue, or other bodily reactions to the prolonged presence of a device. However, by operating a first disease management system and a second disease management system simultaneously in an overlapping scheme, at least one of the administration systems may have a sensor not in a warmup period, stabilization period, and end of life period and insulin storage capacity and shelf life issues can be mitigated.

Figure 2A:
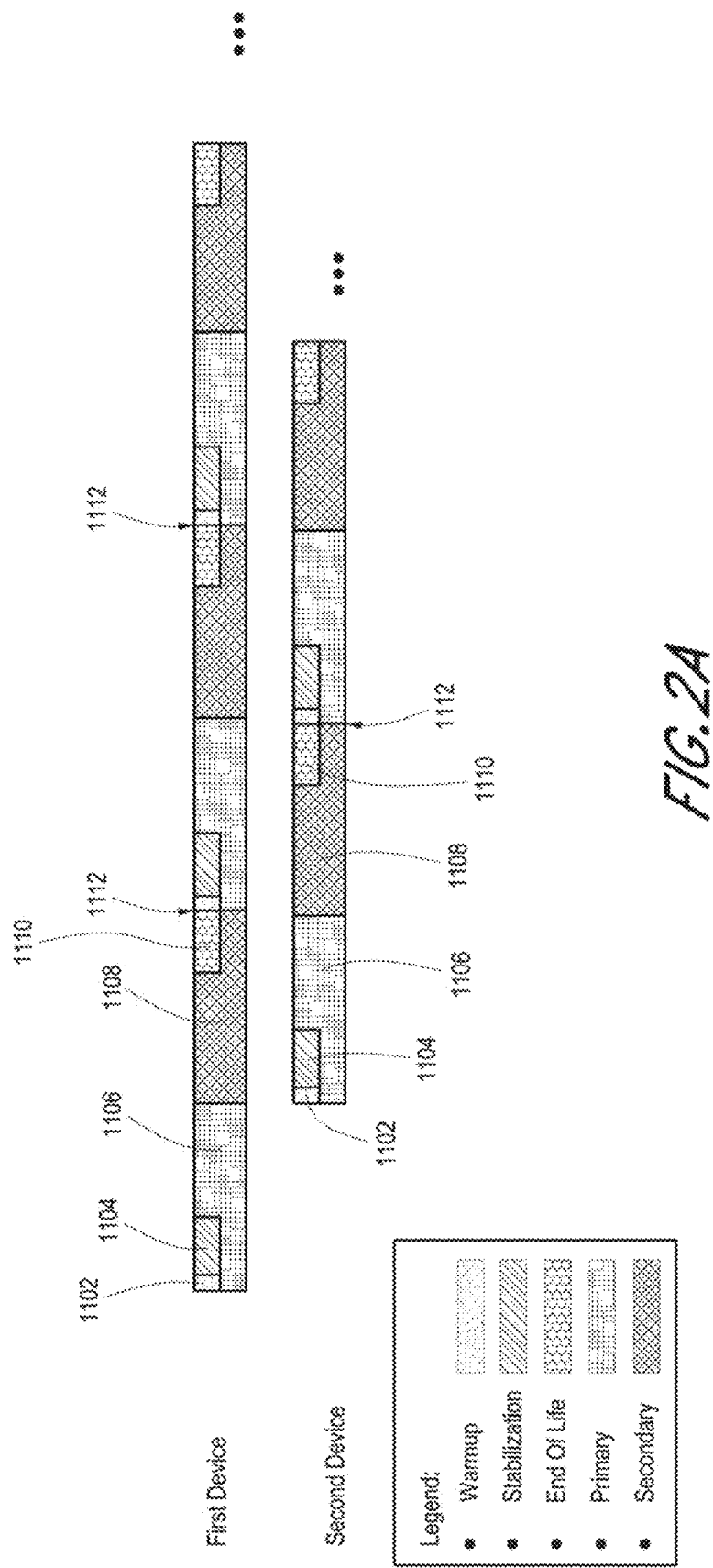

FIG. 2A illustrates a two interleaved device replacement schedule. The schedule includes a first device and a second device. In this schedule, there is a three day insulin supply in each device. The schedule begins with running the first device until its three day insulin supply has run out. A second device is placed on the patient when the first device has run out of insulin. However, the first device may continue to provide glucose measurements while the second device's glucose sensor is in its warmup period 1102 and stabilization period 1104. Once the second device's glucose sensor has exited the warmup period 1102 and stabilization period 1104, the first device's glucose measurements may be used or the second device's glucose measurements may be used or a combination of the first device's glucose measurements and second device's glucose measurements may be used. In some implementations, combining the first device's glucose measurements and second device's glucose measurements may provide a more accurate overall measurement to calculate the patient's insulin dosage. The measurements from the first device may not be used when the first device is in an end of life period 1110 and may be removed from the patient.

After the second device runs out of insulin, the first device may be replaced 1112 and the replacement first device may pump insulin into the patient while the second device is used for glucose measurements while the new first device is in a warmup period 1102 and stabilization period 1104. This operation can continue with the second device being replaced 1112 when the first device runs out of insulin. The schedule illustrates a primary mode 1106 which is a mode where the device is pumping insulin and may be providing glucose measurements whereas a secondary mode 1108 is a mode where the device may be providing only glucose measurements. Of course, it is to be understood that a larger or smaller insulin reservoir may be used that may last longer or shorter than 3 days. Further, it is to be understood that the first pump can continue to pump insulin even after the second device is attached. In this way, the first pump can entirely deplete its insulin reservoir so that no insulin is wasted, and the second pump can seamlessly continue where the first pump left off. In addition, the insertion of the second device can be scheduled to occur at an opportune time for the patient because the handoff between the devices may occur without user intervention. This would avoid alarms which alert a patient to switch one or more treatment devices at inconvenient times (for example, at night when the patient is sleeping) in conventional treatment devices. Thus, depending on the nature and capacities of the respective devices, different overlap time periods can be used as would be understood by the disclosure herein.

Calculating the dosage of insulin for the patient may occur on the first device or the second device or the cloud. The first device may send insulin dosage instructions or glucose measurements to the second device. The second device may send insulin dosage instructions or glucose measurements to the first device. The first device and second device may communicate wirelessly by such a manner as Bluetooth or RF signals. In some implementations, the first device and/or the second device may calculate the dosage of insulin based on an algorithm such as a glucose insulin meal model.

Figure 2B:
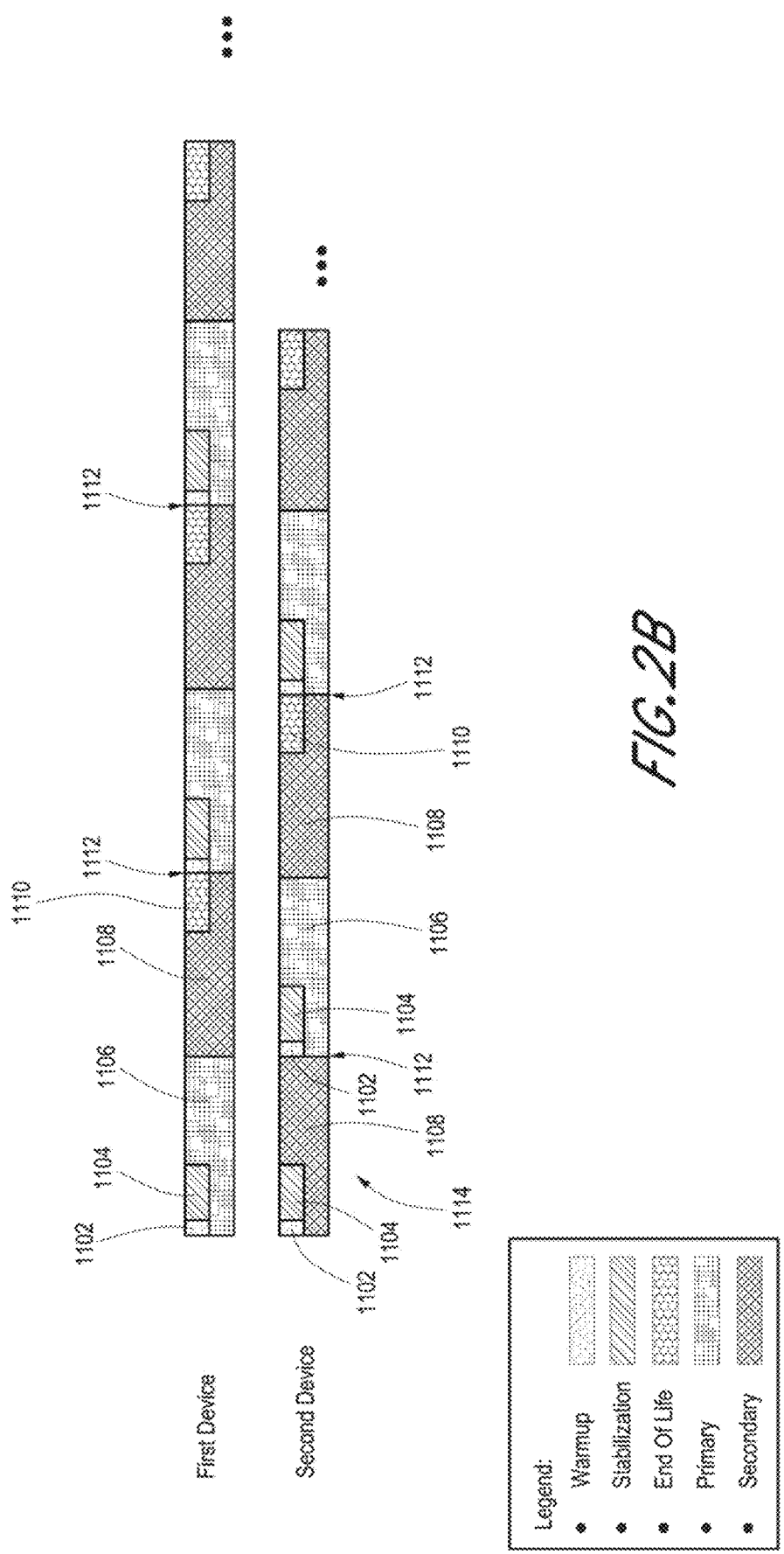

FIGS. 2B-2E depict different scenarios that all share the same features and thus identically labeled elements share the identical description as the description provided in connection with FIG. 2A. It is understood that the two interleaved devices used within the device replacement schedule may be any of the devices described within this specification including the disease management system integrated with an insulin pump and a glucose sensor described in connection with FIGS. 4A and 4B. FIG. 2B depicts another two interleaved device replacement schedule. The schedule is identical to the schedule depicted in FIG. 2A except both a first device and a starting second device 1114 are placed on a patient in the beginning of the treatment. The starting second device 1114 may be a device which does not have insulin and thus does not waste insulin since the starting second device 1114 is merely used for glucose measurement. The starting second device 1114 may supplement glucose measurements from the first device which may create a more accurate glucose measurement during a warmup period 1102 and stabilization period 1104. Since the starting second device 1114 is at a physically different insertion site on the body, the starting second device 1114 may provide parameters that the primary device may not provide based on providing an independent glucose measurement from the primary device. These parameters may include one or more of transport delay, diffusion constants, and/or rates of absorption of insulin. The starting second device 1114 may further provide added psychological effects of getting the patient used to running an interleaved, redundant system. When the first device runs out of insulin, the starting second device 1114 may be replaced with a second device.

Figure 2C:
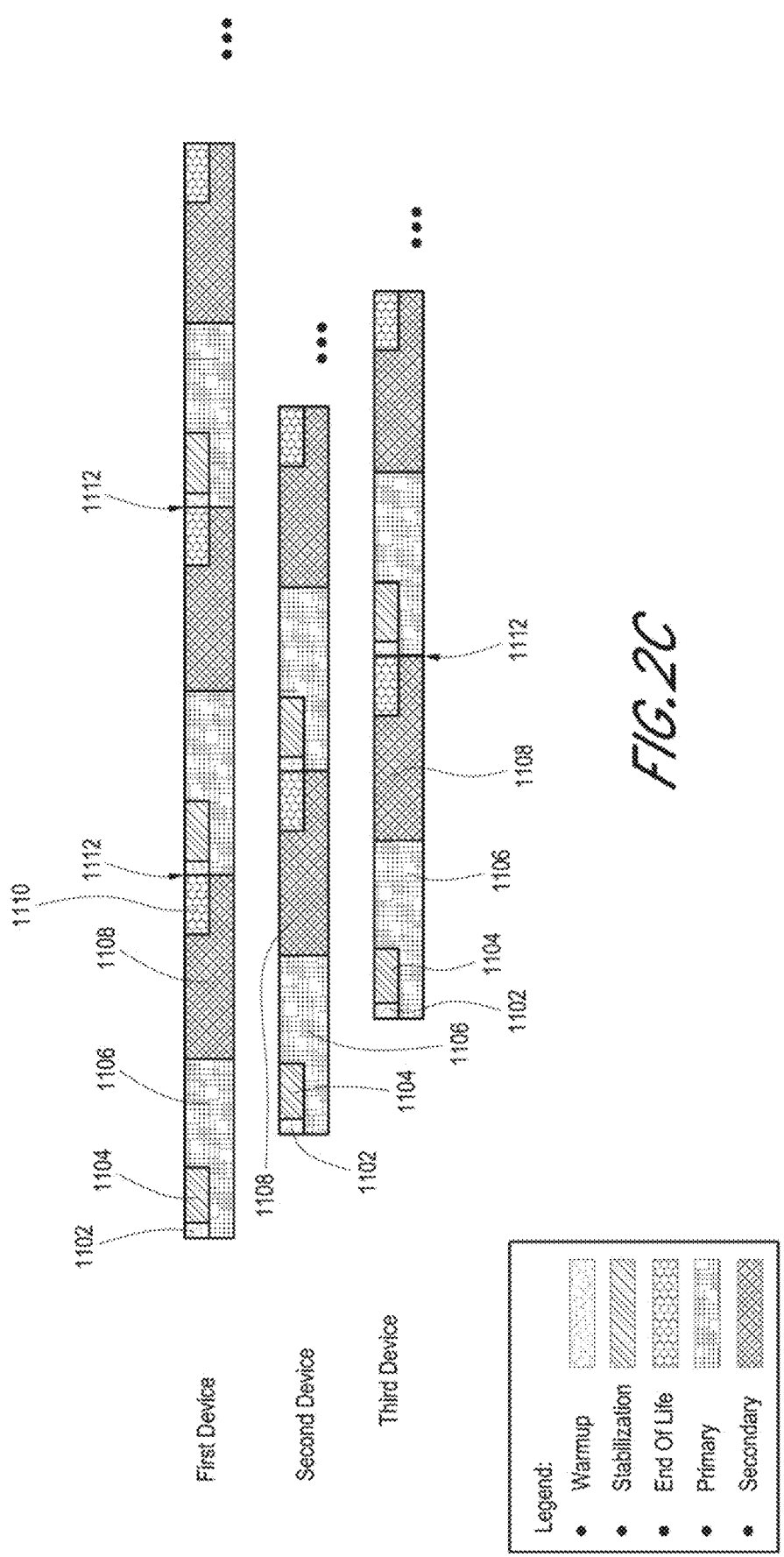

FIG. 2C depicts another interleaved device replacement schedule. This schedule integrates a first device, a second device, and a third device. As depicted, the first device, the second device, and the third device may provide redundant measurement such that at least one device is not in a warmup period 1102, a stabilization period 1104, and an end of life period 1110. Further, one or more of the first device, the second device, or the third device may pump insulin at one time. All of the devices may communicate with each other such that the insulin dosage may be calculated in the first device, the second device, or the third device based on the insulin measurement of at least one of the devices. One of ordinary skill would be able to modify this schedule to accommodate more than three devices.

Figure 2D:
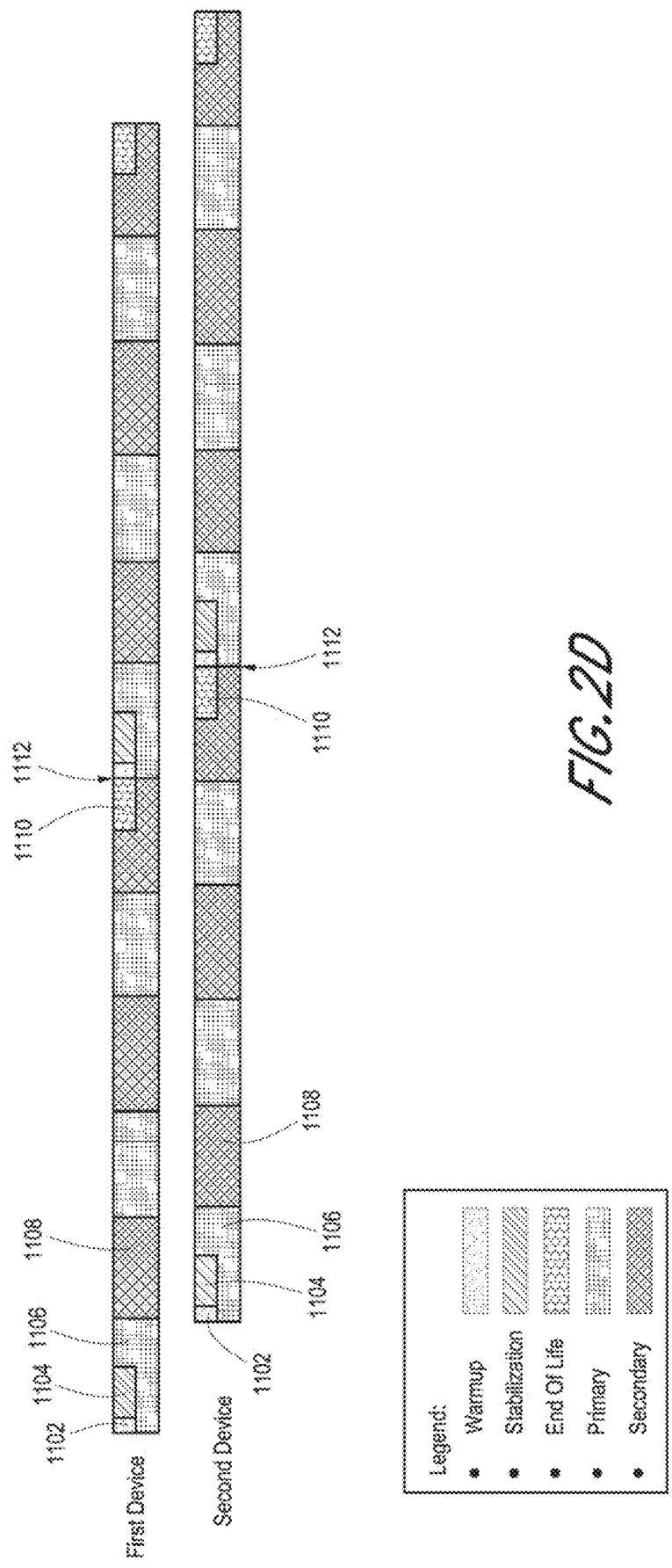

FIGS. 2D and 2E depict a two interleaved device replacement and usage schedule. In FIG. 2D, a first device and a second device each include 6 days of insulin. In FIG. 2E, a first device and a second device each include 4 days of insulin. In both schedules, the first device is operated and delivers insulin for two days and then second device is implanted on the patient and is operated and delivers insulin for two days. The first device and the second device continue to switch off on two day periods until the first device runs out of insulin. The first device may continue to provide glucose measurements however when the sensor is in an end of life period, the first device is replaced before the second device runs out of insulin.

It is understood that a first device is replaced such that the replacement first device ends a warmup period and a stabilization period before the second device begins an end of life period. Further, a second device is replaced such that the replacement second device ends a warmup period and a stabilization period before the first device begins an end of life period. It is also understood that a first device or a second device has insulin supply remaining such that at least one device is capable of supplying insulin to the patient. It is also understood that the insulin supply has natural expiration dates that may alter the device replacement schedule. In some implementations, the patient may be alerted that one or more of the devices should be replaced based on the replacement schedules of FIGS. 2A-2E. The patient may be alerted through a notification on a user device, an indication light on the device, or a vibration of the device.

B. EXAMPLE DISEASE MANAGEMENT SYSTEM

Figure 2F:
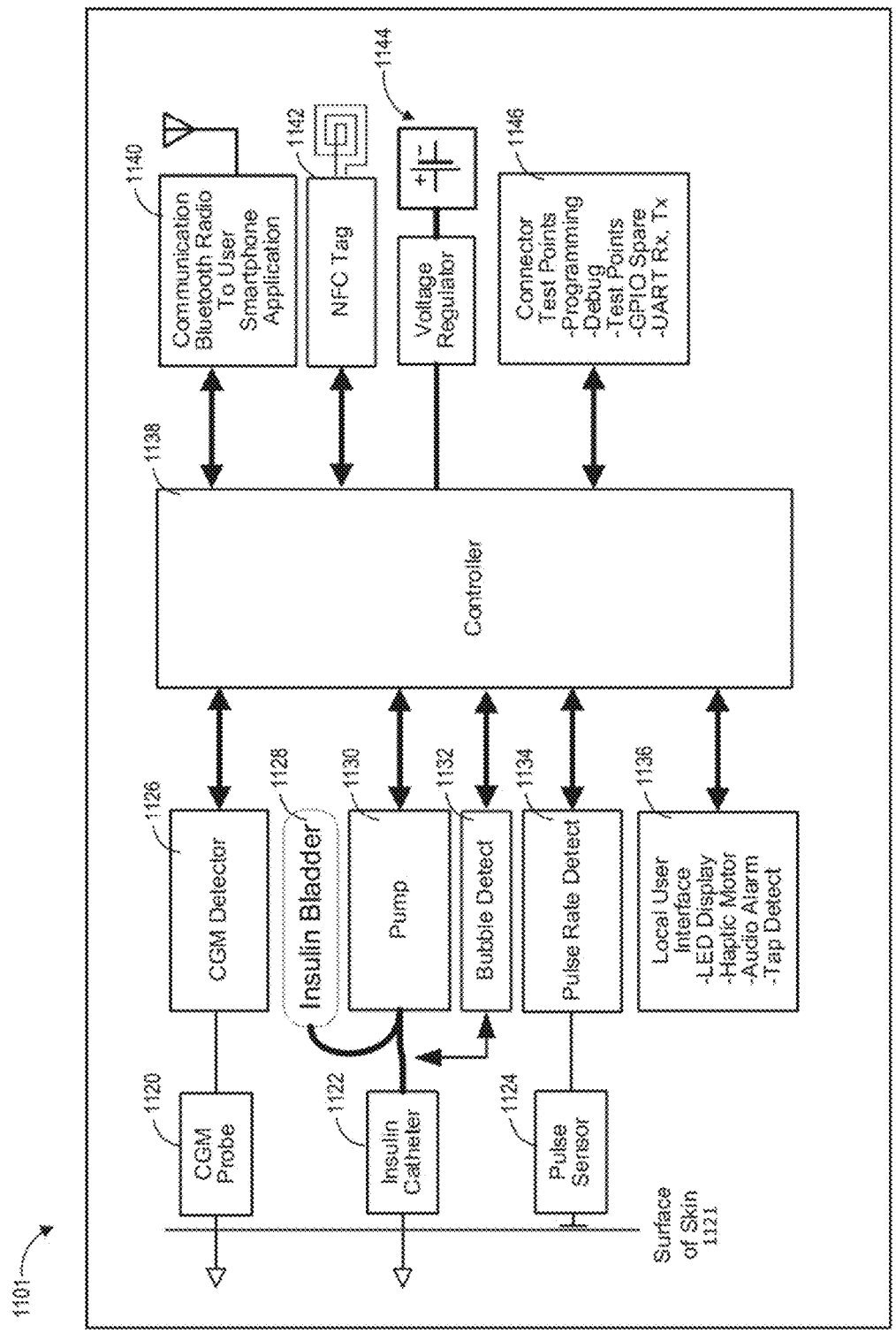
FIG. 2F illustrates an example disease management system that may be part of a disease management environment or used as an interleaved device.

FIG. 2F shows a block diagram of an example disease management system 1101. In some examples, the disease management system 1101 may be part of a disease management environment, such as described above. A disease management system 1101 may be configured to measure one or more physiological parameters of a patient (such as pulse, skin temperature, or other values), measure one or more analytes present in the blood of a patient (such as glucose, lipids, or other analyte) and administer medication (such as insulin, glucagon, or other medication). In some examples, a disease management system 1101 may be configured to communicate with one or more hardware processors that may be external to the disease management system 1101, such as a cloud based processor or user device. A disease management system 1101 may include an NFC tag to support authentication and pairing with a user device (for example, smart phone or smart watch), Bluetooth communication with additional disease management systems or devices, and Bluetooth communication with a paired user device running an associated control application. To support ease of use and safe interaction with the patient, the system may incorporate user input through tap-detecting accelerometer, and provide feedback via audio speaker, haptic vibration, and optical indicators. The system may operate on battery power and support both shelf-life and reliable operation once applied to the patient. Battery life may be managed through control of several planned levels of sleep and power consumption. To support this reliability, a controller can monitor several system-health parameters, and monitor temperatures of the included medication, and ambient temperature for the life of the device.

As illustrated in FIG. 2F, a controller 1138 of the disease management system 1101 may be configured to communicate and control one or more components of the disease management system 1101. The controller 1138 may include one or more hardware processors, such as a printed circuit board (PCB) or the like. The controller 1138 may be configured to communicate with peripheral devices or components to support the accurate measurement of physiological parameters and blood analytes, such as patient pulse, temperature, and blood glucose, using detector electronics. The controller 1138 may subsequently calculate dose or receive a calculated dose value and administer medication, such as insulin, by actuation of an actuated pump. The controller 1139 may record device activity and transfer the recorded data to non-volatile secure memory space. At the end of the life of a device or system, the controller can be configured to lock operation, and create a data recovery module to permit authenticated access to the recorded data if needed.

A disease management system 1101 may include an analyte sensor 1120. The analyte sensor 1120 may be configured to detect analytes in the patient's blood. For example, an analyte sensor 1120 can include a glucose sensing probe configured to pierce the surface of the skin 1121. In some examples, a disease management system 1101 may include a plurality of analyte sensors 1120 to detect one or more analytes. In some examples, an analyte sensor 1120 may be configured to detect a plurality of analytes. Sensed analytes may include, but are not limited to, glucose, insulin, and other analytes. An analyte sensor 1120 may be configured to communicate with an analyte detector 1126. The analyte detector 1126 may be configured to receive a signal of one or more analyte sensors 1120 in order to measure one or more analytes in the blood of the patient. The analyte detector 1126 may be configured to communicate with the controller 1138. For example, the analyte detector 1126 may be configured to, for example, send analyte values to the controller 1138 and receive control signals from the controller.

A disease management system 1101 may include a medication catheter 1122. The medication catheter 1122 may be configured to administer medication, including, but not limited to insulin, to the patient. The medication catheter 1122 may receive medication from a medication bladder 1128 configured to contain medication to be administered. The medication bladder 1128 may be configured to contain medication for a prolonged period, such as 1 day, 3 days, 6 days, or more. The medication bladder 1128 may be configured to contain certain medication types, such as insulin. In some examples, a disease management system 1101 may include a plurality of medication bladders 1128 for one or more reservoirs of the same or different medications. In some examples, a disease management system 1101 may be configured to mix medications from medication bladders 1128 prior to administration to the patient. A pump 1130 may be configured to cause medication to be administered from the bladder 1128 to the patient through the insulin catheter 1122. A pump 1130 may include, but is not limited to, a pump such as described herein with reference to FIGS. 8A-14H.

A disease management system 1101 may include a physiological sensor 1124. The physiological sensor 1124 may include a pulse rate sensor, temperature sensor, pulse oximeter, the like or a combination thereof. In some examples, a disease management system 1101 may be configured to include a plurality of physiological sensors. The physiological sensor 1124 may be configured to communicate with a physiological detector 1134. The physiological detector 1134 may be configured to receive a signals of the physiological sensor 1124. The physiological detector 1134 may be configured to measure or determine and communicate a physiological value from the signal. The physiological detector 1134 may be configured to communicate with the controller 1138. For example, the physiological detector 1134 may be configured to, for example, send measured physiological values to the controller 1138 and receive control signals from the controller.

A disease management system 1101 may include one or more local user interfacing components 1136. For examples, a local user interfacing component 1136 may include, but is not limited to one or more optical displays, haptic motors, audio speakers, and user input detectors. In some examples, an optical display may include an LED light configured to display a plurality of colors. In some examples, an optical display may include a digital display of information associated with the disease management system 1101, including, but not limited to, device status, medication status, patient status, measured analyte or physiological values, the like or a combination thereof. In some examples, a user input detector may include an inertial measurement unit, tap detector, touch display, or other component configured to accept and receive user input. In some examples, audio speakers may be configured to communicate audible alarms related to device status, medication status user status, the like or a combination thereof. A controller 1138 may be configured to communicate with the one or more local interfacing components 1136 by, for example, receiving user input from the one or more user input components or sending control signals to, for example, activate a haptic motor, generate an output to the optical display, generate an audible output, or otherwise control one or more of the local user interfacing components 1136.

A disease management system 1101 may include one or more communication components 1140. A communication component 1140 can include, but is not limited to one or more radios configured to emit Bluetooth, cellular, Wi-Fi, or other wireless signals. In some examples, a communication component 1140 can include a port for a wired connection. Additionally, a disease management system 1101 may include an NFC tag 1142 to facilitate in communicating with one or more hardware processors. The one or more communication components 1140 and NFC tag 1142 may be configured to communicate with the controller 1138 in order to send and/or receive information associated with the disease management system 1101. For example, a controller 1138 may communicate medication information and measured values through the one or more communication components 1140 to an external device. Additionally, the controller 1138 may receive instructions associated with measurement sampling rates, medication delivery, or other information associated with operation of the management system 1101 through the one or more communication components 1140 from one or more external devices.

A disease management system 1101 may include one or more power components 1144. The power components may include, but are not limited to one or more batteries and power management components, such as a voltage regulator. Power from the one or more power components 1144 may be accessed by the controller and/or other components of the disease management system 1101 to operate the disease management system 1101.

A disease management system 1101 may have one or more power and sleep modes to help regulate power usage. For example, a disease management system 1101 may have a sleep mode. The sleep mode may be a very low power mode with minimal functions, such as the RTC (or real time clock) and alarms to wake the system and take a temperature measurement of the system, or the like. In another example, a disease management system 1101 may include a measure temperature mode which may correspond to a low power mode with reduced functions. The measure temperature mode may be triggered by the RTC where the system is configured to take a temperature measurement, save the value, and return the system to a sleep mode. In another example, a disease management system 1101 may include a wake up mode. The wake up mode may be triggered by an NFC device and allow the system to pair with an external device with, for example, Bluetooth. If a pairing event does not occur, the system may return to sleep mode. In another example, a disease management system 1101 may include a pairing mode. The pairing mode may be triggered by an NFC device. When a controlling application is recognized, the system may proceed to pair with the application and set the system to an on condition and communicate to the cloud or other external device to establish initial data movement. In another example, a disease management system 1101 may include a rest mode where the system is configured to enter a lower power mode between measurements. In another example, a disease management system 1101 may include a data acquisition mode where the system is configured to enter a medium power mode where data acquisition takes place. In another example, a disease management system 1101 may include a parameter calculation mode where the system is configured to enter a medium power mode where parameter calculations, such as a blood glucose calculations, are performed and data is communicated to an external device and/or the cloud. In another example, a disease management system 1101 may include a pump mode where the system is configured to enter a higher power mode where the pump draws power to deliver medication to the patient.

A disease management system 1101 may include one or more connector test points 1146. The connecter test points may be configured to aid in programming, debugging, testing or other accessing of the disease management system 1101. In some examples, connector test points 1146 may include, for example, a GPIO spare, UART receiver or transmitter, the like or a combination thereof.

Figure 2G:
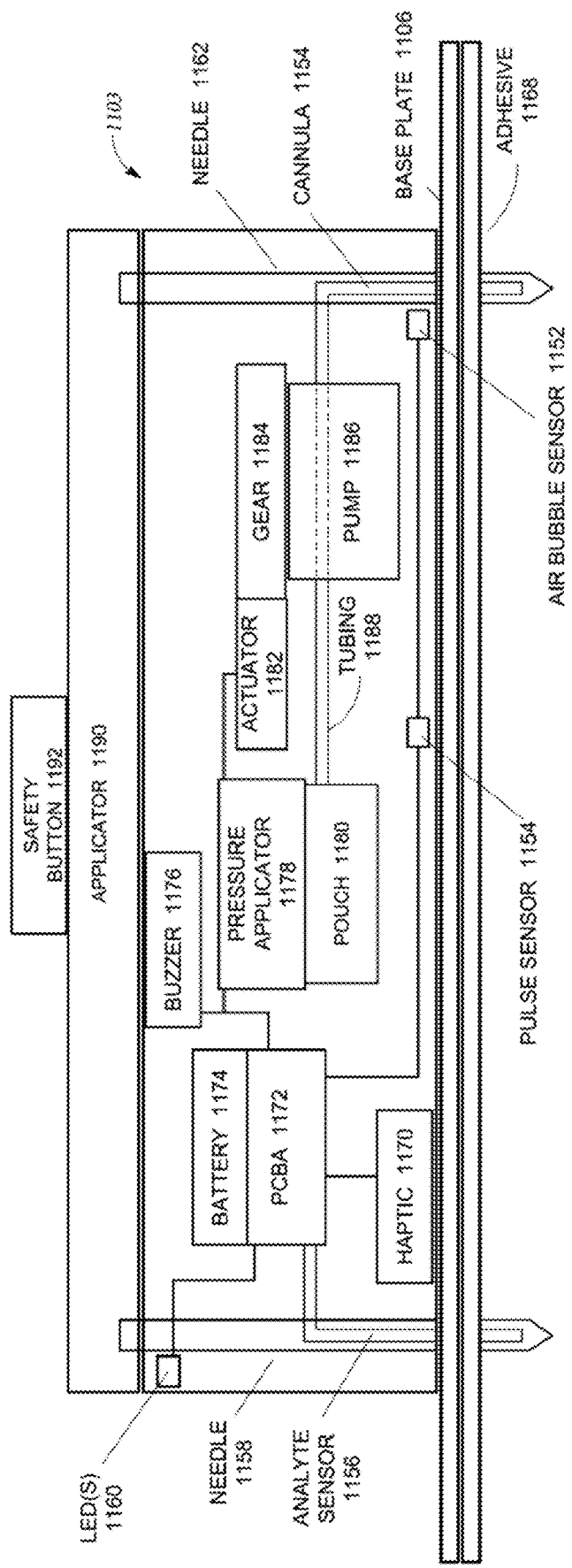
FIG. 2G illustrates an example implementation of a disease management system.

FIG. 2G illustrates an example implementation of a disease management system 1103 and applicator 1190 for applying a disease management system 1103 to a patient. In the illustrated example, an applicator 1190 may be configured to mate with the disease management system 1103. In some examples, an applicator 1190 may include a safety button 1192 for release or other interaction with the applicator 1190. In the illustrated example, a disease management system 1103 may include one or more LEDs 1160 that may be configured to output information using one or more of color, frequency, and length of display. In some examples, the disease management system 1103 may include a buzzer 1176, haptic actuator 1170, or other feedback mechanism, such as a speaker to output information to the patient, such as an alarm. In some examples, a disease management system 1103 may include a battery 1174, controller 1172. In some examples, a disease management system 1103 may include aspects of a medication administration system, such as a bladder 1180, a bladder pressure applicator 1178 to provide pressure on the bladder (such as a component of a pump), actuator 1182, pump gears 1184, and a pump 1186. In some examples, a disease management system 1103 may include one or more needles 1158 that may include one or more analyte sensors (such as a glucose sensor) 1156. In some examples, a disease management system 1103 may include one or more needles 1162 that may include one or more cannulas 1164 configured to administer medication to the patient. In some examples, a disease management system 1103 may include an air bubble sensor 1152 configured to detect the presence of air bubbles in the medication prior to delivery to the patient. In some examples, a glucose control system 1103 may include one or more physiological sensors 1154, such as a non-invasive physiological sensor including but not limited to a pulse sensor. In some examples, the disease management system 1103 may include a base plate 1166 and an adhesive layer 1168 below the base plate 1166 to provide adhesion of the disease management system 1103 to the patient's skin. As described below, a housing of the disease management system 1103 may consist of a combination of flexible and rigid material so as to both provide support for the components of the disease management system 1103 and allow conforming, at least in part, of the disease management system 1103 to the skin of the patient.

The adhesive layer 1168 may be configured to provide adhesion for a prolonged period. For example, the adhesive layer 1168 may be configured to adhere the disease management system 1103 to the skin of a patient for a period of 1 day, 3 days, 6 days, or more or fewer days or hours. In some examples, the adhesive layer may be configured to have an adhesive force sufficient to prevent accidental removal or movement of the disease management system 1103 during the intended period of use of the disease management system 1103. In some examples, the adhesive layer 1168 may be a single layer of adhesive across at least a portion of a surface the disease management system 1103 that is configured to interface with the patient. In some examples, the adhesive layer 1168 may include a plurality of adhesive areas on a surface of the disease management system 1103 that is configured to interface with the patient. In some examples, the adhesive layer 1168 may be configured to be breathable, adhere to the patient's skin after wetting by humidity or liquids such as tap water, saltwater, and chlorinated water. A thickness of the adhesive may be, for example, be in a range of 0.1 to 0.5 mm or in a range of more or less thickness.

In some examples, a needle 1158, 1162 may be inserted at different depths based on a patient age, weight, or other parameter. For example, a depth of insertion of a medication cannula may be approximately 3 mm for 7 to 12 year olds. In another example, a depth of insertion of a medication cannula may be approximately 4 mm for 13 year olds and older. In another example, a depth of insertion of a medication needle may be approximately 4 to 4.5 mm for 7 to 12 year olds. In another example, a depth of insertion of a medication needle may be approximately 5 to 5.5 mm for 13 year olds and older. In another example, a depth of insertion of an analyte sensor may be approximately 3 mm for 7 to 12 year olds. In another example, a depth of insertion of an analyte sensor may be approximately 4 mm for 13 year olds and older. In another example, a depth of insertion for a needle associated with an analyte sensor may be approximately 4 to 4.5 mm for 7 to 12 year olds. In another example, a depth of insertion for a needle associated with an analyte sensor may be approximately 5 to 5.5 mm for 13 year olds and older. However, other values or ranges for any of the inserted components are also possible.

Figure 2H:
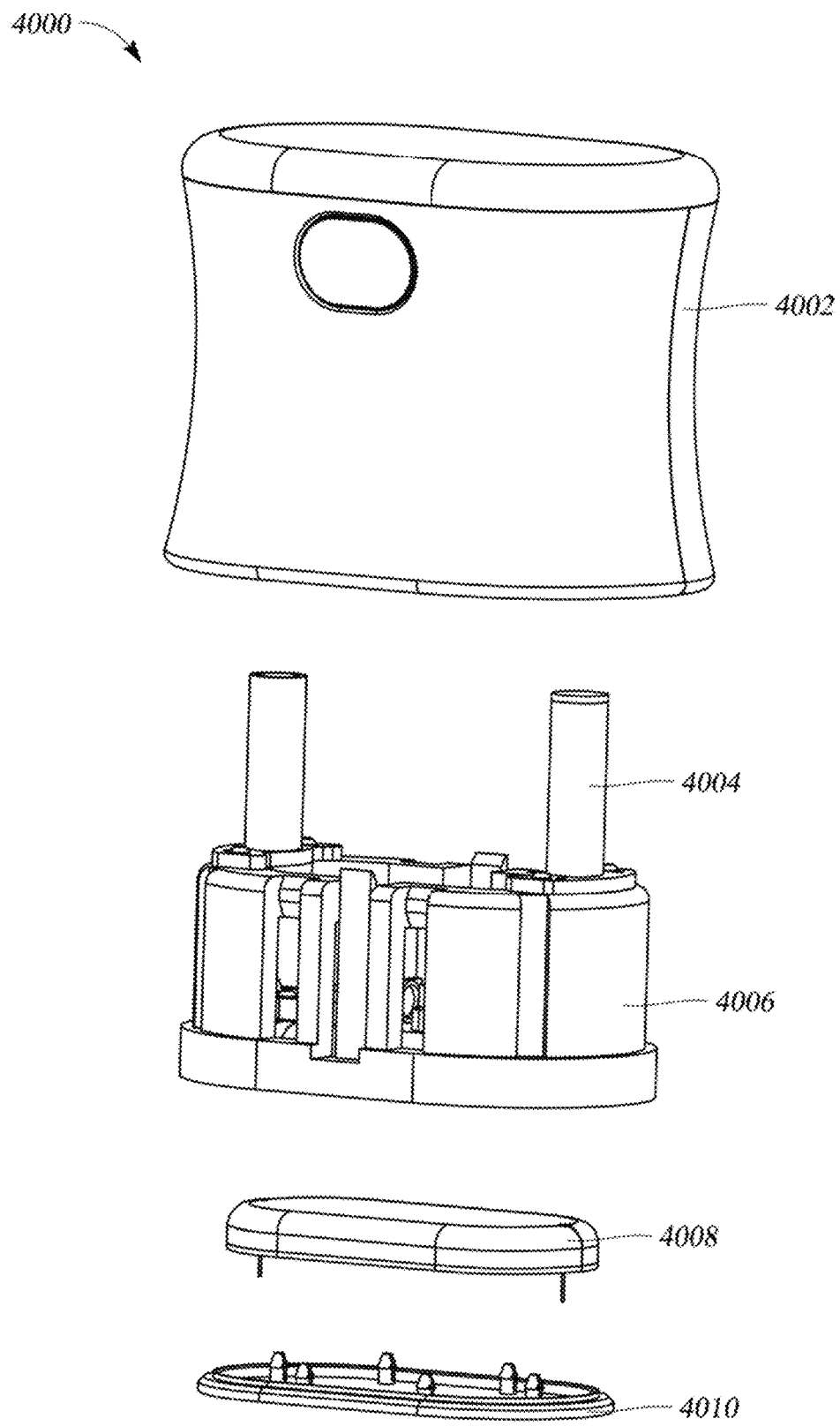
Figure 2J:
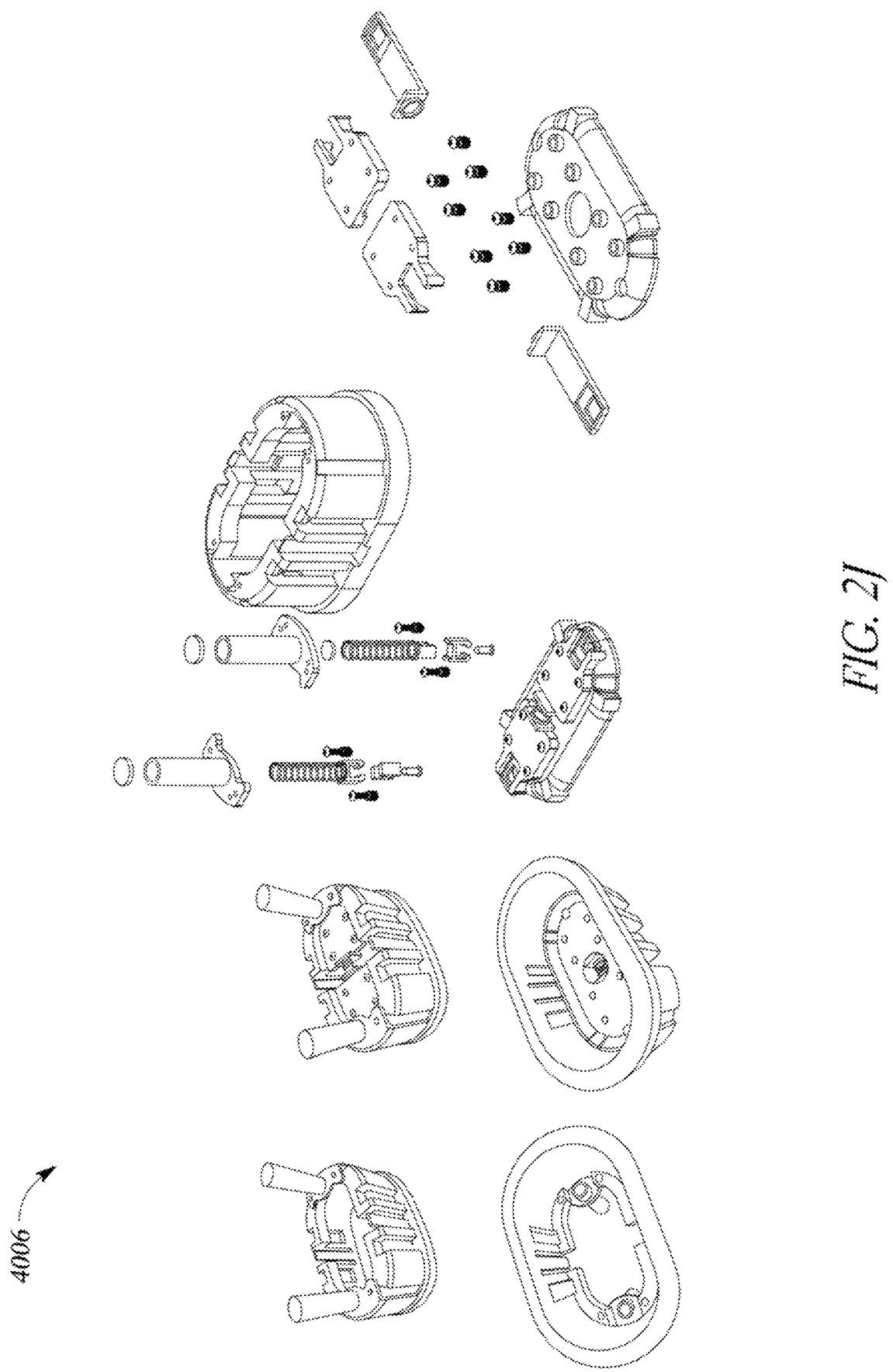

In some examples, one or more components of a disease management system and/or environment may be reusable, disposable, or refurbishable. FIGS. 2H-2K illustrates aspects of an example implementation of a disease management system 4000 that includes a combination of reusable, disposable and refurbishable components. As illustrated in FIG. 2H, a disease management system 4000 may include an applicator having a combination of reusable, disposable, and refurbishable components and a disease management system 4007 having a combination of reusable, disposable, and refurbishable components. FIG. 2I illustrates perspective and exploded views of reusable aspects 4002 of an applicator. FIG. 2J illustrates perspective views of refurbishable aspects 4006 of an applicator. Disposable aspects 4004 of an applicator are illustrated in FIG. 2H.

As shown in FIGS. 2H and 2K, a disease management system 4000 may include a disease management system 4007 composed of refurbishable components 4008 and disposable components 4010. In some examples, refurbishable components 4008 can include a device shell 4102 and light pipes 4104 in the shell 4102. Refurbishable components 4008 in a shell 4102 can include a buzzer and port cover 4108, a haptic motor 4106, an antenna 4114, a pump 4112, sealing rings 4110 or other reusable or recyclable components that can be sterilized and reused. Disposable components 4010 can include an adhesive layer 4130, system battery 4116, pump battery or batteries 4122, cannula 4120, analyte sensor 4128, medication bladder or pouch 4126, insulin or medication access port 4124, peristaltic tubing 4118, or other components that are difficult to sterilize and refurbish, expensive to sterilize and refurbish, designed for limited use or shelf life, or otherwise disposable.

1. Example Insulin Pump and Glucose Sensor System

Figure 3A:
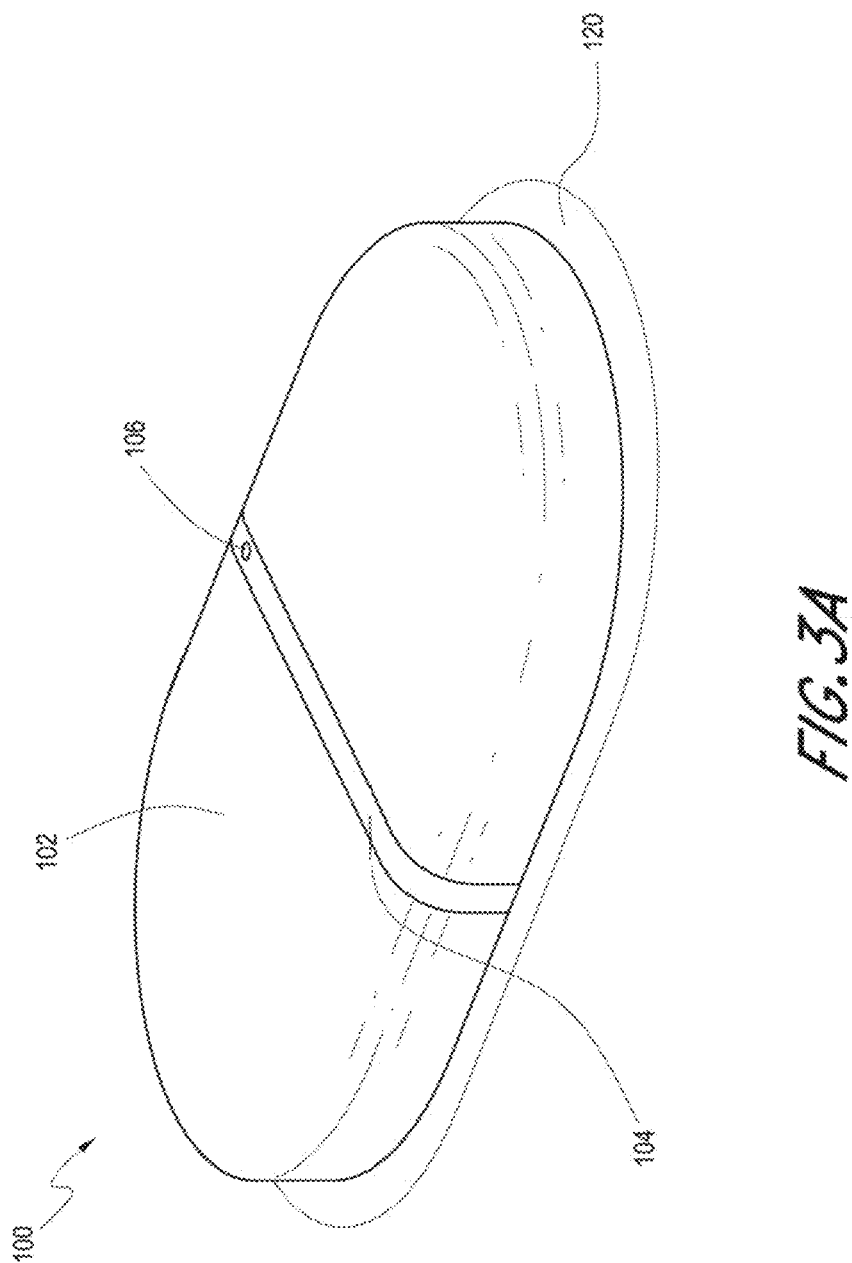
FIGS. 3A and 3B illustrate perspective views of a disease management system integrated with an insulin pump and a glucose sensor.
Figure 3B:
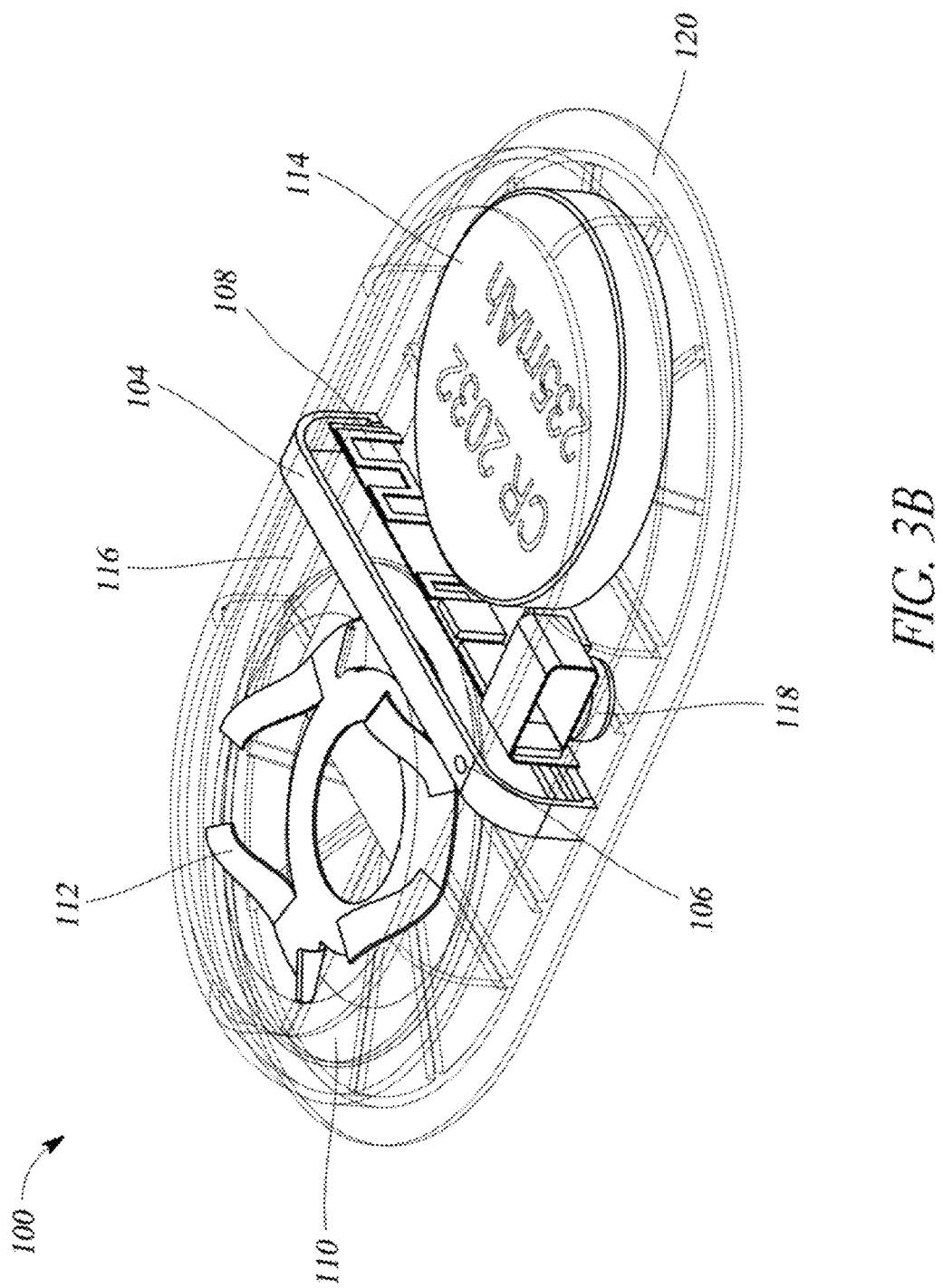

FIGS. 3A and 3B illustrate perspective views of an implementation of a disease management system 100 including a glucose sensor and an insulin pump (such as shown in FIGS. 4A-4C, or FIGS. 6A-6C). The disease management system 100 includes a printed circuit board (PCB) 108 including a computing device where the glucose sensor may be located. The computing device may include an electronic processor and memory with instructions executable by the electronic processor capable of receiving glucose measurements from the glucose sensor and controlling the insulin pump to provide a specific dosage of insulin to a patient based on the glucose measurements. An insulin dosage may be referred to as an insulin bolus. The disease management system 100 further includes an insulin bladder 110 which stores insulin to be administered to the patient. The insulin bladder 110 is connected to the insulin pump. The insulin pump may use pressure on the insulin bladder to force insulin out of the bladder 110. A spring 112 may be included in the disease management system 100 to apply pressure to the insulin bladder 110. The disease management system 100 further includes a battery 114 configured to provide power to the glucose sensor, the computer device, and the insulin pump. An antenna 104 is further included. The antenna 104 is configured to communicate with the computing device to communicate with other devices such as a smartphone, another disease management system, smartwatch, or other electronic device.

In some implementations the insulin bladder 110 may be adapted to store various types of insulin such as U-100 insulin and U-200 insulin. U-200 insulin may be of higher strength and higher concentration than U-100 insulin and thus an insulin bladder 110 filled with U-200 insulin may take up less space for the same dosage when compared to U-100. Other insulin types may be used without departing from the present invention.

A light source 118 such as a light emitting diode (LED) and photodiode may also be included. A vibration device such as a haptic feedback vibrator may also be included. The light source 118 and vibration device may be used to alert the patient of certain events such as a malfunction of a device, when it is time to change the disease management system 100, or alerts that can indicate spikes in glucose.

The antenna 104 can be compatible with Bluetooth or radio frequency (RF) such as Wi-Fi. In some implementations, the insulin bladder 110 can be a flexible insulin pouch capable of flexing under pressure in order to force out insulin. In these implementations, the insulin bladder 110 may be connected to an insulin pump which is a valve. In some implementations, the insulin bladder 110 may be a rigid storage structure. In these implementations, the insulin bladder 110 is connected to an insulin pump which applies pressure to the insulin in order to force out the insulin. The PCB 108 may include an accelerometer, gyroscope, and communications module.

A case 102 houses the PCB 108, the insulin pump, the insulin bladder 110, the battery 114, the spring 112, the light source 118, and the vibration device 116. The case 102 is rigid such that the spring 112 may press against the case 102 when applying pressure to the insulin bladder 110. The case may be made from a metal such as aluminum or plastic. The aluminum may be polished for aesthetic purposes. The case 102 may be mounted on an adhesive 120 in order to mount the disease management system 100 on a patient. The case 102 may include one or more needle insertion pass through 106 which allows a needle to pass from the top of the case 102 through the insulin pump and into the patient. The needle may be used to implant a cannula from the insulin pump into the patient allowing the insulin pump access to the patient's interstitial fluid or blood. The one or more needle insertion pass through 106 may also allow access to the patient's interstitial fluid or blood to the glucose sensor. These one or more needle insertion pass through 106 may be on opposite sides of the device in order to provide adequate spacing for the glucose sensor and the insulin being provided from the pump into the patient. The antenna 104 may be applied on the case 102, embedded with the case, or may divide the case 102 into two portions. The case 102 can further include an auxiliary device space 116 which may include one or more auxiliary devices such as a vibration device (for example, a haptic feedback vibrator).

Figure 4A:
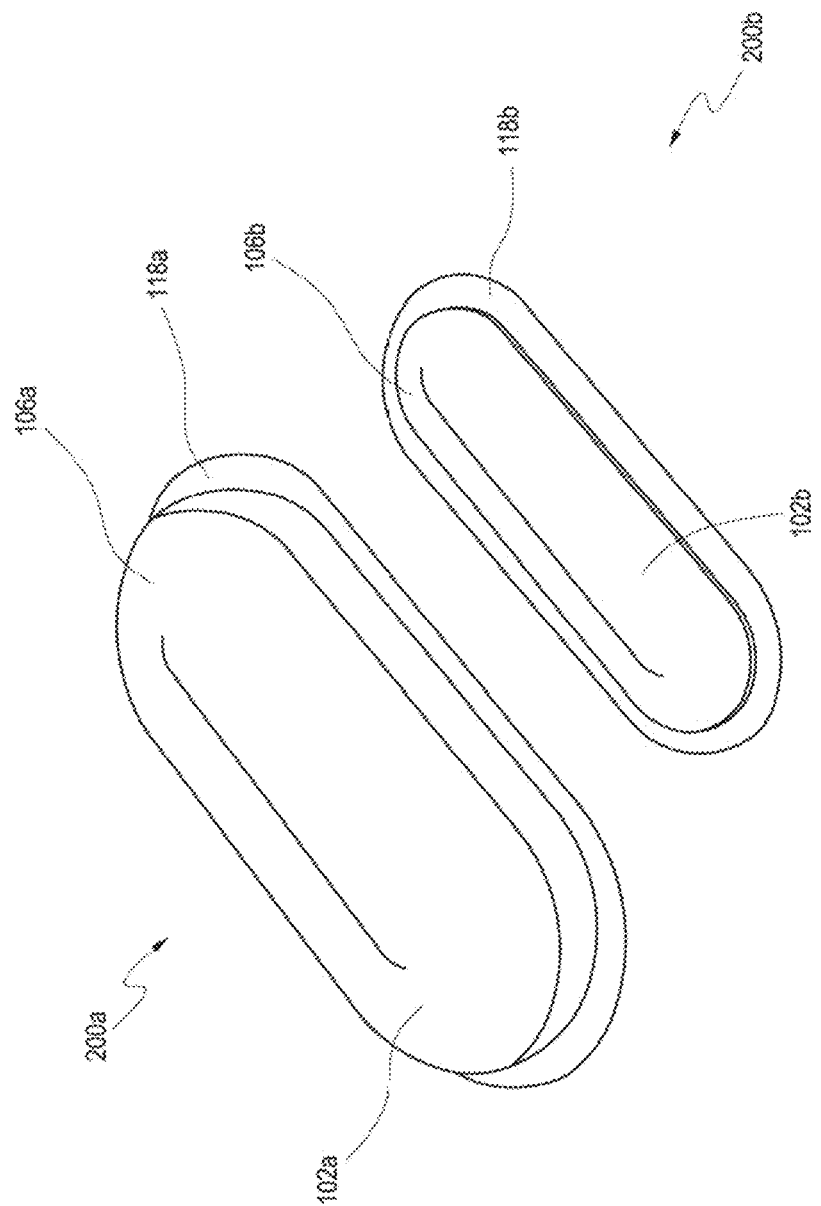
FIGS. 4A and 4B illustrate perspective views of a disease management system including a sensor system and an insulin pump system which are separate.
Figure 4B:
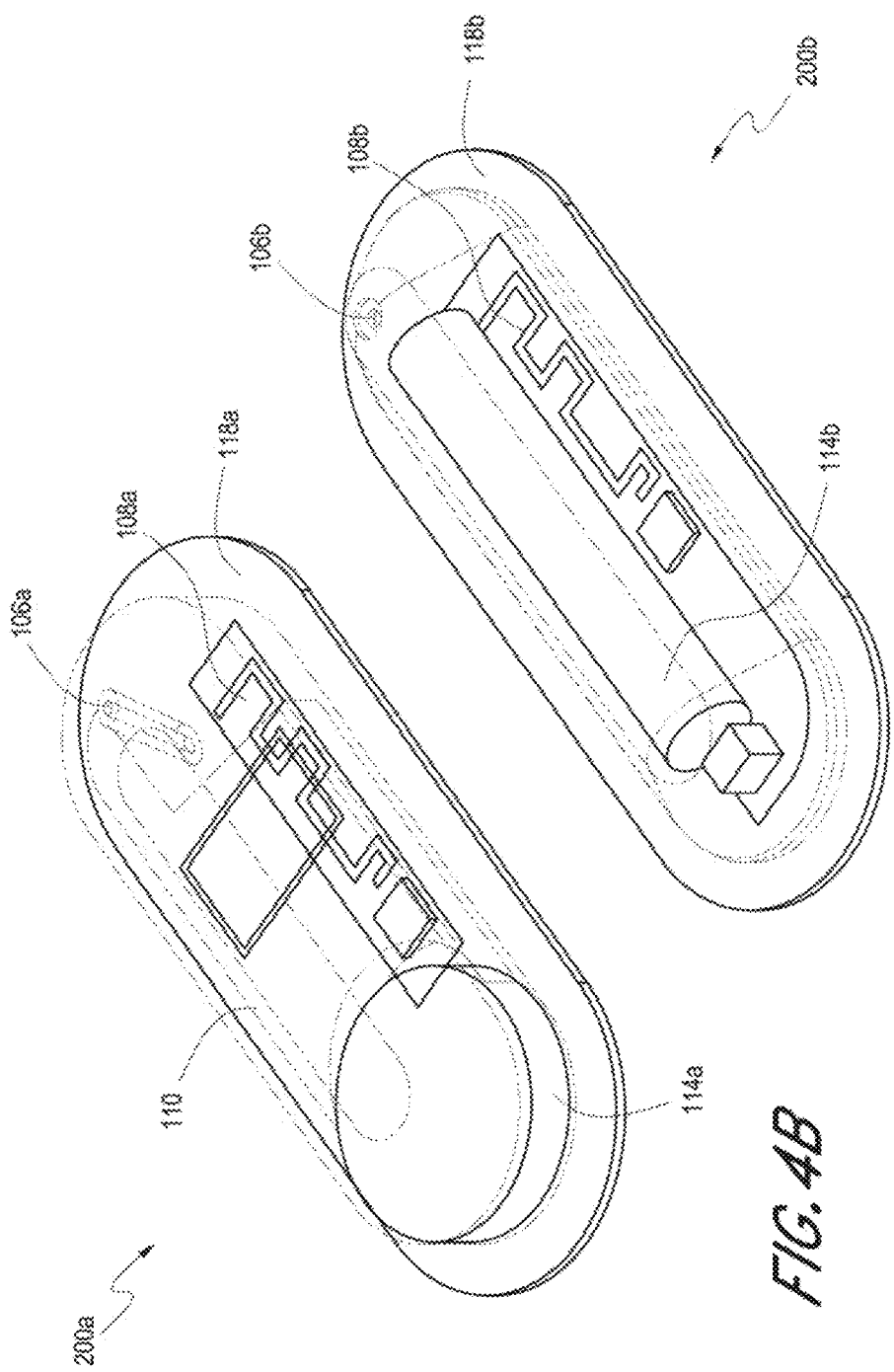

FIGS. 4A and 4B illustrate a perspective view of an implementation of a disease management system including a sensor system 200B and an insulin pump system 200A. FIG. 4C illustrates a cross sectional view of the insulin pump system 200A. The disease management system illustrated in FIGS. 4A-4C share many features with the disease management system which have been identically numbered. The description from FIGS. 3A and 1B are applicable in the description in FIGS. 4A and 4B. In FIGS. 3A-3c, the sensor system 200B and the insulin pump system 200A provide similar functionality to the disease management system described above but broken down into two separate systems.

The sensor system 200B and the insulin pump system 200A may or may not both include a PCB 108B, 108A. The PCBs 108B, 108A may both include a computing device with an electronic processor and memory with instructions executable by the electronic processor capable of receiving glucose measurements from a glucose sensor and controlling an insulin pump to provide a specific dosage of insulin to a patient based on the glucose measurements. In some implementations, the PCB 108B of the sensor system 200B may merely send measurements to the PCB 108A of the insulin pump system 200A and a computing device of the insulin pump system 200A may compute the proper dosage of insulin and operate the insulin pump to administer the proper dosage to the patient. Alternatively, the computing device located on the PCB 108B of the sensor system 200B may calculate the proper insulin dosage and send instructions to the PCB 108A of the insulin pump system 200A to pump the proper dosage of insulin. The insulin pump system 200A may merely follow instructions from the computing device located on the PCB 108B of the sensor system 200B. Further, the PCBs 108A, 108B may both include antennas which may be connected to the computing devices to transmit information between the computing devices and also other devices such as a user device (for example a smartphone or smartwatch) or another disease management system.

The sensor system 200B and the insulin pump system 200A may both include a battery 114B, 114A. The battery 114B of the sensor system 200B may be used to power the PCB 108B which includes the glucose sensor and the computing device. The battery 114A of the insulin pump system 200A may be used to power the PCB 108A which is connected to an insulin pump (not shown) and the computing device. The insulin pump system 200A may further include a spring 112 which applies force to the insulin bladder 110. Similar to implementations of the disease management system described above, the spring 112 may not be present when the insulin pump forces the liquid out of the bladder 110. Rather it can be a valve that gates the flow of insulin.

The sensor system 200B and the insulin pump system 200A both include a case 102B, 102A. The case may be made of the same materials as the implementations of the disease management system described above. Alternatively, the cases 102A, 102B may also be made of a softer material such as silicone. The cases 102A, 102B include needle insertion points 106A and 106B in which needles may be inserted to penetrate from the top of the cases 102A, 102B and into the patient. The cases 102A, 102B may be adhered to a patient with an adhesive 118A, 118B.

Advantageously, the implementations of the disease management system described above, such as disease management system 100 of FIGS. 3A and 3B including combined glucose sensor and insulin pump whereas the disease management system of FIGS. 4A-4C includes a separate insulin pump system 200A and sensor system 200B. Separate systems can add cost and waste. Having one system can allow for shared components which can decrease cost. Further, applying two separate systems to the patient adds additional pain and anxiety to the patient. However, having separate systems may make replacement of the insulin pump and glucose sensor more efficient. Though, with proper replacement timing, the combined system may be as efficient as having separate systems.

C. EXAMPLE IMPLEMENTATION OF A DISEASE MANAGEMENT SYSTEM

Figures 1, 4D:
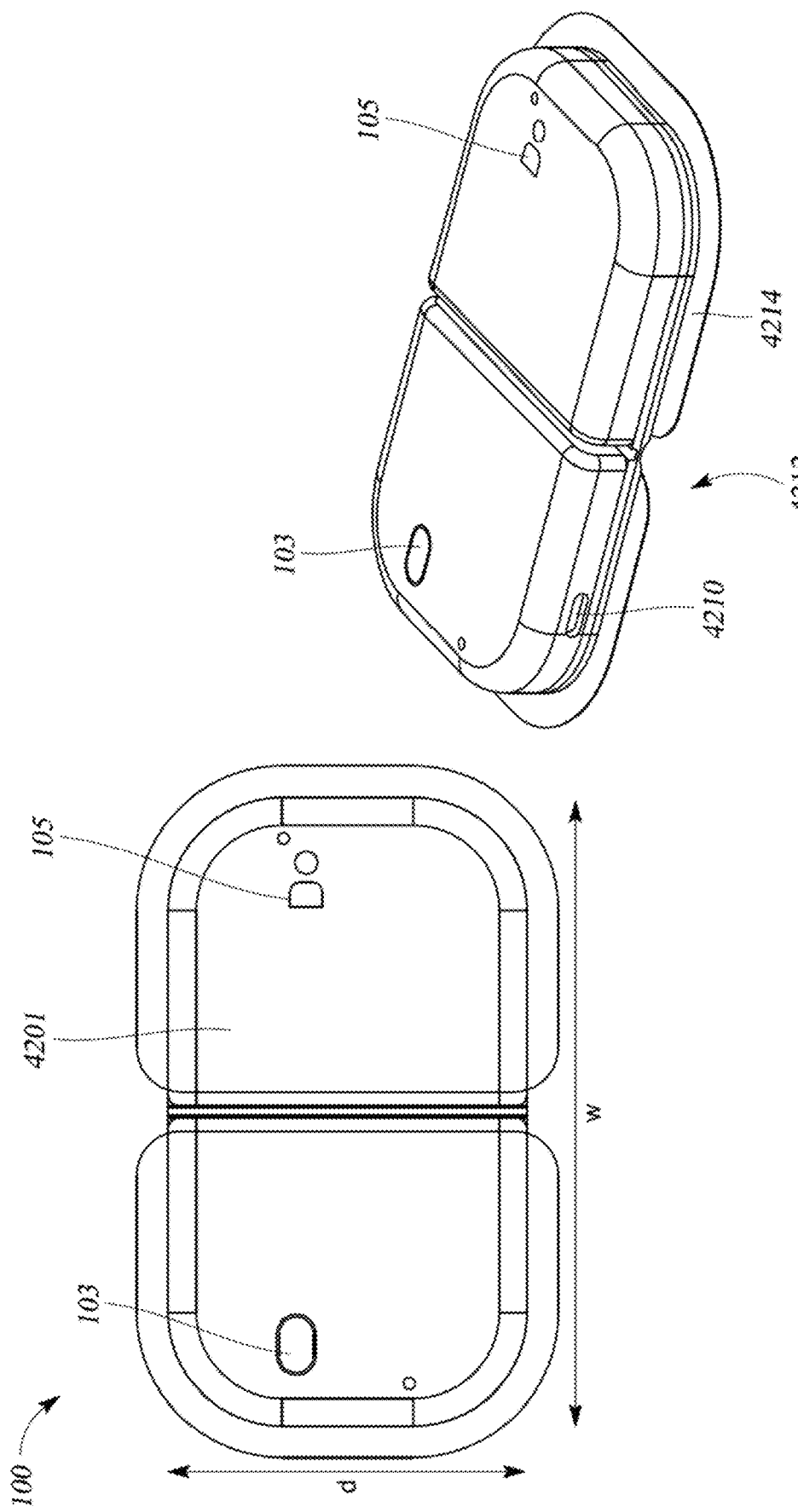
FIG. 4D-1 illustrates perspective views of an example disease management system.
Figures 1, 4E:
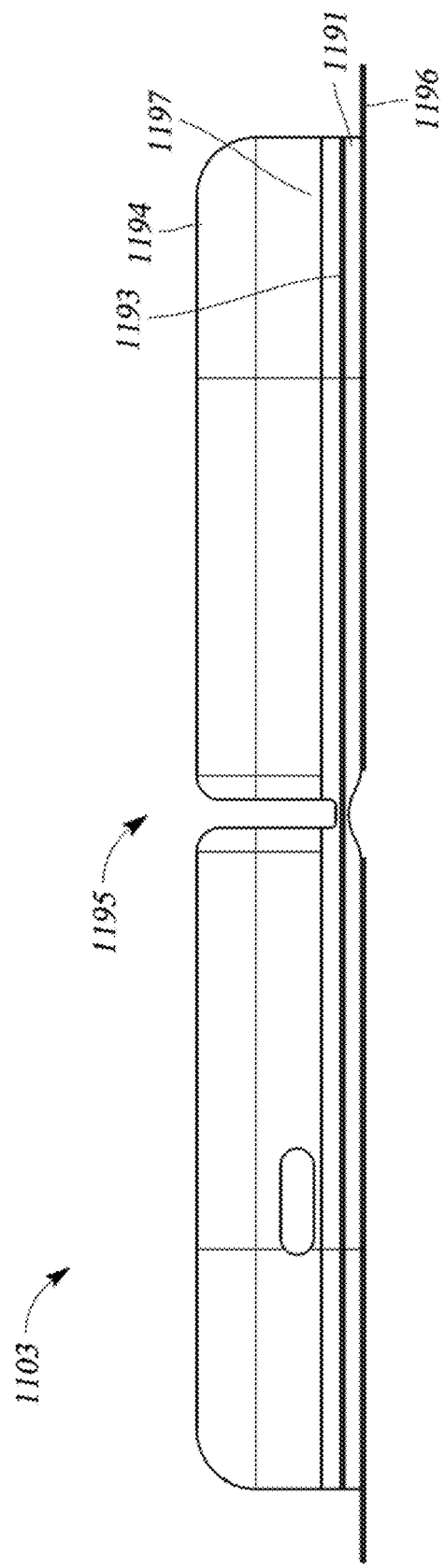
Figures 2, 4E:
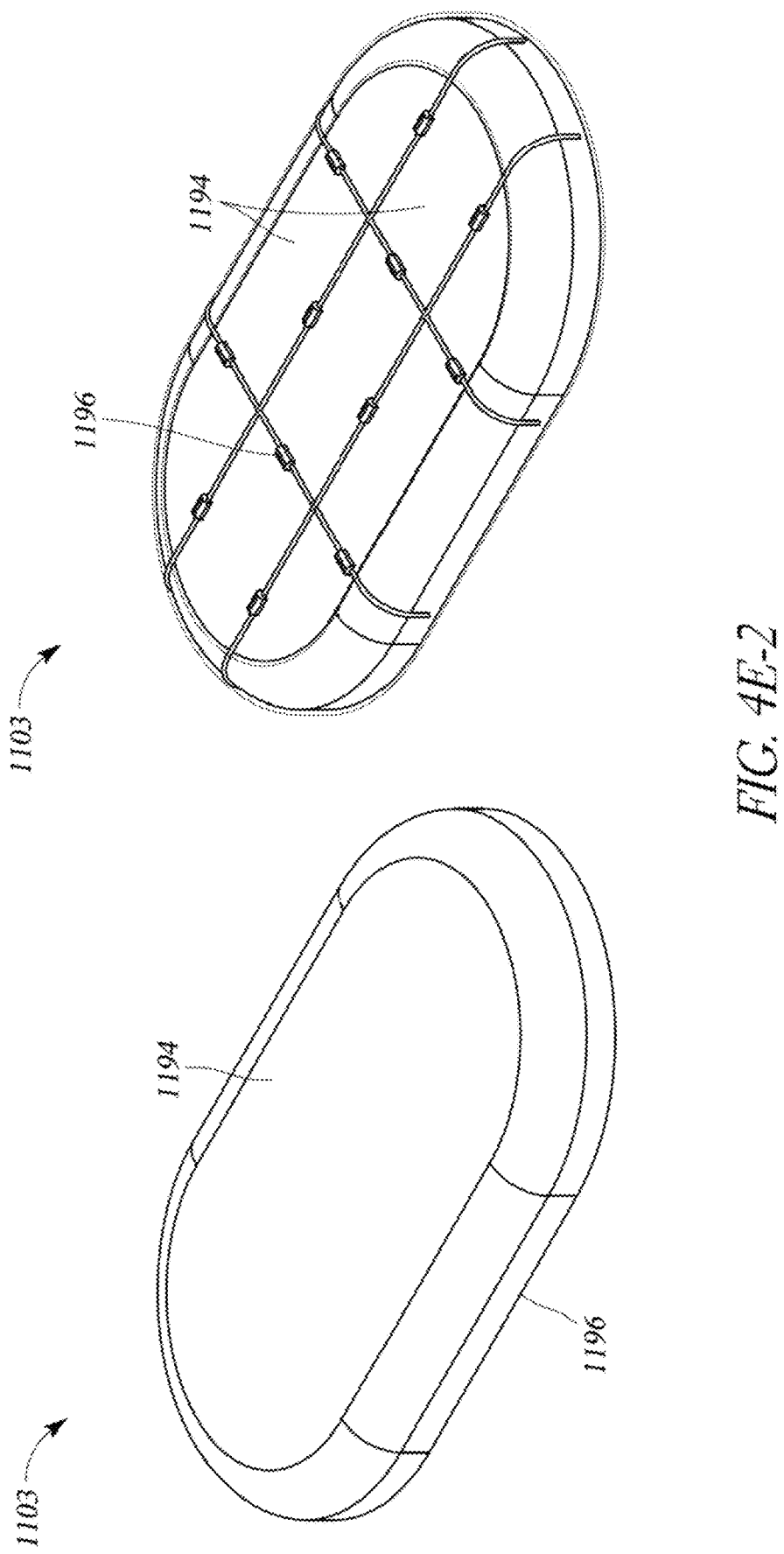

In addition or in the alternative to one or more of the implementations described above, a disease management system may be combined into a compact design, such as illustrated in FIGS. 4D-1 and 4D-2.

For example, as illustrated in FIG. 4D-1, a disease management system 100 can include a combined glucose monitor and insulin pump. In some examples, the depth, d, of a disease management system 100 can be in a range of approximately 20 to 50 mm or a value less than or greater than that range. In some examples, the width, w, of the disease management system 100 can be in a range of approximately 40 to 70 mm or a value less than or greater than that range. In some examples, the height, h, of the disease management system 100 can be in a range of approximately 5 to 10 mm, or a value less than or greater than that range. For example, the dimensions of the disease management system 100 can be approximately 32 mm in depth (d), approximately 56 mm in depth (w), and approximately 7 mm in height (h).

With continued reference to FIG. 4D-1, a disease management system 100 may be configured to have an outer shell 4201. The outer shell 4201 may include one or more portions that are connected, attached, or separate from each other. In some examples, the outer shell may consist of two pieces connected by a bending portion 4212. The bending portion 4212 may be configured to allow the one or more portions that make up the outer shell 4201 to bend or flex in at least a manner suitable to approximately conform to an attachment site on the skin of the patient. For example, the bending portion 4212 may be configured to allow the disease management system 100 to bend so as to substantially conform or partially conform to a curved portion of the patient's skin. The curved portion of the patients skin may, for example, include a portion of a patient's abdomen, arm, buttocks, or other area of a patient. In some examples, such as described below, an outer shell 4201 may be configured to include a plurality of flexible and rigid materials.

In some examples, a disease management system may have one or more buzzers, alarms, or speakers 4210, or optical displays configured to display or communicate information to a patient. For example, a disease management system 100 may include a plurality of light emitting diodes (LEDs) 103, 105. In some examples, a disease management system 100 may include a connection status LED 103 and a patient status LED 105. In some examples, the disease management system 100 may be configured to change a property of illumination of the LED to display information. For example, a disease management system 100 may change color or pattern of illumination of a connection status LED 103 to indicate a connection status of the disease management system with one or more of: user device(s), other disease management system(s), other patient monitoring or treatment system(s), and the cloud. In another example, a disease management system 100 may change color or pattern of illumination of a connection status LED 105 to indicate a patient status, such as a glycemic state or condition.

In some examples, a disease management system 100 may include a port to facilitate delivery of a manual bolus of medication. A port can include an opening in a shell of the disease management system 100. The opening may be configured to receive a medication needle and allow delivery of a manual bolus of medication to the patient from the medication needle. In some examples, the port may be a pass through to the skin of the patient. In some examples, the port may allow an injection of medication through the cannula of the disease management system 100.

FIG. 4D-2 illustrates cross sectional and perspective views of the disease management system 100. As illustrated, a disease management system 100 can include a battery 4204, a PCBA 4202, an analyte sensor mount 4206, an adhesive latch mechanism 4208, a buzzer 4210 and water resistant film or layer, a vibration motor 4209, a medication pouch assembly 4216, a pouch puncture assembly 4228, one or more light pipes 4218, a cannula and needle 4222, and a pump assembly 4220.

A top shell or housing 4201 of the disease management system 100 be configured to cover other components of the disease management system 100. The top housing 4201 can be a thickness in a range of approximately 0.5 mm to 5 mm, or a value less than or greater than that range. For example, a top housing 4201 can be approximately 1 mm thick.

In some examples, a bottom of the disease management system 100 can include a bottom assembly, such as a bottom frame portion 4211. The bottom frame portion 4211 may include a metal plate. The metal plate may, for example, have a thickness of approximately 0.1 to 1 mm, or a value less than or greater than that range. For example, a metal plate can be approximately 0.2 mm thick. In some examples, a bottom assembly can include an adhesive plate 4213 configured to connect the metal plate and/or other portions of the disease management system 100 to an adhesive material or layer of adhesive material 4214. The adhesive plate may, for example, have a thickness of approximately 0.1 to 2 mm, or a value less than or greater than that range. For example, an adhesive plate 4213 may have a thickness of approximately 0.7 mm. The adhesive material or layer of adhesive material 4214 may, for example, have a thickness of approximately 0.05 mm to 1 mm, or a value less than or greater than that range. For example, the adhesive material may have a thickness of approximately 0.15 mm.

In some examples, a disease management system 100 can include a battery 4204. The battery may be configured to rest on or couple to at least a portion of the bottom frame, such as the metal plate 4211. The battery may be electrically connected to a PCBA board 4202. In some examples, the battery 4204 may have a thickness in a range of, for example, approximately 2.5 mm to 5 mm, or a value less than or greater than that range. For example, the battery 4204 may have a thickness of approximately 3.3 mm. In some examples of a PCBA may have a thickness in a range of, for example, approximately 0.1 to 1 mm or a value less than or greater than that range. For example, a PCBA may have a thickness of approximately 0.5 mm. In some examples, a space 4203 between the PCBA and the antenna 4224 may be approximately 1 to 1.2 mm, or a value less than or greater than that range.

FIGS. 4E-1 and 4E-2 illustrate example configurations of an outer portion of a disease management system 1103. For example, as illustrated in FIG. 4E-1, a disease management system 1103 can have a plurality of portions. In the illustrated example, a housing can include at least two portions with a bending mechanism 1195 coupling the two portions. Advantageously, having two portions connected as opposed to two separate devices can reduce an overall footprint of the disease management system 100. For example, having a single device can allow for the use of a single battery system, PCBA, communication components, and antennas. In the case of a split device, many or all of these components would have to be duplicated to ensure full functionality.

In some examples, a disease management system 1103 can include a bottom housing 1197 and top housing 1194. One or more of the top housing 1194 or the bottom housing 1197 can include a plastic, such as polycarbonate (PC) or ABS. At least a portion of the bottom housing can be configured to couple to a metal plate (for example, a stainless steel plate) 1193. The plate 1193 may be configured to support the bend or bending mechanism 1195 of the disease management system 1103. The plate 1193 may be thin. The plate may have a thickness, for example, of approximately 0.005 inches or more or less thickness. In some examples, the plate 1193 may be configured to couple to an adhesive plate 1191. An adhesive layer 1196 may be configured to couple to the adhesive plate 1191. The adhesive layer 1196 may be configured to attach at least a portion of the disease management system 1103 to the attachment site of the patient. The adhesive layer 1196 may be configured to adhere to the patient for a prolonged period, such as 1 day, 3 days, 6 days, a different number of days or more or less time. The adhesive layer 1196 may be configured to adhere to the patient for the intended life or period of use of the disease management system 1103.

A bending mechanism 1195 can include a flexible material or bendable portion of the disease management system 1103. The bending mechanism 1195 may allow at least a portion of the disease management system 1103 to bend or otherwise change shape or configuration to approximately conform to an attachment site on a patient. In some examples, the bending mechanism 1195 may facilitate an improved contact of at least a portion of the disease management system 1103 with the patient.

FIG. 4E-2 illustrates alternative configurations of an external housing of a disease management system 1103. As illustrated, a disease management system 1103 may include one or more rigid portions 1194 and one or more flexible portions 1196. In some examples, the one or more rigid portions 1194 can include a single rigid piece configured to directly or indirectly couple to at least some of the internal components of the disease management system 1103. In some examples, the single rigid piece 1194 may be coupled to a flexible portion 1196 configured to conform to an approximate shape of a patient at the attachment site. For example, the rigid portion 1194 may include a top housing portion and the flexible portion 1196 may include a bottom housing portion, where the bottom housing portion is configured to adapt its shape to a shape associated with the patient skin. In some examples, the one or more rigid portions 1194 can include a plurality of rigid pieces 1194 can be coupled together with a plurality of flexible portions 1196. In some examples, the plurality of flexible portions 1196 can facilitate bending or conforming of at least a portion of the disease management system 1103 to an approximate shape of a patient at the attachment site.

Figure 4F:
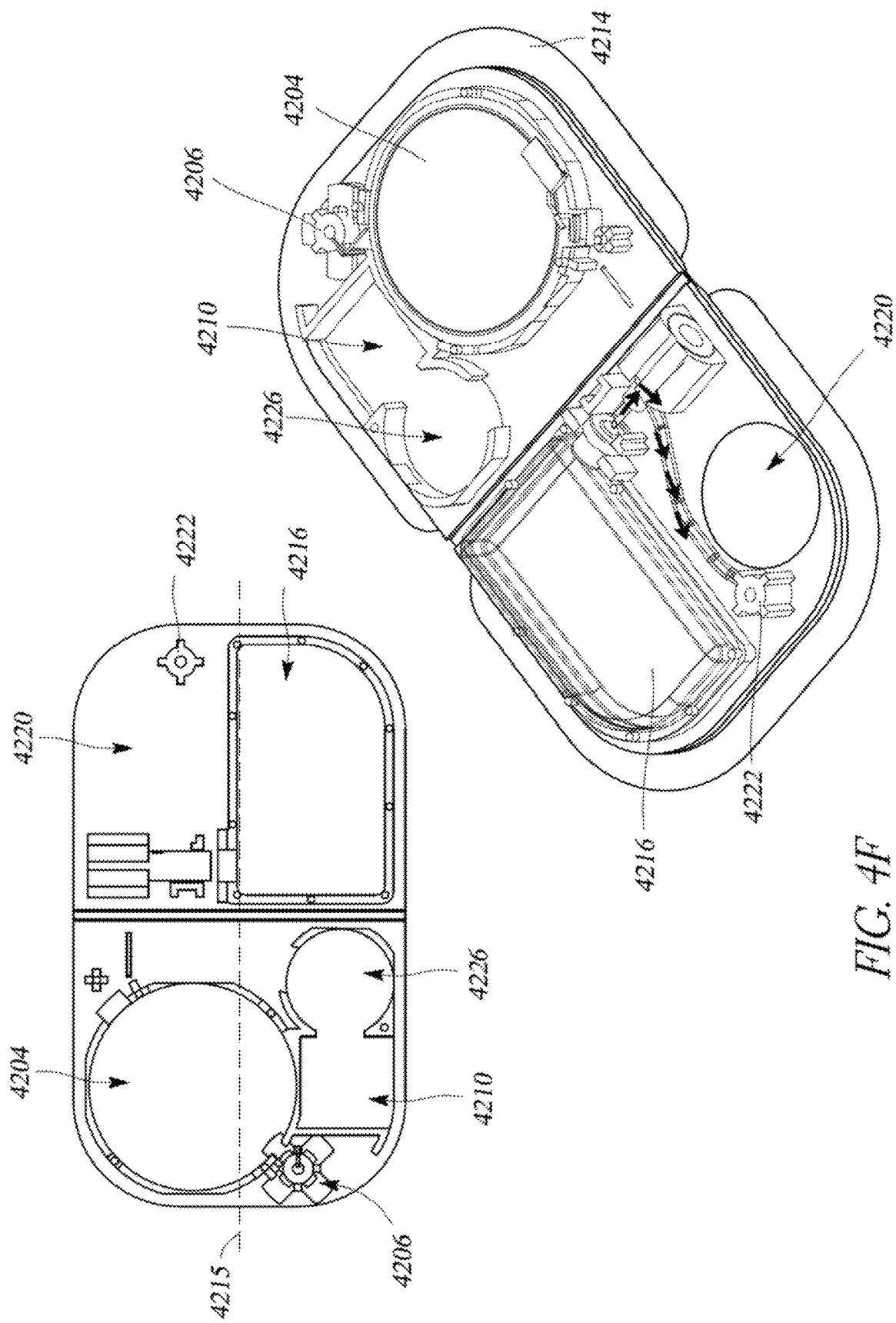
FIG. 4F illustrates example component layout of an implementation of a disease management system including a plurality of components that may be disposable.

FIG. 4F illustrates an example layout of the components of a disease management system 100. For example, a battery 4204 may be configured to sit at a corner of a system 100 in order to maximize internal space of the system 100 for other components. In some examples, an analyte sensor mount 4206 may be placed offset from a centerline 4215. Advantageously, the offset may help reduce the length of the device and facilitate more efficient use of space on the device. In some examples, a vibration motor and mount 4226 may be located away from needles of the device, such as an analyte sensor mount 4206 in order to avoid poking tissue as a result of vibration. In some examples, a pump 4220 can include components, such as a pump gear head and actuator, near a cannula outlet (for example a cannula and needle 4222). Advantageously, having the pump components being close to the cannula outlet can improve effectiveness and efficiency of the pump system and help ensure that the pump mechanism results in reduced waste of medication during operation. In some examples, a medication pouch 4216 may be located at a corner location so that a pouch shape is relatively simple and easier to manufacture.

With continued reference to FIG. 4F, in some examples, one or more of the components may be disposable. In some examples, disposable components can include an adhesive layer 4214, battery 4204, medication pouch 4216, metal layer 4440, analyte sensor mount 4206, and cannula and needle 4222.

Figures 1, 4G:
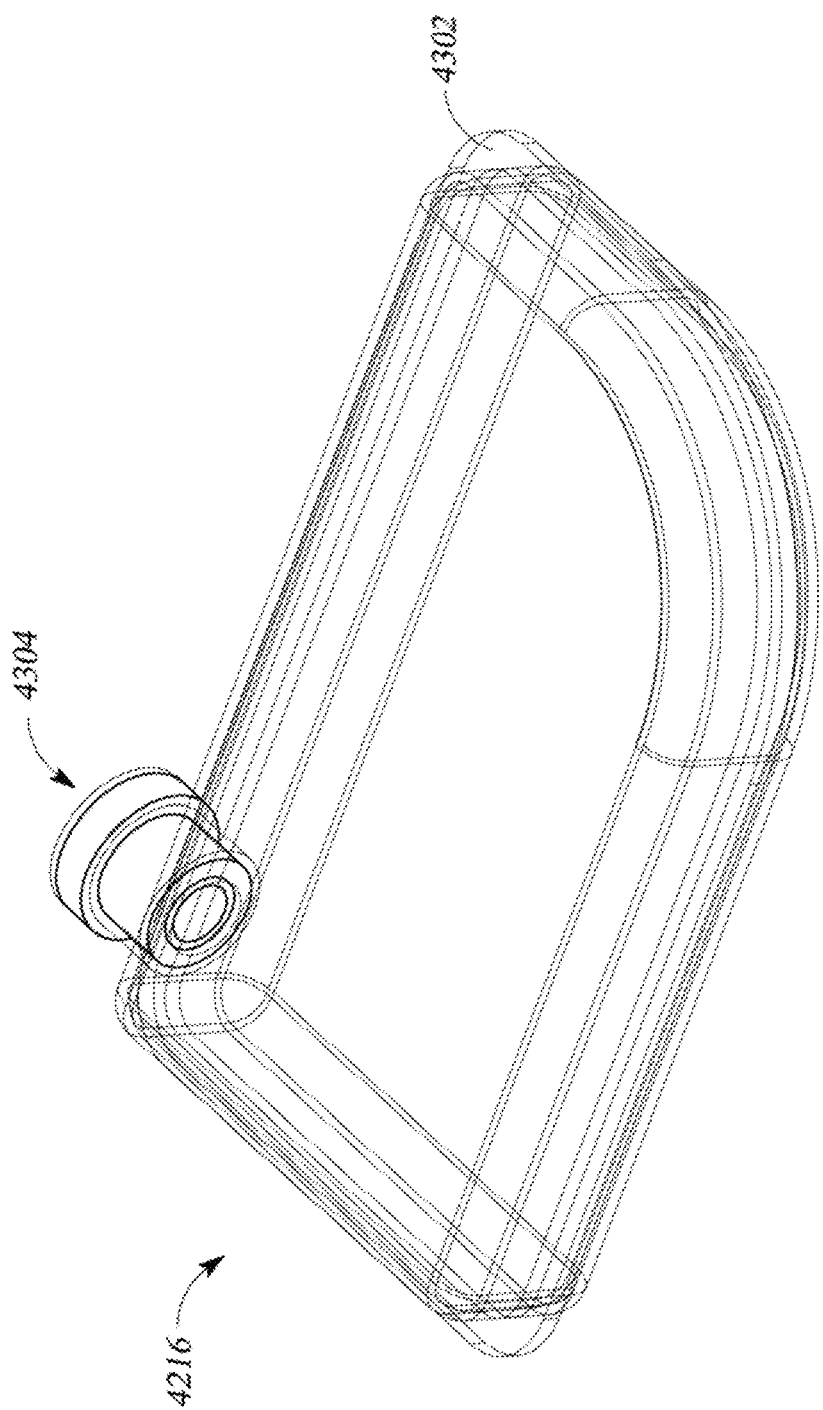
Figures 2, 4G:
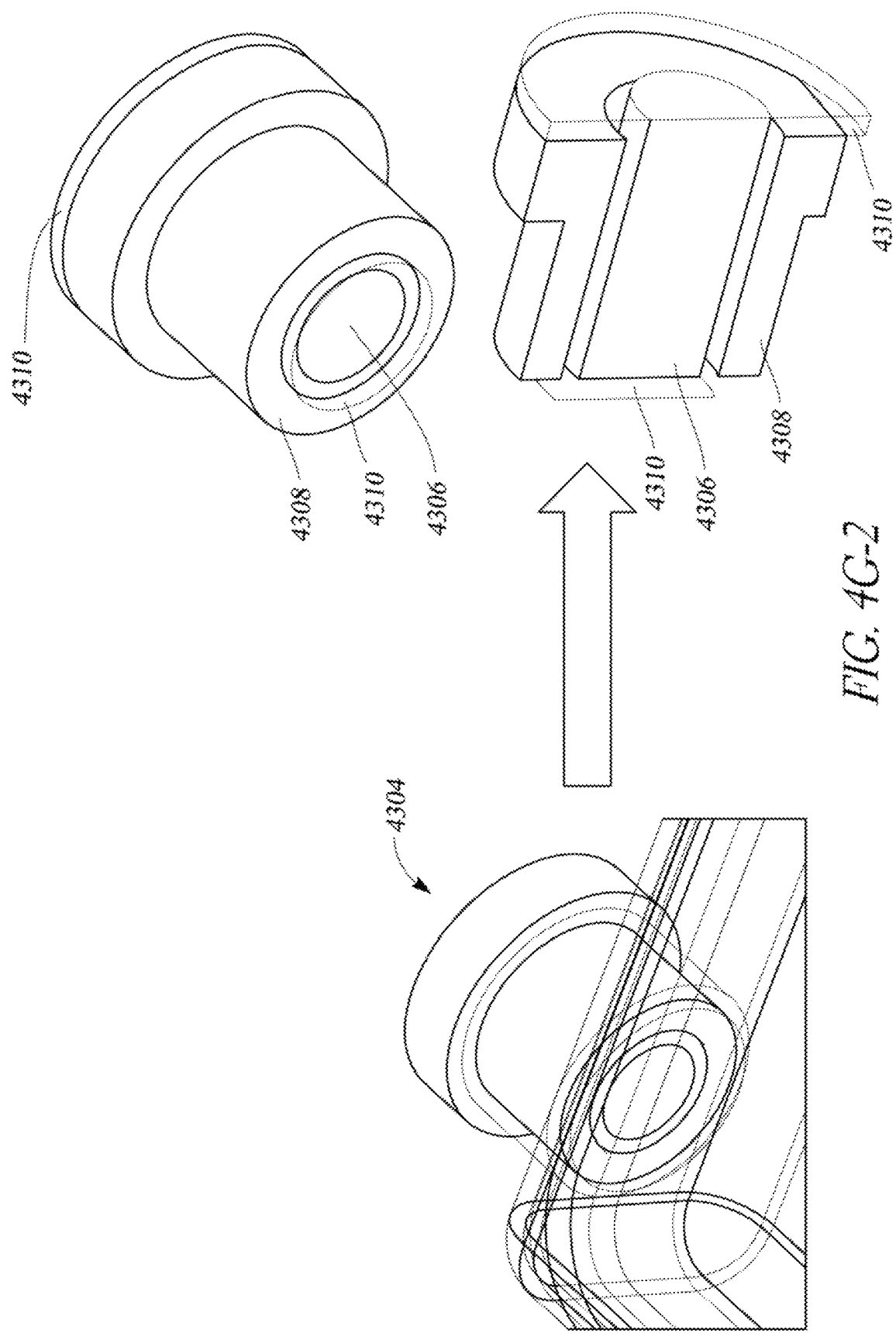

FIG. 4G-1 illustrates an example medication pouch or bladder 4216. The pouch may be configured to contain, for example, approximately 1.5 mL, 3 mL, or a different amount of medication. In some examples, the capacity of the pouch may be large enough to contain medication for the intended life of the disease management system. For example, a pouch may be configured to contain 3 days of medication, 6 days of medication, or more or less medication. In some examples, a disease management system can include a plurality of pouches containing the same or different medications. For examples, the disease management system can include a plurality of medications in different pouches configured to combine or be administered at different times to a patient. In some examples, the medication can be insulin, glucagon, or the like.

A medication pouch 4216 may include one or more sealed or sealable portions 4302. For example, a medication pouch 4216 may include a sealed flange. The sealed flange may be heat sealed or otherwise sealed. The flange may be configured to allow for the pouch to be mounted to the glucose storage system or vice versa. The flange may be configured to help ensure that the medication pouch collapses flat. For example, as the medication pouch 4216 is emptied, the flange may help ensure that the medication pouch collapses flat instead of in another shape. One or more surfaces of the medication pouch may be covered in a film, such as a polymer film (for example, a COC film). The film may advantageously help ensure integrity of the pouch and/or medication during storage, sterilization of the pouch, or other manufacturing or refurbishing processes.

As illustrated in FIG. 4G-2, a pouch 4216 may have a pouch seal 4304. The pouch seal 4304 may be configured to allow access to the medication in the pouch 4216. The pouch seal 4304 may be sealed after the medication is added to the pouch during manufacture. For example, a pouch seal 4304 may include a plug 4306 configured to allow for needle penetration and in order to facilitate access by a needle to medication in the pouch. The plug may include a material, such as polyisoprene or other material configured to allow for needle penetration. The plug 4306 may be sealed using one or more materials 4310, such as a polymer (for example COC). The plug 4306 may be configured to be received by a receiving portion 4308 of the seal 4304. The receiving portion 4308 may be configured to have a pass through that can be filled with the plug 4306. In some examples, the receiving portion 4308 may be configured to have a mating shape with the plug 4306.

Figures 3, 4G:
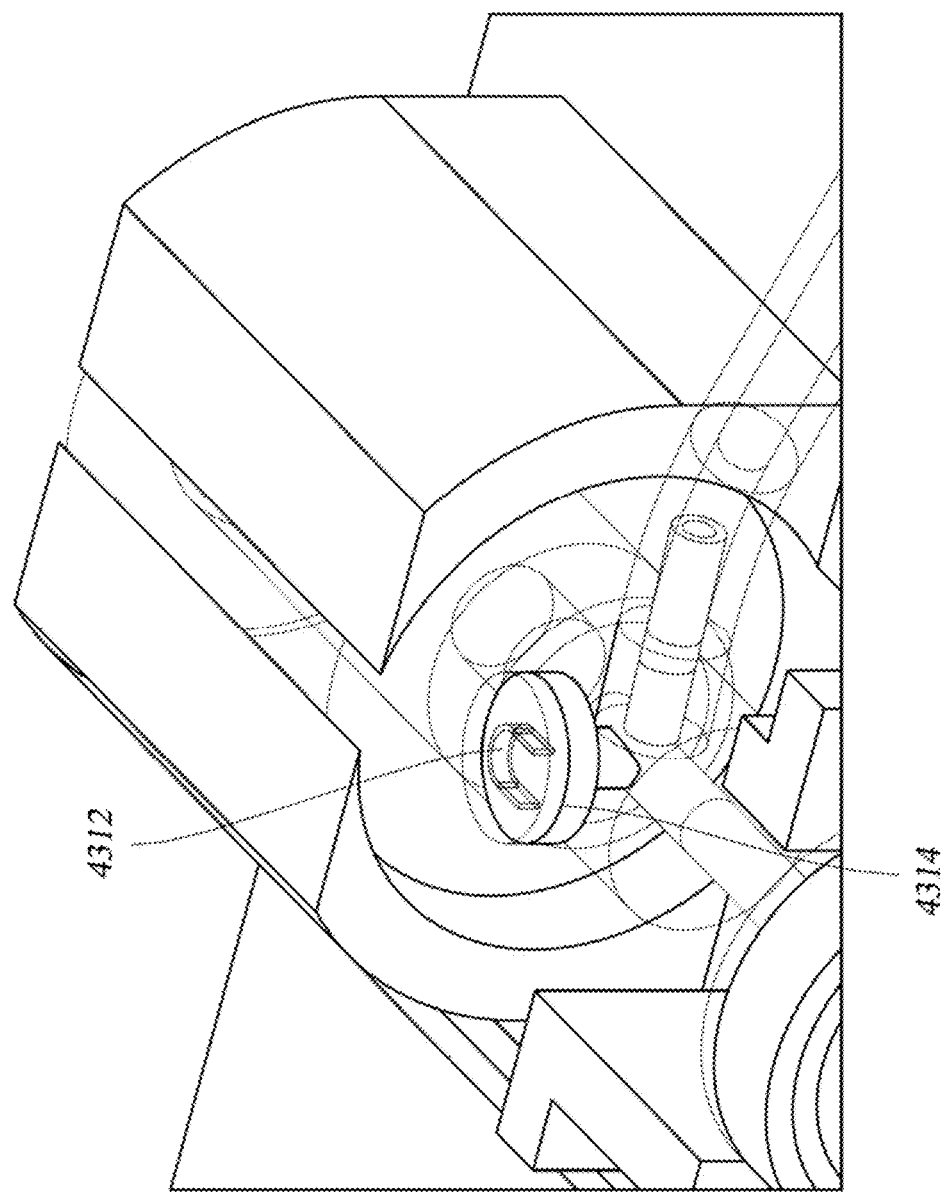

FIG. 4G-3 illustrates an example pressure release valve mechanism that may be configured to be attached to at least a portion of a pouch assembly, such as the seal 4304. In some examples, the pressure release valve may be configured to safely release pressure from one or more of the cannula, pouch, or other parts containing medication. For example, the pressure release valve may be configured to release pressure in the cannula, pouch, or other parts containing medication in the event of excessive pressure on the device or in the flow of medication, such as caused in the event of a crushed device. As illustrated in FIG. 4G-3, a pressure control valve 4312 may be used as a pressure control. The pressure control valve 4312 may be composed of, for example, silicone. In some examples, the pressure control valve 4312 may be configured to release pressure from a line containing medication at a pressure of approximately 200 mmHg or more or less pressure. In some examples, a drilled hole in the valve mechanism or other flow rate control mechanism may facilitate control of a flow rate of medication from the pouch to other components of the disease management system. In some examples, a valve may include a metal (such as a stainless steel) orifice 4314. Advantageously, the metal orifice 4314 may help minimize thermal expansion of components.

Figure 4H:
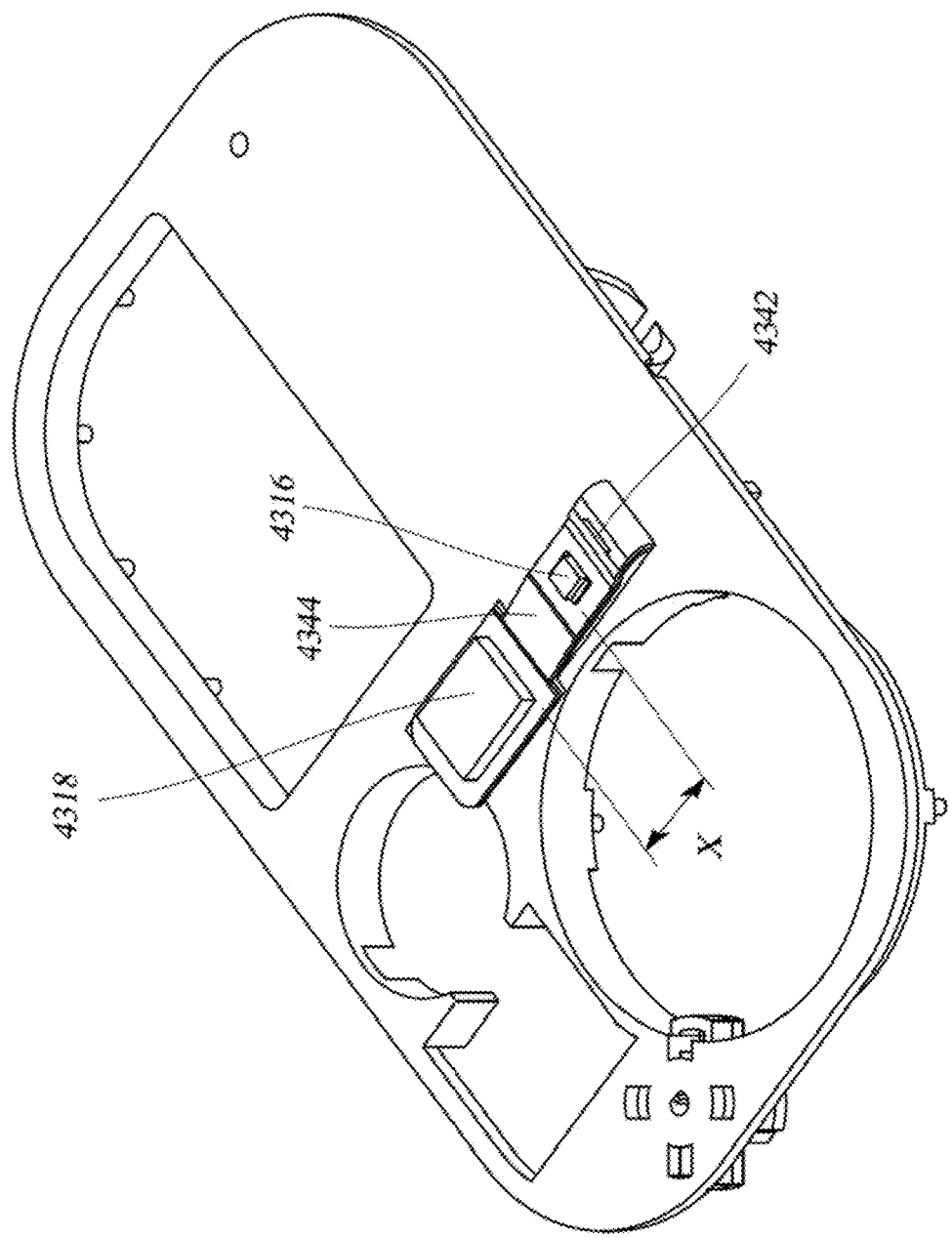
FIG. 4H illustrates an example pulse rate and thermistor mount for an implementation of a disease management system.

FIG. 4H illustrates example sensors and mounts for the sensors for a disease management system. In some examples, a disease management system may include one or more non-invasive sensors, including, but not limited to a pulse rate sensor or pulse oximeter and thermistor. The pulse rate sensor can include some combination of light source 4316 and detector 4318. The distance, x, between a light source 4316 and a detector 4318 may be, for example, approximately 5 mm, or more or less distance. In some examples, the light source 4316 may include a green LED (for example, having a wavelength of approximately 525 nm or 550 nm), or a plurality of LEDs having a single or a plurality of colors. In some examples, a photo detector 4318, light source 4316, and thermistor 4342 may be configured to couple to each other and/or other components of a disease management system using a flex cable 4344. In some examples, the flex cable may be configured to electrically and/or communicatively couple the components to each other and/or other components of the disease management system. In some examples, a thermistor 4342 (or other temperature sensor) may be configured to measure a temperature of components of the disease management system and/or patient.

Figure 4I:
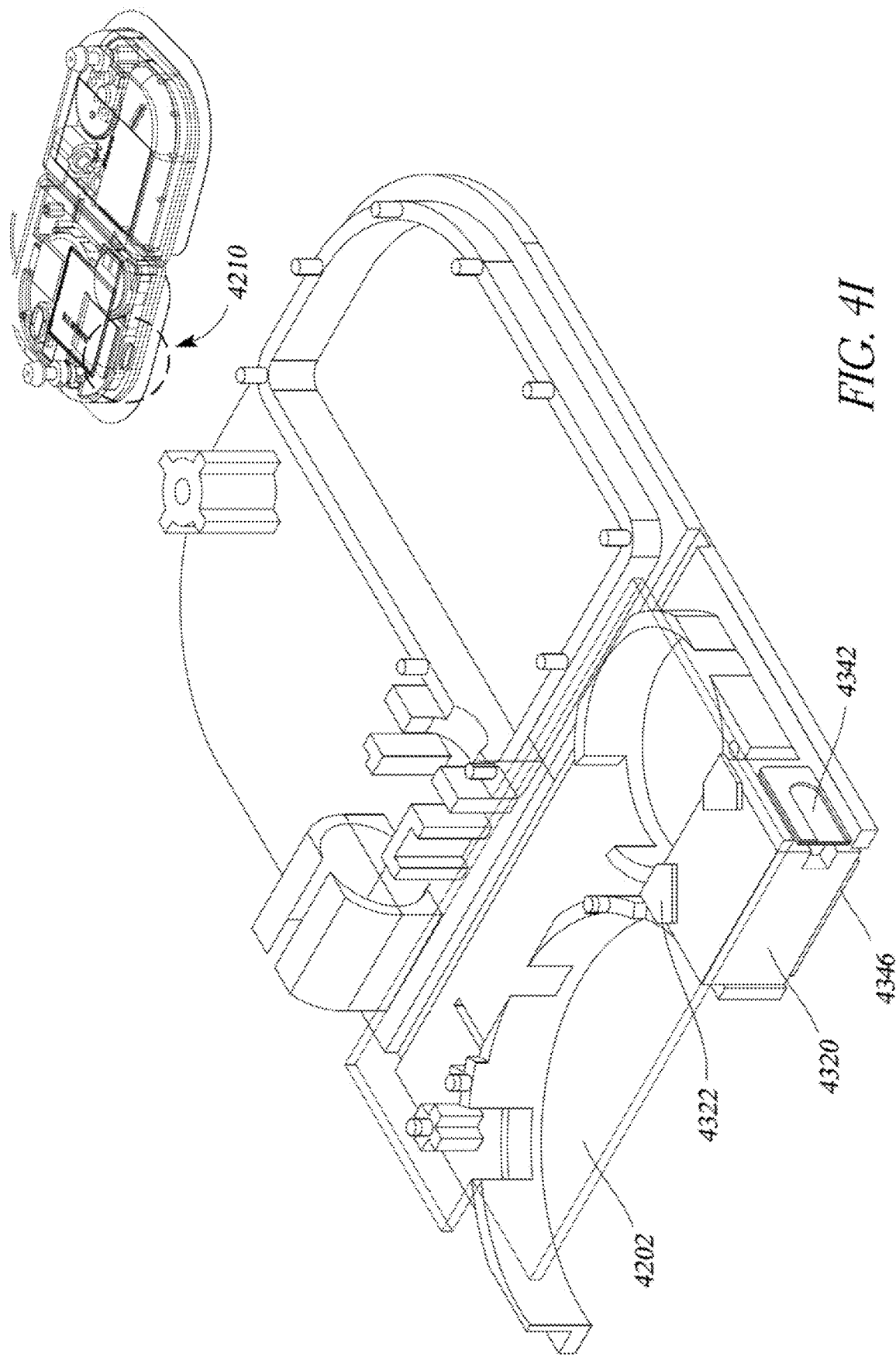
FIG. 4I illustrates an example buzzer mount for an implementation of a disease management system.

FIG. 4I illustrates an example buzzer and mount 4210. In some examples, a buzzer 4320 may be directly coupled to a PCBA 4202. For example, the buzzer 4320 may be soldered (at, for example, one or more soldered points 4322) or otherwise electrically connected to the PCBA 4202. In some examples, the buzzer 4320 may be indirectly connected to the PCBA 4202. In some examples, a buzzer 4320 may include an alarm, speaker, or other noise making device or mechanism. In some examples, the buzzer 4320 may be configured to output a sound at an audible frequency and volume in response to a signal from a controller (such as the PCBA 4202). For example, a buzzer 4320 may receive a signal to output an alarm in response to one or more alarm conditions of the device or patient, such as a hypoglycemic state of a patient, a malfunction of a device, or during certain operations of the device, such as during calibration processes, bolus processes, or for another reason. In some examples, properties of the audible output of the buzzer (such as pitch, frequency, volume), may be modified based on the alarm condition. In some examples, the volume output of the buzzer may be up to and including 88 dB or more. In some examples, the buzzer may be covered by a film or membrane 4342 configured to prevent excessive environmental damage to the buzzer 4320. For example, a membrane 4342 may include a material configured to protect the buzzer 4320 from water damage or penetration for a sustained period of time (for example, 30 minutes) and up to a maximum pressure (for example, 4 meters or 10 meters submersion). In some examples the buzzer 4320 may be coupled to other components of the disease management system using an adhesive 4346, such as a double sided tape. Advantageously, double sided tape can be good for e-beam that the device may be exposed to during manufacture.

FIG. 4J illustrates an example vibration motor and mount 4226 of a disease management system. In some examples, a vibration motor 4326 may include a motor configured to vibrate at a determined frequency. In some examples, the vibration motor 4326 and/or components of the glucose sensor system may be configured to transfer vibration to the skin of the patient. In some examples, the vibration motor 4326 may be configured to output a sound at an audible frequency and volume in response to a signal from a controller (such as the PCBA 4202). For example, a vibration motor 4326 may receive a signal to output an alarm in response to one or more alarm conditions of the device or patient, such as a hypoglycemic state of a patient, a malfunction of a device, or during certain operations of the device, such as during calibration processes, bolus processes, or for another reason. In some examples, properties of the audible output of the vibration motor 4326 (such as vibration frequency), may be modified based on the alarm condition. The vibration motor 4326 may be soldered (at, for example, one or more soldered points 4328) or otherwise electrically connected to the PCBA 4202. In some examples, the vibration motor 4326 may be indirectly connected to the PCBA 4202. In some examples the vibration motor 4326 may be coupled to other components of the disease management system using an adhesive 4324, such as a double sided tape. Advantageously, double sided tape can be good for e-beam that the device may be exposed to during manufacture.

Figure 4K:
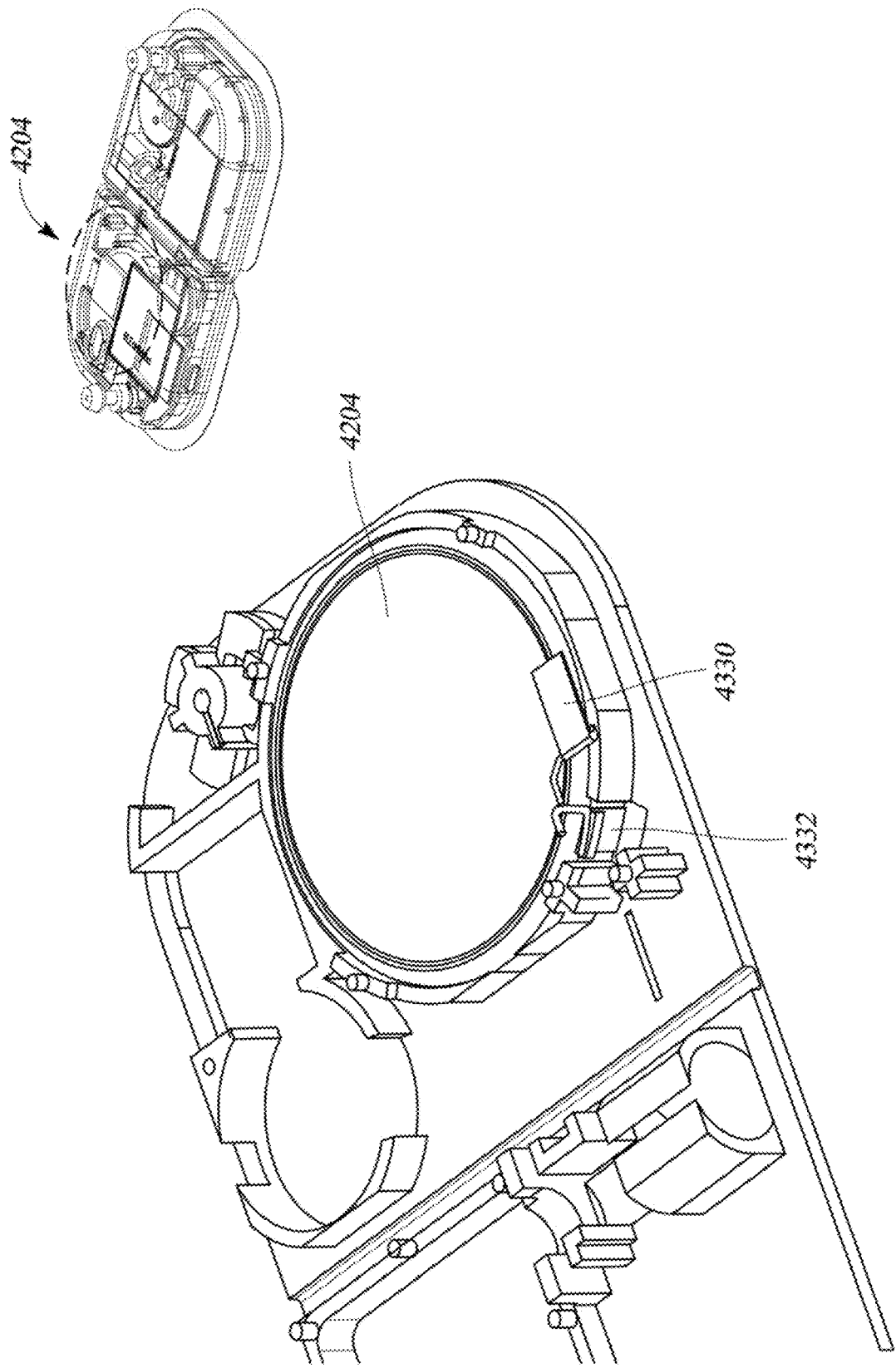
FIG. 4K illustrates an example battery mount for an implementation of a disease management system.

FIG. 4K illustrates an example battery 4204 and mount for a disease management system. In some examples, a battery 4204 may be electrically connected to other components of the disease management system through, for example, one or more electrical connections 4330, 4332. In some examples, the battery 4204 may have a thermal or laser weld connection 4330. In some examples, the connection may additionally include conductive adhesive to help improve reliability of an electrical connection. In some examples, a battery 4204 may have a side connection 4332. Advantageously, the side connection may facilitate electrical connection without adding to the overall height or thickness of the disease management system.

Figure 4L:
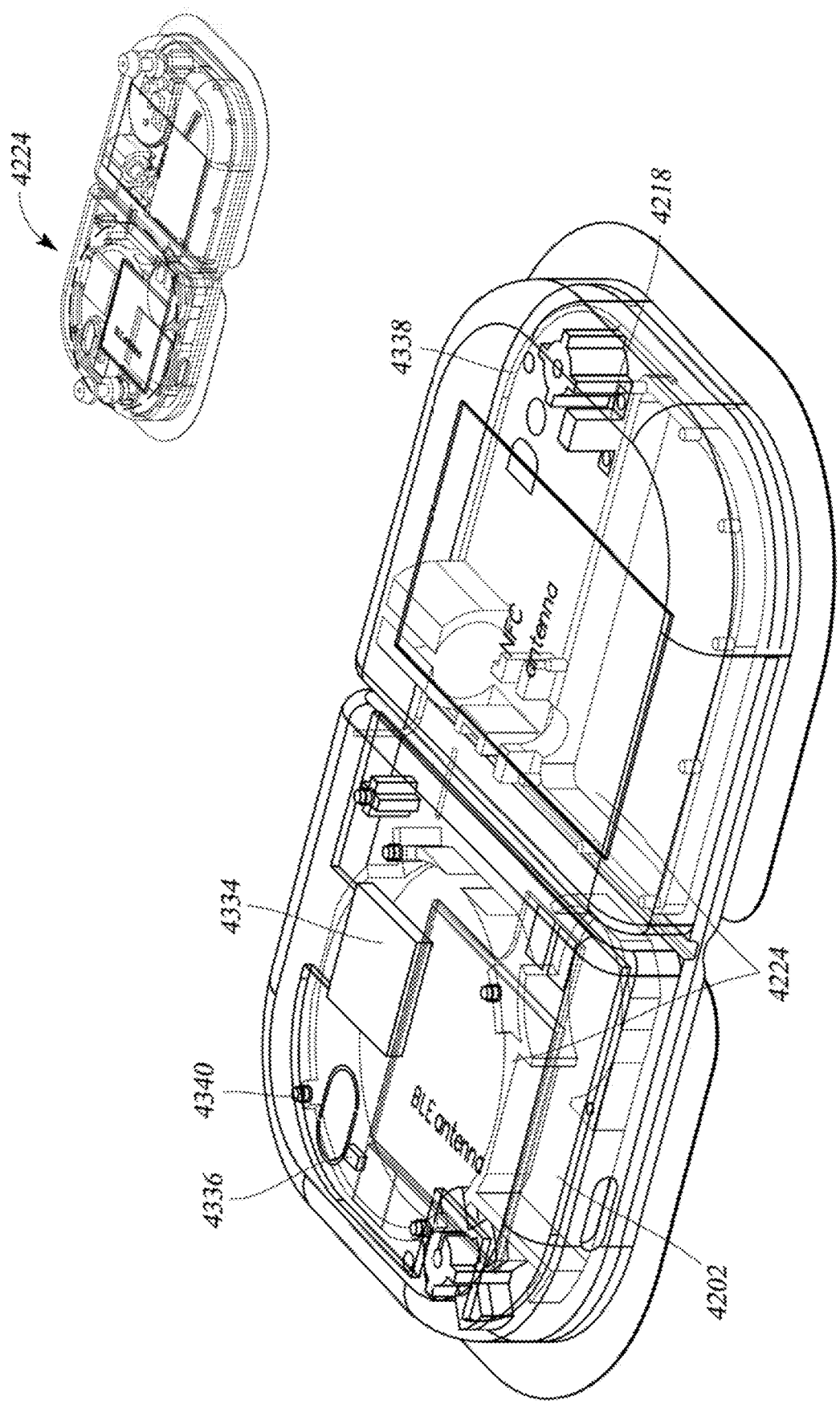
FIG. 4L illustrates an example PCBA mount for an implementation of a disease management system.

FIG. 4L illustrates an example PCBA 4202 and antenna mount 4224. In some examples, a PCBA mount can include one or more support and/or alignment features 4340 to help affix the PCBA within the disease management system. In some examples, an LED 4336 associated with, for example, a connection status indicator on the disease management device, can be configured to be on top of the PCBA. This orientation may, for example, simplify assembly and configuration of the device. In some examples, an LED may have an associated light piper 4218 in order to bring light to a status indicator, such as a patient status indicator. In some examples, an SOC (or system on a chip) 4334 can be coupled to (or mounted to) the PCBA 4202. In some examples, one or more antennas 4224 may be electrically connected to the PCBA 4202. For example, a Bluetooth antenna and NFC antenna may be electrically connected to the PCBA. In some examples, wires 4338 may be configured to connect electrical components from one side of the device to the other.

FIG. 4M illustrates an example adhesive plate mounting mechanism 4442. In some examples, a disease management system may include an adhesive plate 4214. The adhesive plate may be configured to lock, mount to, or mate with a bottom housing of the disease management system and/or a metal plate 4440 using an adhesive plate mounting mechanism 4442. In some examples, a disease management system may include a latch 4444 to lock or secure the disease management system to the adhesive plate 4214. In some examples, the mounting mechanism 4442 may include a sponge 4448 or other moldable or flexible material. The sponge 4448 or other material may advantageously help accommodate hard parts tolerance and make sure that the latch is not too loose. In some examples, the mechanism 4442 may include a plug 4446 to help seal a hole or other open area of the locking mechanism that may be present as a result of manufacturing methods.

Figure 4N:
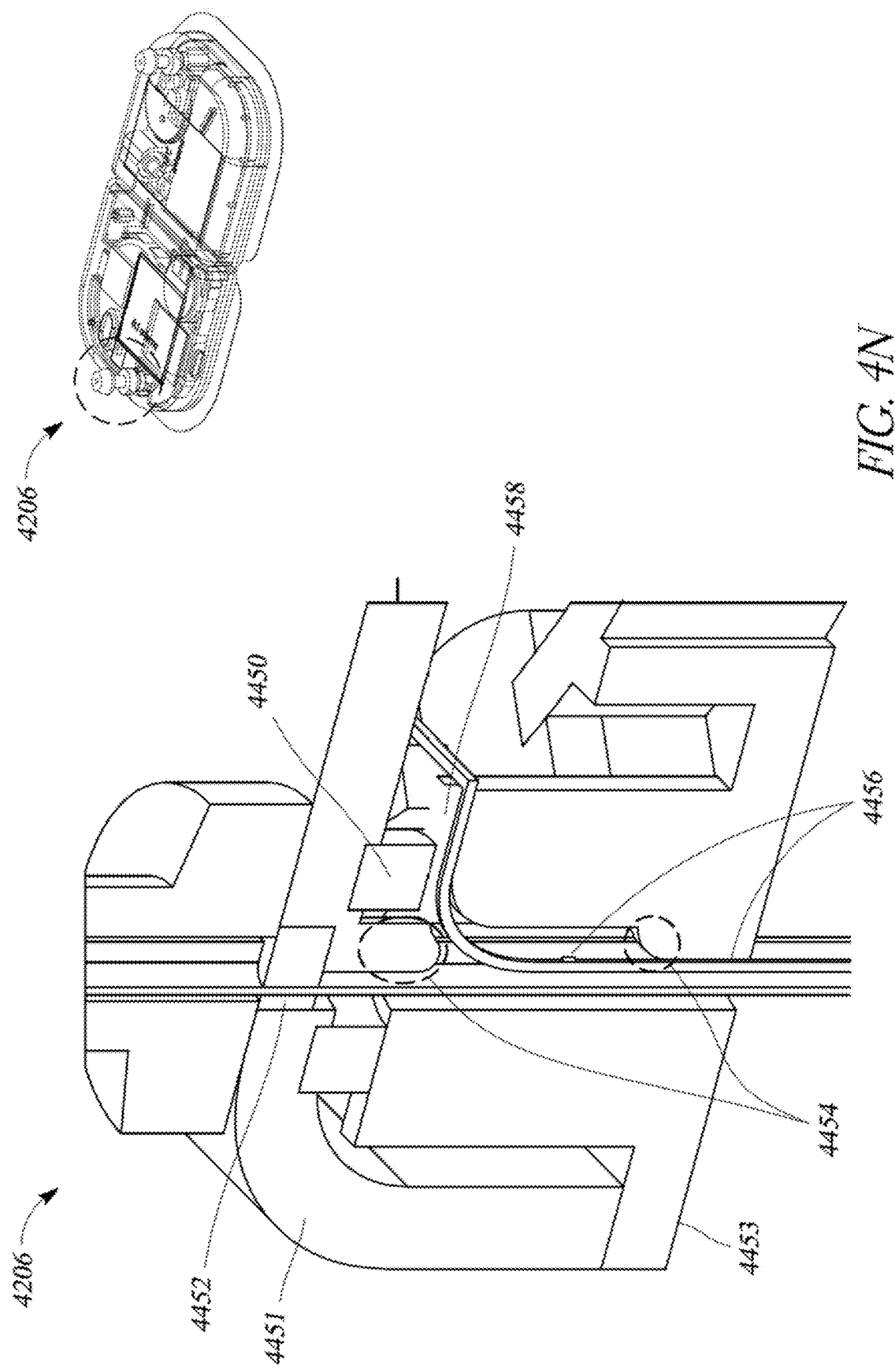
FIG. 4N illustrates an example analyte sensor seal and mount for an implementation of a disease management system.

FIG. 4N illustrates an example analyte sensor and mount 4206 of a disease management system. In some examples, an analyte sensor mount 4206 can include a gasket 4550. The gasket can be configured to seal the sensor from external fluids that may otherwise flow into the disease management system. In some examples, the gasket may be sandwiched or compressed by a top housing 4451 and a bottom housing 4453. In some examples a compression force provided between the top housing 4451 and the bottom housing 4453 may help provide the seal. In some examples, other areas 4458 of the sensor mount, such as in and around the sensor or needle itself may be sealed using, for example, an adhesive or epoxy. In some examples, a pass through section of the mount may include a plastic (for example, TPU) overmold 4452. The overmold may be configured to seal a hole that may be left in the mount after the sensor needle is removed.

In some examples, a mount 4206 may include features to position the analyte sensor and needle properly. For example, a mount 4206 may include portions 4454 configured to position the sensor properly so as to avoid upward shift of the sensor before, during, or after insertion. In some examples, one or more of a needle and sensor can include dimples 4456 or other positioning features to help prevent a sensor from touching the needle and being damages when the needle is withdrawn.

Figure 5A:
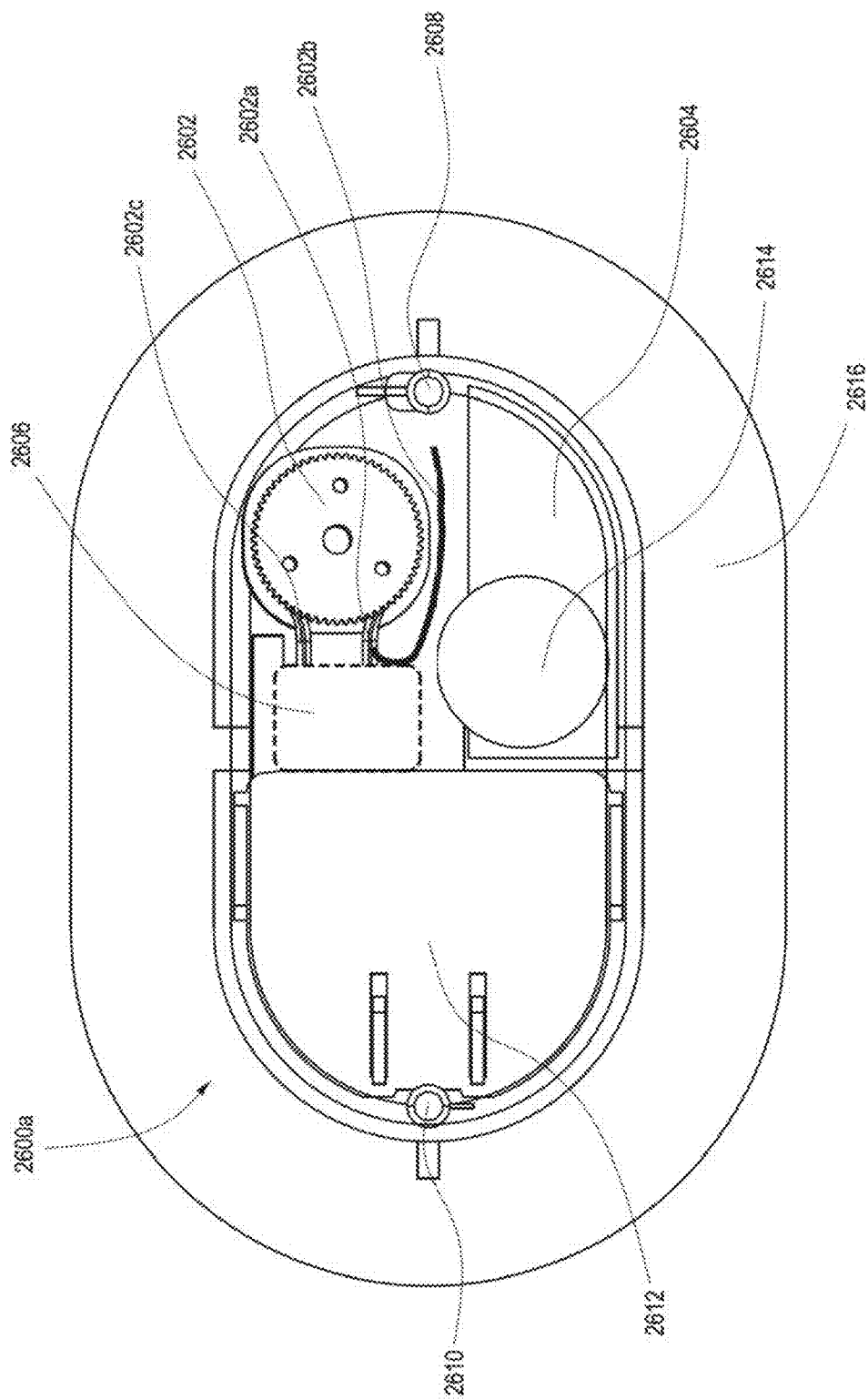
FIG. 5A illustrates an exemplary implementation of a disease management system.

FIG. 5A illustrates an exemplary implementation of aspects of a disease management system 2600A. The disease management system 2600A includes an insulin pump 2602. While as illustrated the insulin pump 2602 is a peristaltic pump such as the peristaltic pump 300 described in connection with FIGS. 4A and 4B, other pumps may be implemented. The insulin pump 2602 includes an inlet 2602C and an outlet 2602A. The outlet 2602A may be connected to a cannula through a pipe 2602B. The cannula may be implanted into the patient to provide insulin to the patient. A needle holder 2608 may be connected to a needle which may be used to implant the cannula into the patient. Further, the inlet 2602C may be connected to an actuator and/or a connector which may be placed at a position 2606 between the insulin pump 2602 and an insulin source such as an insulin bladder filled with insulin. The insulin source may be placed below a spring 2612 such as a disc spring capable of applying pressure to the insulin source in order to force the insulin out of the insulin source. In some implementations, the spring 2612 may be excluded when the insulin pump 2602 is capable of pumping out the insulin without aid from the spring 2612.

The disease management system 2600A may further include a battery 2614 capable of powering components such as a circuit board 2604 and the insulin pump 2602. The circuit board 2604 may be in communication with the insulin pump 2602 and/or the actuator in order to power and control these components. The disease management system 2600A may further include a glucose probe. The glucose probe may be connected to a glucose sensor which may reside on the circuit board 2604. A needle holder 2610 may be connected to a needle which may be used to implant the glucose probe into the patient. The disease management system 2600A mounted on a patient through an adhesive pad 2616.

Figures 1, 5B:
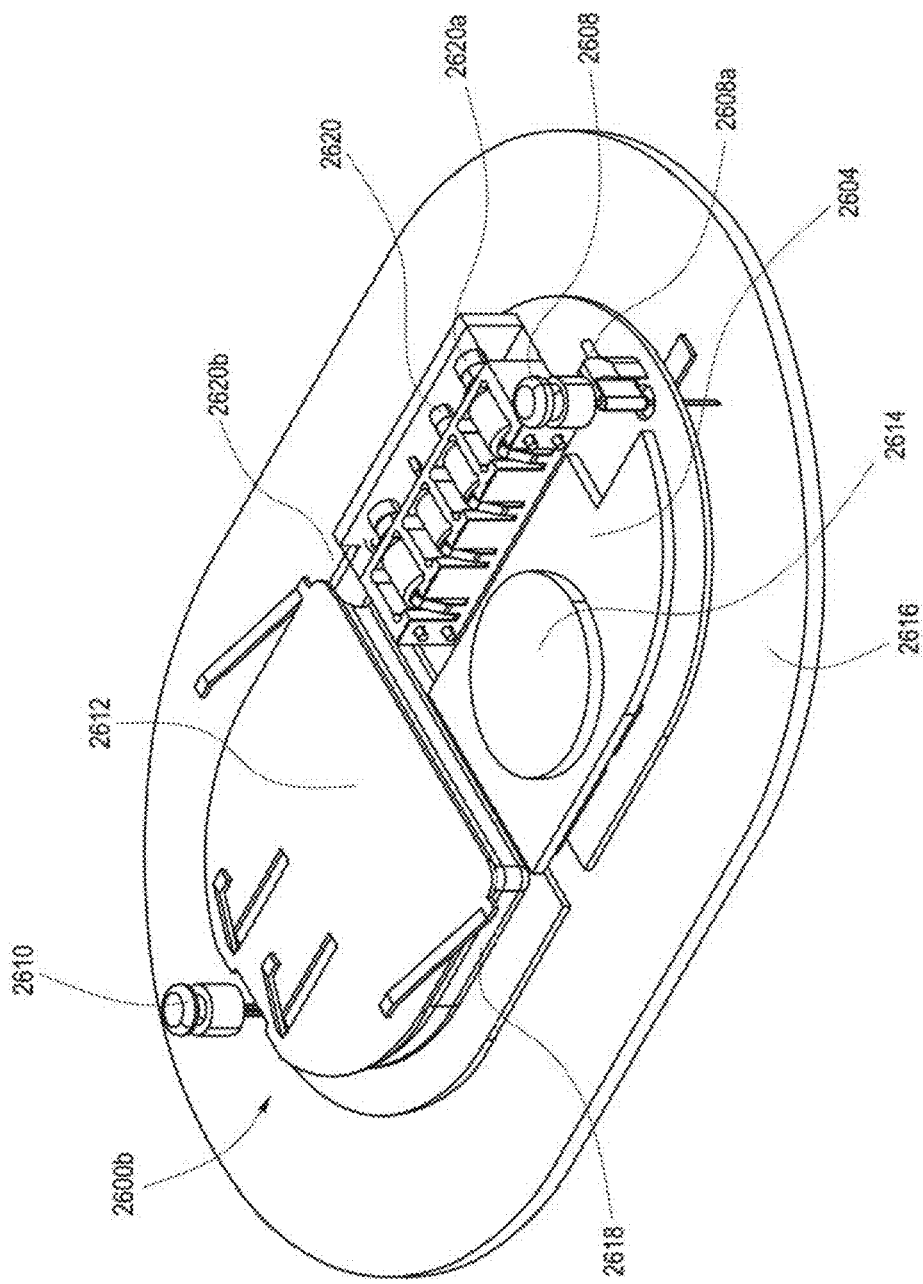
Figures 2, 5B:
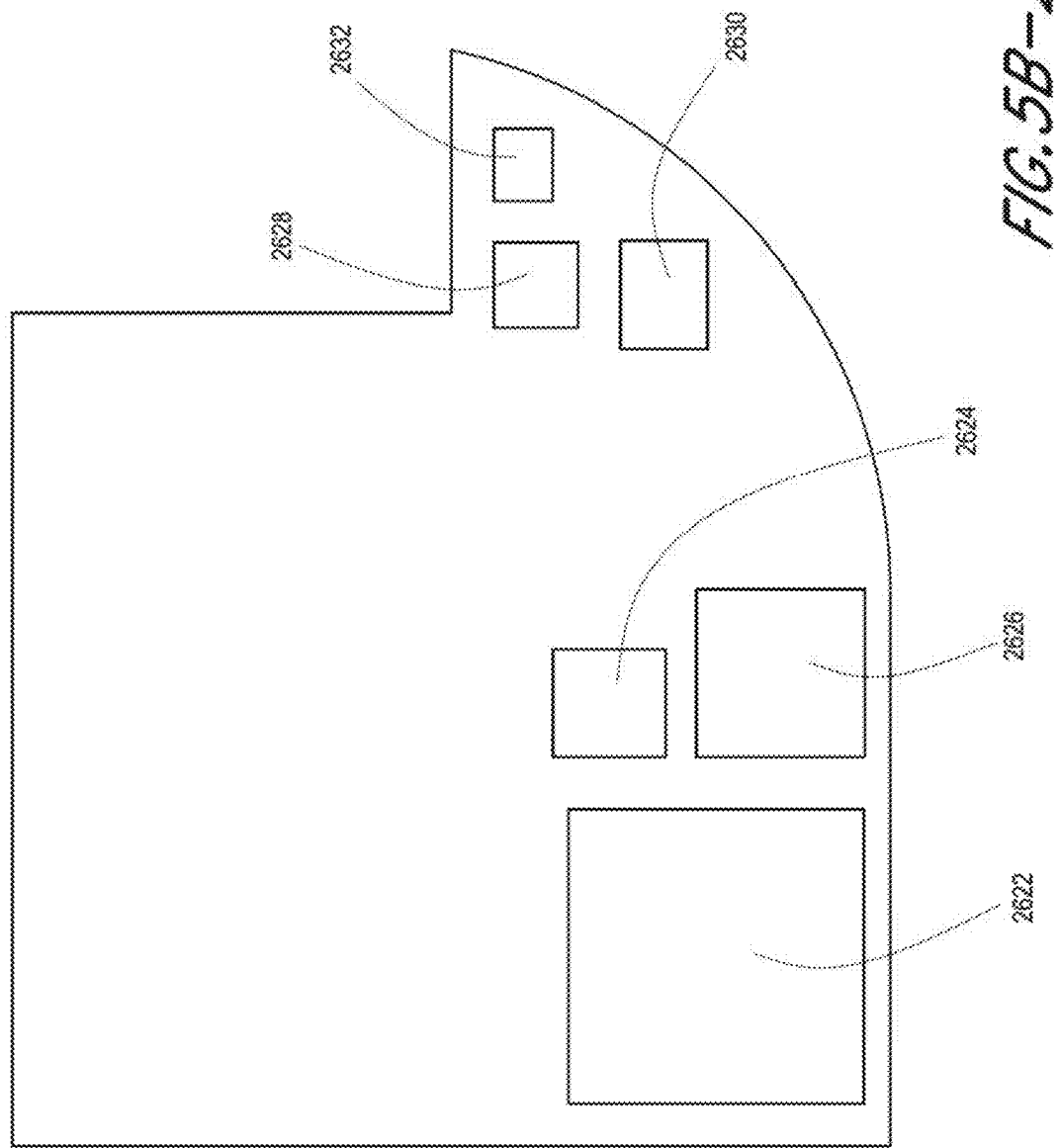
Figures 3, 5B:
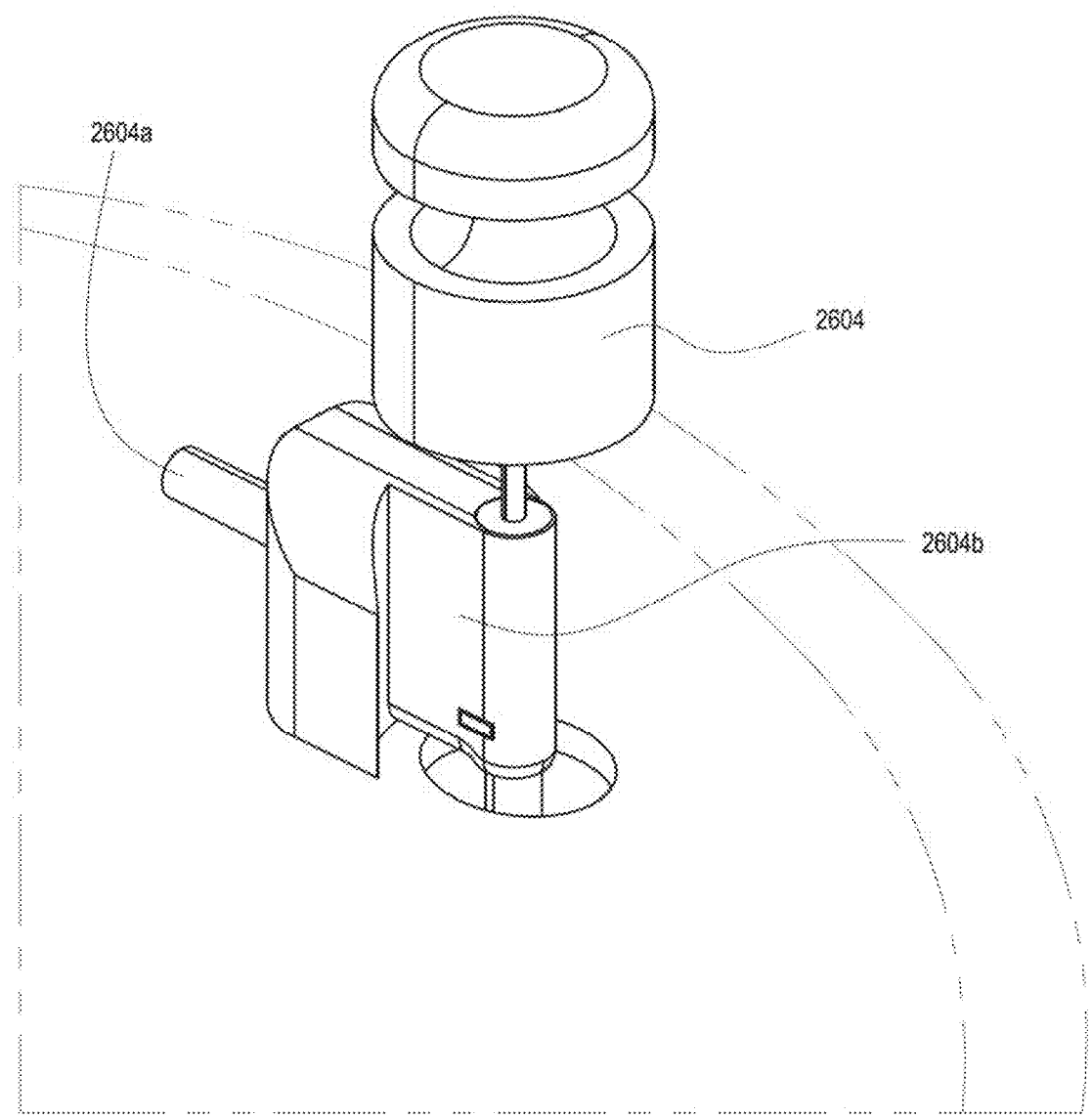

FIG. 5B-1 is a perspective schematic view of an exemplary implementation of a disease management system 2600B. The disease management system 2600B shares many components with the disease management system 2600A described in connection with FIG. 5A. The description of these components will not be repeated. The disease management system 2600B includes an insulin pump 2620 which includes an inlet 2620B and an outlet 2620A. The inlet 2620B is connected to an insulin source 2618 such as an insulin bladder. As illustrated, the insulin pump 2620 is a valve style insulin pump 930 as described in connection with FIGS. 9E through 9H however other insulin pumps have been implemented. The outlet 2620A may be connected to a cannula 2608A which may be implanted into a patient. A spring 2612 such as a disc spring may apply pressure to the insulin source 2618 in order to force insulin out of the insulin source into the insulin pump 2620.

FIG. 5B-2 is a schematic view of an exemplary implementation of a circuit board 2604 which may be used in the disease management system 2600A as described in connection with FIG. 5A or the disease management system 2600B as described in connection with FIG. 5B-1. The circuit board 2604 may include a computing component 2622 such as a system on chip. A system on chip may include both a memory and a processor which may be configured to control the other components on the circuit board 2604. The computing component 2622 may be connected directly or indirectly to a communication module 2624, a pump driver 2626, an accelerometer 2628, a pulse oximetry sensor 2630, and/or a NFC module 2632. The communication module 2624 may be a Bluetooth chip or Bluetooth low energy chip. The pump driver 2626 may be directly or indirectly connected with the insulin pump in order to drive the insulin pump. The pulse oximetry sensor 2630 may be connected to a probe such as a photo sensor which may be used to sense oxygen saturation. The NFC module 2632 may be an NFC tag 1303A as described in connection with FIGS. 36A and 36B.

FIG. 5B-3 illustrates a perspective view of an implementation of an insulin cannula 2604A as may be implemented within the disease management system 2600A as described in connection with FIG. 5A and the disease management system 2600B as described in connection with FIG. 5B-1. As illustrated, the insulin cannula 2608A may be connected with a photo sensor 2604B. The photo sensor 2604B may be used to test and confirm various aspects such as sense for air bubbles within the insulin in the insulin cannula 2608A, the oxygen saturation of the patient, and/or the pulse rate of the patient.

Figure 6B:
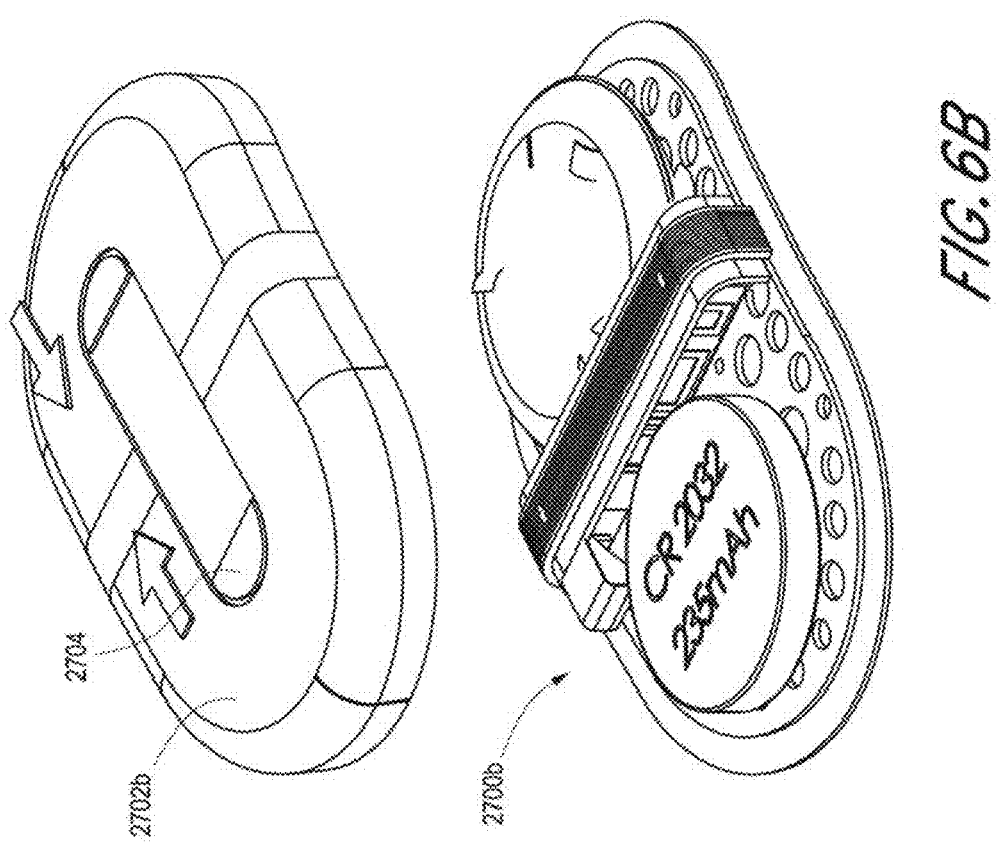
FIG. 6B illustrates an exemplary implementation of a disease management system.
Figure 6A:
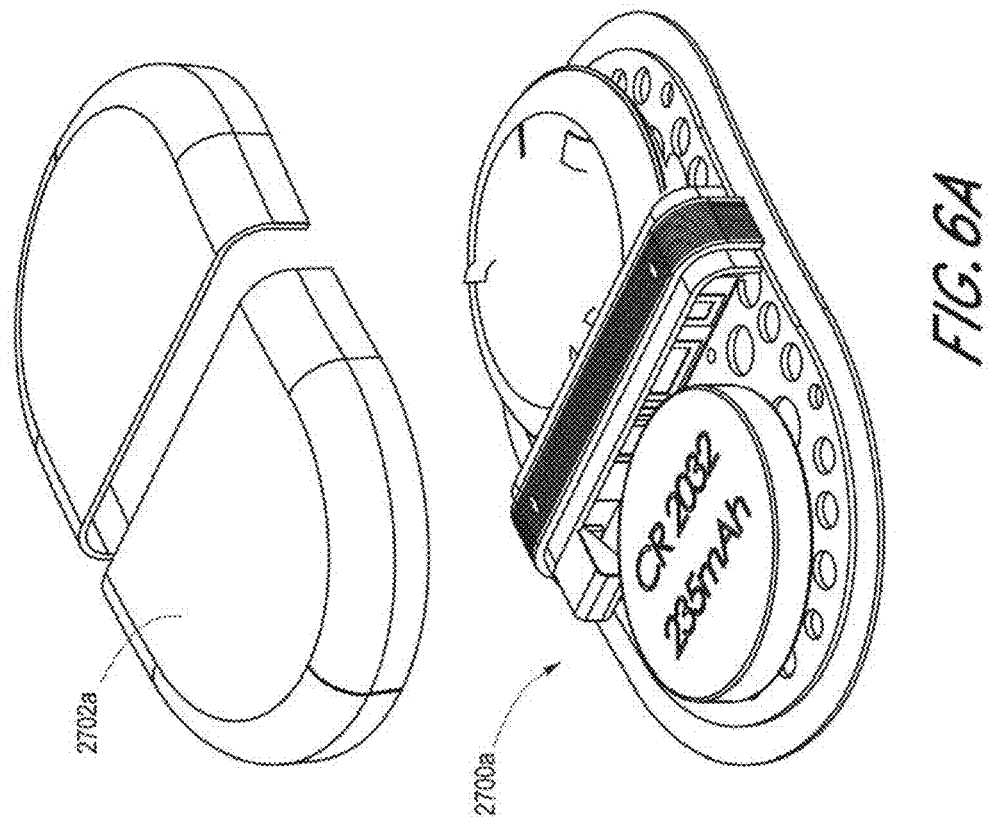
FIG. 6A illustrates an exemplary implementation of a disease management system.
Figure 35A:
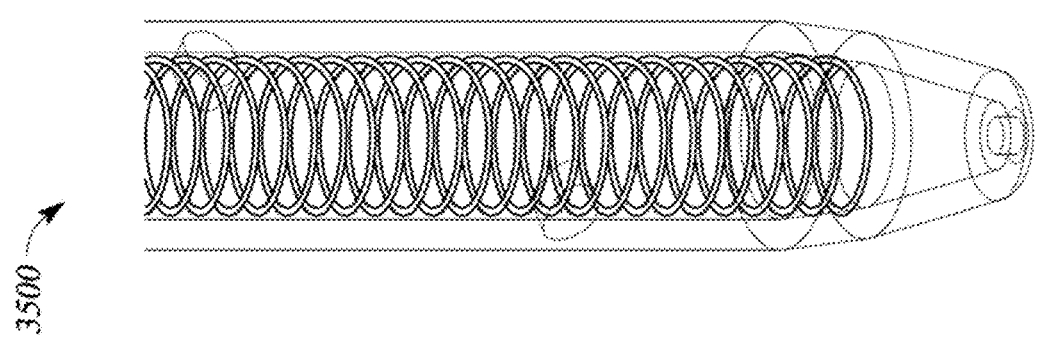
FIGS. 35A-35D illustrate different configurations of non-kinking cannulas.
Figure 35B:
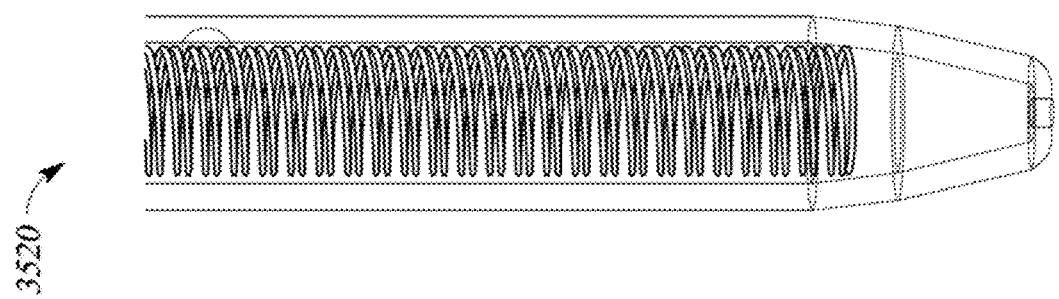
Figure 35C:
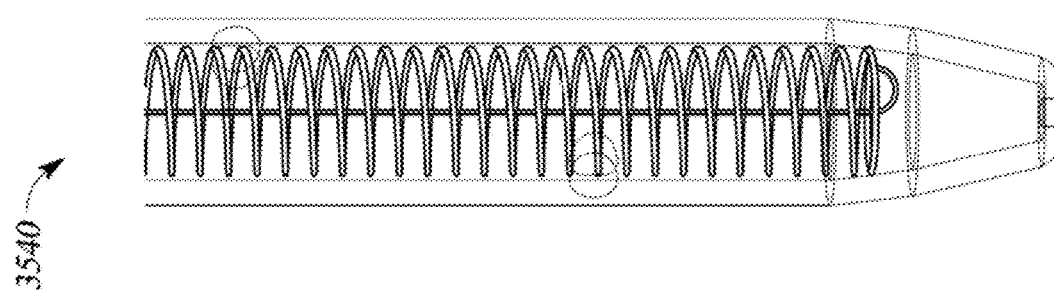

FIG. 6A illustrates an implementation of a disease management system 2700A. The disease management system 2700A may include the components described in connection with other disease management systems and disease management systems described above such as the disease management system 2600A described in connection with FIG. 5A or the disease management system 2600B described in connection with FIG. 5B-1. The disease management system 2700A may include a case 2702 without buttons which is capable of protecting the components within the disease management system 2700A. The disease management system 2700A is controlled through the programming and administers dosages of insulin based on a schedule determined through the disease management system 2700A. The disease management system 2700A may be trigger to administer a manual dosage of insulin to the patient through communication with an NFC device as described in connection with FIGS. 36B and 36C or a user device as described in connection with FIGS. 35A-35C.

FIG. 6B illustrates an implementation of a disease management system 2700B. The disease management system 2700B may include components described in connection with other disease management systems and disease management systems described above such as the disease management system 2600A described in connection with FIG. 5A or the disease management system 2600B described in connection with FIG. 5B-1. The disease management system 2700B includes a case 2702B which includes a mechanism 2704 to trigger the disease management system 2700B to administer a manual dosage of insulin to the patient. The mechanism 2704 may be a button, switch, slide toggle, or touch interface. The touch interface may be resistive or capacitive. The mechanism 2704 may be engaged through pressing or tapping. The mechanism 2704 may also require a complex operation in order to trigger the manual dosage such as a two finger pinch or combination press down and slide in order to prevent accidental engagement. Similar to the disease management system 2700A of FIG. 6A, the disease management system 2700B may be triggered to manually administer a dosage to the patient through an NFC device and a user device.

In some implementations, the mechanism 2704 may only trigger the disease management system 2700B to communicate with a NFC device or a user device to trigger the disease management system 2700B to administer a manual dosage of insulin to the patient. Thus, the mechanism 2704 may only be a safety mechanism to keep unwanted dosages from reaching the patient. In some implementations, the case 2702B described in connection with FIG. 27B and the case 2702A described in connection with FIG. 6A may be removable and swappable such that a disease management system equipped with the case 2702A described in connection with FIG. 6A may be replaced with the case 2702B described in connection with FIG. 6B.

Figure 7B:
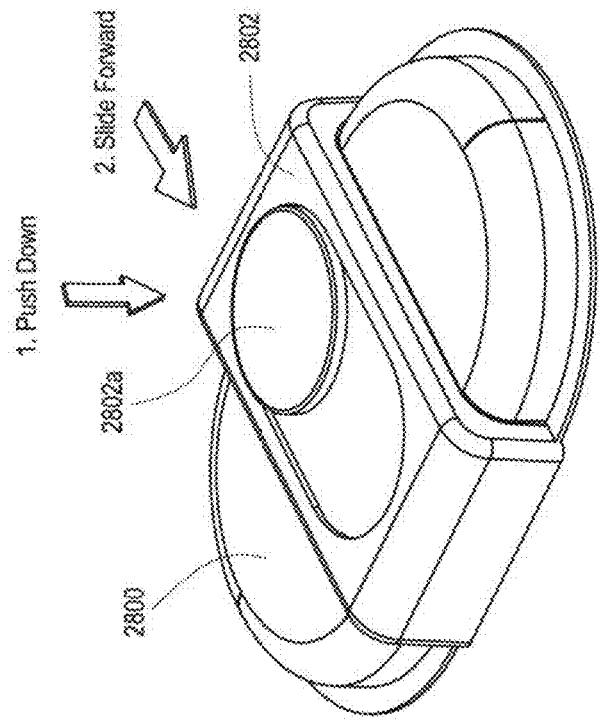
FIGS. 7A and 7B illustrate an exemplary implementation of a disease management system including an additional manual dosage trigger component.
Figure 7A:
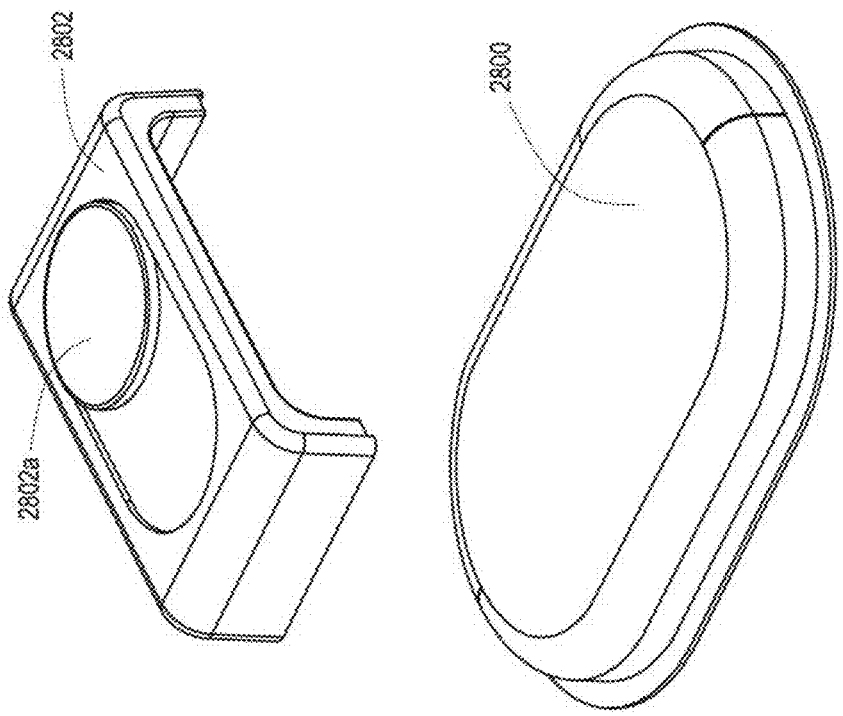

FIGS. 7A and 7B illustrate an implementation of a disease management system 2800 which includes an additional manual dosage trigger component 2802. The disease management system 2800 may be any of the disease management systems or disease management systems described above such as the disease management system 2700A described in connection with FIG. 27A. The manual dosage trigger component 2802 may manually trigger the disease management system 2700A to administer a dosage of insulin to a patient. FIG. 7A illustrates the additional manual dosage trigger component 2802 before installation on the disease management system 2800. FIG. 7B illustrates the manual dosage trigger component 2802 after installation on the disease management system 2800. After installation, the manual dosage trigger component 2802 may communicate with the disease management system 2800 to manual trigger the disease management system 2800 to administer a dosage of insulin to the patient. The manual dosage trigger component 2802 may be installed and removed from the disease management system 2800. The manual dosage trigger component 2802 includes a mechanism 2802A which may be applied by a user to activate the manual dosage trigger component 2802. As illustrated, the mechanism 2802A uses multiple actions such as pushing a button and then sliding the button forward in order to activate the mechanism 2802A.

D. EXAMPLE PUMP IMPLEMENTATION OF A DISEASE MANAGEMENT SYSTEM

Figure 7C:
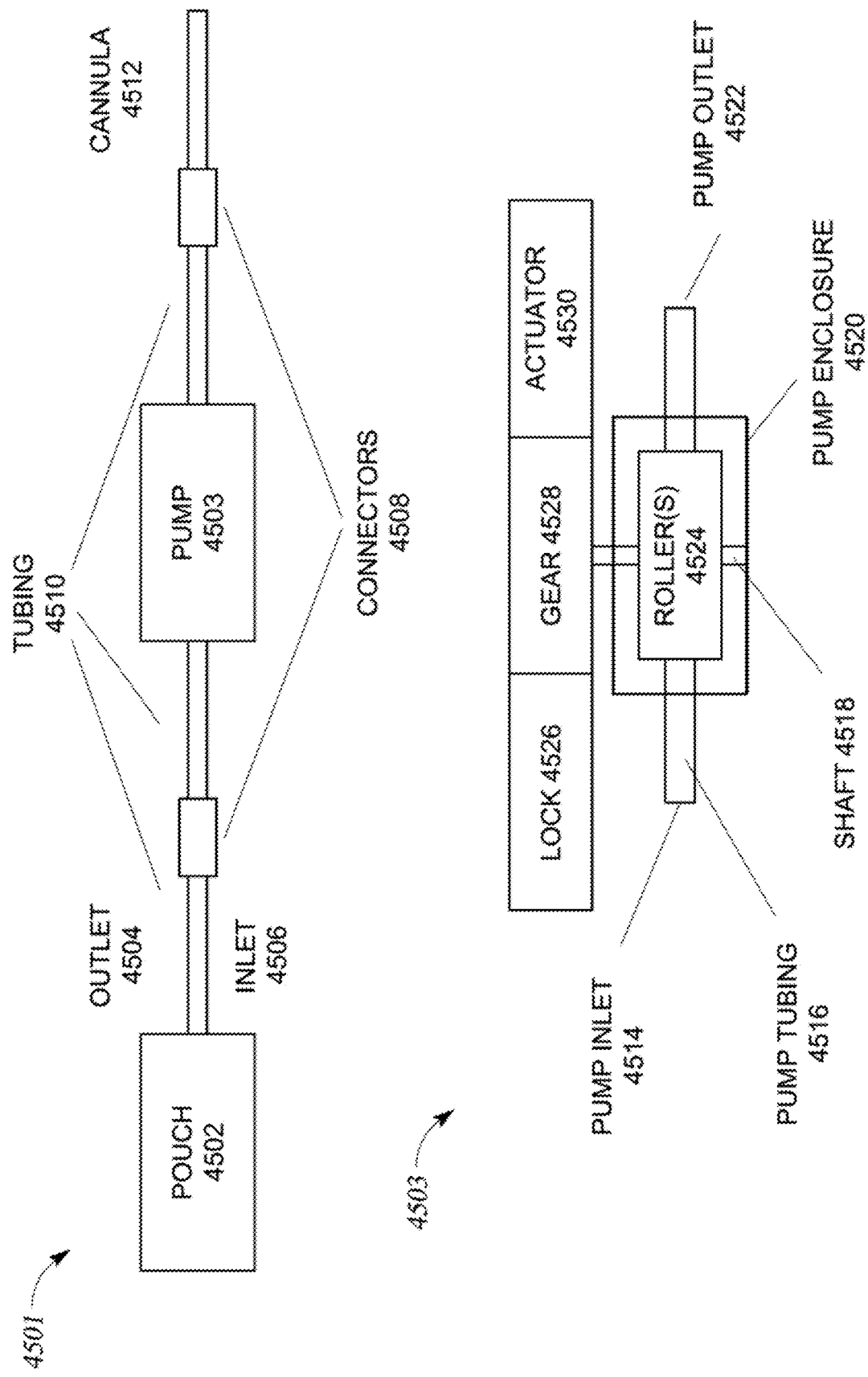
FIG. 7C illustrates an example configuration of a peristaltic pump.

Described herein are a plurality of different types of pumps and fluidic paths of a medication, such as insulin, from a medication reservoir (such as a pouch) to a patient. FIG. 7C illustrates an example fluidic path utilizing a peristaltic pump. However, other pump systems are also possible, such as described herein. Pump systems can include, but are not limited to a peristaltic pump, valve pump, nitinol or muscle wire pump, piston pump, other pump, or some combination thereof.

FIG. 7C illustrates an example fluidic path 4501 of medication from a pouch 4502 to a cannula 4512 that may be inserted or implanted into a patient. As shown in FIG. 7C, a medication may be stored in a pouch 4502. The pouch 4502 may be manufactured with thin film plastic material. An inlet 4506 and outlet 4504 tube may be attached and sealed to the pouch 4502. The inlet tube 4506 may be configured to allow medication to fill in the pouch. After filling, an inlet tube 4506 may be sealed. Outlet tube 4504 may be connected or otherwise come into contact with a pump 4503 through tubing 4510. In some examples, one or more connections 4508 may connect tubing 4510 to an outlet tube 4504 between the pouch 4502 and the pump 4503. In some examples, one or more connections 4508 may connect tubing 4510 to a cannula 4512 between the pump 4503 and cannula 4512, which may be inserted into the patient.

A pouch material may be made of a material configured to contain a medication for a prolonged period. In some examples, a pouch material may be a silicone material (including platinum cure) or Cyclic Olefin Copolymer a special polymer. The pouch material may be soft enough to flatten up when the drug is pumped out and the pouch internal volume is reduced. The pouch material may be strong enough to handle pressure inside the pouch when pressurized. Other materials can be used as that does not degrade the medication contained in the pouch 4502 and the desired mechanical properties (such as the strength and flexibility of the pouch) is met. The tubing 4510, inlet 4506, or outlet 4504 can be made with a material having similar or the same properties as the pouch 4502. For example, the material can be a silicone material (including platinum cure).

One or more types of insulin may be utilized in the pump system(s) described herein. For example, a pump may utilize a fast acting insulin. Fast acting insulin is one that creates glucose concentration changes in less than 20 minutes. It is important that this change happens in less than 20 minutes so that a person with Type 1 diabetes who eats a meal (which can also appear within 20 minutes) can counteract their blood sugar change to food in a timely manner.

The two states of insulin: monomeric and hexameric, are two insulin states generally correspond to fast and slow body response, respectively. Traditionally, insulins used in pumps are of the relative concentration U100 and are fast acting. In some embodiments of the systems and methods described herein, an insulin pump may utilize U200 insulin, reducing storage size by half and allowing for a smaller pump apparatus.

As illustrated in FIGS. 7C, a pump system 4503 can include a ratcheting peristaltic pump. A pump system 4503 can include some combination of one or more locks 4526, gears 4528, actuator(s) 4530 and rollers 4524. In some examples, an actuator 4530 may be coupled to a pump gear 4528. The gear(s) 4528 may be configured to rotate one or more rollers 4524 along a portion of tubing 4516 configured to engage with the pump 4503. A shaft 4518 may be used to transfer power to the rollers 4524. Rollers 4524 may rotate along the tubing 4516 to squeeze medication along the path from a pump inlet 4514 towards a pump outlet 4522 in the tubing 4516. In some examples, rollers 4524 may be within a pump enclosure 4520. The lock 4526 can allow the gear 4528 to rotate forward with minimal interference but will induce high blocking force to prevent reverse operation.

Figure 7D:
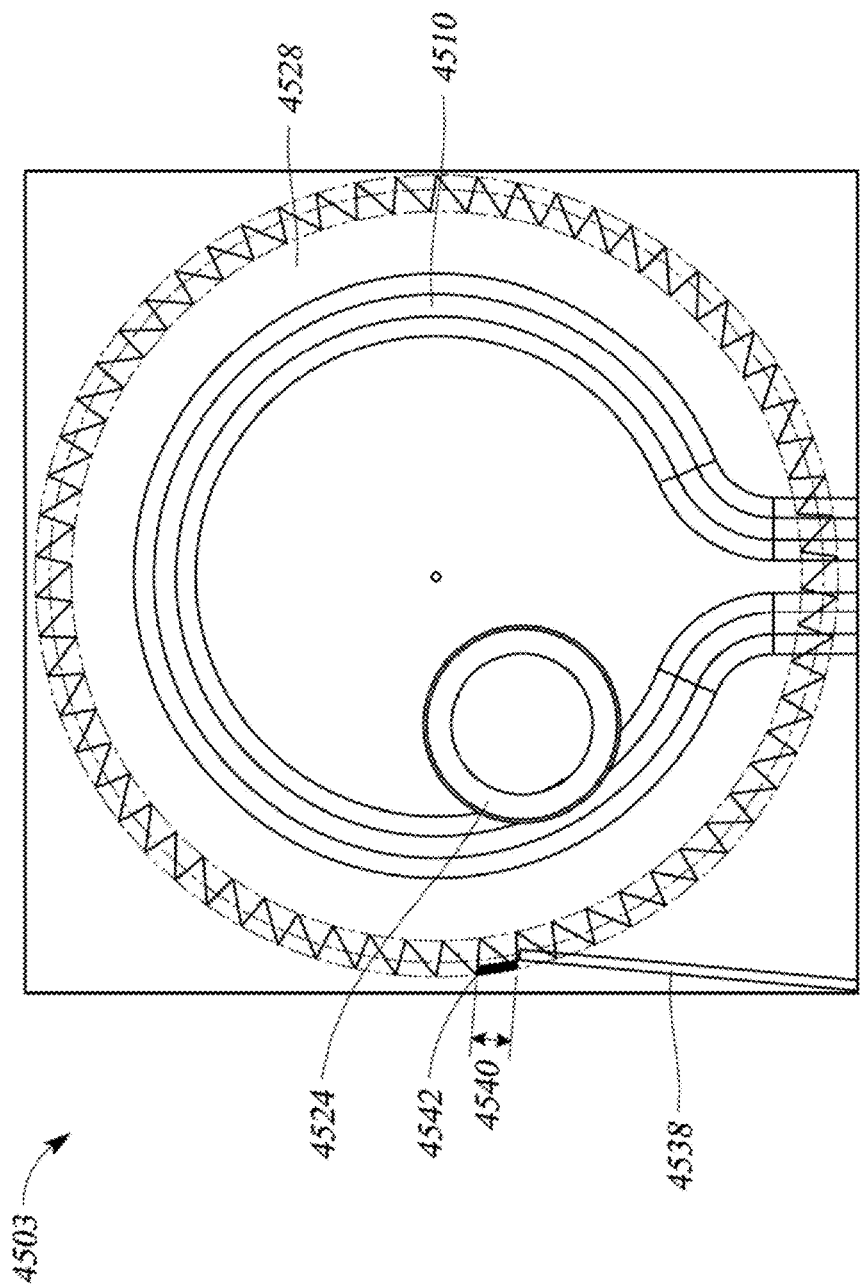
FIG. 7D illustrates an example peristaltic pump head, such as illustrated in FIG. 7C.

FIG. 7D illustrates a first example configuration of a peristaltic pump, such as described with reference to FIG.

7C. As illustrated in FIG. 7D, the actuator 4530 may be configured to engage the gears 4528 of the pump 4503 using, for example, an actuation component 4538 (such as a moment arm) may be configured to contact teeth 4542 of a gear 4532. An actuator stroke 4540 may be based on the configuration of the teeth 4542. In the illustrated configuration, rollers may be oriented vertically in order to squeeze tubing 4516 configured to wrap circumferentially in the pump head with respect to the rollers.

Figure 7E:
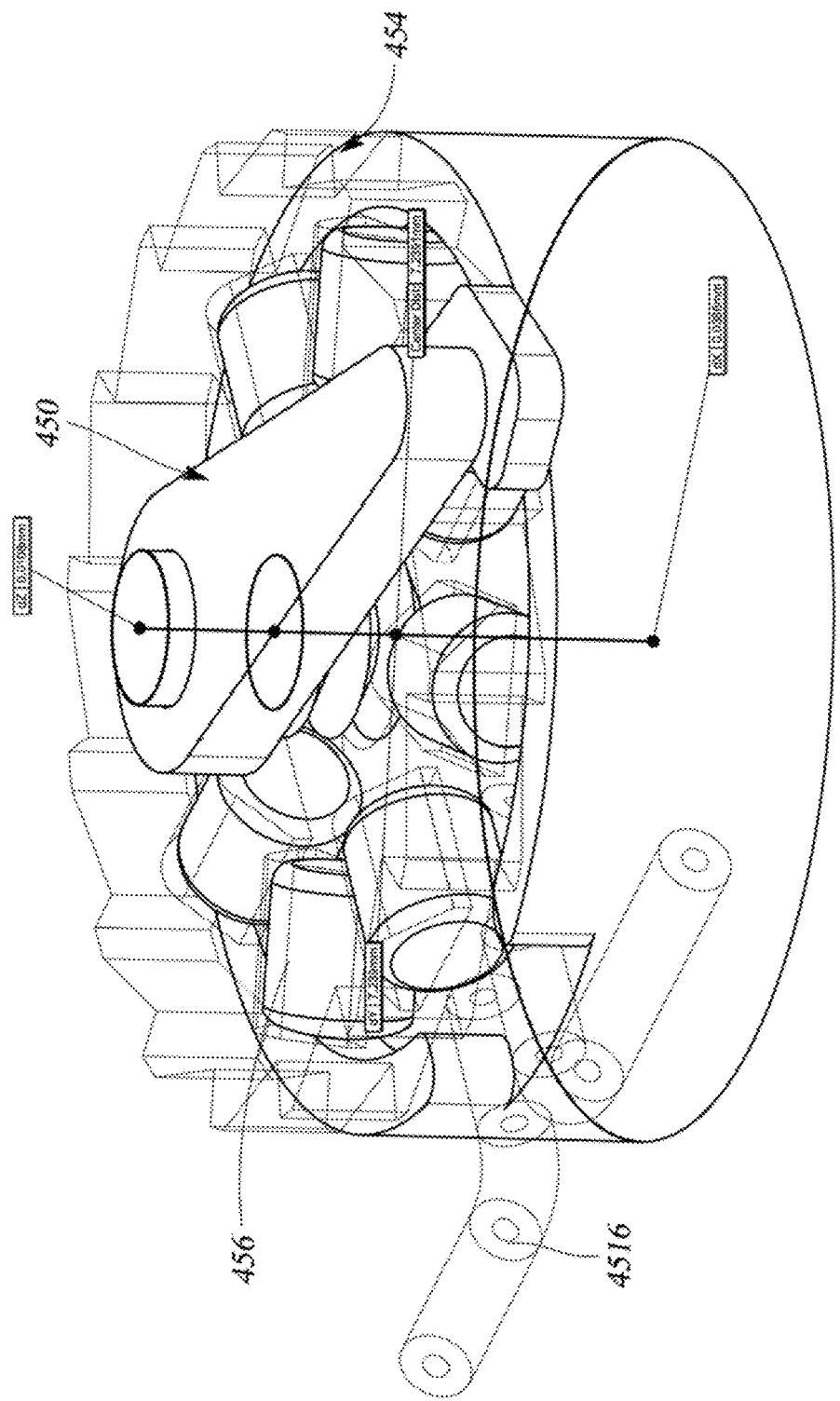
FIG. 7E illustrates another example of a peristaltic pump head.

FIG. 7E illustrates a second example alternative configuration of a peristaltic pump, such as described with reference to FIG. 7C. As illustrated in FIG. 7D, an actuation mechanism may be located in the center of the pump head and engage gear teeth 454 using a movement arm 450. In the illustrated example, rollers may be orientated horizontally in order to squeeze tubing 4516 oriented below the rollers.

The exit 4522 of the pump 4503 can connect to the tubing 4510. The tubing 4510 can extend into the cannula 4512, which may be inserted under patient skin. The pump 4503 may be configured to push the drug into the patient tissue under skin. A bolus mechanism may accordingly be a set of repeated pump actions in a short time that yields a desired bolus size.

The pouch 4502, tubing 4510, and cannula 4512 are part of the fluidic system of the disease management system. Pump tubing 4510 may be internal to the device with the exception of the insulin cannula 4512. While the tubing 4510 will transfer fluid from the pouch 4502 to the cannula 4512, the roller 4524 inside the peristaltic pump will stop and control the un-desire leakage or dosage. The peristaltic pump 4503 is able to lock and hold up designated pressure from the pouch 4502. The pouch 4502 may be designed such that it will not deliver pressure more than the pressure the pump 4503 cannot hold. In addition, the fluidic system may be designed to prevent users to alter the prefilled insulin pouch 4502 by adding or extracting medication from it. In some examples, the disease management system may have no refill capability to ensure high quality closed loop performance. The pump may allow discrete usage by maintaining low audible noise levels.

A pump controller may include one or more hardware processors configured to cause the pump to perform one or more pumping actions. In some examples, a pump controller may include a PCBA of the device or separate electronics. The pump may be connected to and controlled by the controller. In pump configurations with actuator components, the controller may be configured to have a microprocessor and actuator control circuit.

In some examples, the controller may be configured to provide notifications of pump activity to a patient. For examples, the controller may be configured to display a notification using audible, tactile, or visual means using components of the disease management system or associated device. In some examples, the controller may be configured to communicate pump activity or status to a user device or the cloud.

The pump activity or status may be displayed on a device interface through, for example, an associated application. Aspects of a pump may be controlled by the associated or companion mobile device application (for example, on a smart phone and smart watch). For example, settings, controls, and alarms can all be set and managed in this interface. Additionally or alternatively, the pump can have a mechanical mechanism for dosing of a predetermined bolus insulin amount. The mechanical interface can have a two-step interface to reduce chance of accidental dosing. In some examples, the pump may have visual feedback of system status and alerts. In some examples, the pump may have a haptic feedback motor to communicate alarm events to the user as well as assist with device replacement process.

Figure 7F:
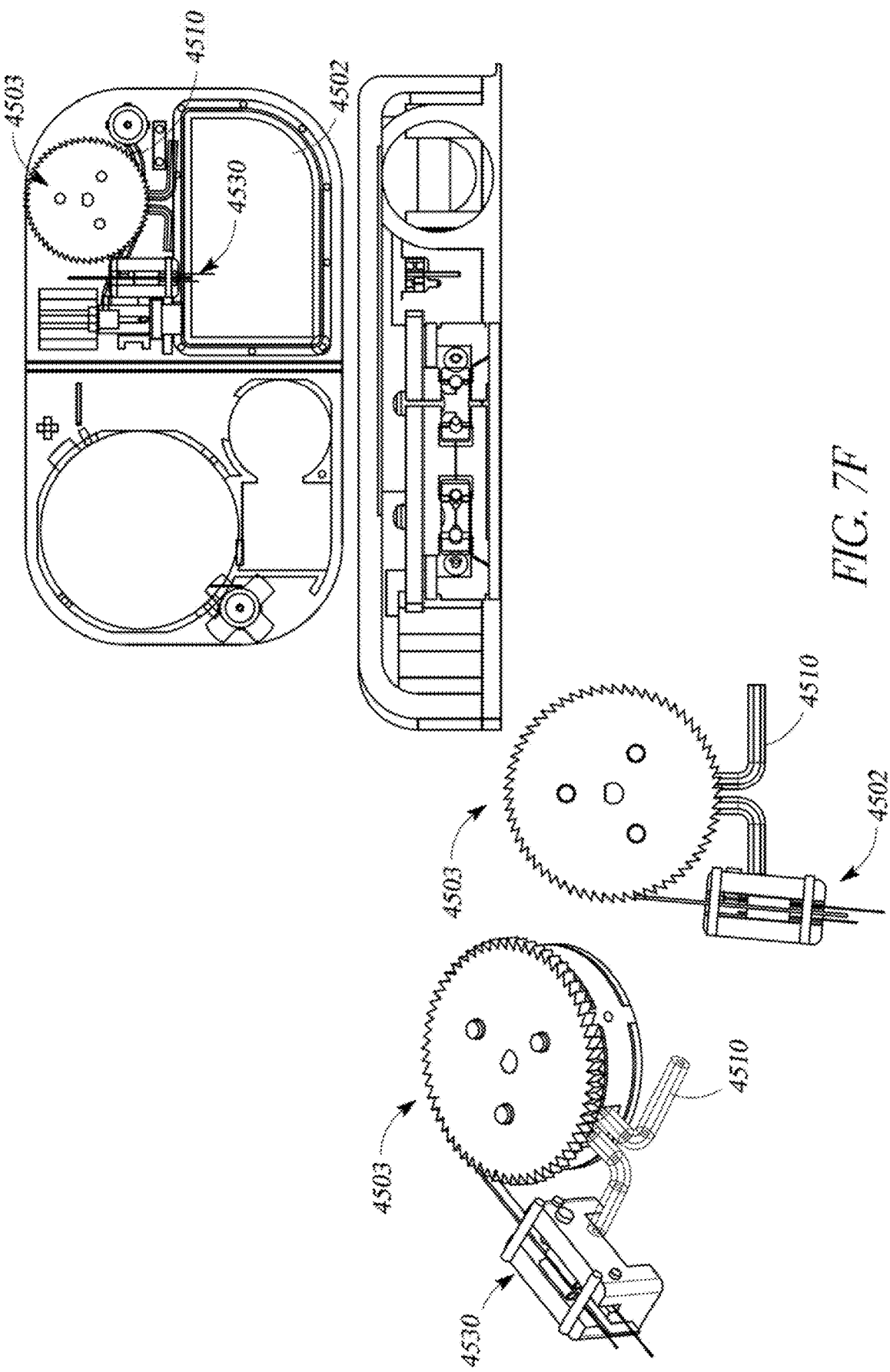
FIG. 7F illustrates an example pump head configuration.

FIG. 7F illustrate example views of a first configuration of an example peristaltic pump 4503 that may be used for pumping medication, such as insulin, from a medication pouch to a cannula. As illustrated in FIG. 7F, an actuator 4350 may be configured to mechanically actuate a pump head 4503 so that medication is transmitted through tubing 4510. In some examples, the fluidic system of disease management system may be on a separate side of the disease management system than an analyte sensor and other electronic components, such a buzzer and haptic motor.

1. Example Peristaltic Pump System

Figure 8A:
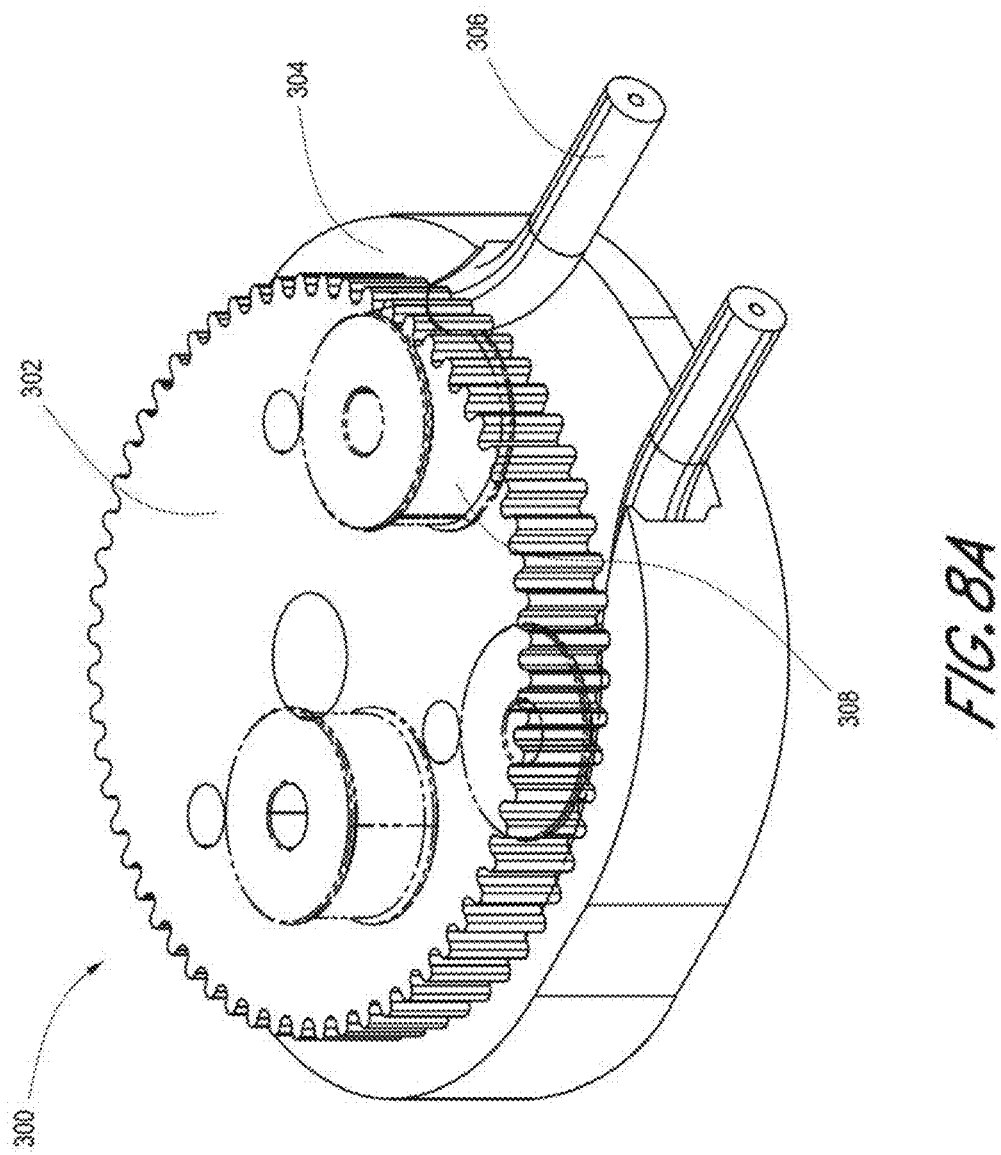
FIGS. 8A and 8B illustrate various perspective views of an example peristaltic pump.
Figure 8B:
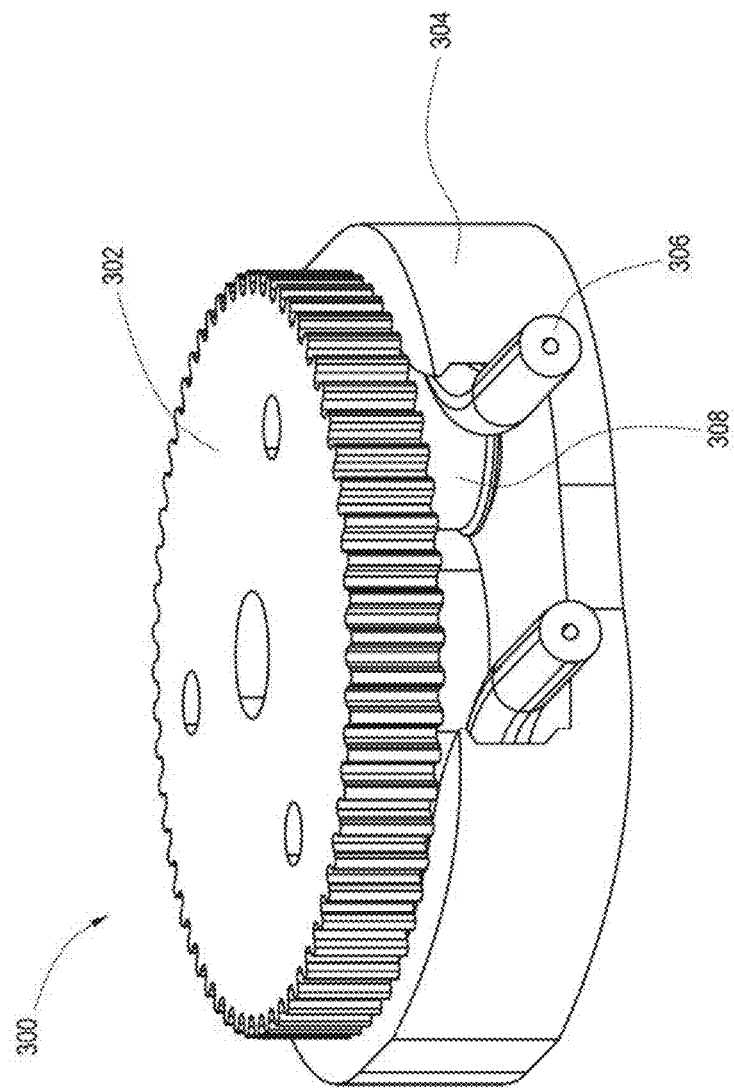
Figure 8D:
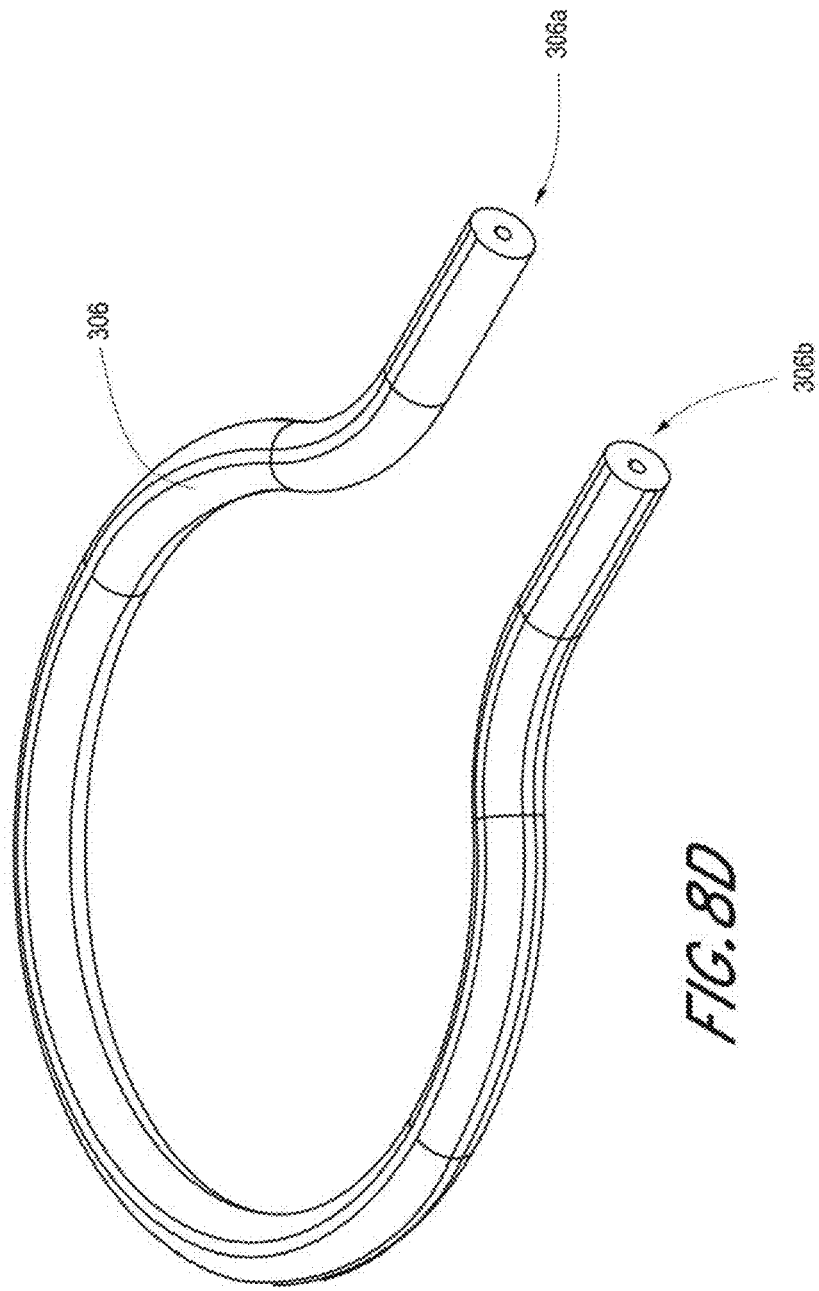
FIG. 8D illustrates a perspective view of the tubing of the peristaltic pump of FIGS. 8A-8C.

FIGS. 8A and 8B illustrate various perspective views of an example peristaltic pump 300 for pumping insulin. This pump may be incorporated into any of the above implementations of a disease management system or device, such as a disease management system 100 of FIGS. 3A and 3B, the insulin pump system 200A of the disease management system of FIGS. 4A-4C or the disease management system of FIGS. 4D-4N. FIG. 8C illustrates a cross-sectional view of the peristaltic pump 300 going through the tubing 306. FIG. 8D illustrates a perspective view of the tubing 306 alone outside the rest of the peristaltic pump 300 components. The peristaltic pump 300 includes a circular gear 302 including an upper portion that is connected to a lower circular portion 302A. When the circular gear 302 rotates, the circular portion 302A rotates at the same rotational speed. The circular gear 302 may be ratcheted by a ratcheting actuator capable of turning the teeth of the circular gear 302 by one tooth at a time. In some implementations, the ratcheting actuation may be accomplished by solenoid, muscle wire, ratchet motor, and/or direct current (DC) motor.

As illustrated, three or more rollers 308 are in physical contact with the circular portion 302A such that when the circular portion 302A rotates, the rollers 308 rotate. A casing 304 wraps around the circumference of the rollers 308 and the circular portion 302A. The casing 304 and the rollers 308 cooperate to form a circular channel. The rollers 308 are located at an inside portion of the circular channel and the casing 304 is located on the outside of the circular channel. A tubing 306 is located within the circular channel and the tubing physically contacts both the casing 304 and the rollers 308. When the circular gear 302 rotates, the circular portion 302A drives the rollers 308 which apply pressure to the tubing 306 such that insulin is driven from an inlet 306A of the tubing 306 to an outlet 306B of the tubing 306.

In some implementations, the number of rollers 308 can vary. There can be as few as two rollers however there can also be more than three rollers depending on the application. Further, while the primary operation of the peristaltic pump 300 is driving insulin from the inlet 306A of the tubing 306 to the outlet 306B of the tubing, the peristaltic pump 300 may also operate in reverse where insulin is driven from the outlet 306B to the inlet 306A. Further, the peristaltic pump 300 may pump other liquids than insulin such as a saline buffer solution.

Figure 9A:
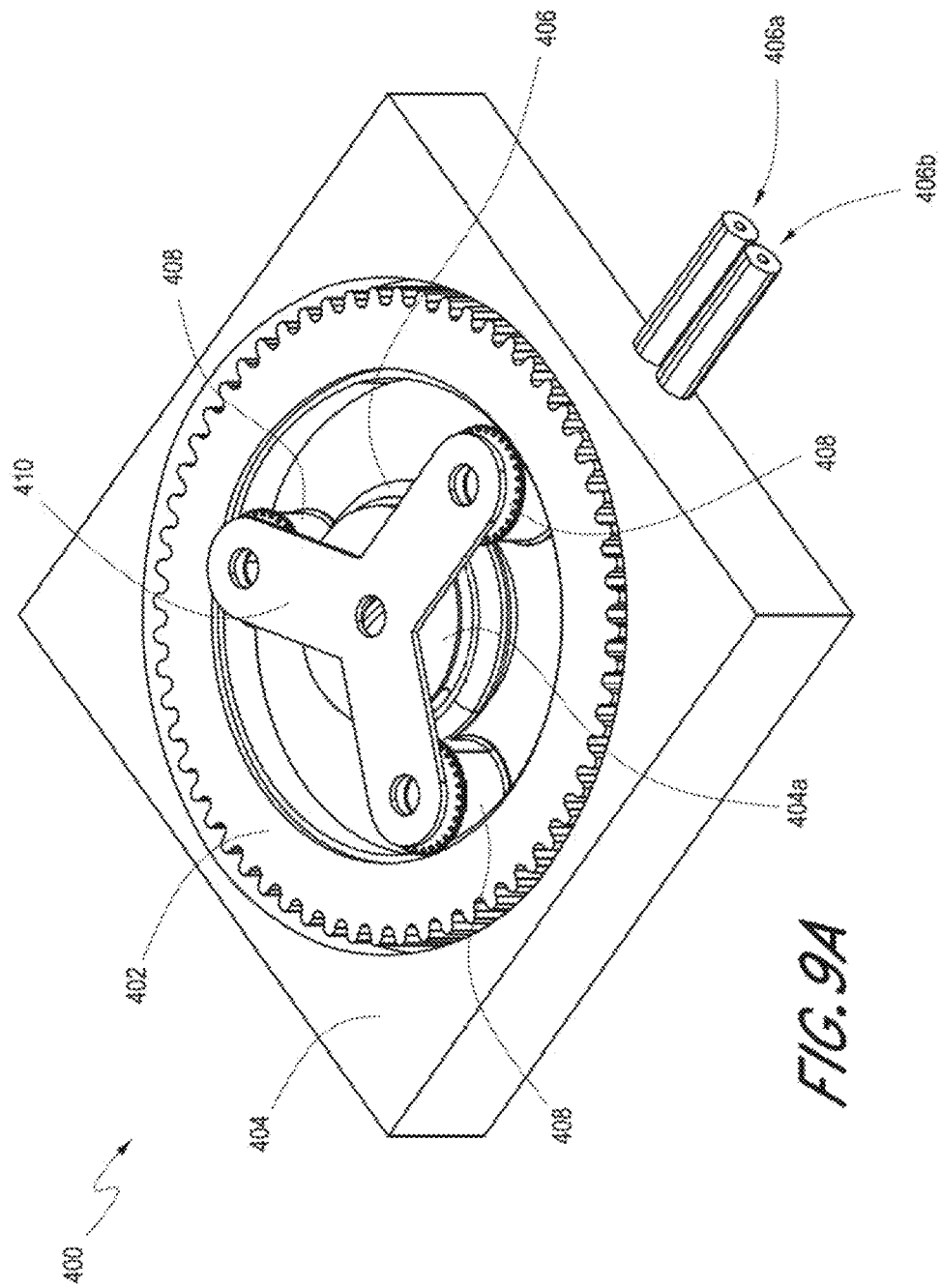
FIGS. 9A and 9B illustrate various perspective views of a peristaltic pump.
Figure 9B:
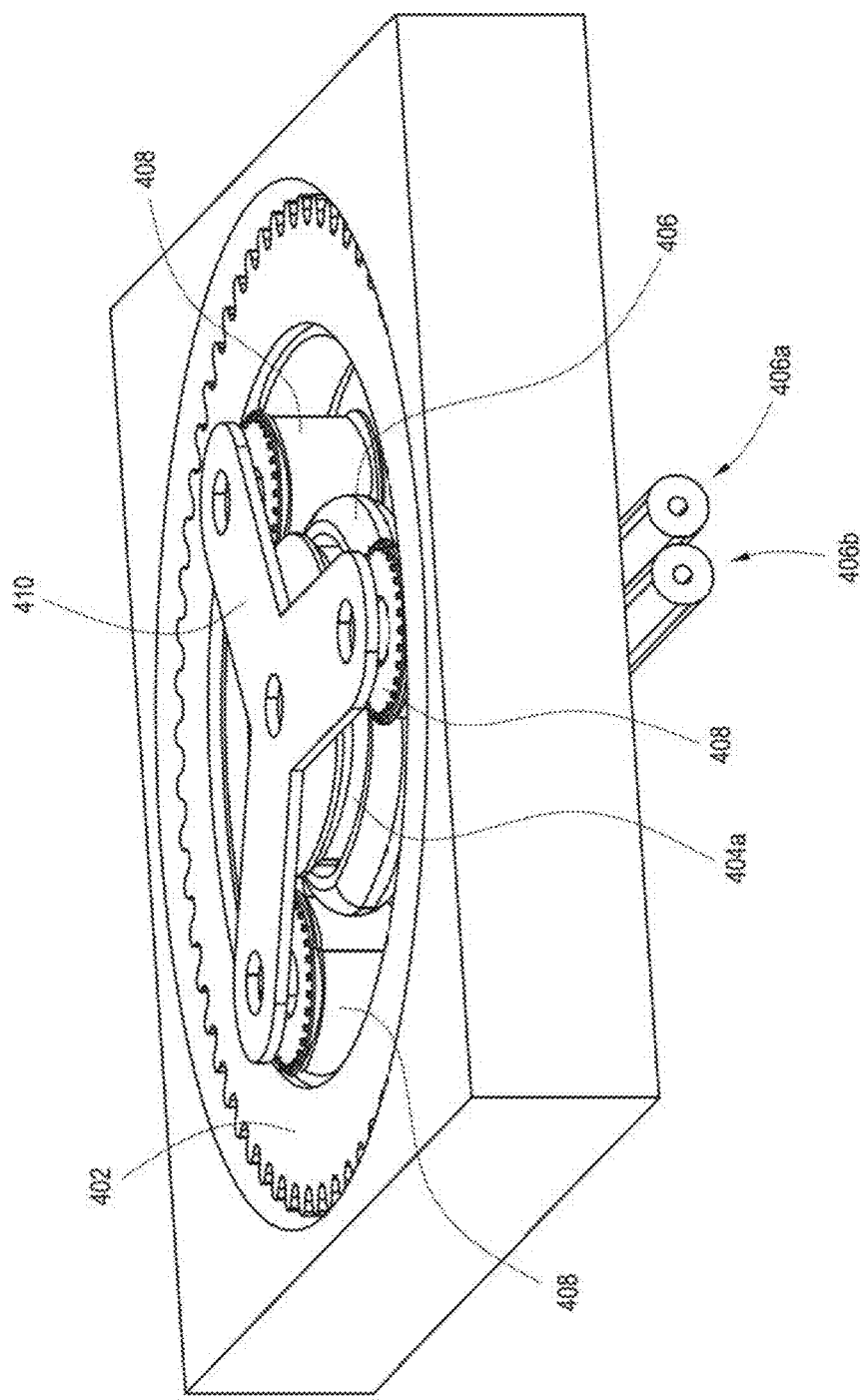
Figure 9C:
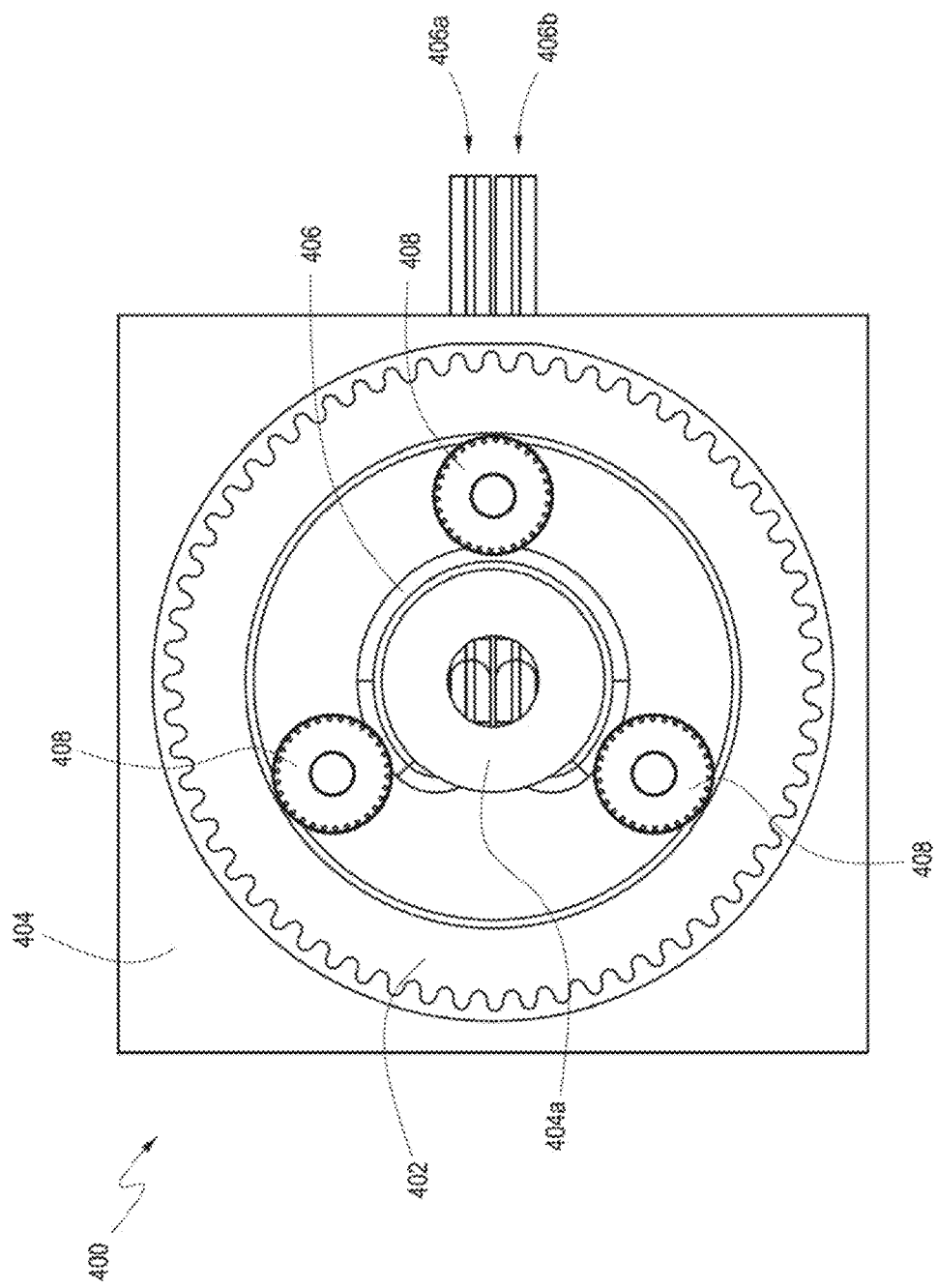
FIG. 9C illustrates a top down cross sectional view of the peristaltic pump of FIGS. 9A and 9B.
Figure 9D:
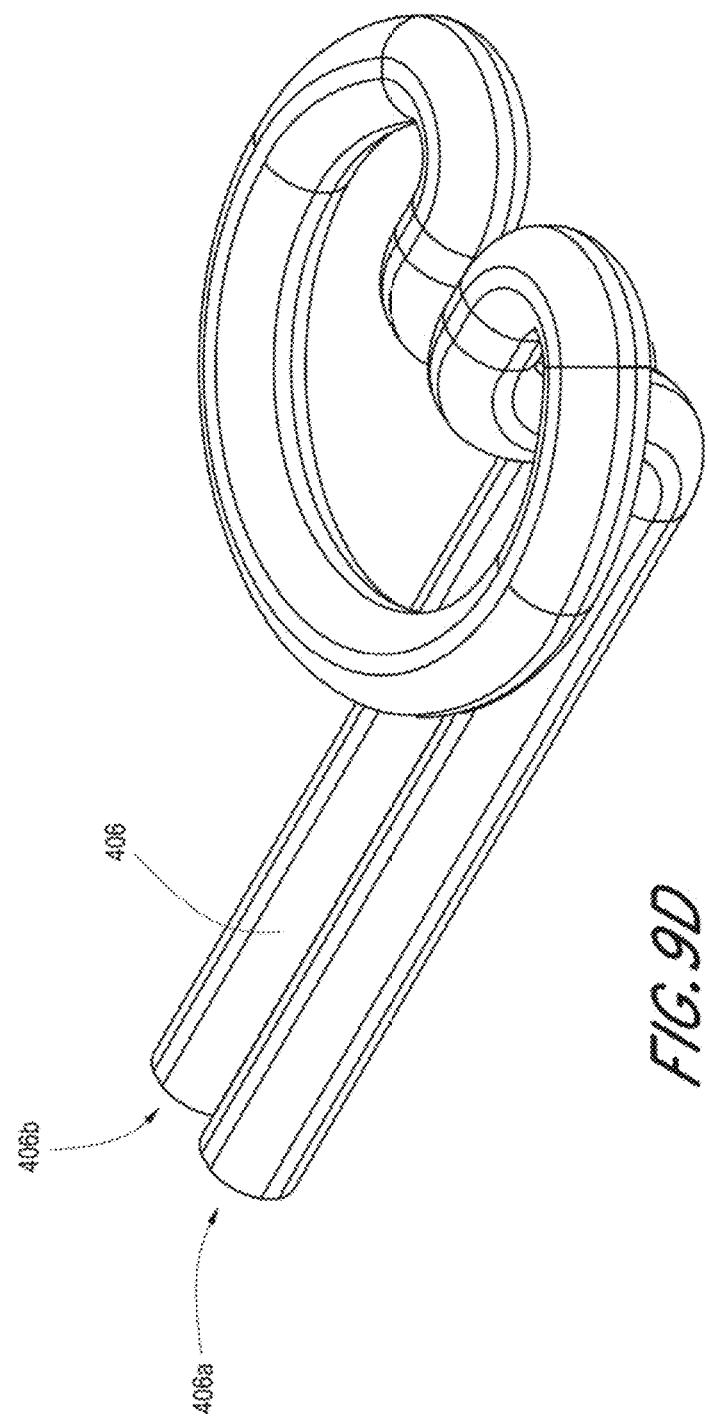
FIG. 9D illustrates a perspective view of the tubing of the peristaltic pump of FIGS. 4A-4D.

FIGS. 9A and 9B illustrate various perspective views of a peristaltic pump 400 for pumping insulin. FIG. 9C illustrates a top down cross sectional view of the peristaltic pump 400 through a stationary inner portion 404A and the rollers 408. FIG. 4D illustrates a perspective view of the tubing 406 alone outside the rest of the peristaltic pump 400 components. This pump may be incorporated into any implementation of a disease management system described herein, such as a disease management system described above with reference to FIG. 2F, or FIGS. 3A and 3B, or the insulin pump system 200A of the disease management system of FIGS. 4A-4C. This peristaltic pump 400 is similar to the peristaltic pump 300 of FIGS. 8A and 8B except for the rollers 408 are located inside a circular gear 402 with a circular hollow center. The rollers 408 make physical contact with an inner wall of the circular gear 402 such that the rollers 408 rotate when the circular gear 402 rotates. In some examples, the rollers 408 may be connected through a connecting portion 410 so that they roll at a similar rate. The casing 404 includes a stationary inner portion 404A which cooperates with the rollers 408 to form a circular channel. The rollers 408 are located at an outside portion of the circular channel whereas the stationary inner portion 404A is located at the inner portion of the channel. The stationary inner portion 404A includes holes within the center to allow a tubing 406 to exit. The tubing 406 is located within the circular channel such that the tubing 406 physically contacts both the casing 404 and the rollers 408. When the circular gear 402 is rotated, the circular portion drives the rollers 408 which applies pressure to the tubing 406 such that insulin is driven from an inlet 406A of the tubing 406 to an outlet 406B of the tubing 406. As is seen in FIG. 9D, the inlet 406A and the outlet 406B are on a separate vertical level from the portion of the tubing 406 located within the circular channel.

In some implementations, the number of rollers 408 can vary. There can be two or more rollers 408 and the number of rollers 408 can depend on the application. Further, similar to the peristaltic pump 300 of FIGS. 8A and 8B, while the primary operation of the peristaltic pump 400 is driving insulin from inlet 406A of the tubing 406 to the outlet 406B of the tubing 406, the peristaltic pump 400 may also operate in reverse where insulin is driven from the outlet 406B to the inlet 406A. Further, the peristaltic pump 400 may be pump other liquids than insulin such as a saline buffer solution.

Advantageously, the peristaltic pump 400 of FIG. 9A-9C may have a narrower height than the peristaltic pump 300 of FIGS. 8A-8C due to the fact that the circular gear 402 is on the same level as the rollers 408. The smaller diameter of the circular path of the tubing 406 in the circular channel than the tubing 306 of FIG. 8A-8C may lead to a higher level of stress on the tubing. However, for applications where the peristaltic pump 400 is not used for extended periods of time, the stress on the tubing 406 is unlikely to lead to failure. Further, before operation of the peristaltic pump, the tubing 306, 406 for either peristaltic pump 300, 400 may be stored without stress from the rollers 308, 408.

2. Example Insulin Priming in a Pump System

Insulin priming is a frequent concern among persons with type 1 diabetes. An unprimed insulin pump can result in hyperglycemia. However, a primed insulin pump may have leaky insulin due to pressure differentials during insertion. Conventional solutions often require user awareness and visual observation of properly primed insulin at the tip of a cannula and can leading to sometimes unexpected results. Systems and methods described herein may improve the priming process to reduce issues of leaky insulin and provide more consistent and expected results.

Peristalsis gears may lock fluid in place and prevent diffusion between gears and insulin reservoirs. Let us define tubing track 1 as between the cannula tip, gear 1, and gear 2 where there exists a buffered solution with no insulin. This region could also be air but a buffered solution is considered more advantageous so as to prevent air bubbles. A buffered solution can be safely injected into interstitial space. Let us define tubing track 2 as beyond gear 2 and all the way to the insulin reservoir resides pre-filled insulin. The quantity of buffered solution in tubing track 1 is known due to the inner diameter and length of tubing track 1. This value in one embodiment will be less than 0.25 U of equivalent insulin. The device may also contain or be connected to a CGM which can be monitored to determine if it is safe to bolus the equivalent of 0.25 U of insulin (Even though, at this stage there is no insulin in tubing track 1). Once a CGM verifies the users interstitial (or plasma if regressed) glucose is in a safe range the peristaltic system will move forward to inject the buffered solution into user.

The above injection could occur during a "warmup" period for the device which has just been inserted. This situation is especially beneficial to interleaved CGM devices. To double check only saline has been administered another device, CGM, can monitor glucose levels to determine if the body is or is not responding to insulin over a 1 hour period. If the body does appear to be responding to an insulin injection the device could be flagged as a faulty unit or a flag of possible insulin injection could be passed to a closed loop controller.

Once the system has gone through this procedure (which may be up to and including 1 hour), the insulin pump can be considered primed and ready for full and normal operation.

Figure 10:
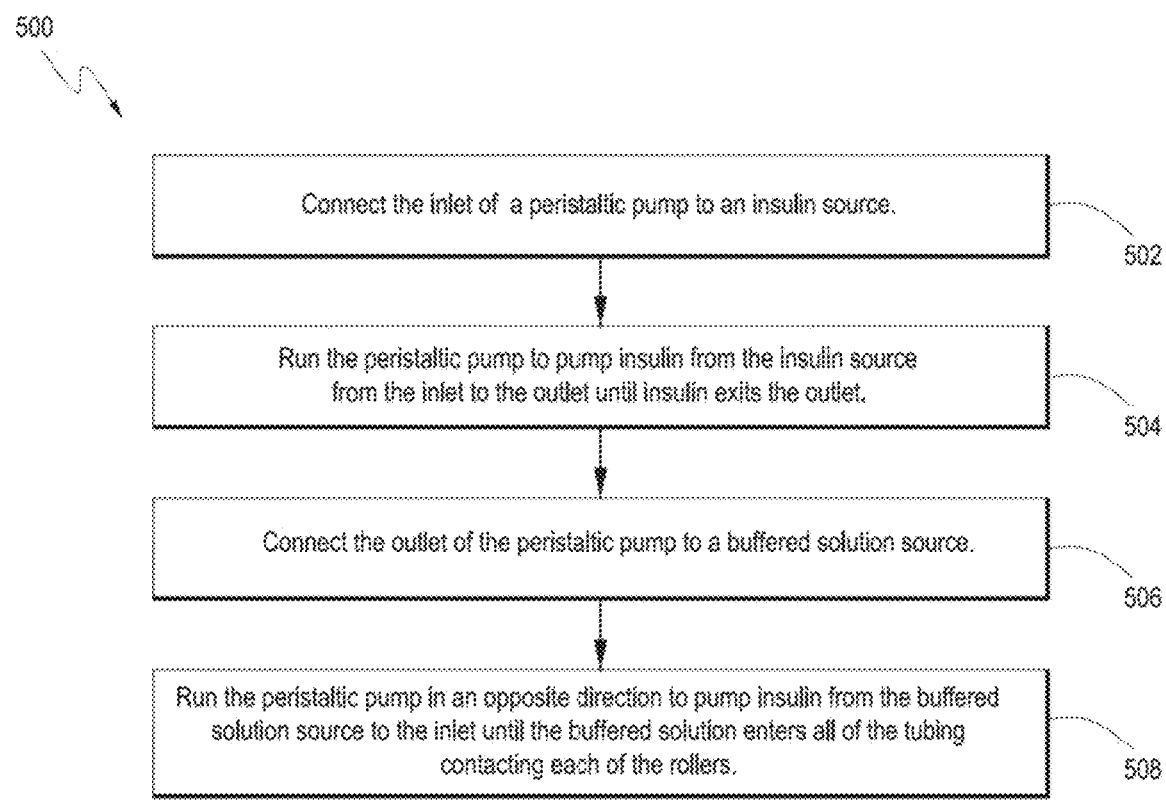
FIG. 10 illustrates an exemplary process for priming a peristaltic pump.
Figure 11A:
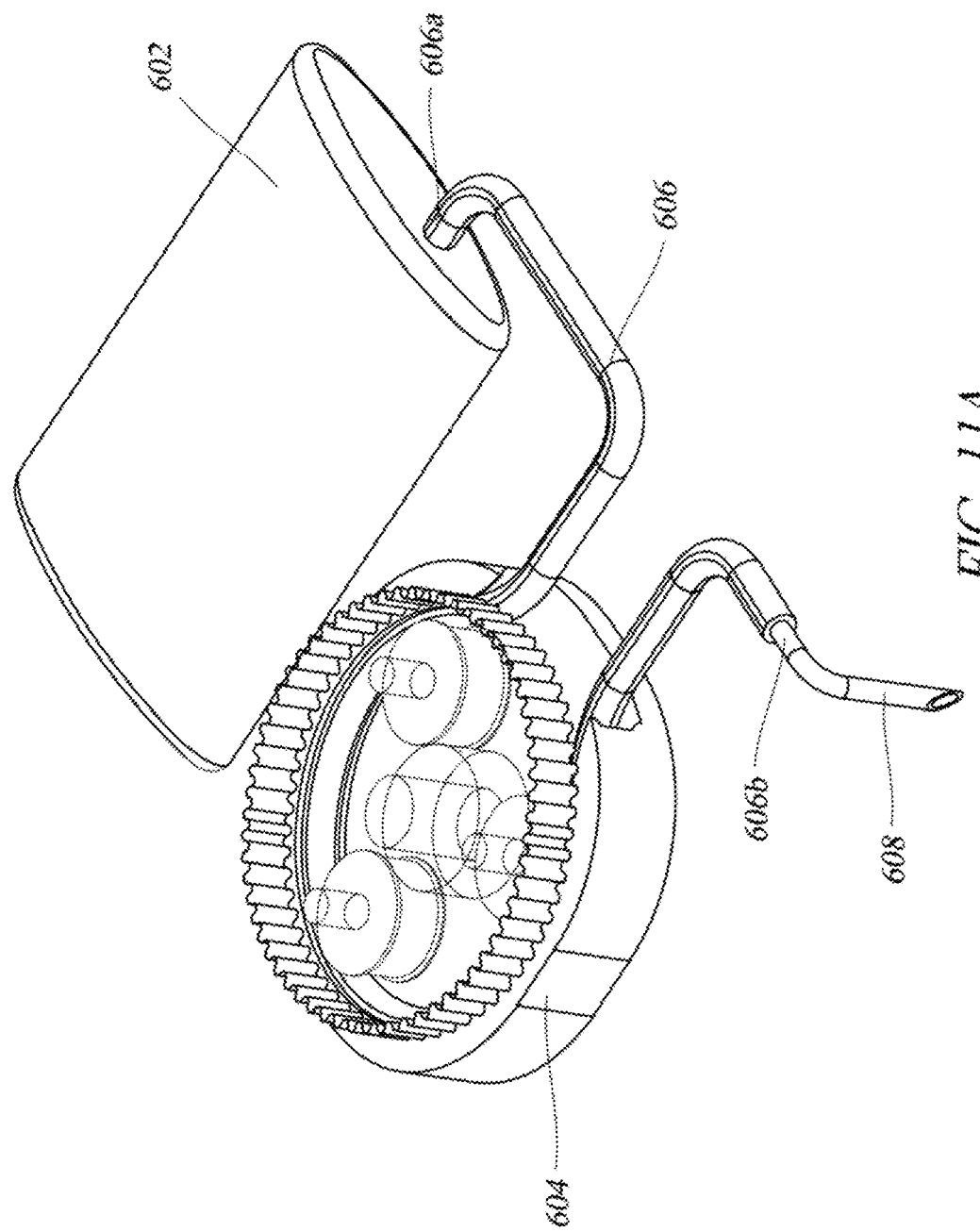
FIGS. 11A-11D illustrate various views of the process of FIG. 10 for priming a peristaltic pump.

FIG. 10 illustrates a process 500 for priming a peristaltic pump according to an example embodiment. The peristaltic pump may be the peristaltic pump 300 of FIGS. 8A-8C or the peristaltic pump 400 of FIGS. 9A-9C. FIGS. 11A-11D illustrate various views of the process 500 of FIG. 10 while performed on the peristaltic pump 300 of FIGS. 8A-8C. The process 500 of FIG. 10 will be explained using the views of FIGS. 11A-11D. In block 502, the inlet of a peristaltic pump is connected to an insulin source. In some implementations, the insulin source may be an insulin bladder which holds insulin. FIG. 11A illustrates an insulin bladder 602 that has been fluidly connected to the inlet 606A of the tubing 606 of the peristaltic pump 604. The outlet 606B of the tubing 606 may be connected to a needle 610 which may be implanted into a patient.

Figure 11B:
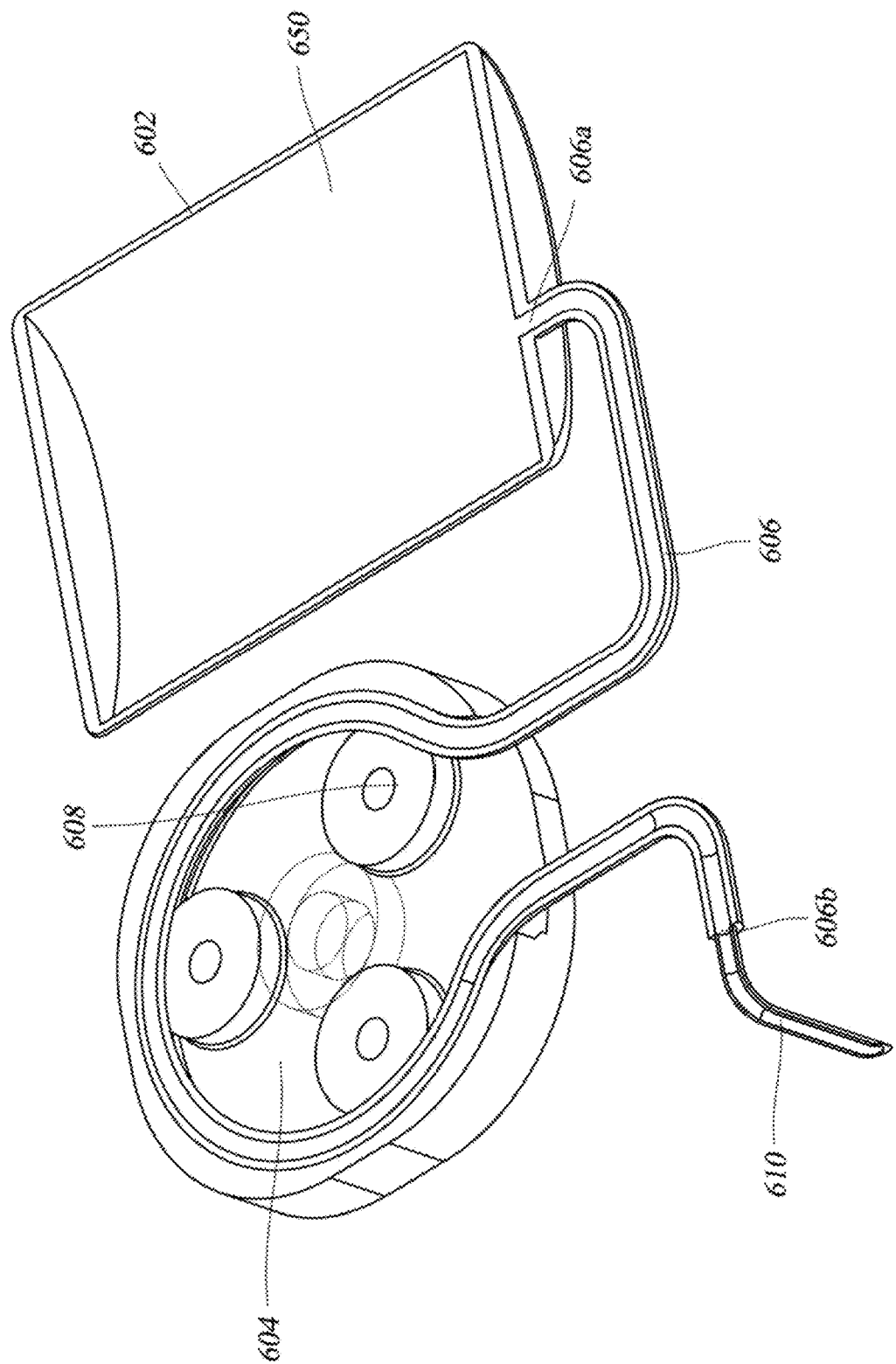
Figure 11C:
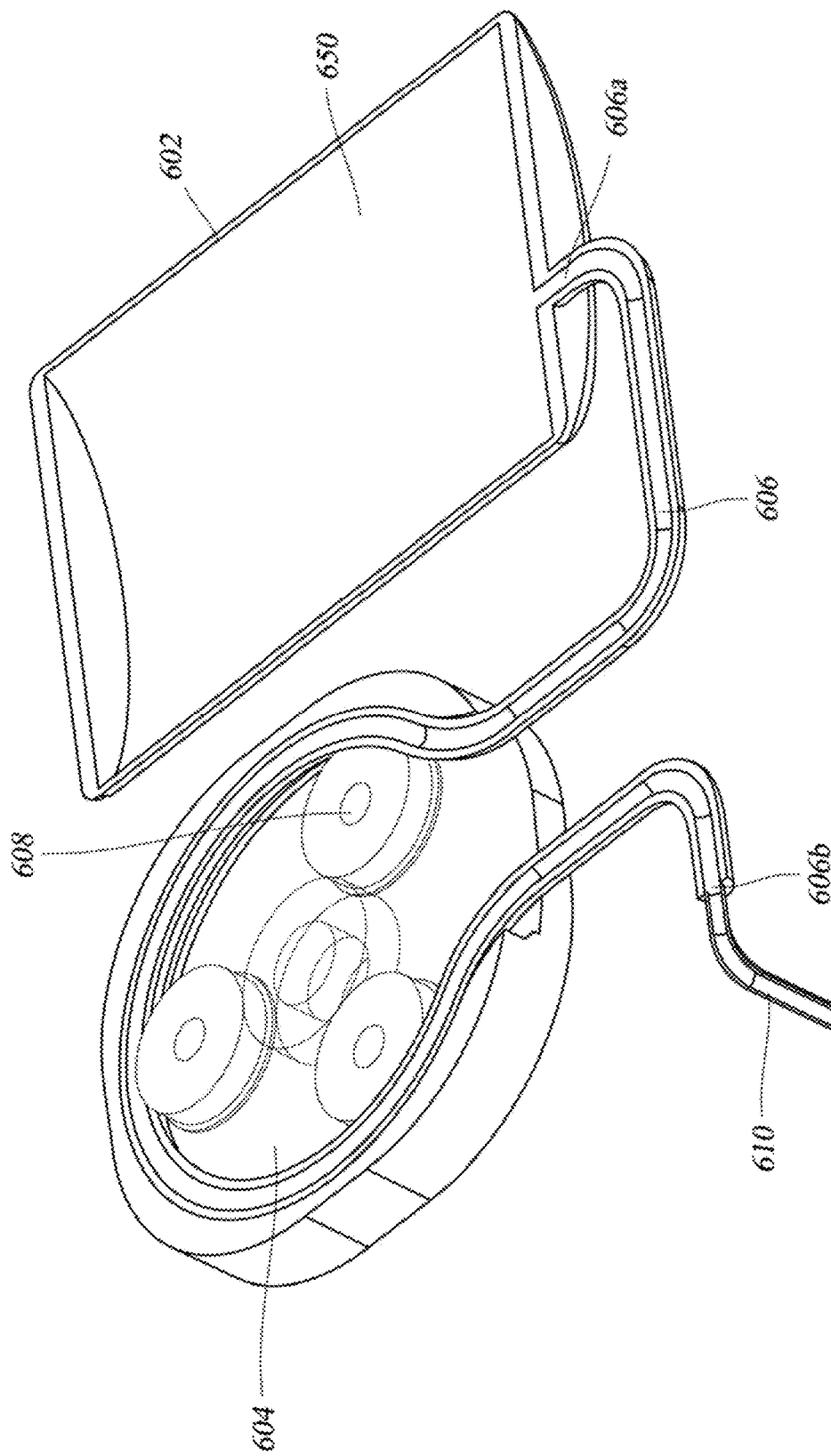

In block 504, the peristaltic pump 604 is run to pump insulin 650 from the insulin source 602 through the inlet 606A to the outlet 606B until insulin exits the outlet 606B. FIG. 11B illustrates operationally when the insulin 650 has entered the inlet 606A and gone into the tubing 606 until the roller 608 adjacent to the inlet 606A. FIG. 11C illustrate operationally when the insulin 650 completely circulated through the tubing 606 and is exiting the inlet 606A into the needle 610.

In block 506, the outlet 606B of the peristaltic pump 604 may be connected to a buffered solution source. In some implementations, the buffered solution in the buffered solution source may be saline. The buffered solution source may be connected to the outlet 606B through the needle 610. The needle 610 may also be removed or not present and installed after priming the peristaltic pump.

Figure 11D:
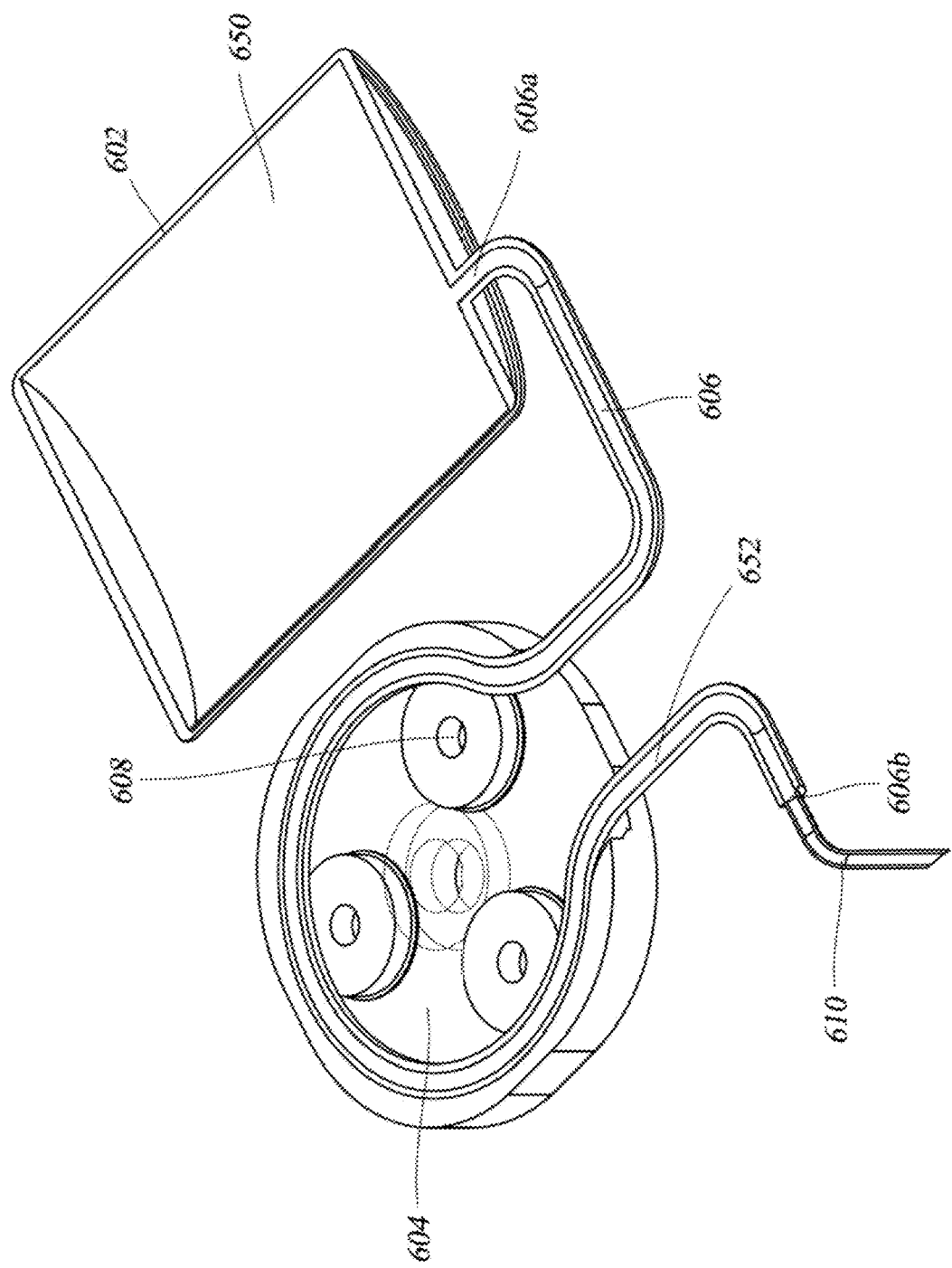

In block 508, the peristaltic pump 604 is run in an opposite direction to pump insulin from the buffered solution source to the inlet until the buffered solution 652 enters all the tubing 606 contacting each of the rollers 608. FIG. 11D illustrates operationally after the peristaltic pump 604 has been run until the buffered solution 652 entered the tubing 606 contacting the roller 608 adjacent to the inlet 606A. In some implementations, the peristaltic pump 604 is run until a specific amount of buffered solution 652 and the buffered solution 652 may be used to calibrate the pump. Advantageously, by allowing the buffered solution 652 to be housed within the tubing 606 where the tubing 606 contacts the rollers 608, the buffered solution 652 keeps stress off the tubing 606.

During the manufacturing procedure, a brand new, empty device can be preloaded with insulin by following the procedure:

1. Rotate the pump forward (CCW in the sketch) to drain air from the reservoir, creating thus a small amount of vacuum pressure.
2. Connect the cannula to an external insulin vial or insulin source.
3. Rotate the pump reverse (CW in the sketch) to pre-fill the insulin reservoir with the desired amount of insulin. The correct volume can be metered by the angular displacement of the pump.
4. Disconnect the cannula from the insulin source and reconnect it to the saline source.
5. Rotate the pump reverse, to pre-fill the cannula tubbing with the desired amount of saline As an additional quality to prevent buffer leakage/dehydration, the system can be capped with a hydrogel matrix or silicone that is removed at time of insertion by an applicator or user.

Figure 11F:
Figure 12:
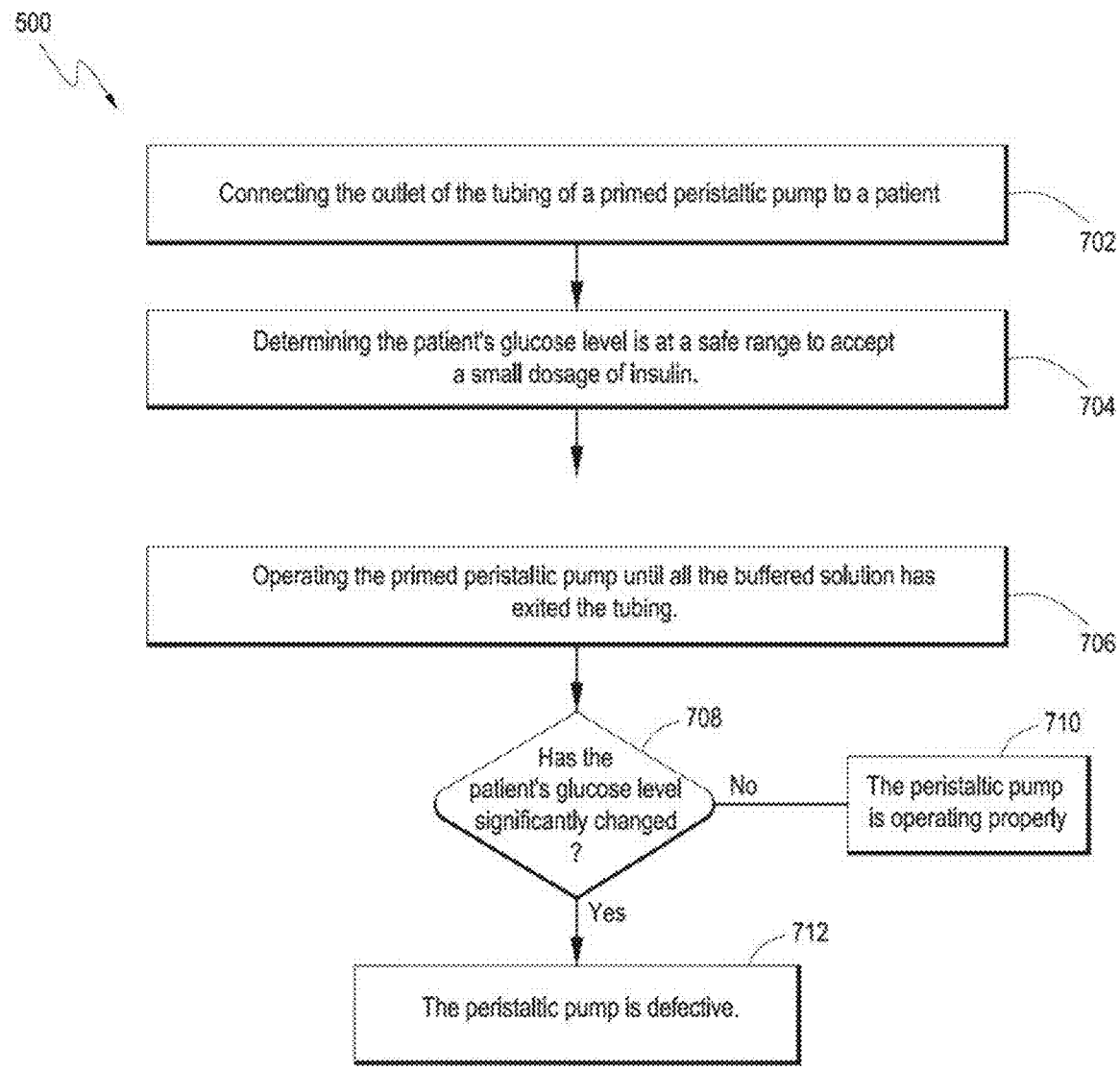
FIG. 12 illustrates a process for using a primed peristaltic pump.

FIG. 12 illustrates a process 700 for using a primed peristaltic pump. The peristaltic pump may be primed using the process 500 of FIG. 10. Further, the peristaltic pump may be the peristaltic pump 300 of any implementation of a disease management system described herein, such a disease management system of FIGS. 3A-3c, or the peristaltic pump 400 of FIGS. 9A-9C. Portions of the process 700 will be explained using the views of FIGS. 11D-11F. At block 702, the outlet 602B of the tubing 606 of a primed peristaltic pump 604 is connected to a patient. FIG. 11D illustrates the primed peristaltic pump 604 where a buffered solution 652 is stored within the tubing 606 at least to the roller 608 adjacent to the inlet 606A. In some implementations, the buffered solution 652 is stored in more or less of the tubing 606. The patient may be connected to the tubing 606 through a needle 610 which may be connected to the outlet 606B.

At block 704, it is determined whether the patient's glucose level is at a safe range to accept a small dosage of insulin. This step is performed to make sure that if the peristaltic pump 602 malfunctions while operating, that the patient is not harmed with a dosage of insulin 650. The patient's glucose level may be determined through the use of a glucose sensor such as the glucose sensor of any implementation of the disease management system described herein which may include a glucose sensor and insulin pump as one system or glucose sensor of the sensor system 200B of FIGS. 4A and 4B where the glucose sensor and the glucose pump are in separate systems.

At block 706, the peristaltic pump 602 is operated until all the buffered solution 652 within the tubing 606 has exited the tubing 606. FIG. 11E illustrates the peristaltic pump as the buffered solution 652 exits the tubing 606 however has not completely exited the tubing. As the buffered solution 652 is pumped from the tubing 606, the insulin 650 is pumped into the tubing 606 following the buffered solution 652. FIG. 11F illustrates the peristaltic pump when the buffered solution 652 has completely exited the tubing 606 and thus insulin 650 may enter the patient through the needle 610.

At block 706, it is determined whether the patient's glucose level significantly changed. As in block 704, the glucose level may be determined using a glucose sensor such as those mentioned above. If it is determined that the patient's glucose level has significantly changed then, at block 712, the peristaltic pump is determined to be defective since insulin was likely administered to the patient when only the buffered solution should be administered to the patient. If it is determined that the patient's glucose level has not significantly changed, then, at block 710, the peristaltic pump is determined to be operating properly since it is likely that only buffered solution was administered to the patient.

3. Example Valve Style Insulin Pump System

FIGS. 13A-13G illustrate different operational views of a valve style insulin pump 800. The valve style insulin pump 800 includes three or more valves 802A-c. The three or more valves 802A-c may be driven by difference mechanisms such as piezoelectric, voice coil, solenoid, muscle wire such as nitinol wire, or DC motor. The valve style insulin pump 800 is in fluid connection with an insulin storage container 804. The insulin storage container is a flexible container such as a bladder. The insulin storage container 804 is filled with insulin 810. The insulin storage container 804 is fluidly connected to a tube 812 where the valve style insulin pump 800 is located. The tube 812 includes an outlet 814 which may be connected to a needle 816 that is connected into a patient. In some implementations, the outlet 814 may be connected into the patient through use of a cannula that is implanted into the patient. The insulin storage container 804 is placed between a pressure applying portion 806 which may include a spring and a wall portion 808 such as a portion of a case. The pressure applying portion 806 applies pressure to the insulin storage container 804 while the wall portion 808 remains firm against the opposite side of the insulin storage container. Thus, a pressure is applied to the insulin storage container 804 which forces out the insulin 810 into the tubing 812. In some implementations, pressure may be applied to the insulin storage container 804 from both sides and thus the pressure applying portion 806 may be joined by another pressure applying portion between the wall portion 808 and the insulin storage container 804 or the wall portion 808 may be substituted for another pressure applying portion such as a spring. The valve style insulin pump 800 regulates the application of insulin 810 to the patient by the use of valves 802A-c. The operation of the valve style insulin pump 800 is describing using FIGS. 13A-13G.

Figure 13A:
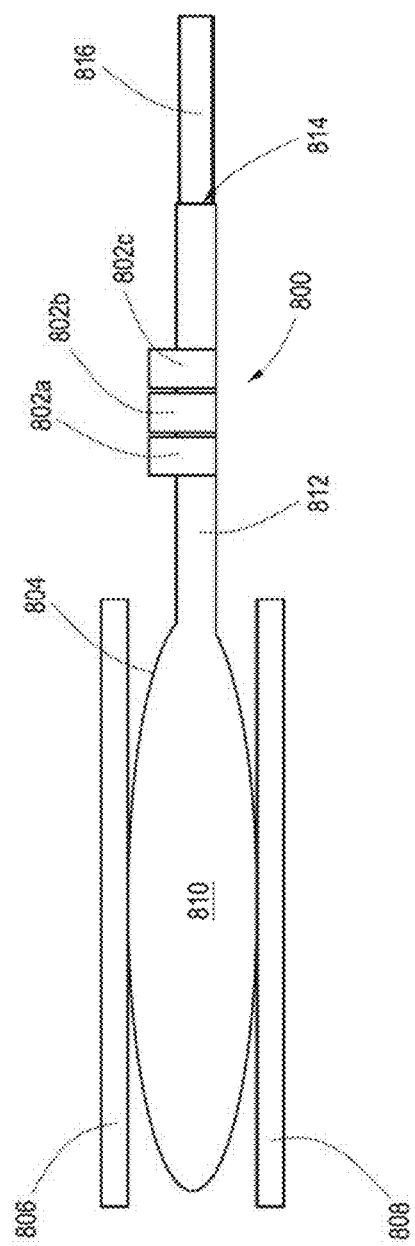
Figure 13C:
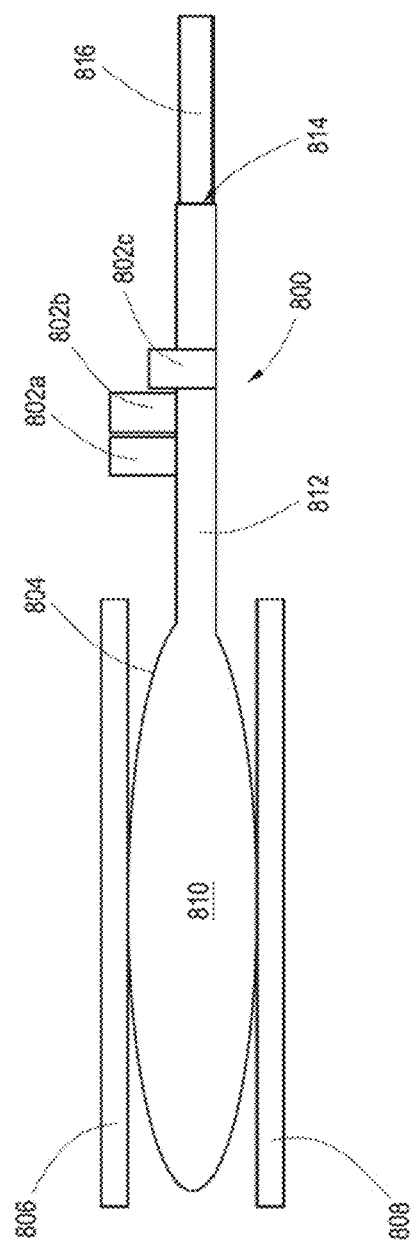
Figure 13F:
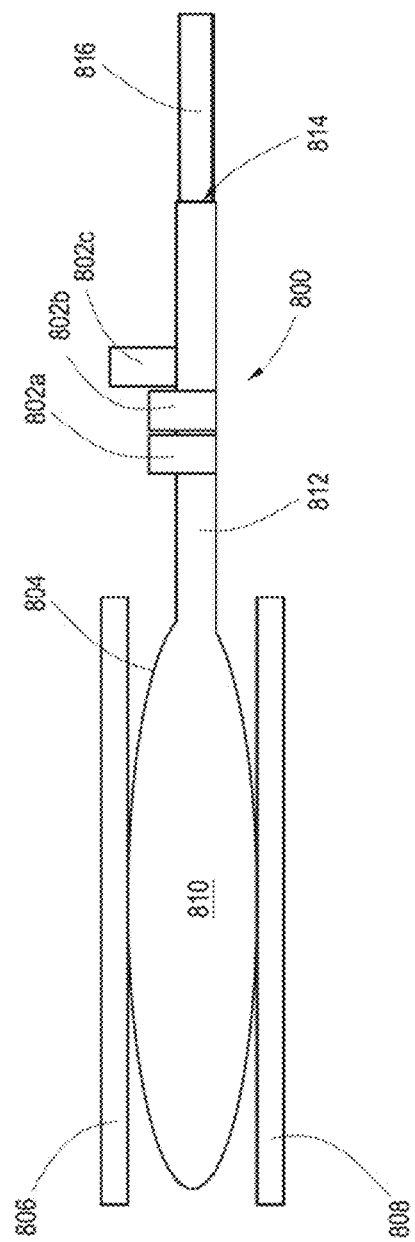
Figure 13G:
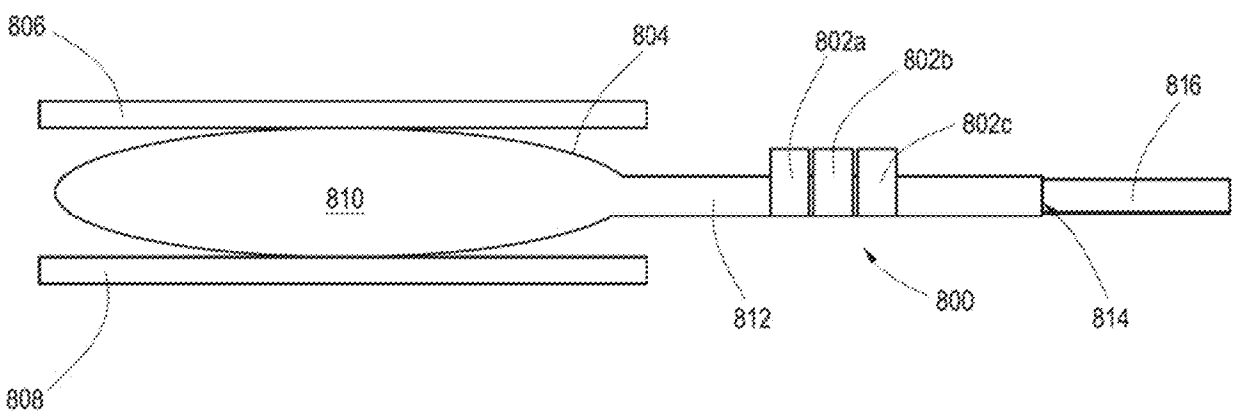

FIG. 8A illustrates a first valve 802A, a second valve 802B, and a third valve 802C being all closed and thus no insulin 810 will flow to the patient. FIG. 13B illustrates a first valve 802A being in an open position and thus insulin 810 will flow into the area within the first valve 802A however the insulin 810 will still be prevented from flowing into the patient by a second valve 802B and a third valve 802C. FIG. 13c illustrates the second valve 802B and the first valve 802A in an open position and thus insulin 810 is allowed to flow into the area within the second valve 802B but the insulin still does not enter the patient since the third valve 802C remains closed. In FIG. 8D, the first valve 802A is in a closed position and thus a dose of insulin is trapped within the area within the second valve 802B. In FIG. 13E, the third valve 802C is opened while the second valve remains open 802B and the first valve 802A remains closed and thus the insulin 810 is in fluid connection with the patient. In FIG. 13F, the second valve 802B is closed and thus insulin 810 is forced out from the space within the second valve 802B towards the third valve 802C. In FIG. 13G, the third valve 802C is closed and thus insulin 810 is forced out from the space within the third valve 802C and toward the patient.

In some implementations, the intermediate second valve 802B may be multiple valves in order to vary the dosage. For example, there may be two valves and only one is opened to provide a smaller dosage than if both valves were opened. Further, the intermediate second valve 802B may be an adjustable valve which may not open fully depending on an input such as a voltage applied to the second valve 802B. In some implementations, there may be a filter at the output 814 or someplace from the output 812 to the valve style insulin pump 800 in order to avoid particles from the patient from being trapped between actuator components within the valves 802A-c. At the stage of FIG. 13E, when the third valve 802C is opened, there will a backflow of fluid from the output 812 which may contain particles and a filter may prevent the particles from flowing into the valves 802A-c and causing failure of the valves 802A-c. The steps illustrated in FIGS. 8A-8g may be repeated to dispense more insulin 810.

Figure 14A:
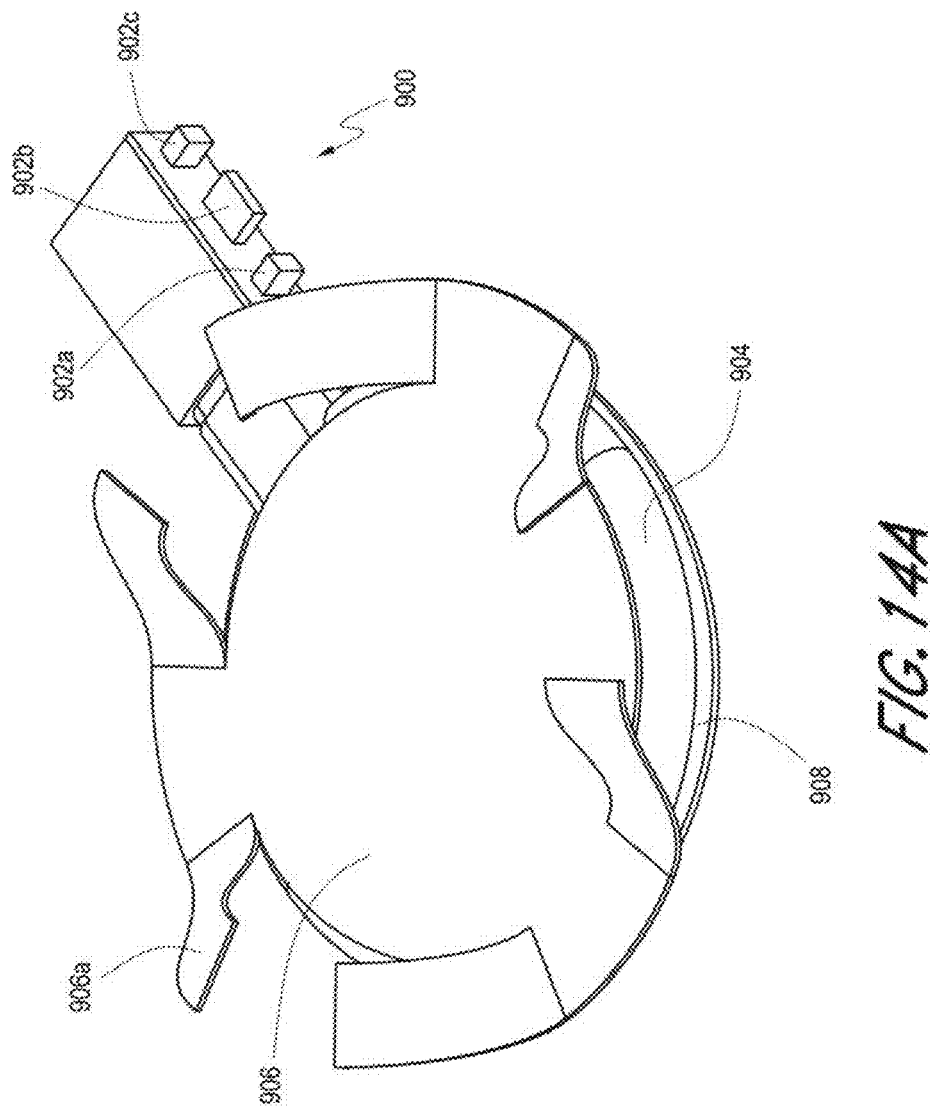

FIG. 14A illustrates a perspective view of an exemplary implementation of a valve style insulin pump 900. As illustrated, the valve style insulin pump 900 includes three valves 902A, 902B, 902C which are in fluid connection with an insulin storage container 904. The three valves 902A, 902B, 902C are piezo crystal valves which may be made from a piezo crystal such as PZT. In some implementations, the three valves 902A, 902B, 902C may also be voice coil valves, solenoid valves, or muscle wire such as nitinol wire. Piezo crystal valves are operated through the application of a voltage. A certain voltage will open the valves whereas another voltage will close the valves. The valves 902A, 902B, 902C are independently accessible in order to allow the valves 902A, 902B, 902C to be independently opened and closed. These valves can also be synchronized. A pressure applying portion 906 cooperates with a wall portion 908 to apply pressure to the insulin storage container 904 to force insulin out. The pressure applying portion 906 includes six springs 906A connected to a plate. In some implementations, the number of springs 906A may depend on various factors such as the amount of force to be applied to the insulin storage container 904. FIG. 14B illustrates a close up view of the valve style insulin pump 900. The valve style insulin pump 900 includes three valves 902A, 902B, 902C which may open and shut to dispense insulin based on the operations described in connection with FIGS. 13A-13G. As shown, the intermediate second valve 902B is a wide rectangular valve. The length of this valve 902B may be modified depending on the desired insulin to be dispensed.

The piezo crystal valves may be manufactured using a piezoelectric ceramic, fine PZT powder mixed in specific proportions and then heated to form a uniform powder. The piezoelectric powder may be mixed with an organic binder and formed into structural elements having a certain shape (for example, discs, rods, or plates). Piezo crystal valves provide adequate power while being a small form factor and low power consumption.

Figure 14C:
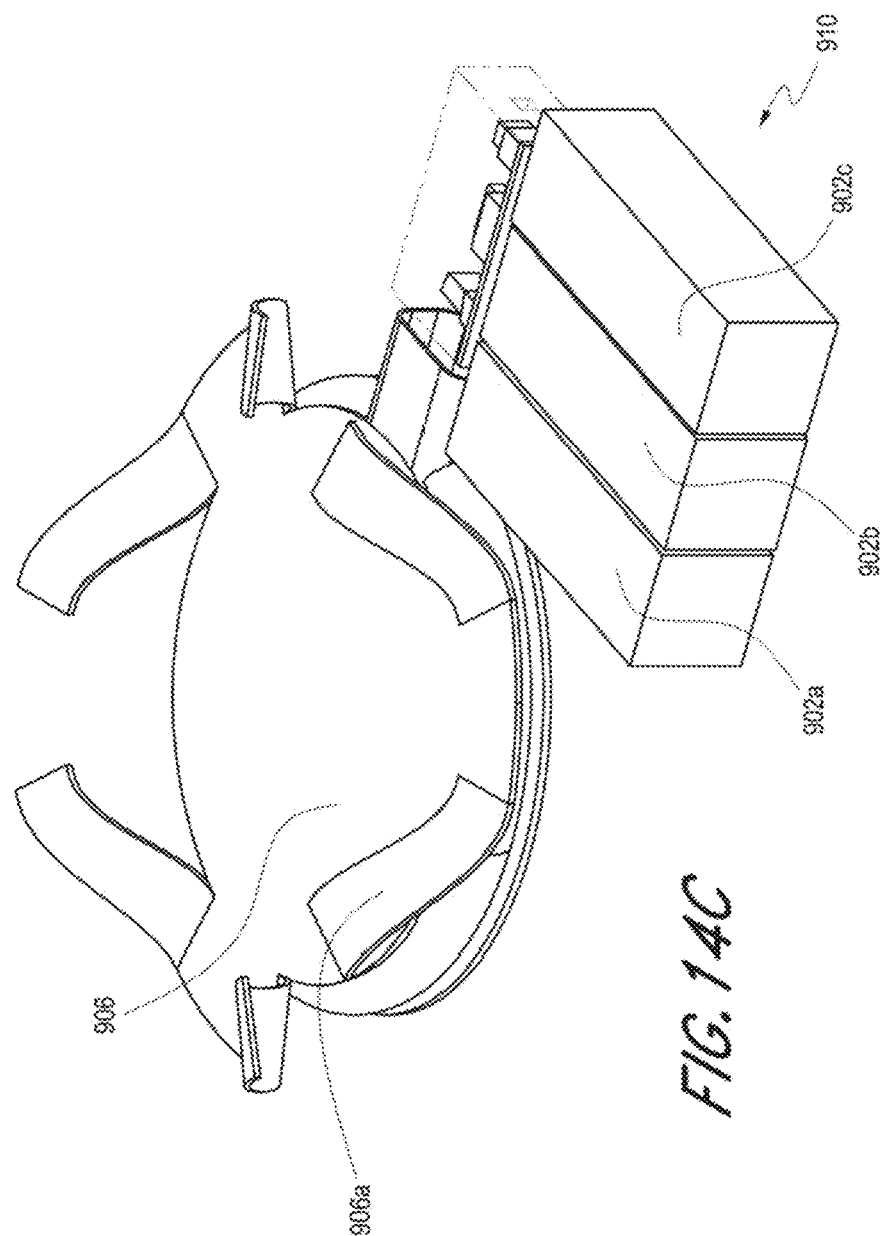
FIG. 14C illustrates a perspective view of an implementation of a valve style insulin pump.

FIG. 14C illustrates a perspective view of another exemplary implementation of a valve style insulin pump 910. The implementation of FIG. 14C shares features from the implementation of FIGS. 14A and 14B. Identical features have been identically numbered and will not be described again. FIG. 14C uses piezo stack valves for the three valves 912A, 912B, 912C. A piezo stack valve can include multiple piezoelectric chips which combine to form one valve. Advantageously, piezo stack valves may have increased power and displacement while not significantly increasing response time when compared to a single layer piezo crystal valve. In some implementations, the valves may be solenoid actuators. In some implementations, the valves may be voice coil actuators. Voice coil actuators may include a permanent magnet as a piston and a coil. Energizing the coil will change the polarity of the magnetic field inside the coil which will push or pull the piston. Advantageously, voice coil actuators may allow for more power without increased size when compared to solenoid actuators.

Figure 14D:
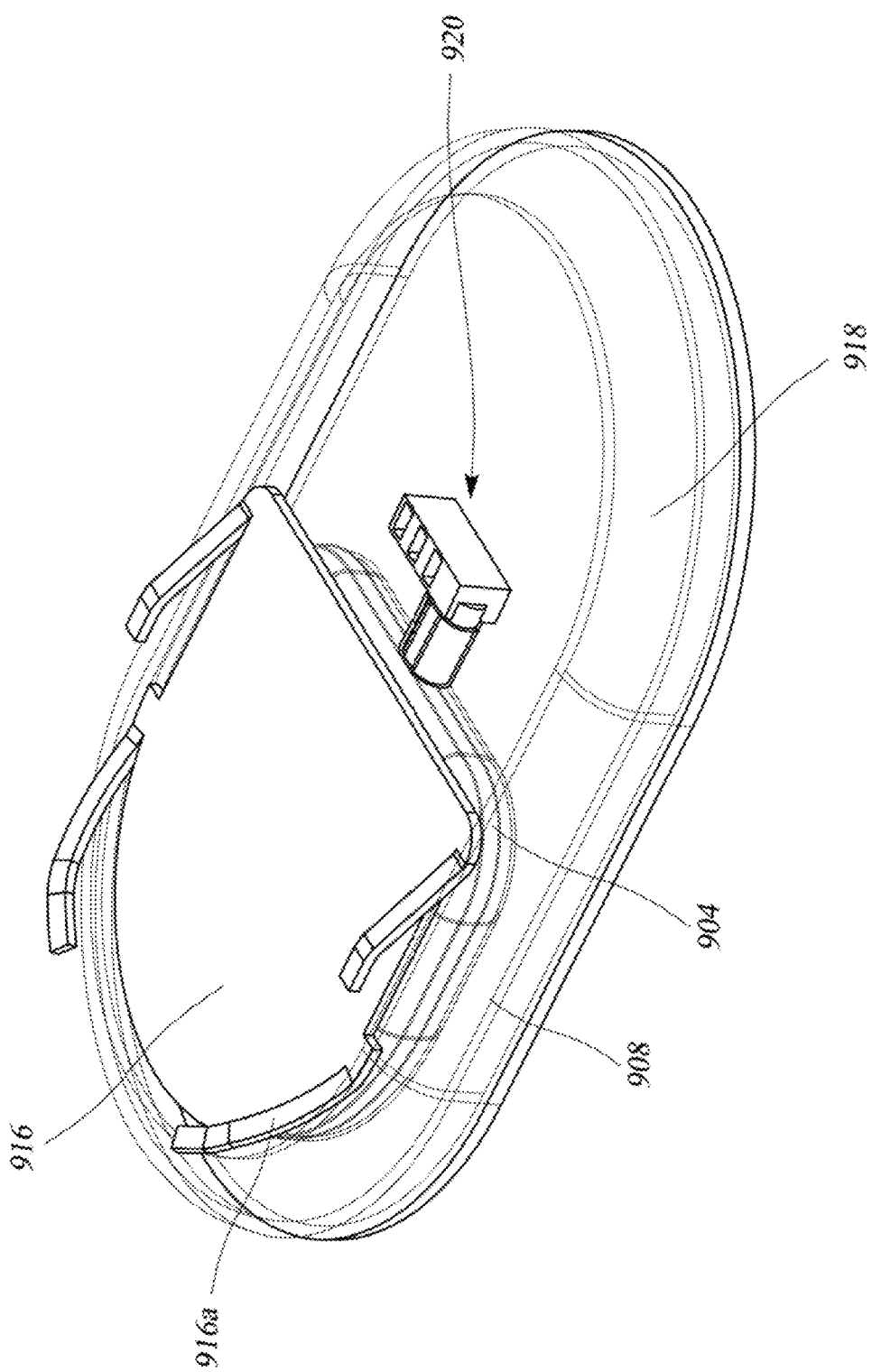
FIG. 14D illustrates a perspective view of an implementation of a valve style insulin pump.

FIG. 14D illustrates a perspective view of another exemplary implementation of a valve style insulin pump 920. In this implementation, similar to the implementation of FIGS. 14A and 14B, an insulin storage container 904 is between a pressure applying portion 916 and a wall portion 908. The pressure applying portion 916 includes springs 916A and cooperates with the wall portion 908 to apply pressure to the insulin storage container 904. The insulin storage container 904 is in fluid connection with the valve style insulin pump 920 which includes three or more valves. The valve style insulin pump 920 diverts the insulin in a perpendicular direction to the tubing connected to the valve style insulin pump 920. The valve style insulin pump 920 is housed within a casing 918 and depending on the dimensions of the casing 918 and other components within the implementation, a perpendicular connection may be easier to integrate within the casing 918.

Figure 14E:
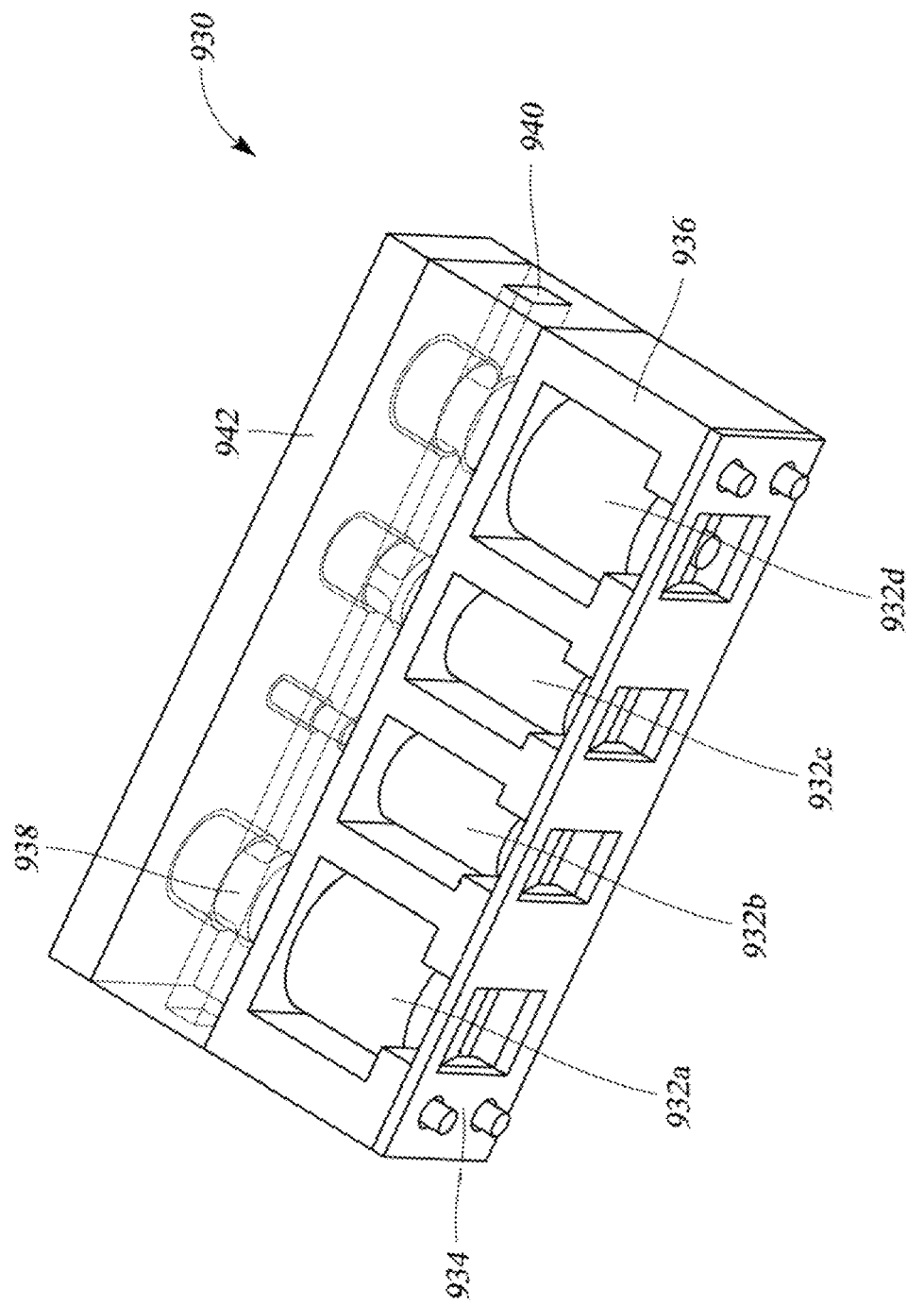
FIG. 14E is a perspective view of an implementation of a valve style insulin pump.
Figure 14F:
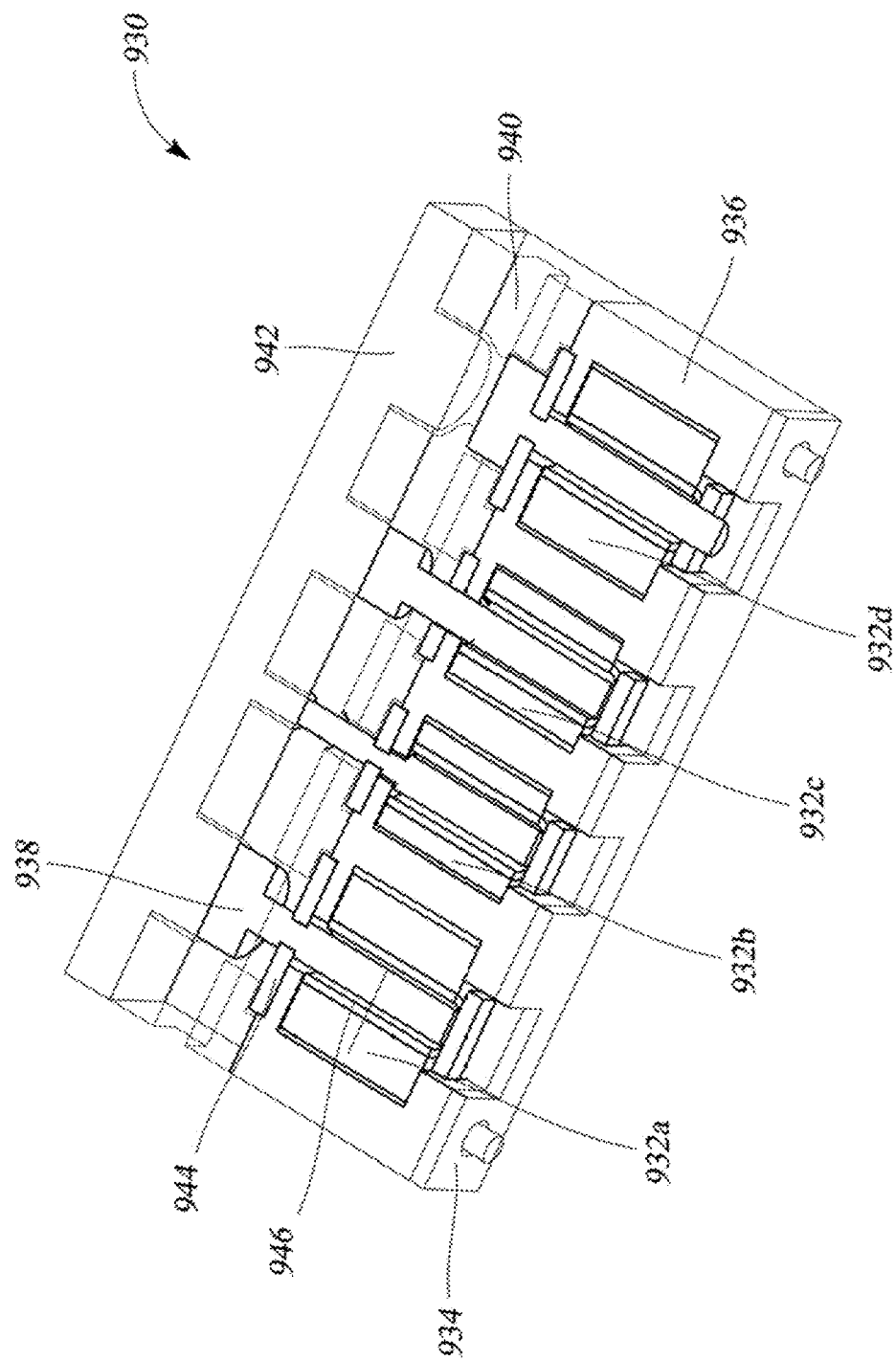
FIG. 14F is a cross-sectional view of an implementation of a valve style insulin pump.

FIG. 14E illustrates a perspective view of another exemplary implementation of a valve style insulin pump 930. FIG. 14F illustrates a cross sectional view of the exemplary implementation of the valve style insulin pump 930 of FIG. 9E. As illustrated, the valve style insulin pump 930 includes four solenoids 932A, 932B, 932C, 932D each positioned around a valve 938. The valve 938 contacts a spring 934 located at the bottom of the valve style insulin pump 930. When the solenoid 932 is not operating the valve 938, the spring 934 pushes the valve 938 upwardly against a sealer 942. The sealer 942 may be made out of a pliable material such as silicone which can ensure an adequate seal with the valve 938 by conforming to the valve 938 when the valve 938 pushes against the sealer 942. The valve 938 moves in and out of an insulin flow channel 940. One end of the channel 940 may be in fluid connection with an insulin source and the other may be in fluid connection with a patient.

The valve style insulin pump 930 may operate similar to the valve style insulin pump 800 described in connection with FIGS. 13A-13G. In order to pump insulin, first, a first solenoid 932A, a second solenoid 932B, a third solenoid 932C, and a fourth solenoid 932D operate their respective valves 938 to be closed. Second, each of the first solenoid 932A, the second solenoid 932B, and the third solenoid 932C sequentially operate their respective valves 938 to be open while the fourth solenoid 932D operates its valve 938 to remain closed. Third, the first solenoid 932A operates its valve 938 to be closed. Fourth, the fourth solenoid 932D operates its valve 938 to be opened. Fifth, the second solenoid 932B and/or the third solenoid 932C may operate their respective valves 938 to be closed. As illustrated, the valve style insulin pump 930 includes both the second solenoid 932B and the third solenoid 932C which may be operate intermediate valves 938 whereas the valve style insulin pump 800 described in connection with FIGS. 13A-13G includes only one intermediate valve 802B. Including more intermediate valves allows for the dosage of insulin pumped to be adjusted. When the second solenoid 932B and/or the third solenoid 932C operates their respective valves 938 to be closed, the valves 938 will force insulin out of the insulin flow channel 940 into the patient. While the valve style insulin pump 930 is described and illustrated with four solenoids, it is appreciated that more solenoids may be included to allow the user more dosage options.

FIG. 14F further illustrates a sleeve 946 within each of the solenoids 932A, 932B, 932C, 932D. The sleeve 946 may be made of a smooth material such as nylon which may allow the valves 938 to glide up and down. Further, the sleeve 946 may protect wires within the solenoids 932A, 932B, 932C, 932D from damage while the valves 938 move up and down. The solenoids 932A, 932B, 932C, 932D may be housed within a holder 936. Each solenoid 932A, 932B, 932C, 932D may further include a sealer 944 which surrounds the valve 938 and is positioned above the holder 936. The sealer 944 may be made out of a sealing material such as silicone or rubber in order to ensure that insulin does not leak down from the valves 938 through the holder 936 into the solenoids 932A, 932B, 932C, 932D. The sealer 944 may be omitted if the viscosity of the insulin is thick enough such that the insulin does not leak through the intersection of the valve 938 and the holder 936 into the solenoids 932A, 932B, 932C, 932D.

Figure 14G:
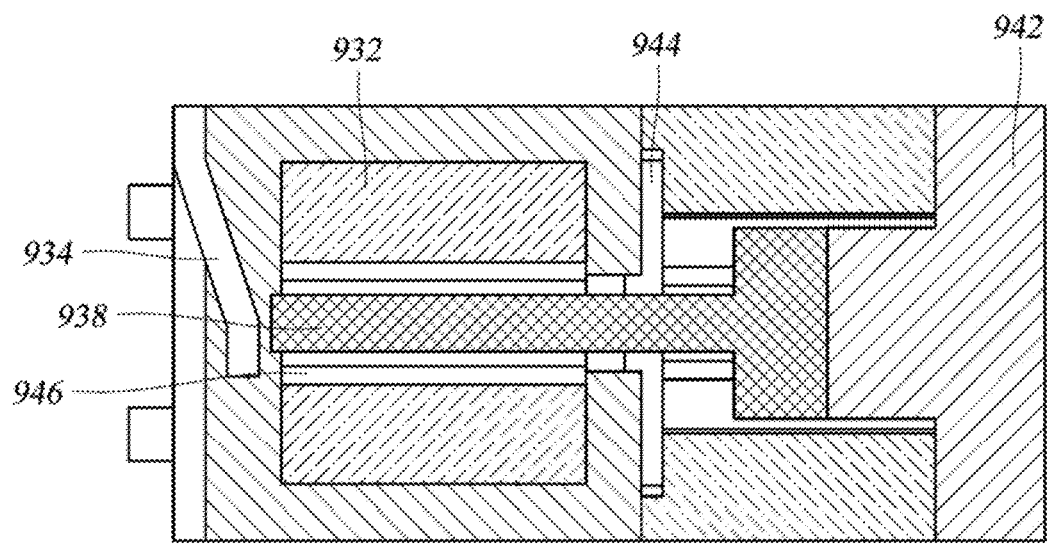
FIGS. 14G and 14H are various cross-sectional views demonstrating the operation of an implementation of a valve style insulin pump.
Figure 14H:
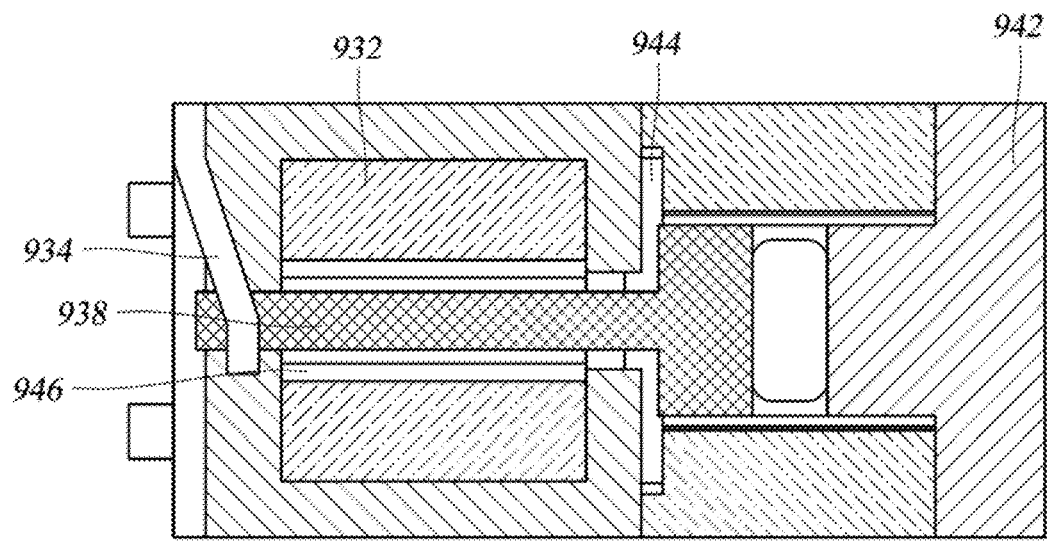

FIGS. 14G and 14H illustrate the operation of a solenoid 932 with a valve 938. The solenoid 932 may be any of the solenoids 932A, 932B, 932C, 932D of the valve style insulin pump 930. FIG. 9G illustrates the operation of the solenoid 932 when the solenoid 932 is not energized and thus the spring 934 pushes the valve 938 up into the sealer 942 which will close the insulin flow channel. FIG. 9H illustrates the operation of the solenoid 932 when the solenoid 932 is energized. When the solenoid 932 is energized, the valve 938 will push against the spring 934 and be forced downwards opening the insulin flow channel. The valve 938 may be forced against the top portion of the sealer 944. In some implementations, the valve 938 may not contact the top portion of the sealer 944.

In some implementations, the valve style insulin pump 930 may include a flow chamber which may control the maximum flow rate when all the solenoids 932A, 932B, 932C, 932D. In some implementations, a photo sensor may be included at the exit of the insulin flow channel 940. The photo sensor may detect whether the exit valve is open or closed and may measure the presence of air bubbles. In some implementations, a membrane made out of a permeable material such as polytetrafluoroethylene (PTFE) or one or more small holes may be added to vent accumulated air.

4. Example Gear and Plunger Pumps

Figure 14I:
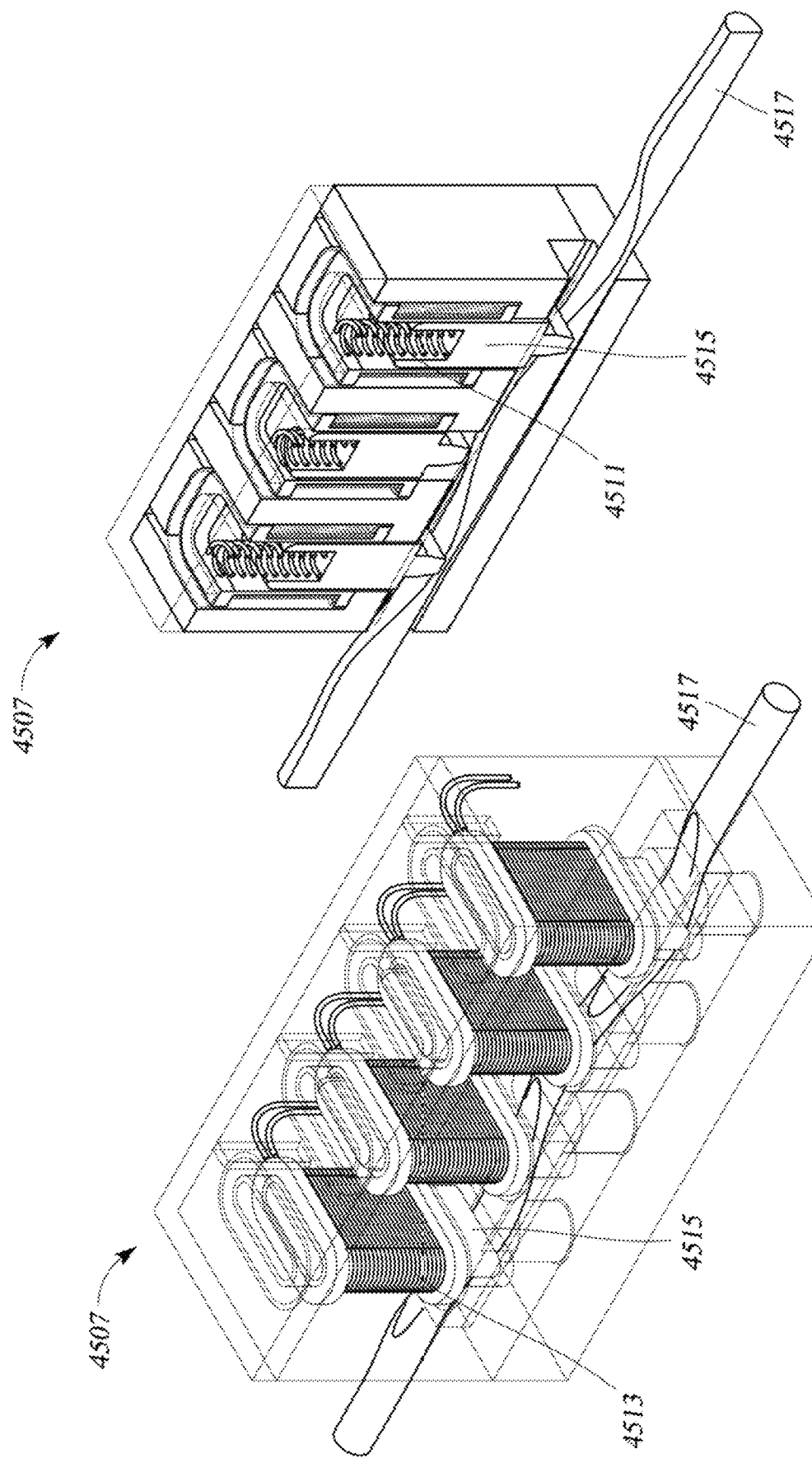
FIG. 14I illustrates an example plunger style pump of a disease management system.

In some examples, a pump head can utilize plungers to squeeze tubing and cause fluid to flow from a medication pouch to a cannula. FIG. 14I illustrates an example plunger style pump 4507 using a set of solenoids 4513 to drive plungers 4515 to squeeze tubing 4517. As illustrated, a solenoid plunger style pump 4507 may include a combination of components, including, but not limited to at least one solenoid, 4513, at least one plunger 4515, and at least one core spring 4511.

When not powered, a core spring 4511 may cause a plunger 4515 to extend at least part of its length outside the solenoid assembly. The plunger 4515 may be configured to squeeze or pinch tubing 4517 when extended. In some examples, a controller may send current through a solenoid 4513. When powered, the plunger 4515 inside the solenoid assembly may pull the plunger 4515 back into the solenoid assembly. As illustrated, a pump 4507 may include a plurality of solenoid assemblies and plungers. By controlling the power to each of the solenoid assemblies, a controller may be configured to cause the pump 4507 to alternate the application of pressure to different areas of tubing 4517 to, for example, deliver a bolus to a patient.

FIGS. 14J-1, 14J-2, and 14J-3 illustrates an example plunger style pump 4602 using an actuator. For example, as illustrated, a plunger style pump assembly 4602 may include some combination of tubing 4702, actuator(s) 4704, spring 4708, lock(s) 4718, gear(s) 4712, plunger(s) 4710, and cleat(s) 4714.

The tubing 4702 may, in some examples, be composed of a silicon material, such as a platinum cured silicon. An inner diameter of the tubing may be in a range of 0.1 to 1 mm, or a value outside that range, such as a value more or less than in that range. For, example, an inner diameter may be approximately 0.5 mm. An outer diameter of the tubing may be in a range of 0.1 to 2 mm, or a value outside that range, such as a value more or less than in that range. For example, an outer diameter may be approximately 1 mm. A working temperature of the tubing may be approximately 80 to 500 degrees Fahrenheit or a value outside that range. In some examples, a durometer hardness may be approximately 50 A or a value greater or less than 50 A. The tubing may be configured to hold fluid at a desired pressure when force is applied. For example, if a 20 gF is applied to the plunger, the tubing may be configured to hold fluid in the tubing at a pressure of 300 mmHg or more or less. This holding force can, advantageously, help ensure proper operation of a pouch bursting safety mechanism.

Figures 1, 14J:
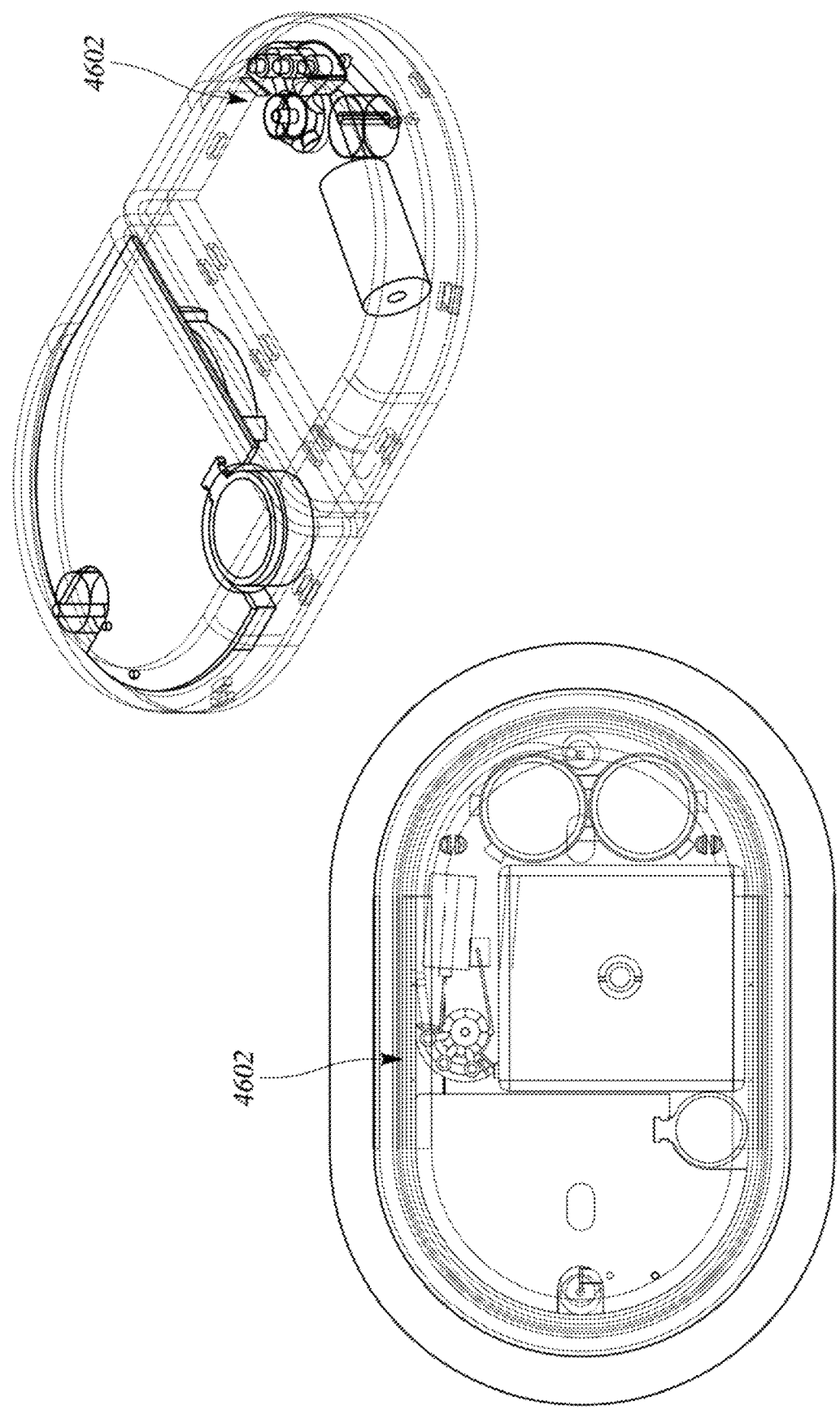
Figures 2, 14J:
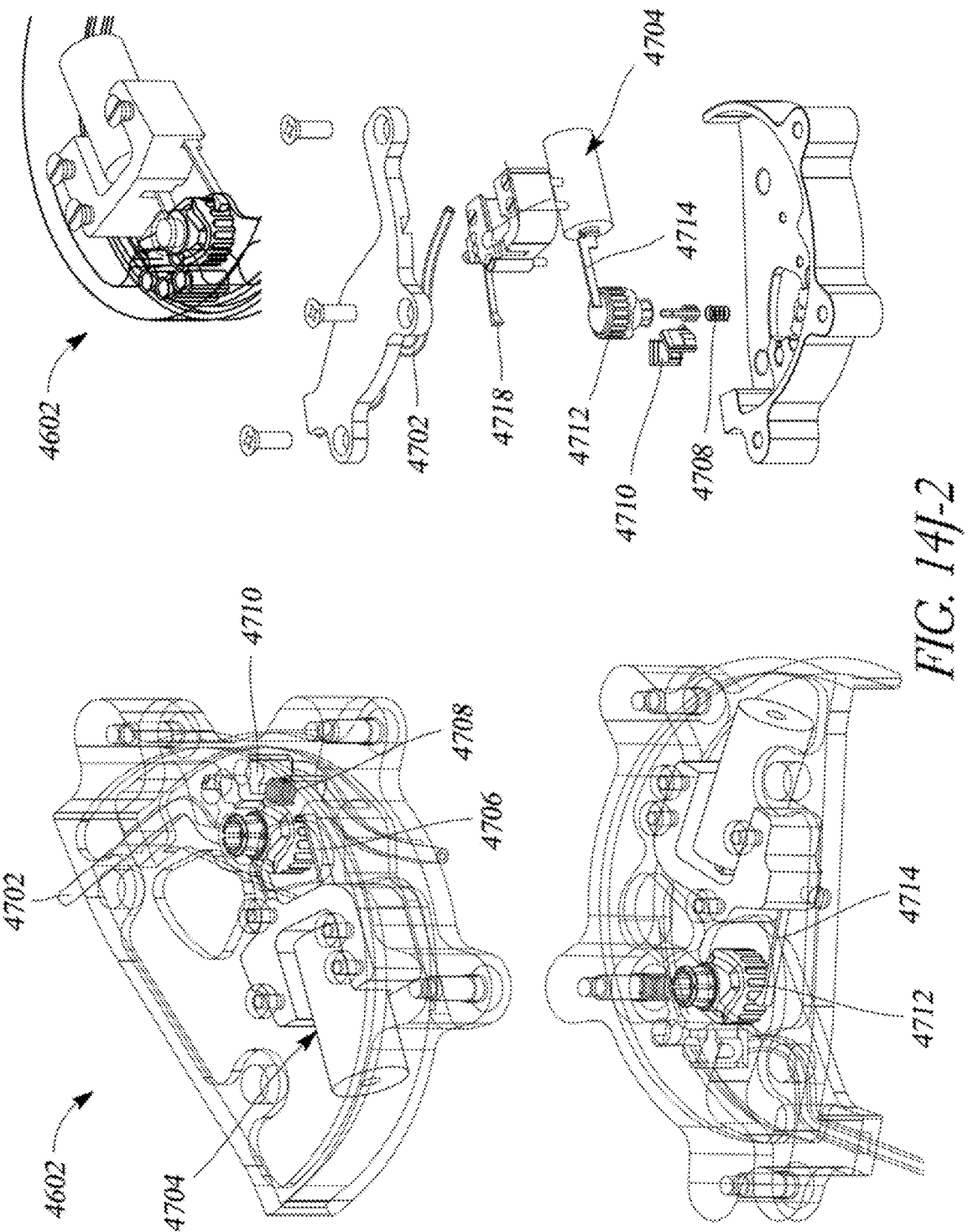
Figures 3, 14J:
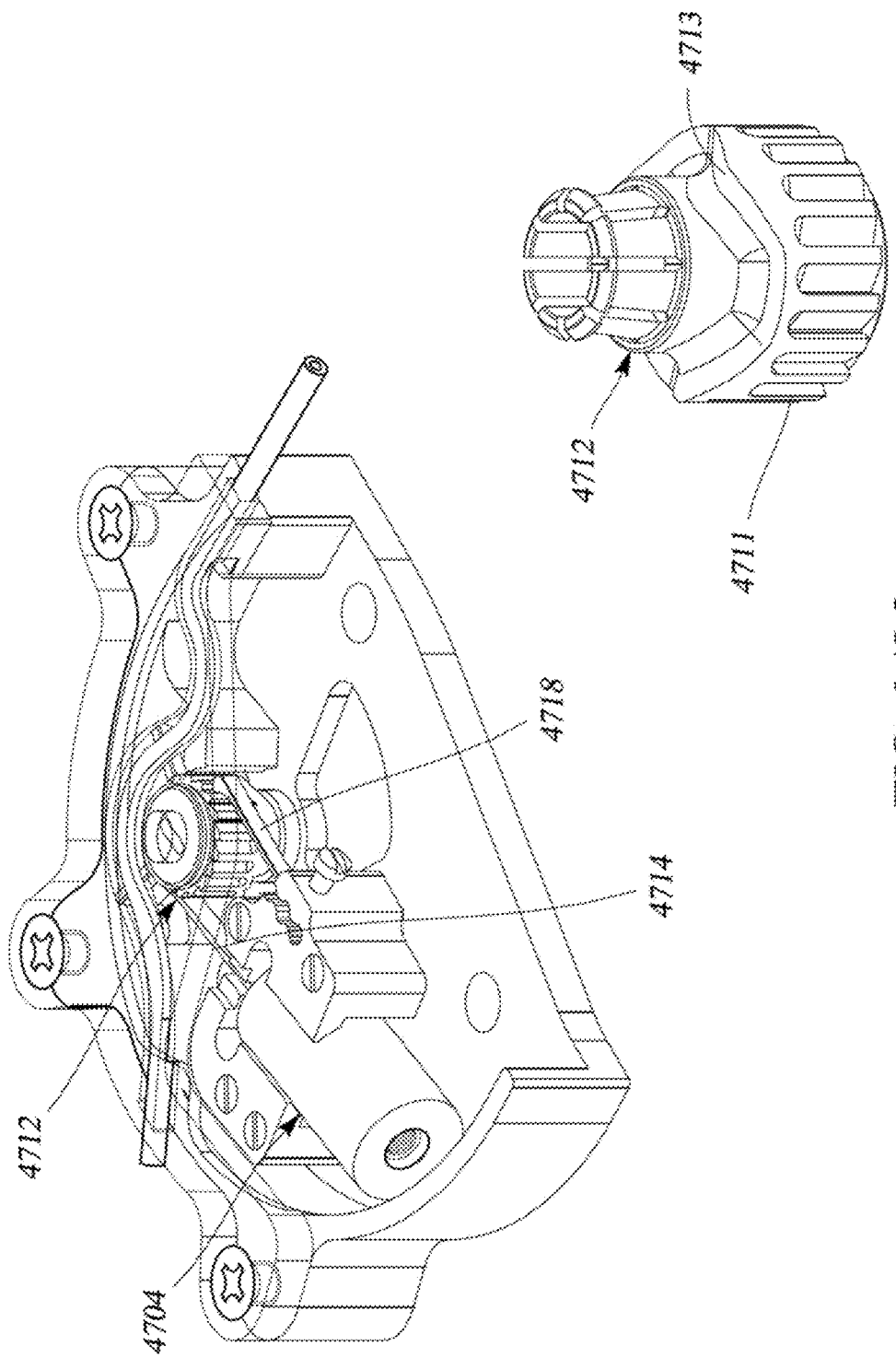

In some examples, such as illustrated in FIG. 14J-3, a gear 4712 may have a plurality of humps 4713 configured to engage one or more plungers 4710 as it turns. For example, a gear 4712 may have 3 humps. The humps may have a slope. For example, the humps may have approximately 30 degree slope. Advantageously, using a plurality of approximately 30 degree sloped humps may help avoid excessive side load on the gear 4712 and accordingly reduce the likelihood of jamming. However, other slopes are also possible. For example, a slope may be between 0 and 45 degrees, or in a value outside that range. A gear diameter may be in the range of 1 to 10 mm, or a value outside that range. For example. A gear diameter may be 5 mm. In some examples, a number of gear teeth 4711 may be 18. However, other values are also possible.

The actuator(s) 4704 may be configured to engage with the gear(s) 4712 using at least one cleat(s) 4714. The actuator(s) 4704 may be configured to include a solenoid coil and metal rod. The metal rod may be coupled to the cleat 4714. By controlling the power to the solenoid coil, the actuator 4704 may be configured to move the metal rod and accordingly, the cleat 4714. The positioning of the actuator may be such that the cleat 4714 engages with teeth 4711 of the gear 4712, rotating the gear a set amount. The hardness of the cleat 4714 may be similar to the hardness of the gear and/or gear teeth. Advantageously, this may help prevent failure by encouraging equal wear between components. Also helpful in preventing wear is the reduction of strain or force needed to actuate. A longer cleat may help reduce strain and accordingly, reduce fatigue rate.

A lock 4718 may be used to help prevent unintended rotation of the gear. For example, the lock 4718 can allow the gear 4712 to rotate forward with minimal interference but will induce high blocking force to prevent reverse operation.

Figures 1, 14K:
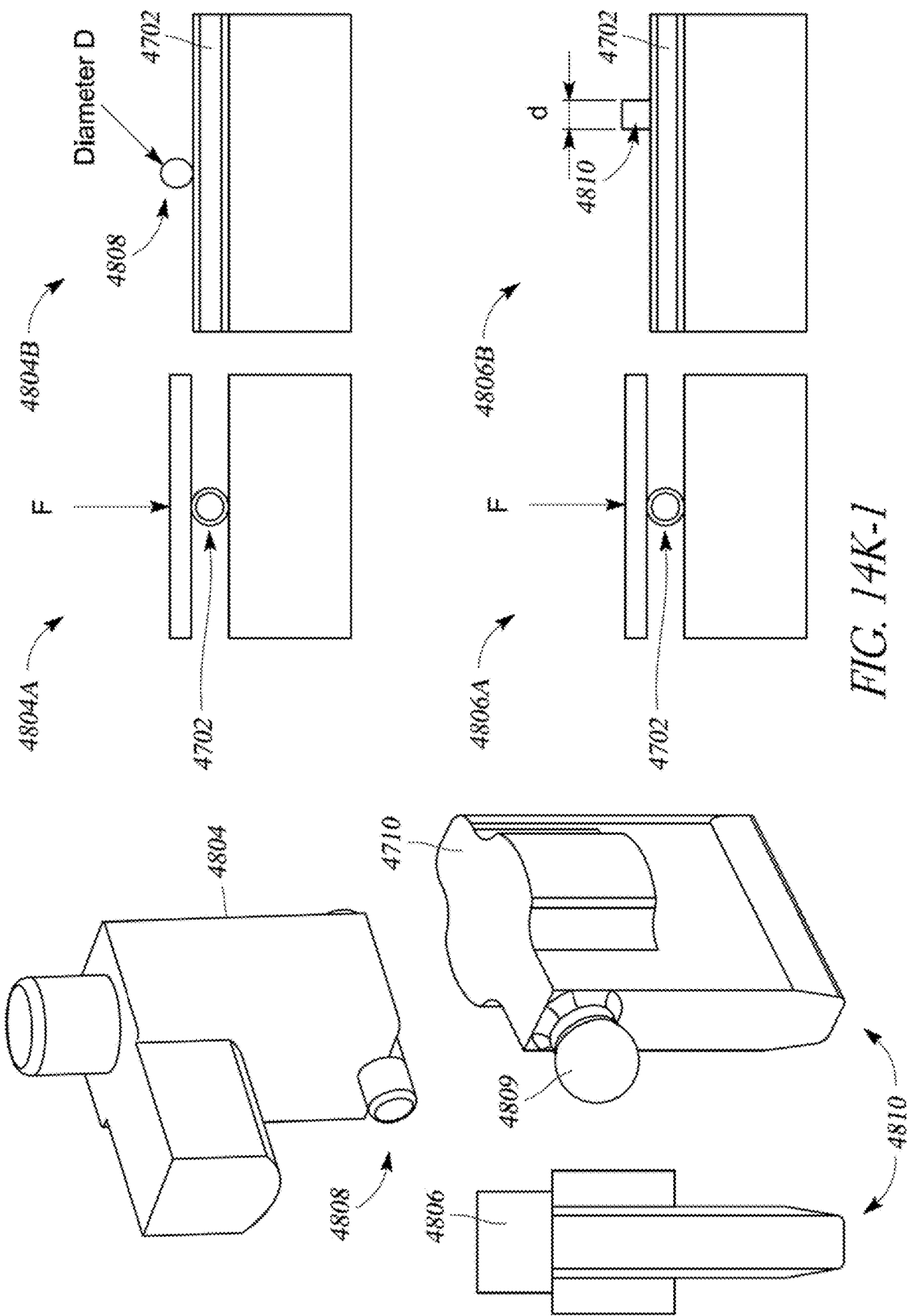
Figures 2, 14K:
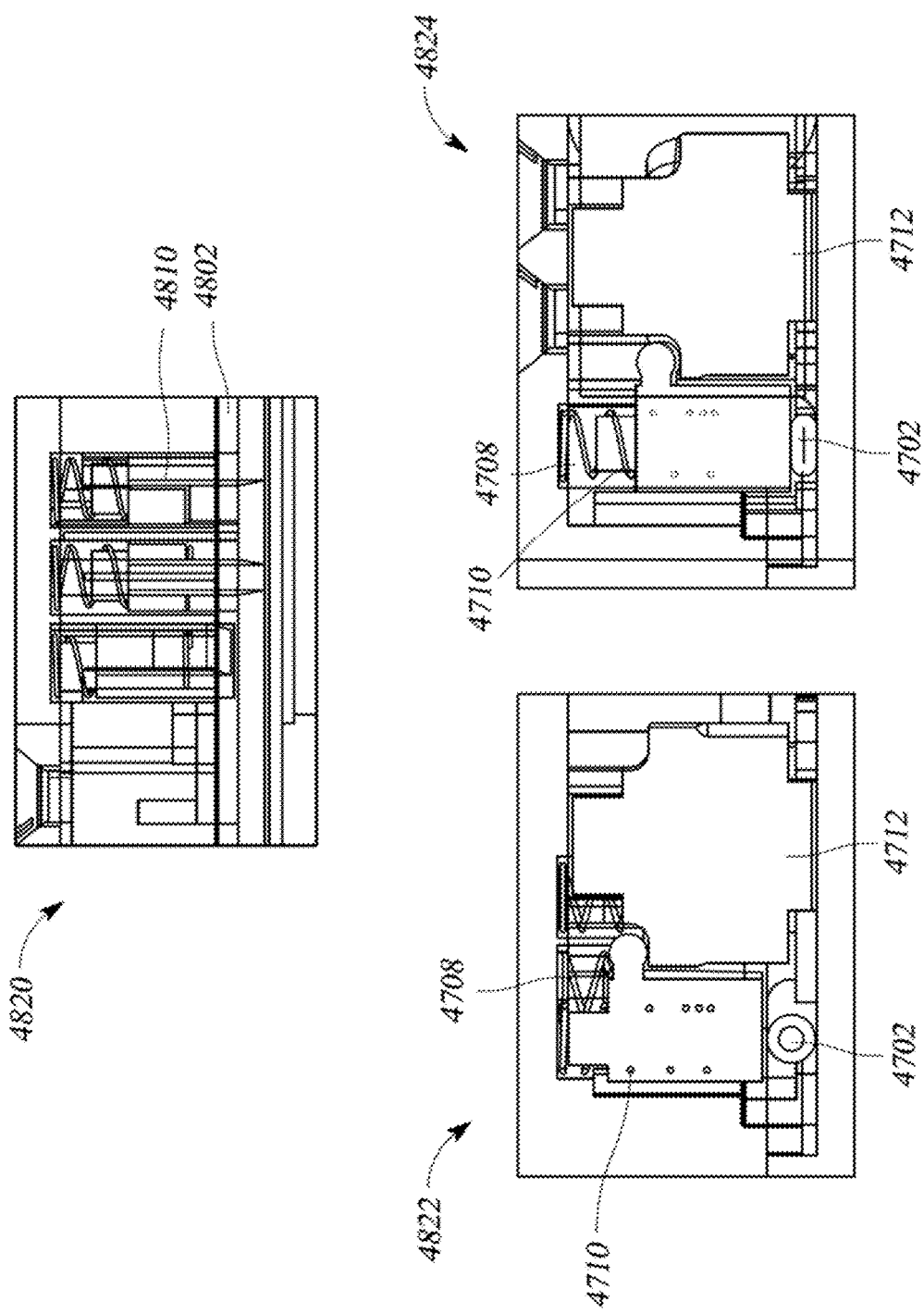
Figure 14K:
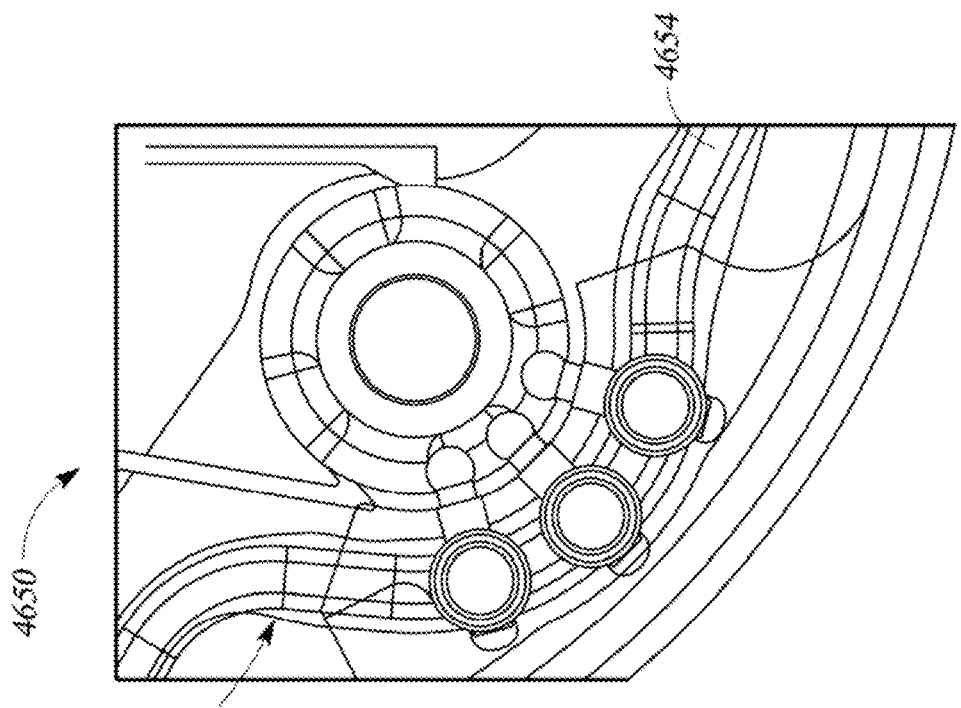
Figure 3:
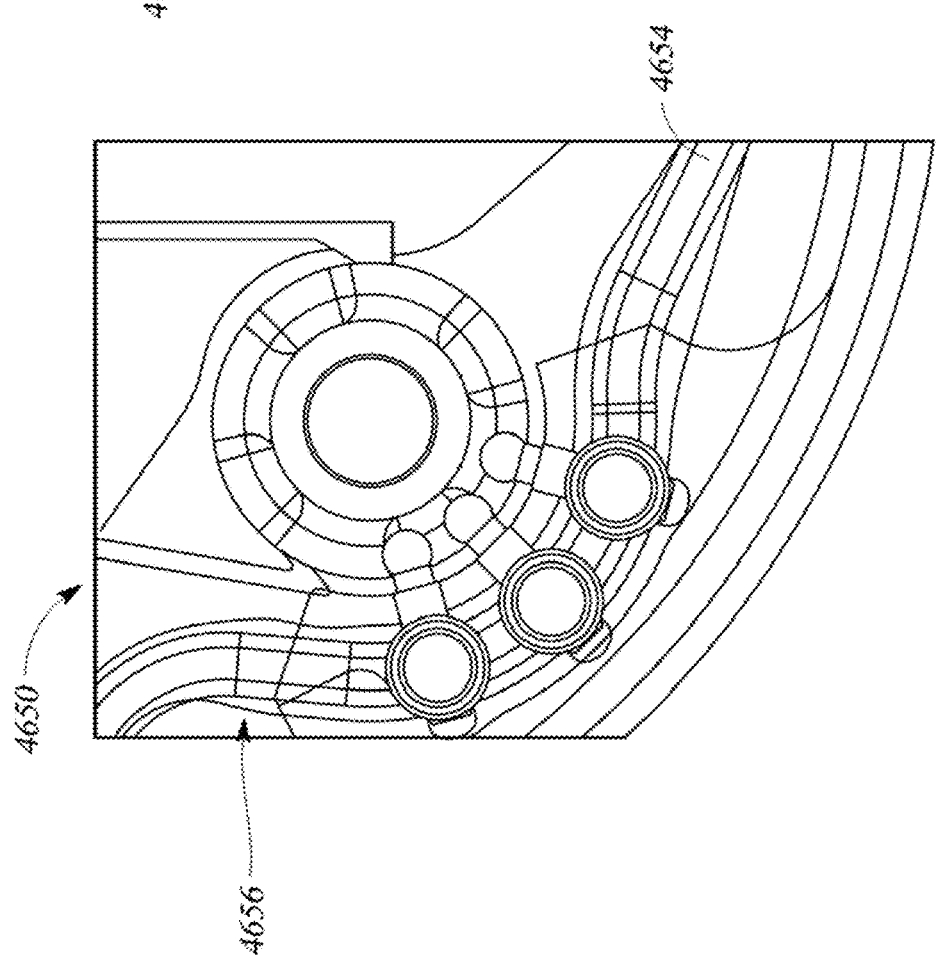

One or more plungers 4710 may be configured to apply pressure to the tubing 4702 upon being engaged by the gear 4712. FIG. 14K-1 illustrates an example plunger 4710 and a variant plunger 4804. A plunger 4710 may be configured to have an approximately flat contact area 4810 configured to press against tubing 4702. The plunger shape may be selected to reduce the force necessary to collapse the tube. If a plunger has a steep slope (such as plunger 4804), then additional lateral spring forces are exerted onto the plunger.

In turn, higher force needed to apply pressure will increase the amount of power that a battery must supply to operate the pump. Views 4806A and 4806B illustrate side and head one views of a plunger contact area 4810 pressing on a tube 4702. Advantageously, as compared to the variant 4804, which may be used in some configurations of the pump system, such as illustrated in FIG. 14M, a smaller diameter d for the contact area 4810 cross section is needed as compared to the plunger variant 4804 using a circular or cylindrical contact portion 4808 in order to achieve equivalent force on the tubing 4702. Thus, the plunger 4710 may be more efficient.

As illustrated in FIG. 14K-1, a plunger 4710 may include a portion 4809 configured to be engaged by the gear 4712. FIG. 14K-2 illustrates example engagement of the plungers 4710 by the gear 4712. For example, view 4820 illustrates a storage state of the device where the plungers 4710 are up and not applying pumping pressure to the tubing 4702. View 4822 illustrates a side view of a plunger up state of the device where the gear 4712 is in a position so that an engagement portion 4809 of the plunger 4710 rests at an apex or near apex position of the hump, lifting the plunger 4710 up. View 4824 illustrates a side view of a plunger down state of the device where the gear 4712 is in a position so that an engagement portion 4809 of the plunger 4710 rests at a valley or near valley of the hump portion of the gear 4712. The spring 4708 may then press the plunger 4710 down and squeeze the tubing 4702. Thus, as the gear rotates, the engagement portion 4809 may travel along the humps and valleys of gear, lifting and pressing down on the tubing 4702 periodically.

A storage state of the device may have two plungers down that are, for example, the plungers closest to the pouch. This storage state may reduce the number of air pockets possible to form during manufacture or fill of the pouch. Advantageously, starting at this state may give a reliable starting state for programming in priming the disease management system for first time use. FIG. 14K-3 illustrates an example priming process or cycle. For example, view 4650 shows a pre-primed state and view 4652 shows a primed state.

A device priming cycle may be configured to perform quickly. For example, a device priming cycle may be performed in less than 1 minute, less than 30 seconds, less than 15 seconds, less than 10 seconds, or other amount of time more or less than 1 minute. In some examples, a priming cycle may occur in roughly thirteen seconds. This time may be defined by the tube length and diameters from the cannula tip to the middle peristaltic plunger. The priming process may occur prior to, during, or after application of the device to the user. For example, the priming process may occur between the removal of the device from packaging and the application to the patient's body. The priming process may be initiated by firmware through a decision logic based on wireless connections to another device or the cloud. The pressure generated from the priming process may cause the fluid 4654 to blow through a sterilization gel cap in the fluidic path 4656. Where priming occurs prior to application, upon application, the remaining gel cap may be ripped off by the applicator action.

Figure 14L:
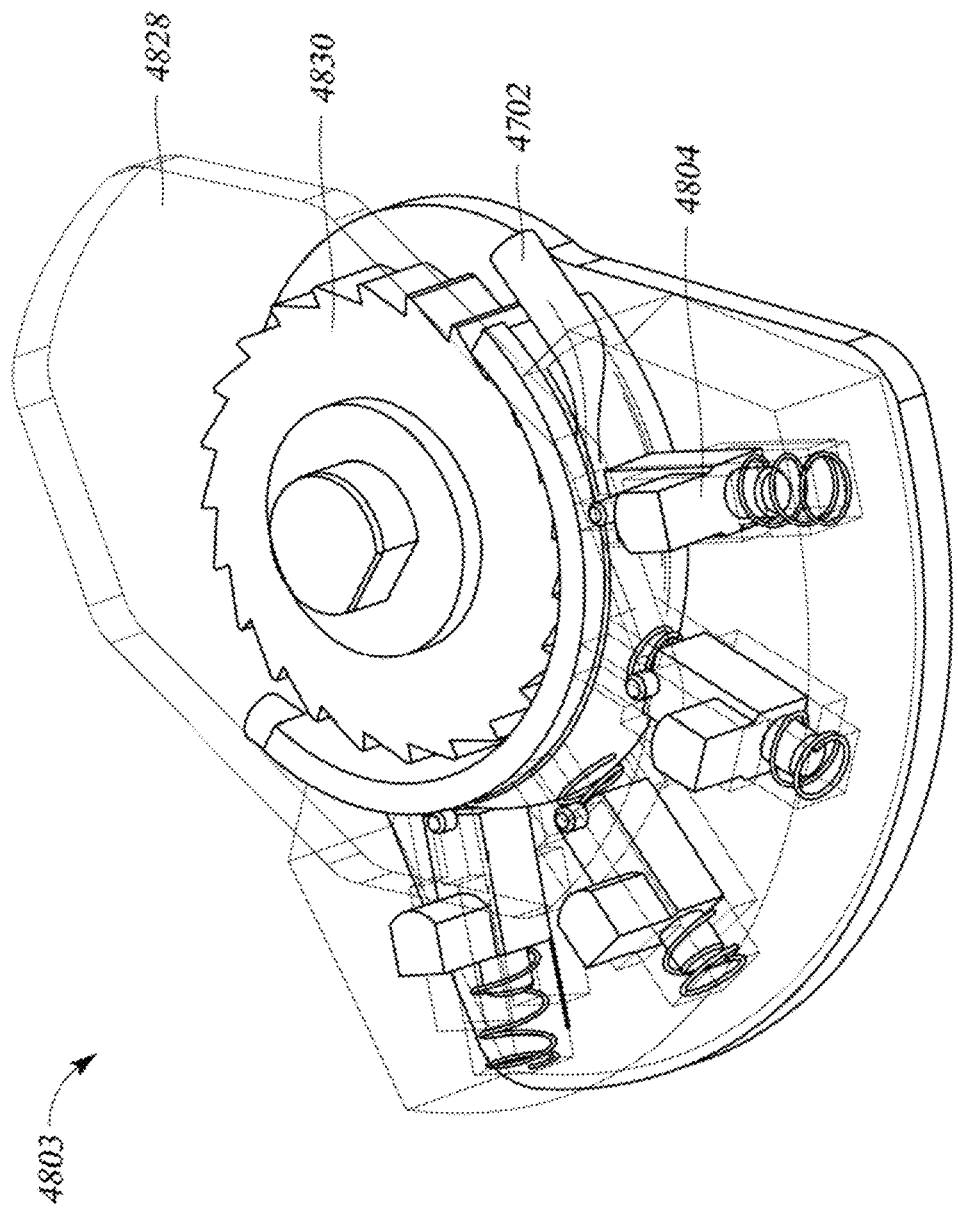
FIG. 14L illustrates another example plunger style pump of a disease management system.
Figure 14M:
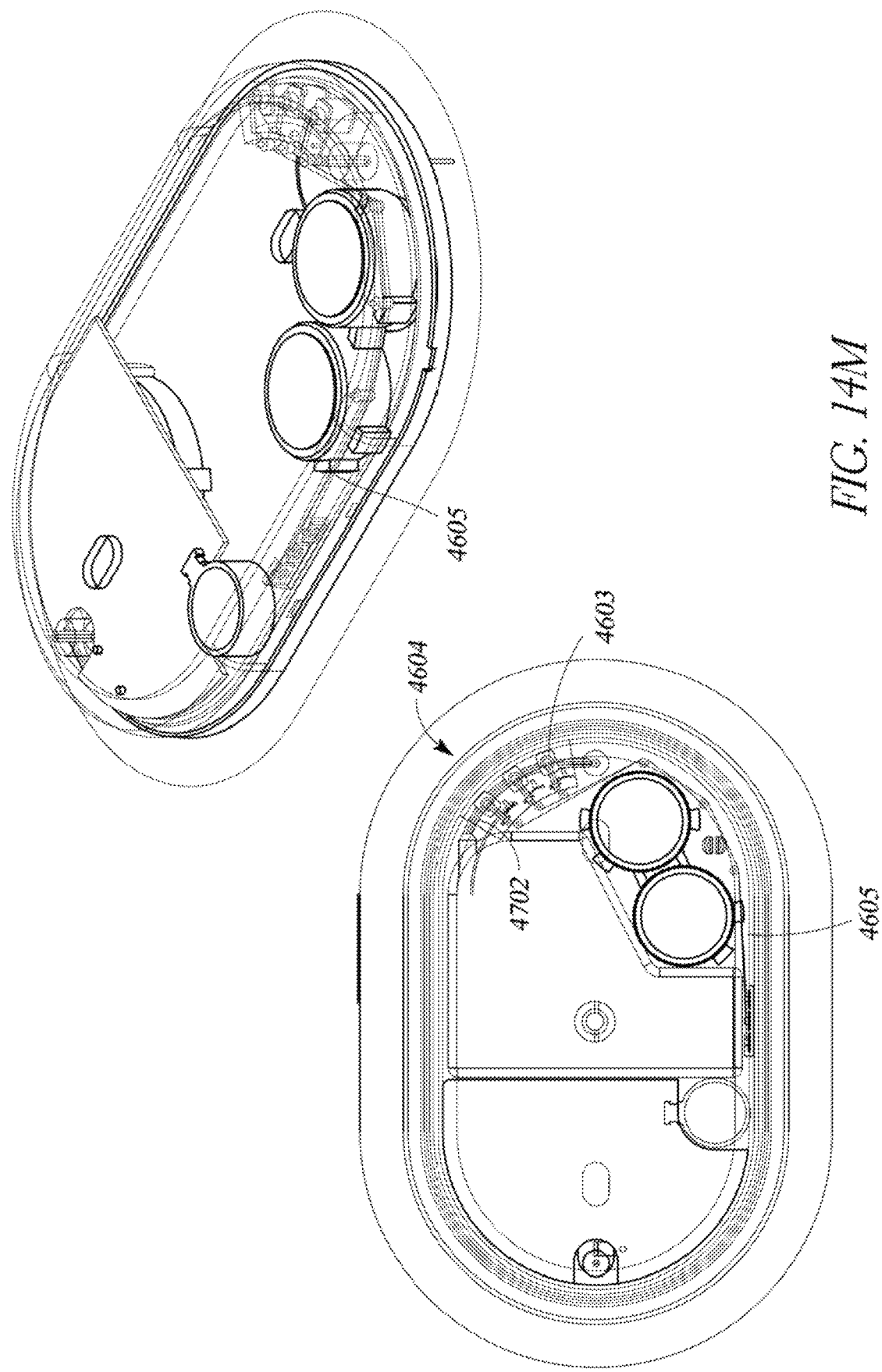
FIG. 14M illustrates an example muscle wire pump of a disease management system.
Figure 140:
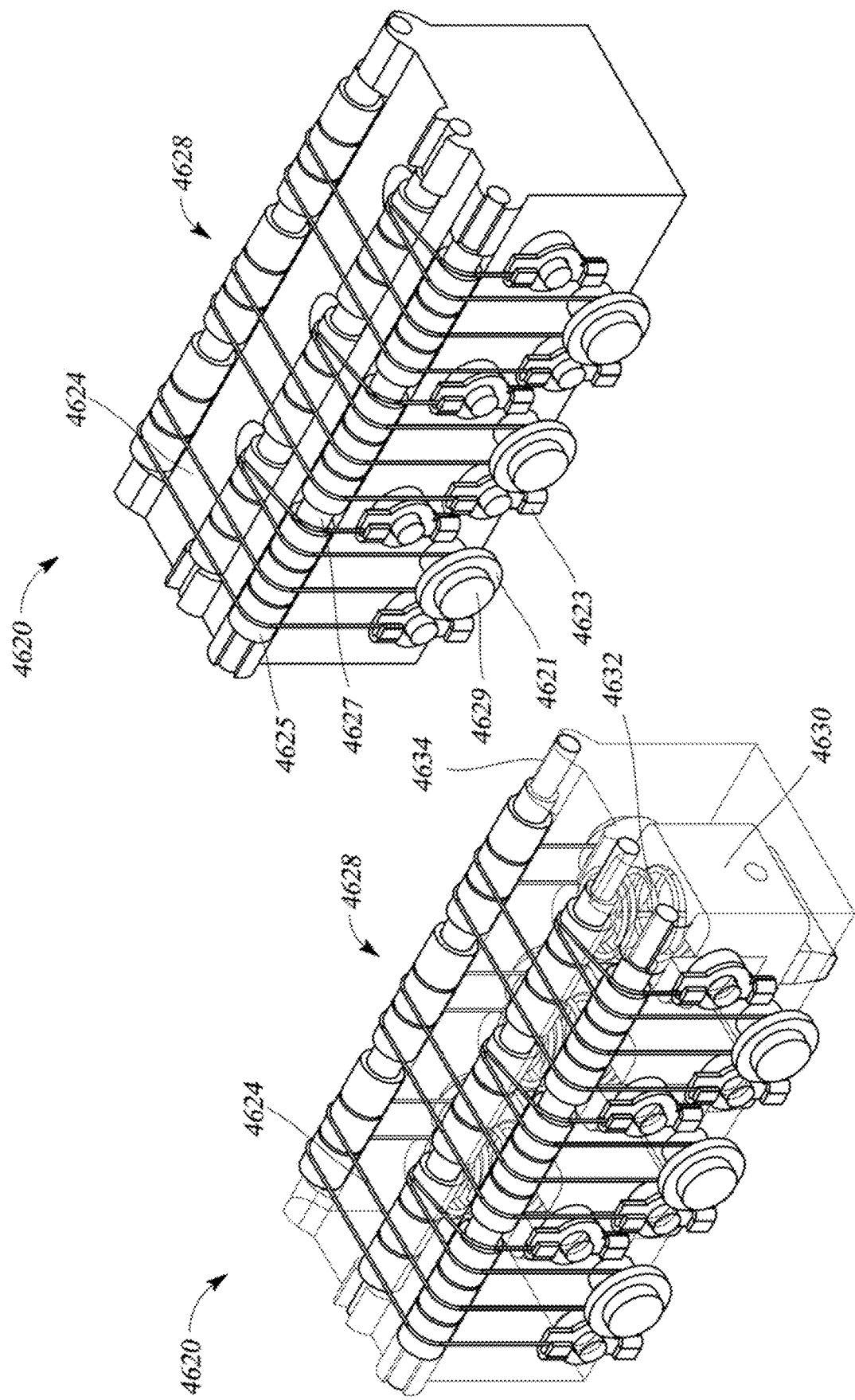

FIG. 14L illustrates an example plunger style pump 4803. In the illustrated pump, an actuator may be configured to engage a gear 4830, the gear 4830 may be configured to engage one or more plungers 4804 through movement of an engagement portion 4828. The engagement portion 3828 may include a plate or disk shaped to cause at least one of the one or more plungers to move outward when engaged with a larger portion of the plates radius and move inward, with the help of springs, when engaged with a smaller portion of the plates radius. As the plungers move in and out, the plungers 4804 may be configured to apply a force to a tubing 4702 orientated horizontally in relation to the plungers 4804. As illustrated, a tubing 4702 may be oriented to lie between the gear 4830 and the plungers 4804. Thus, as the plate or disk is rotated, the one or more plungers may periodically apply pressure to the tubing 4702.

5. Example Muscle Wire Pumps

FIG. 14M illustrates an example plunger style pump 4604 using muscle wire 4605. In the illustrated example, plungers 4603 are engaged with muscle wire 4605. The muscle wire 4605 may include nitinol wire. The muscle wire 4605 may be configured to undergo deformation in response to the application of current. For example, when an electrical current is applied, the muscle wire 4605 may contract, allowing a spring to push the plunger down onto tubing 4702. When no power is applied, the muscle wire 4605 may loosen, compressing a spring and lifting the plunger 4603. Other configurations of muscle wire, springs, and plungers may also be possible. By modifying the power to the wires 4605, the plungers 4603 may squeeze and perform pumping actions on the tubing 4702, facilitating transfer of medication from a pouch to the cannula.

FIG. 14N illustrates another example plunger style pump 4601 using muscle wire. In the illustrated example, one or more plunger(s) 4610 may be configured to apply force to tubing 4612 as a result of an interaction between at least a spring 4608 and muscle wire 4606. In the illustrated example, muscle wire 4606 may be configured to be in the shape of a spring. The muscle wire 4606 may be configured to deform when an electrical current is applied. For example, when an electrical current is applied, the muscle wire 4606 may contract, allowing a spring 4608 to push the plunger down onto tubing 4612. When no power is applied, the muscle wire 4606 may loosen, compressing the spring 4608 and lifting the plunger. Other configurations of muscle wire, springs, and plungers may also be possible. By modifying the power to the muscle wire spring 4608, the plunger 4610 may squeeze and perform pumping actions on the tubing 4612, facilitating transfer of medication from a pouch to the cannula.

FIG. 14O illustrates another example plunger style pump 4620 using muscle wire. In the illustrated example, one or more plungers 4630 may be configured to apply force to tubing (not shown) as a result of interaction between at least a spring 4632 and muscle wire 4628. In the illustrated example, muscle wire 4628 may be wrapped around or otherwise in contact with one or more rollers 4635 resting on spacers 4627 on a center cam 4634. The spacers 4627 and center cam 4634 may be located on a top side of the pump assembly. However, other configurations are also possible. Additionally or alternatively, the muscle wire 4628 may be wrapped around one or more rollers 4621 configured to rotate around at least one pin 4629 placed on a side of the pump assembly. However, other configurations are also possible. The muscle wire 4624 may be coupled to one or more plungers 4630. The muscle wire 4624 may be configured to receive electrical current through a wire terminal 4623. When powered, the muscle wire 4624 may contract and move with rollers, causing a plunger 4630 to lift. When no power is applied, the muscle wire 4624 may loosen and allow a spring 4632 to push the plunger down onto tubing (not shown). By modifying the power to the muscle wire 4624, the plunger 4630 may squeeze and perform pumping actions on the tubing, facilitating transfer of medication from a pouch to the cannula.

Figure 14P:
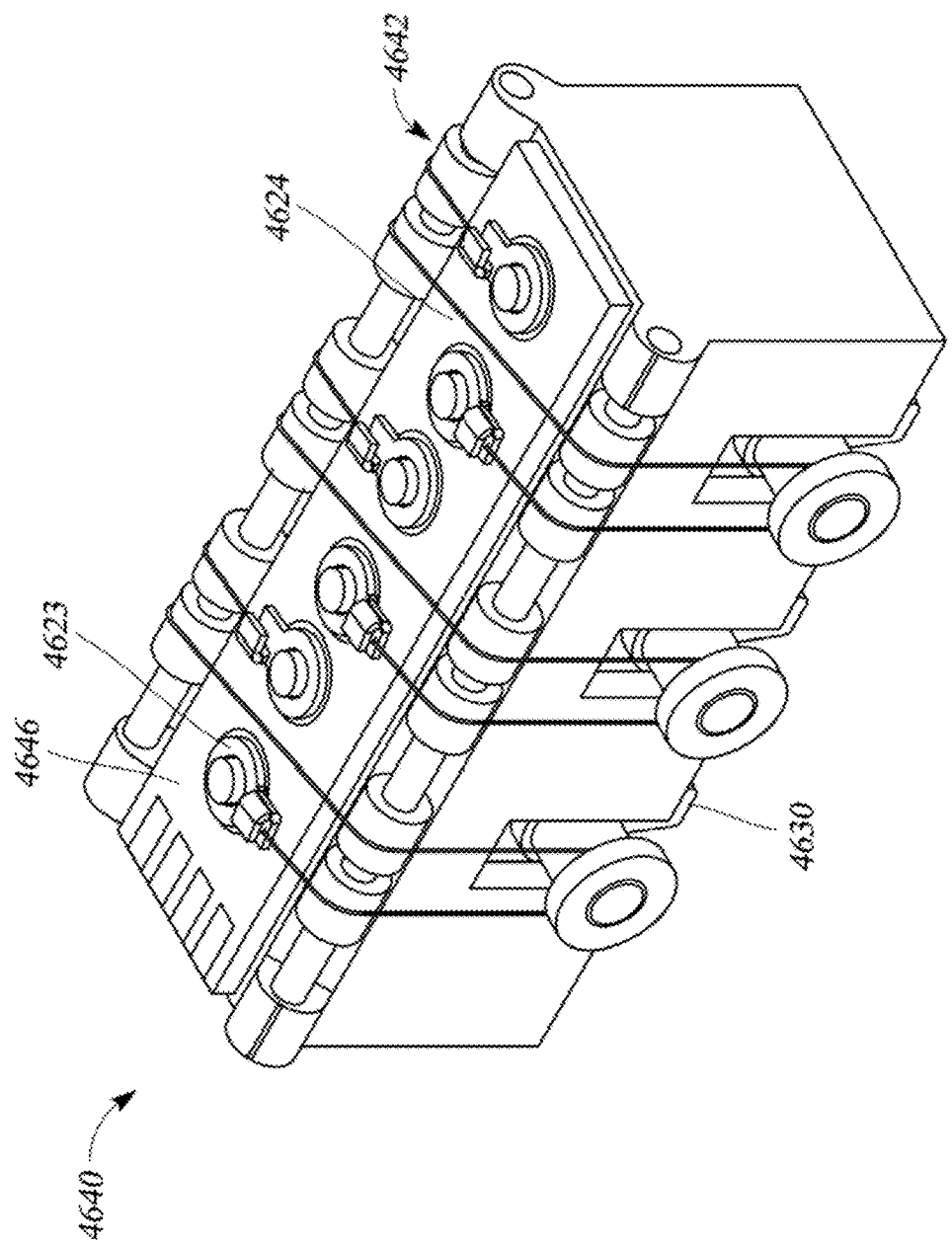
FIG. 14P illustrates a perspective view of another example muscle wire pump of a disease management system.

FIG. 14P illustrates an alternative configuration 4640 of a pump assembly using rollers and muscle wire such as discussed with reference to FIG. 14N. In the illustrate example, a circuit board 4646 is configured to rest on a first surface of the assembly (for example, the top surface). The circuit board 4646 may include one or more wire terminals 4623 configured to be in electrical connection with the muscle wire 4624. The muscle wire 4624 may be in contact with one or more rollers 4642. The one or more rollers 442 may be configured to rotate around a center cam located at a corner location on the side of the circuit board 4646. However, other configurations are also possible. The muscle wire 4624 may be configured to receive electrical current through the wire terminal 4623. When powered, the muscle wire 4624 may contract and move with rollers, causing a plunger 4630 to lift. When no power is applied, the muscle wire 4624 may loosen and allow a spring (not shown) to push the plunger down onto tubing (not shown). By modifying the power to the muscle wire 4624, the plunger 4630 may squeeze and perform pumping actions on the tubing, facilitating transfer of medication from a pouch to the cannula.

6. Example Piston Pump

Figure 14Q:
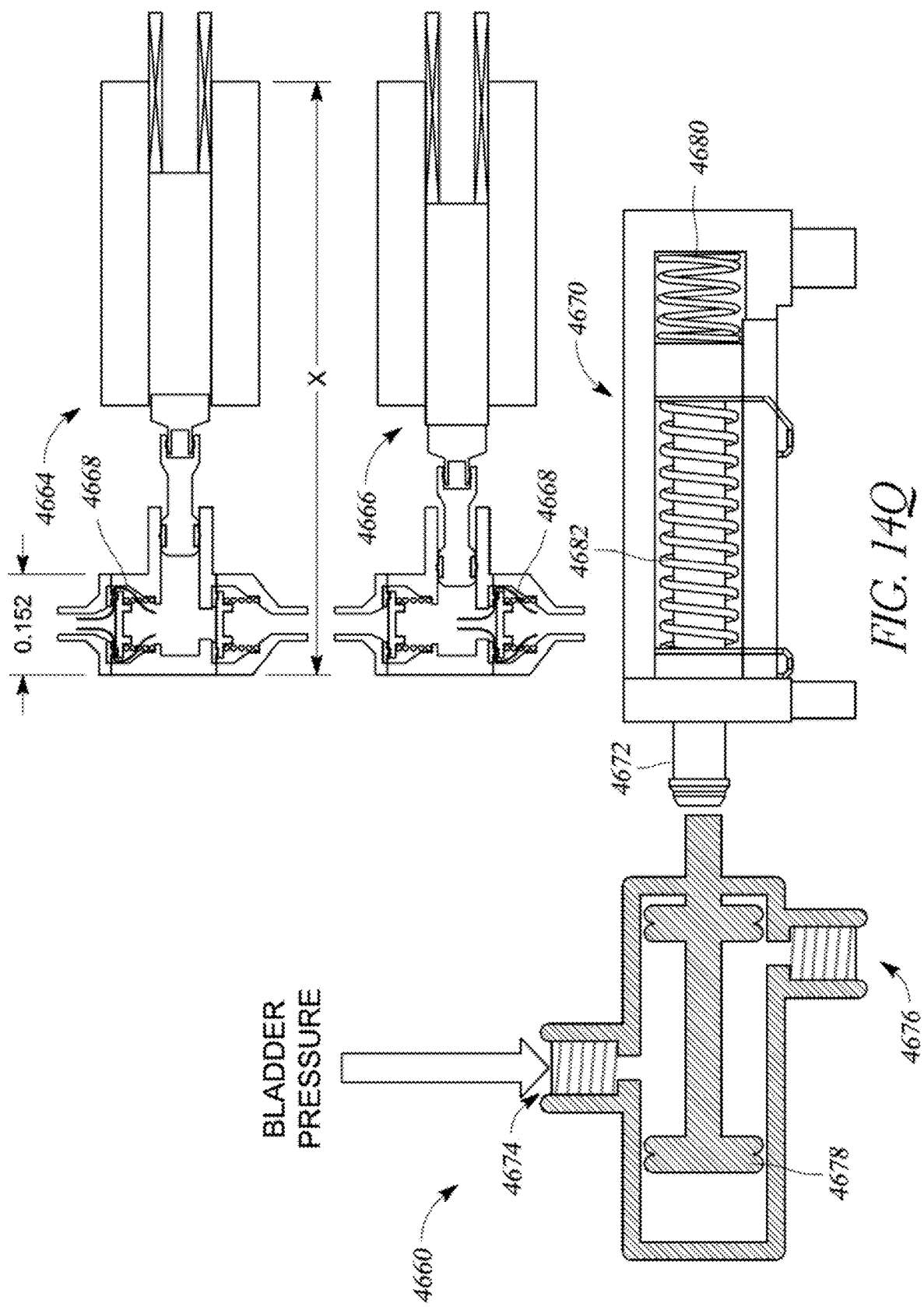
FIG. 14Q illustrates an example piston pump of a disease management system.

FIG. 14Q illustrates an example piston pump that may be used as part of a pump assembly in a disease management system. In the illustrated example, a pump assembly may include a piston assembly 4670 and valve assembly 4660.

The piston assembly 4670 may include a combination of one or more standard springs 4680 and muscle wire springs 4682. The muscle wire springs 4682 may be configured to contract when powered, causing a rod 4672 to extend outward from the piston assembly 4670 and engage a valve assembly 4660. In some examples, the valve assembly 4660 may include a valve 4678 configured to move fluid from an inlet 4674 to an outlet 4676 as it changes position horizontally in response to engagement by the piston 4672. The valve 4678 may include a cylindrical valve with two or more larger cylinders on ends of the valve. In some examples, the larger cylinders may form a seal with the inner diameter of the valve such that fluid 4668 is moved with the movement of the valve. In some examples, the valve 4678 may include a spool valve or other directional control valve. As illustrated, a piston assembly may be in a contracted state 4664, drawing fluid 4668 from a pouch or bladder. When the piston assembly is in an extension state 4666, fluid 4668 may be pushed out of the valve assembly 4660 and towards a cannula.

E. EXAMPLE AIR BUBBLE DETECTION OR REMOVAL

Air bubbles pumped into a user through an insulin pump can pose a serious health risk during closed loop care. While air bubbles alone entering into the interstitial space may not be considered a significant risk to a patient, there are some concerns about air bubbles entering vasculature when they reach a size upwards of 20 mL. In some examples, risk may also arise where an air bubble displaces insulin such that a patient becomes underdosed, which may lead to a patient becoming hyperglycemic. This alone may be a minor risk as the volumes of underdosed insulin are on the order of less than 1 unit. In some examples, risk may arise if underdosing occurs frequently enough an algorithm that personalizes dosing begins estimating that a person with type 1 diabetes is insulin resistant, which may over time pose significant risk to a patient.

A treatment system described herein may include one or more air bubble detection sensors for monitoring or detecting air bubbles from drug delivery devices, such as an insulin pump, infusion pump for saline, or other drug delivery device. An air bubble detection sensor can determine an amount of air bubble in an insertion tube, so that a drug delivery device can compensate for air bubble displacement of a drug in an injection dose and/or notify a user to perform an action to remove the air bubble. In some examples, long-term air bubble quantification can be tracked and used to correct for potentially wrongly assigned insulin resistance by an algorithm that personalizes dosing of insulin.

An air bubble detection sensor may include an optical sensor system (using light emitting diode and photodiode), pressure sensor system (mechanical), ultrasonic sound system, and/or capacitive sensor system.

Figure 15A:
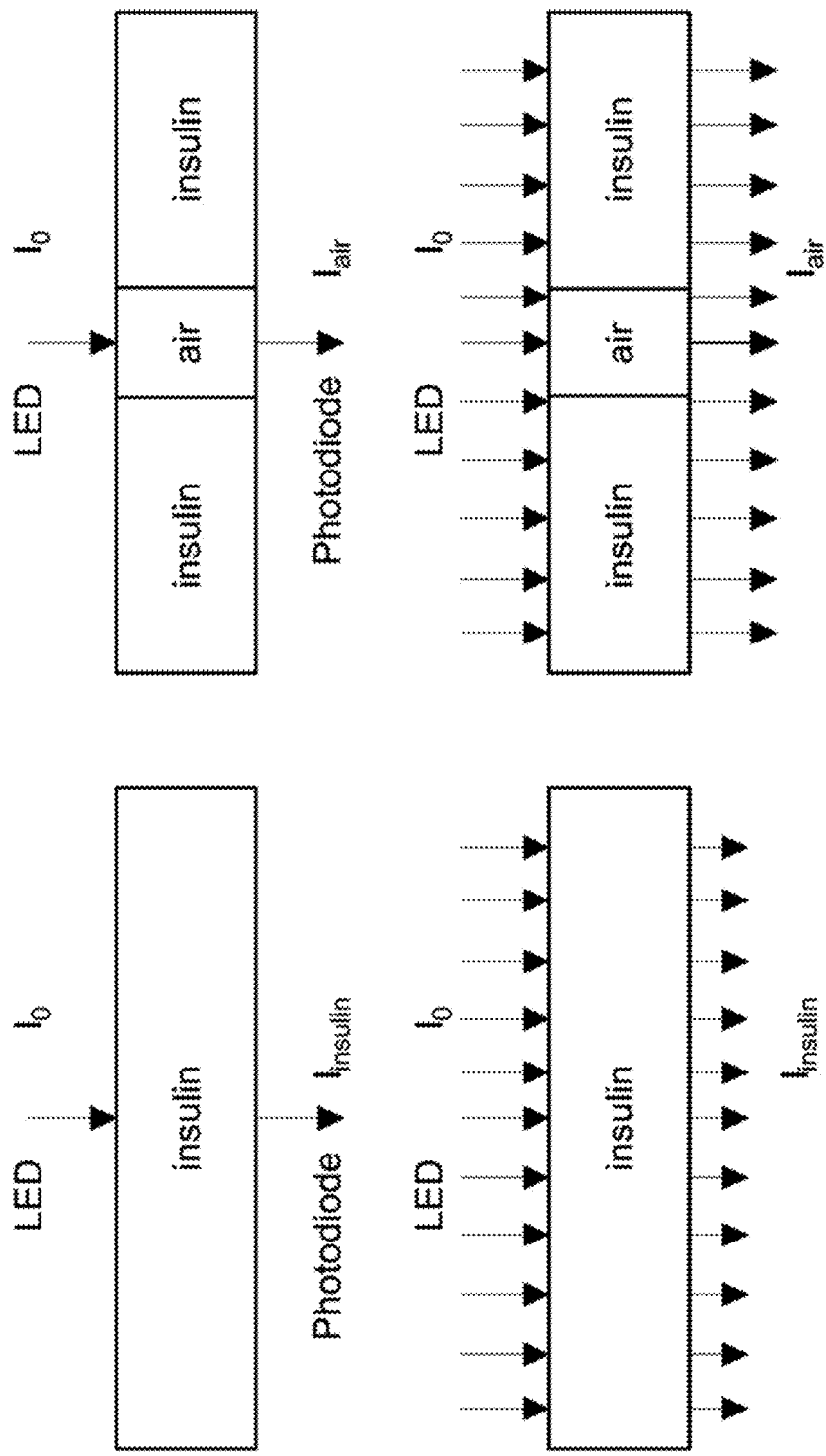

In some examples, an air bubble detection sensor may include an optical detection system. For example, an optical detection system may include absorptive, scattering, or other optical sensing method to detect air bubbles. For example, detection may occur if knowledge of an initial intensity Jo of light from a light source (such as an LED) is known or characterized and a change in signal as the light passes through a channel containing the insulin, such as an insertion tube. Drugs or nutrition have higher light absorption or scatter than air. As illustrated in FIG. 15A, when air enters an insertion tube, the absorbance from the light will be lower than if there was no air. Thus, a signal associated with no air bubbles ($I_{insulin}$) may be lower than a signal associated with the presence of air bubbles ($I_{air}$). In some examples, an optical detection system may emit light from one or more light sources, such as an LED, narrowly or across a larger area of a channel containing insulin from a first side of the channel. One or more detectors may be configured to receive the attenuated or absorbed light on the other side of the channel containing insulin.

Figure 15B:
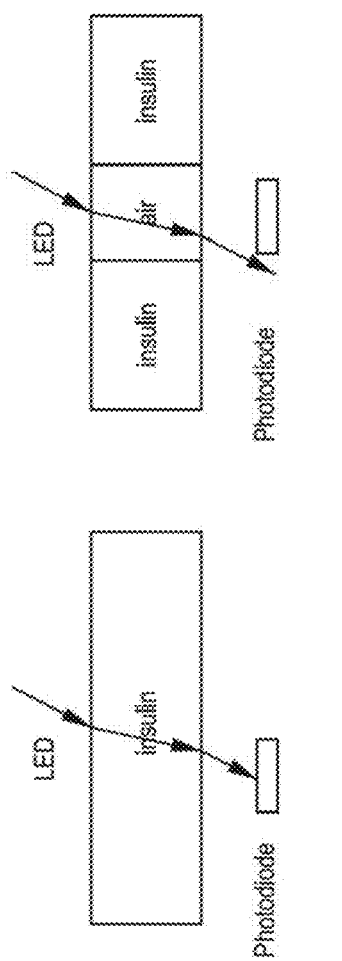

In another example, an optical detection system may include a system based on refraction. For example, drugs or nutrition may have refractive index different than air. An orientation of at least one light source and matching detector may be positioned so as to take advantage of the different angle of refraction that may occur as a result of the different refractive indices of air and nutrition or drugs, such as insulin. For example, as illustrated in FIG. 15B, when air enters an insertion tube, a detector (or photodiode) can be positioned such that when light is redirected due to a refractive index change of the inclusion of air in the channel, there will be lower signal levels than without the inclusion of air.

Figure 15C:
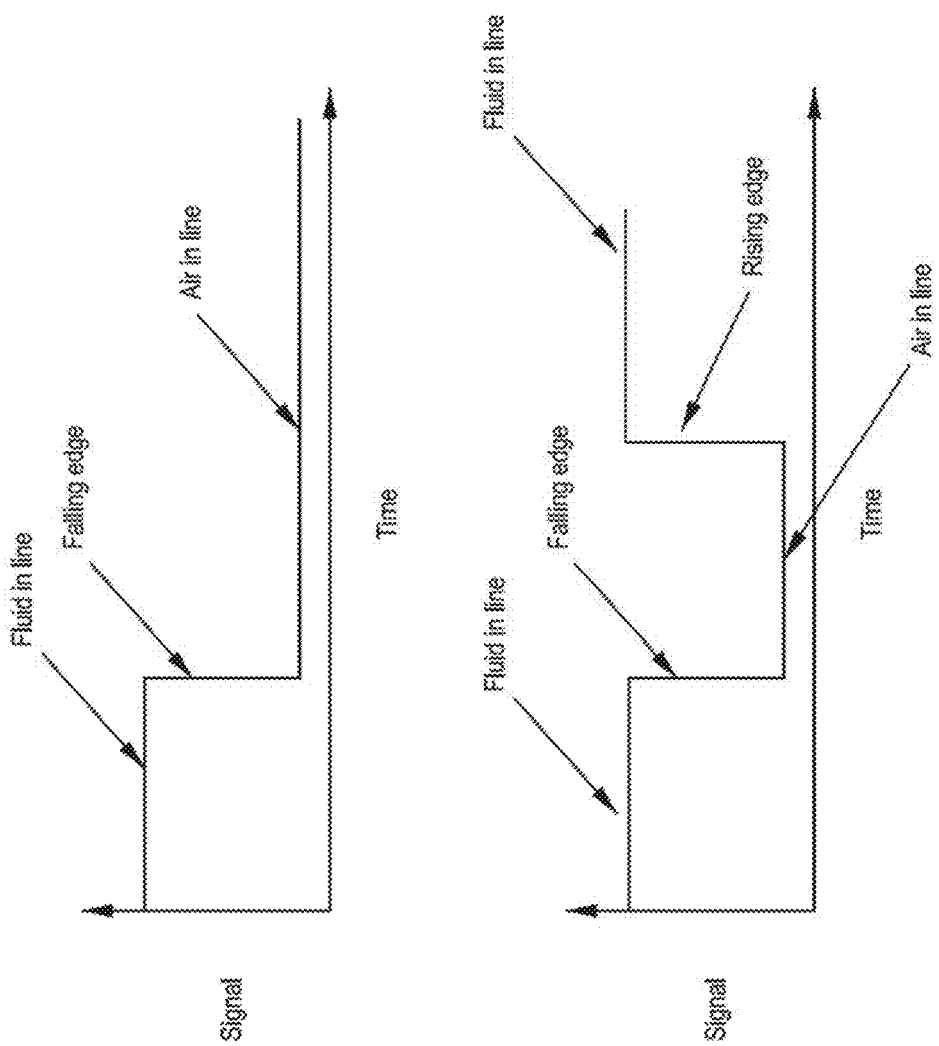

In another example, an optical detection system may include a system based on a detected discontinuity in a signal. For example, as illustrated in FIG. 15C, a discontinuity may be observed over time that is sufficient to distinguish and quantify that an air bubble event has occurred. On the observation of a falling edge, an air bubble or continuous air in line can be observed. On the observation of a falling edge and a rising edge an air bubble can be observed. In contrast, the lack of a falling edge in a signal change, such as illustrated in FIG. 15D, may be a result of other factors, such as environmental stress, and not an air bubble event.

Figure 16:
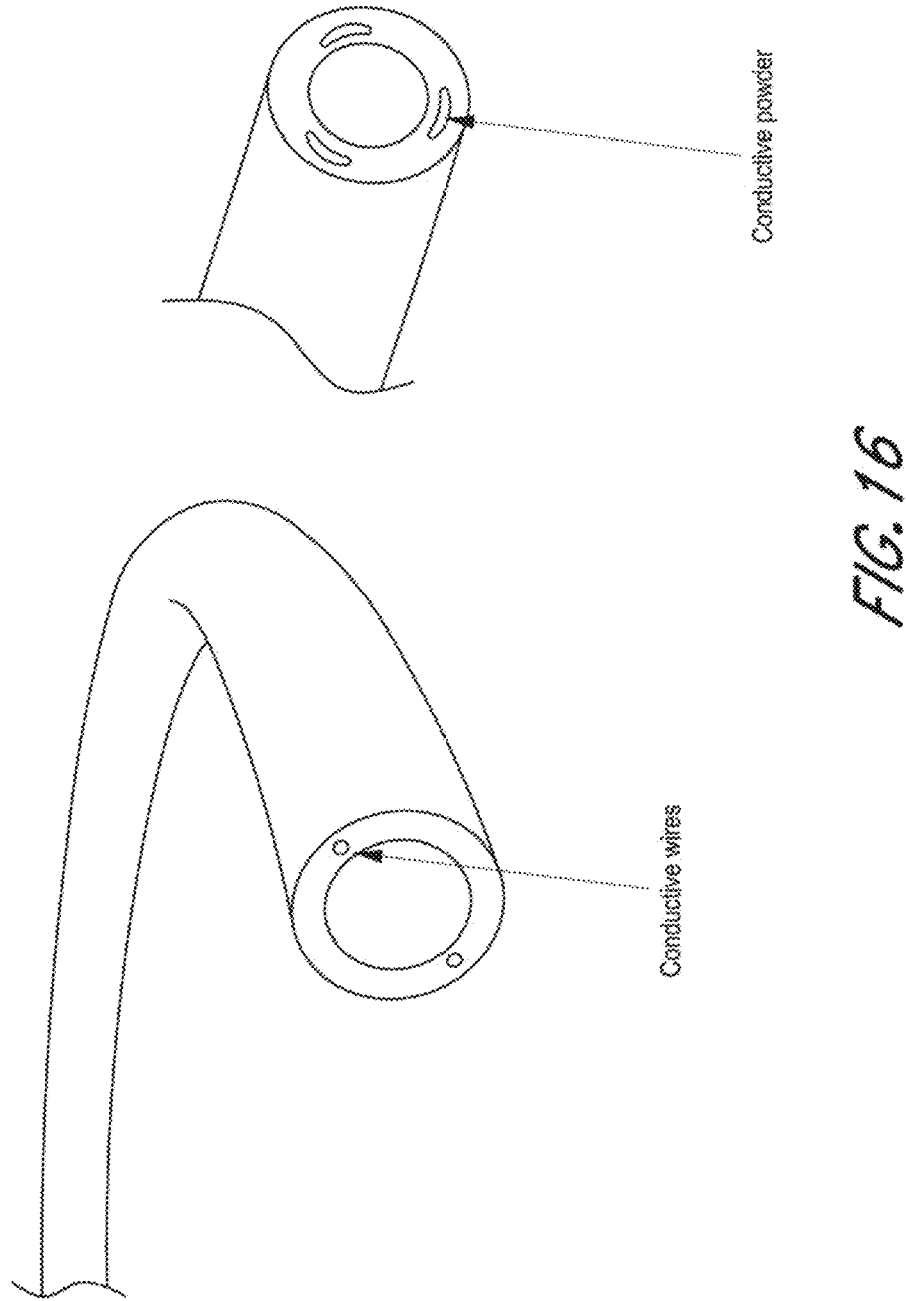
FIG. 16 illustrates an example capacitive air bubble detection system.

Another example method to measure air bubble volume is using a capacitor along an insertion tube. When a current is applied between two conductive wires, or conductive powder layers, as shown in FIG. 16, an electric field can be created between them. Thus, a capacitor may be formed dependent on a dielectric medium (dielectric constant) of material between the two conductive wires or powder layers. Capacitance of a channel having an air bubble and a channel not having an air bubble may be different. For example, the capacitance of a whole tube with insulin can be as:

$$C_{ins} = \frac{\varepsilon_{ins} A}{d}$$

A capacitance of a whole tube with air bubbles can be written as:

$$C_{air} = \frac{\varepsilon_{ins}(A - A_{air})}{d} + \frac{\varepsilon_{air} A_{air}}{d} = \frac{\varepsilon_{ins} A}{d} - \frac{(\varepsilon_{ins} - \varepsilon_{air}) A_{air}}{d} C_{air}/C_{ins} = 1 - (A_{air}/A)(\varepsilon_{air}/\varepsilon_{ins})$$

For example, where a tube length is 6 mm, a conductive width is 0.2 mm, an inner diameter is 0.5 mm, then a capacitance may be around 1 pF. In another example, where a tube length is 12 mm, a conductive width is 0.2 mm, an inner diameter is 0.3 mm, then a capacitance may be around 2.9 pF. An air bubble volume or insulin to air ratio in the tube or channel may be determined based on a capacitance value.

In some examples, a treatment system may remove air bubbles in order to reduce risk associated with delivering air bubbles to a user via a drug delivery device. For example, an air bubble removal system can include utilizing a micro mesh, membrane, or holes along a cannula. Air bubble can pass through a small hole on a hydrophobic surface but a liquid will not pass through. Using this concept, an air bubble can be removed by micro-holes or micro-membrane using a hydrophobic or hydrophilic (surface tension) mechanism. For example, an air bubble can be removed by micrometer holes or micrometer membrane at certain pressures by using the concept of hydrophobicity. A pressure needed to remove air bubbles can be described as:

$$P_{leak} = (P_{liquid} - P_{atm})_{max} = \frac{4\gamma_{lv} \cos(180 - \theta_{max})}{d}$$

Thus, the size of the holes may be reduced when the liquid pressure is increased. A number of membranes can be used to remove air bubbles, including but not limited to polypropylene and polyester membranes having pore sizes between 0.1 and 5 micron, thickness between 3 and 10 mil, air permeability between 0.05 and 8 ft3/min-fit2 at 125 Pa, water entry pressure of between 1 greater than 60 psi, an IPA bubble point of between greater than 0.5 and 20 psi, a surface treatment of hydrophobic or oleophobic, or some other combination of parameters, that have greater or lesser values.

Figure 21C:
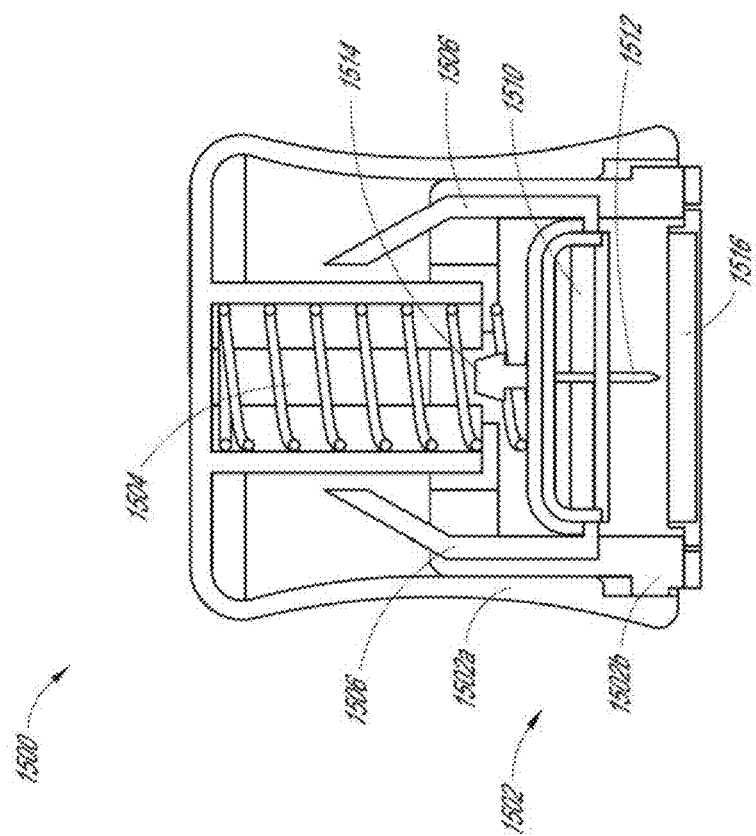
Figures 1, 21F:
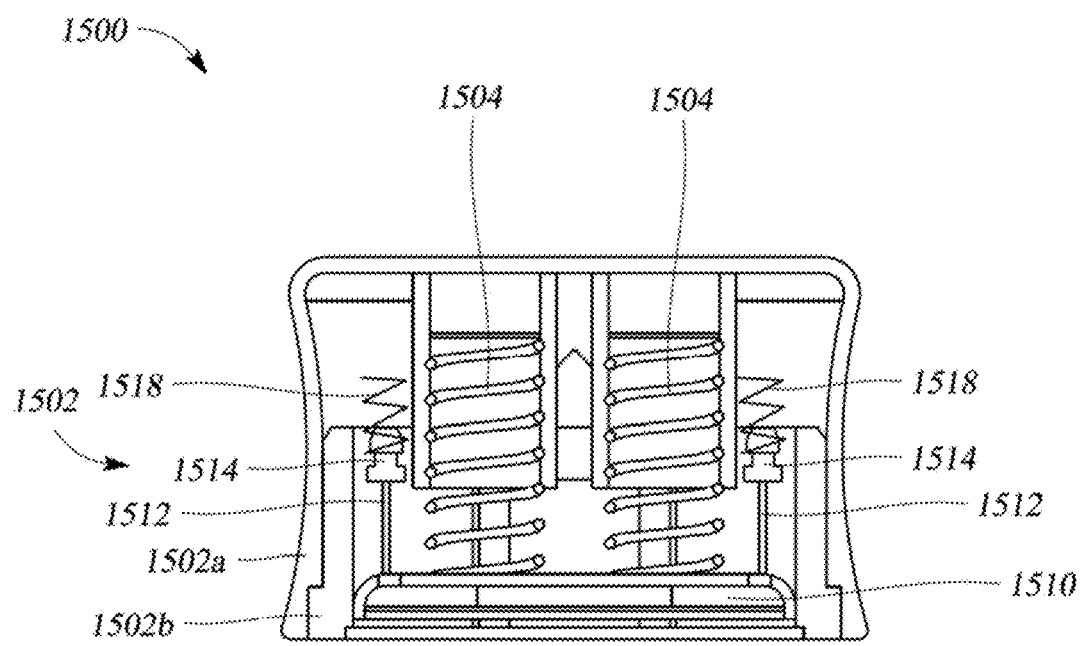
Figures 2, 21F:
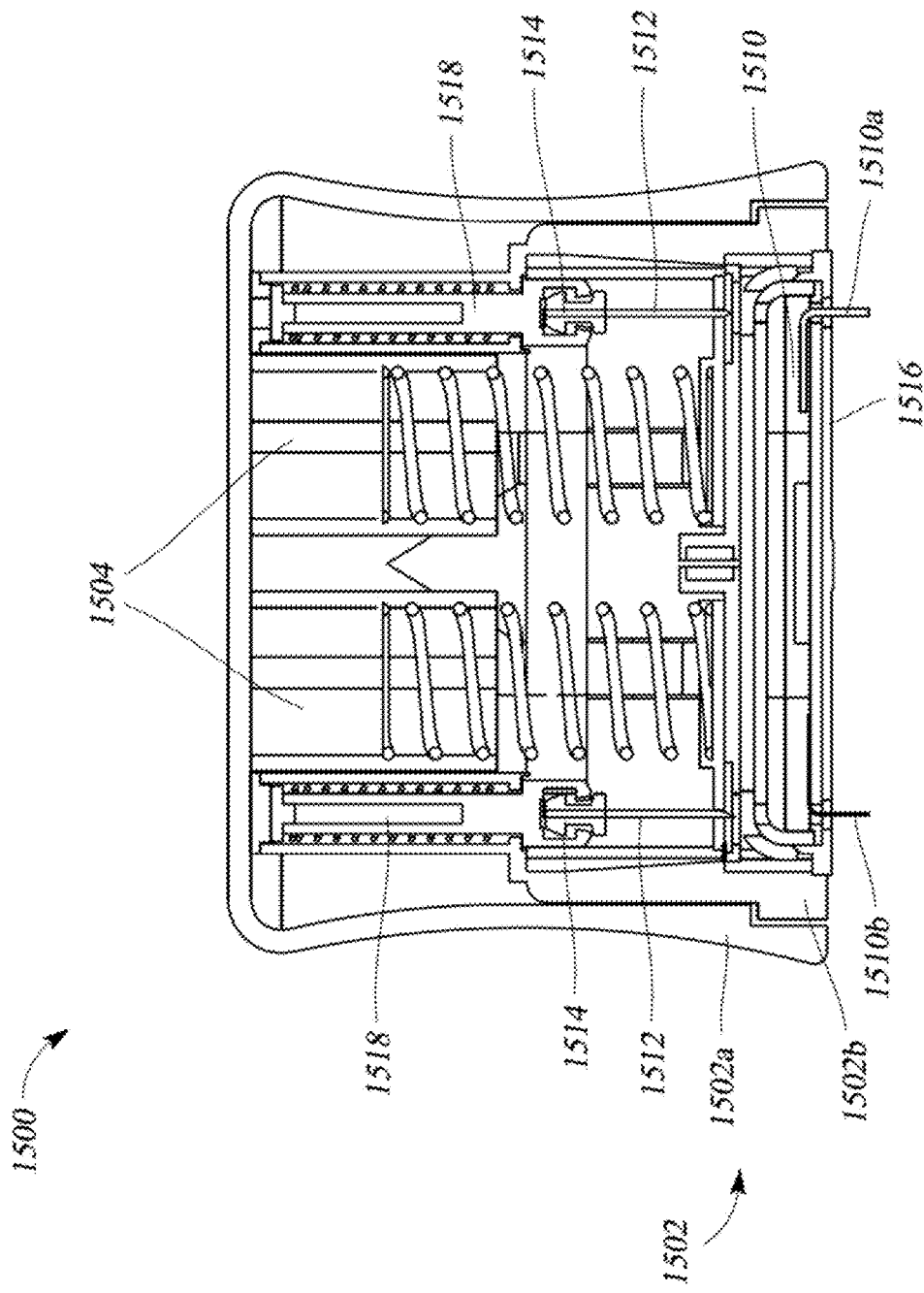
Figures 3, 21F:
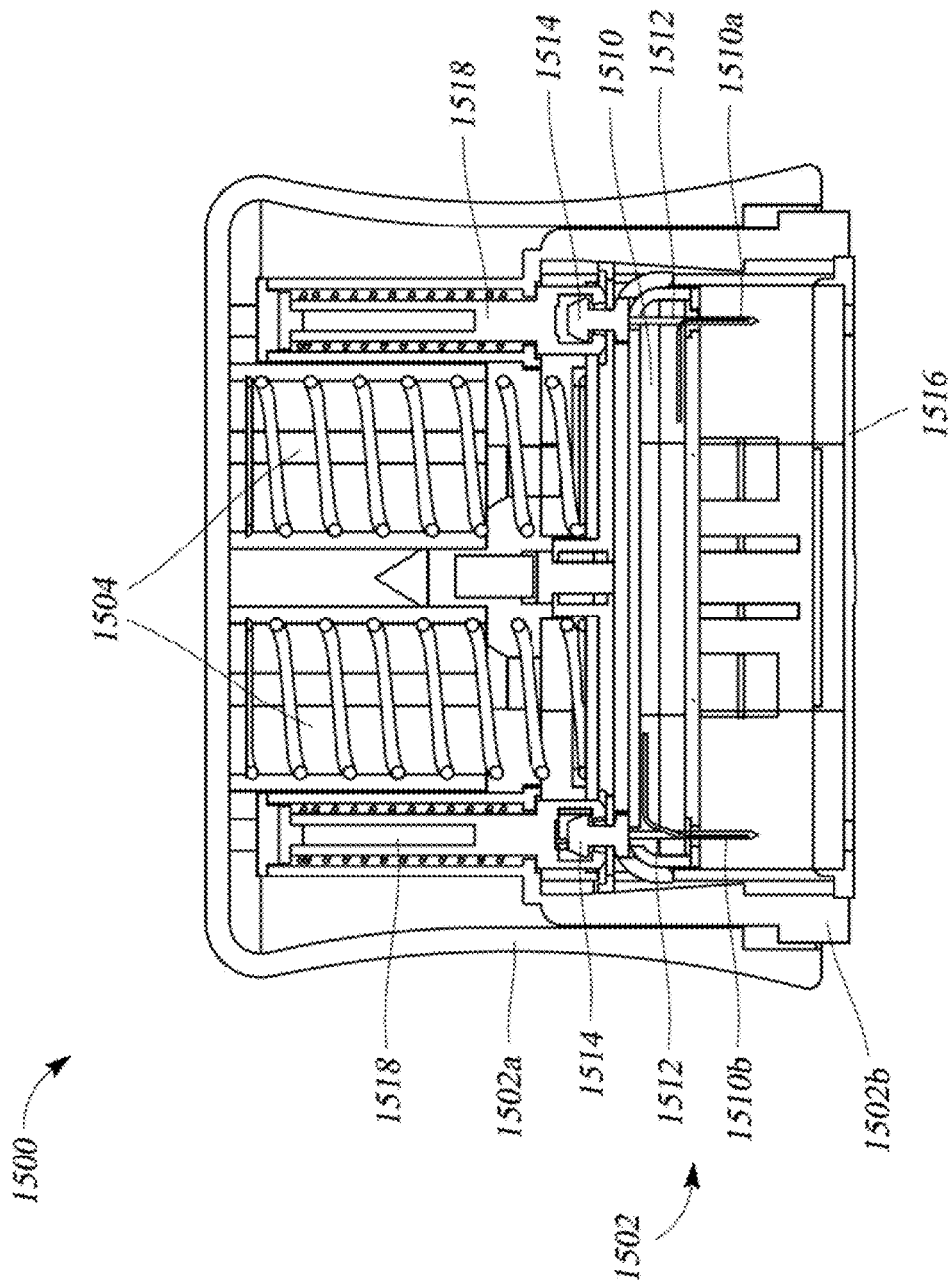
Figures 4, 21F:
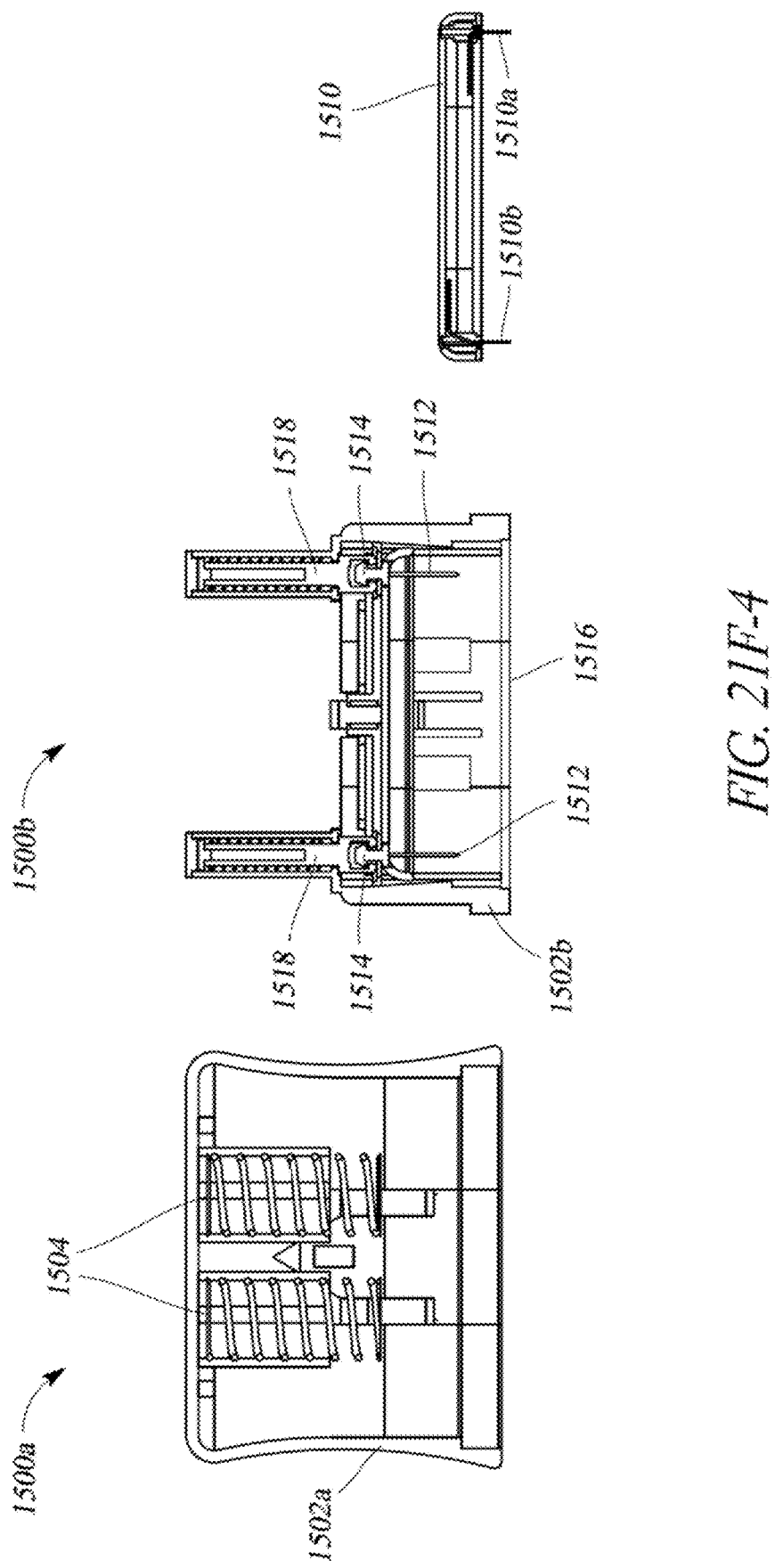
Figures 6, 21F:
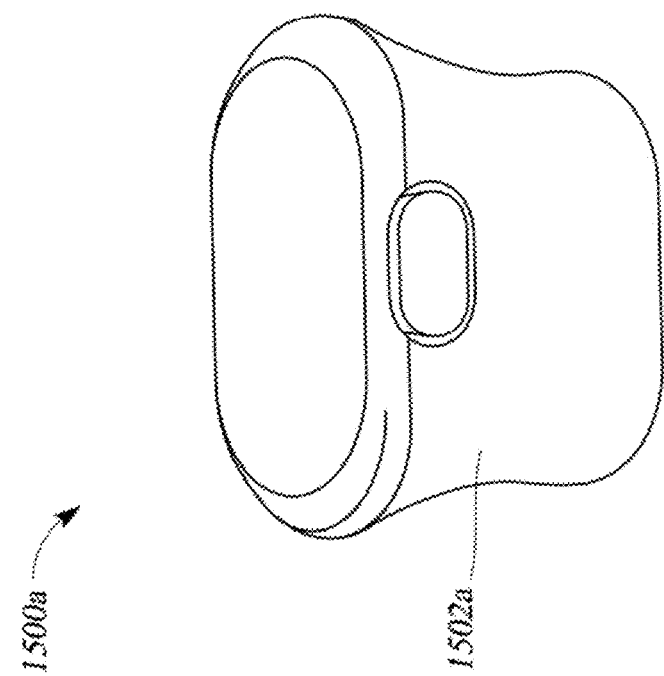
Figures 5, 21F:
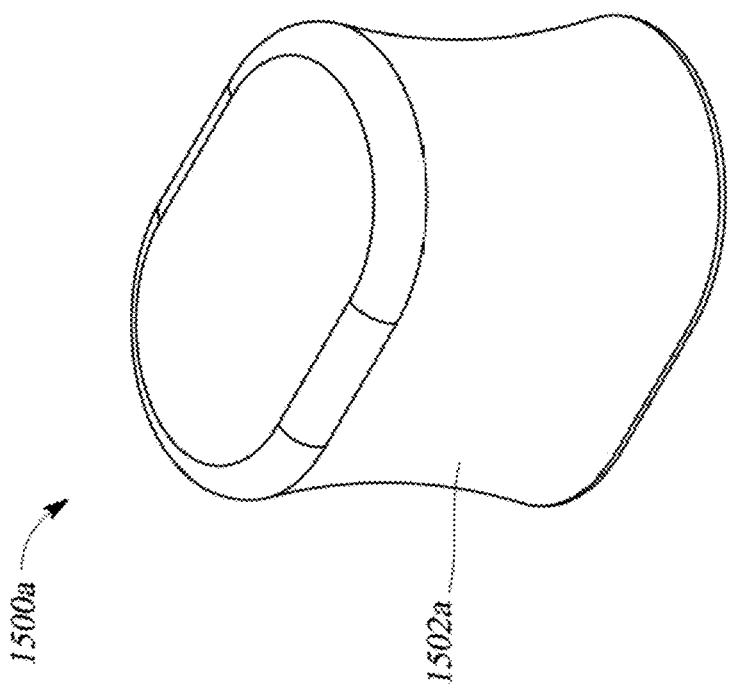
Figures 9, 21F:
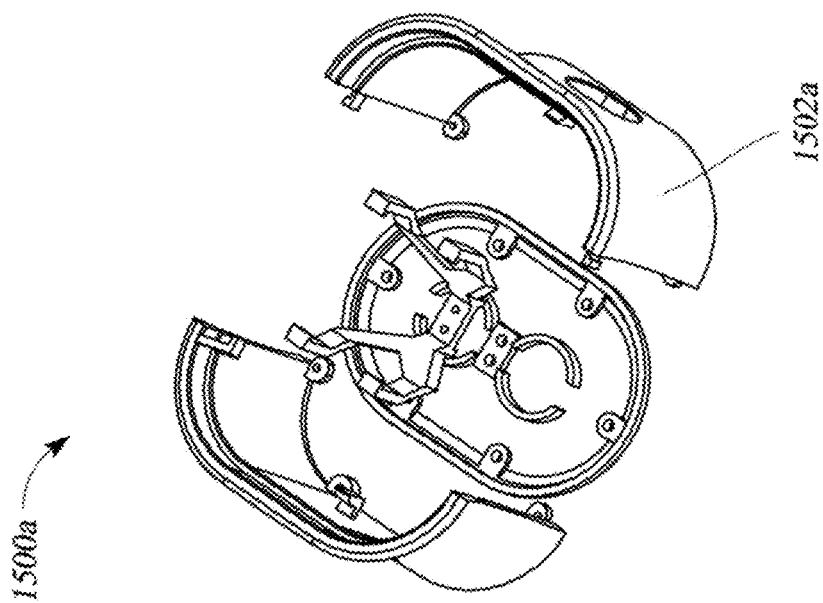
Figures 8, 21F:
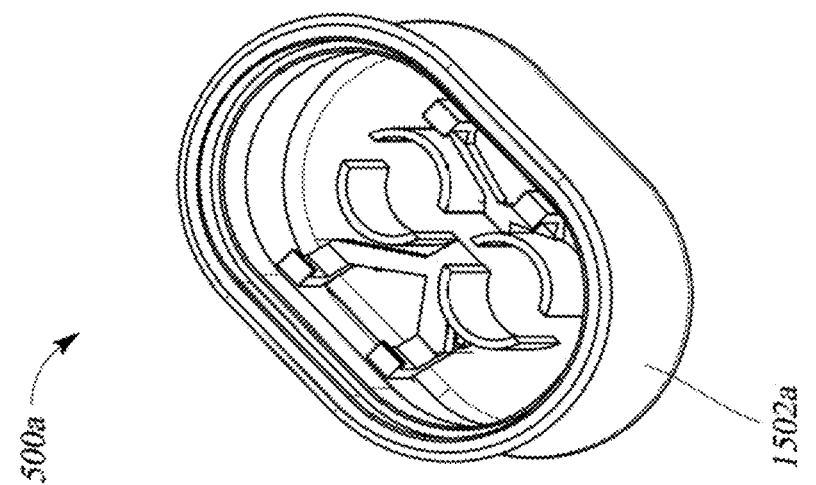
Figures 7, 21F:
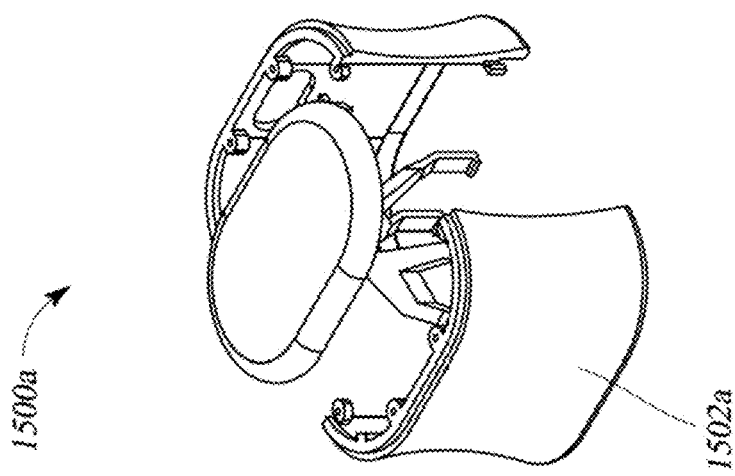
Figures 11, 21F:
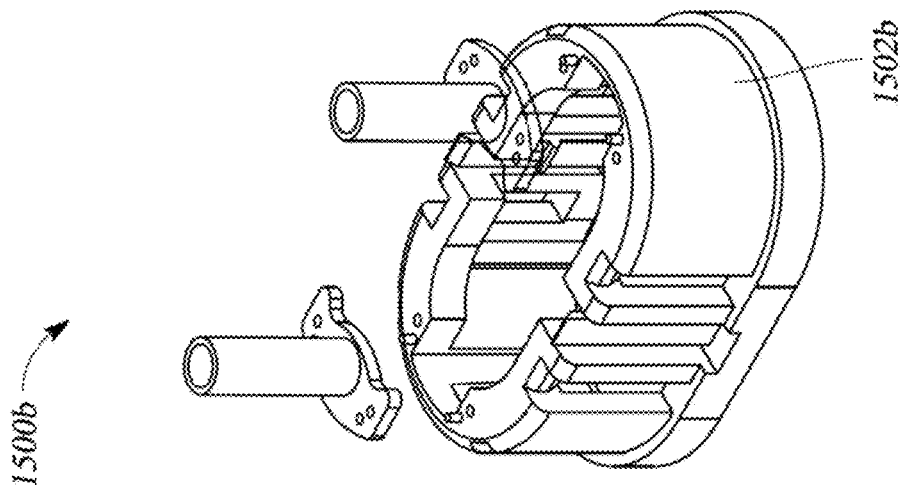
Figures 10, 21F:
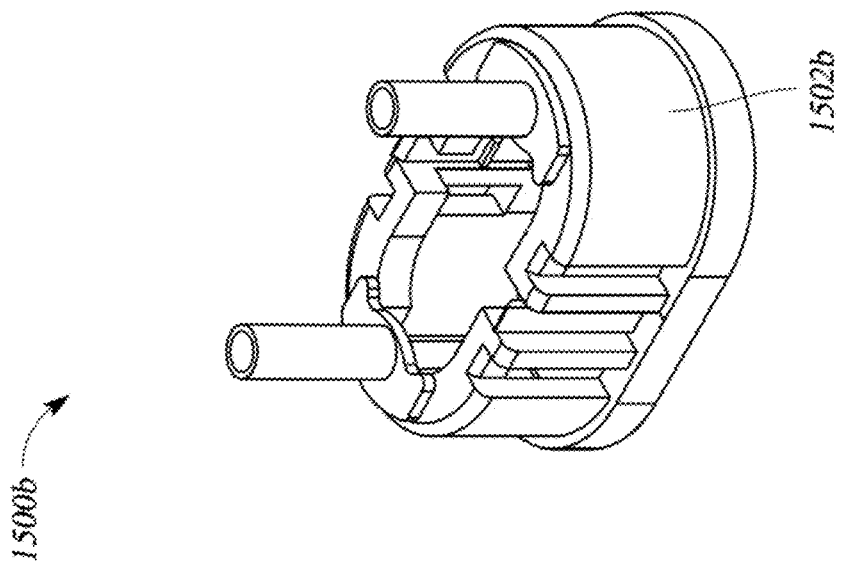
Figures 12, 21F:
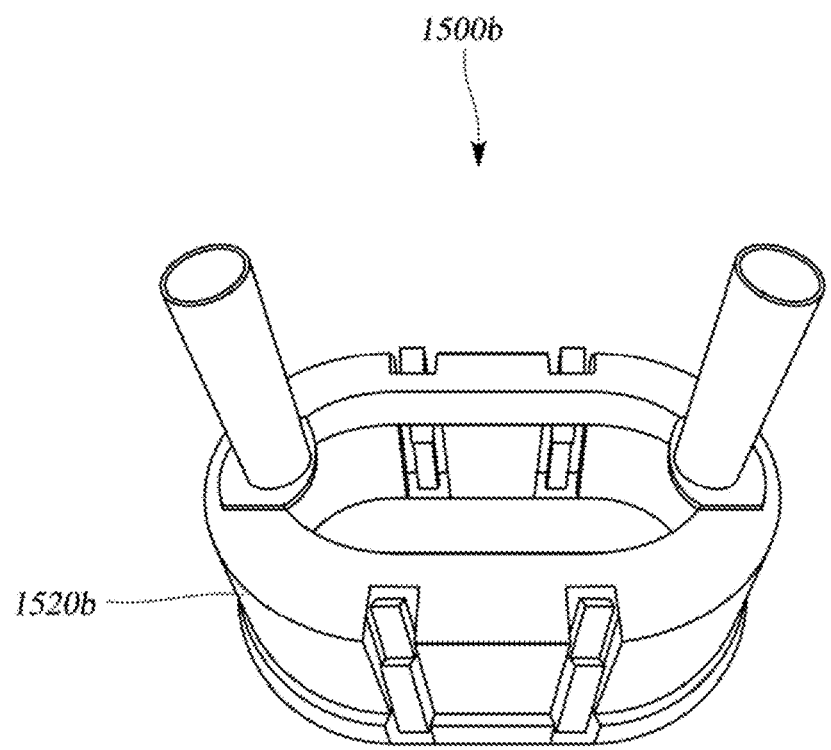
Figures 14, 21F:
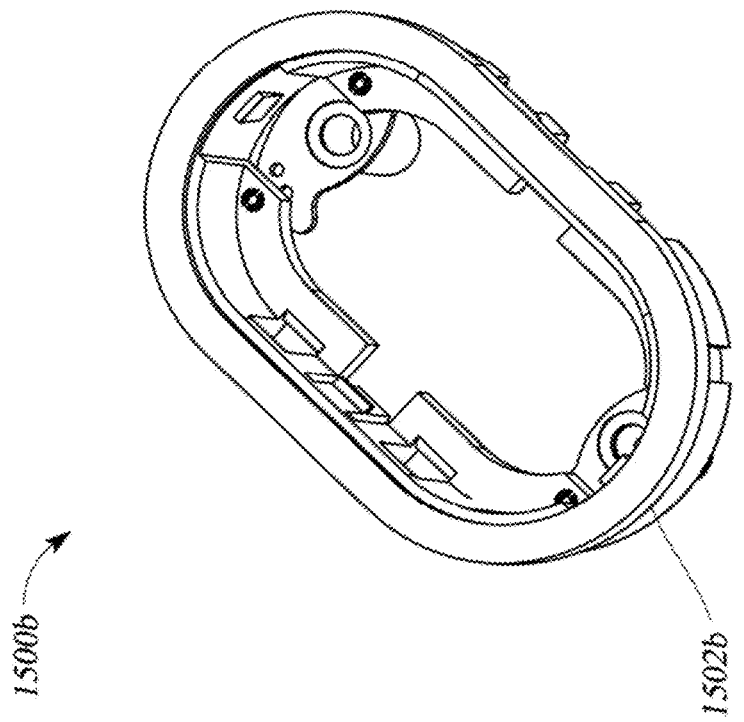
Figures 13, 21F:
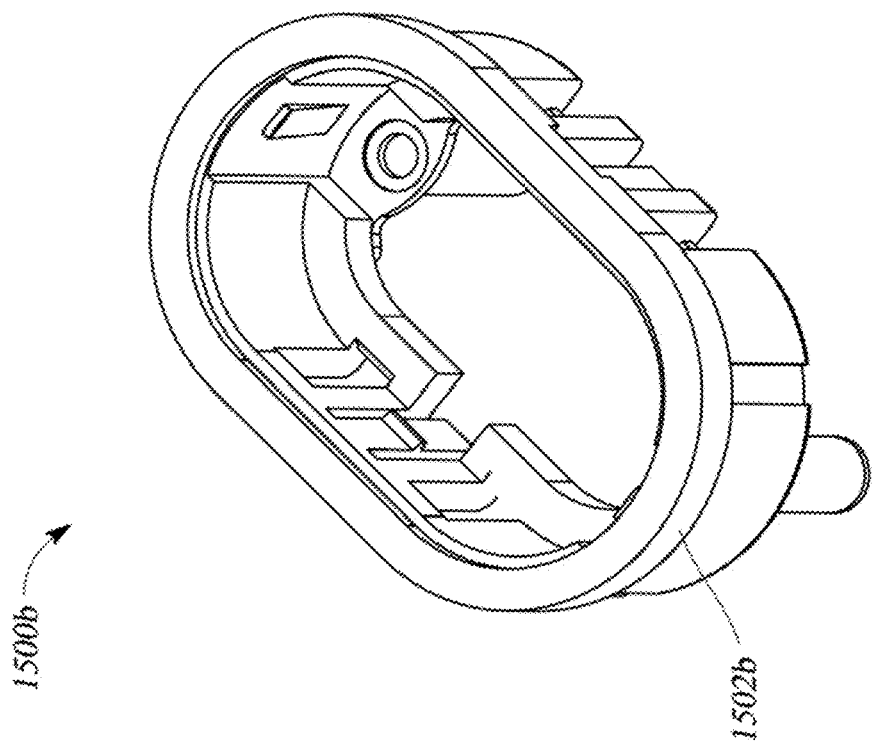
Figures 16, 21F:
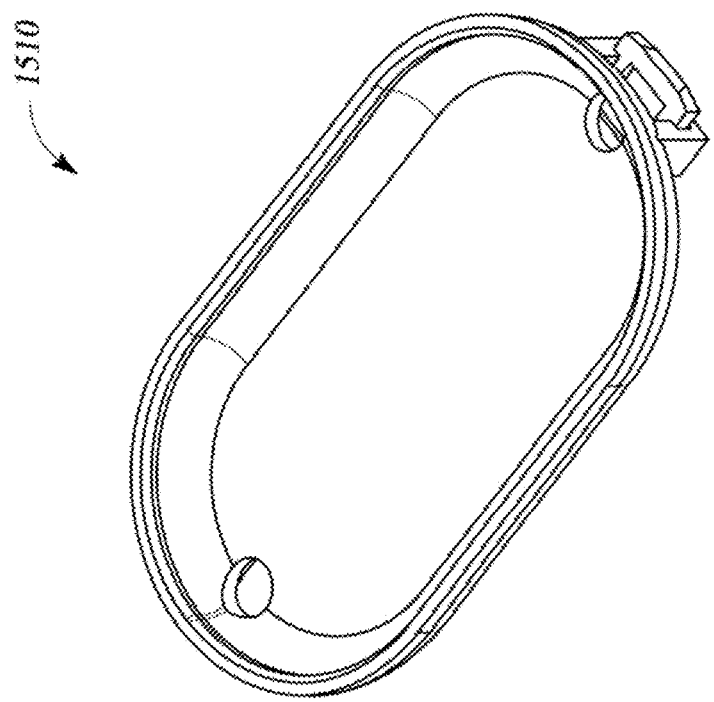
Figures 15, 21F:
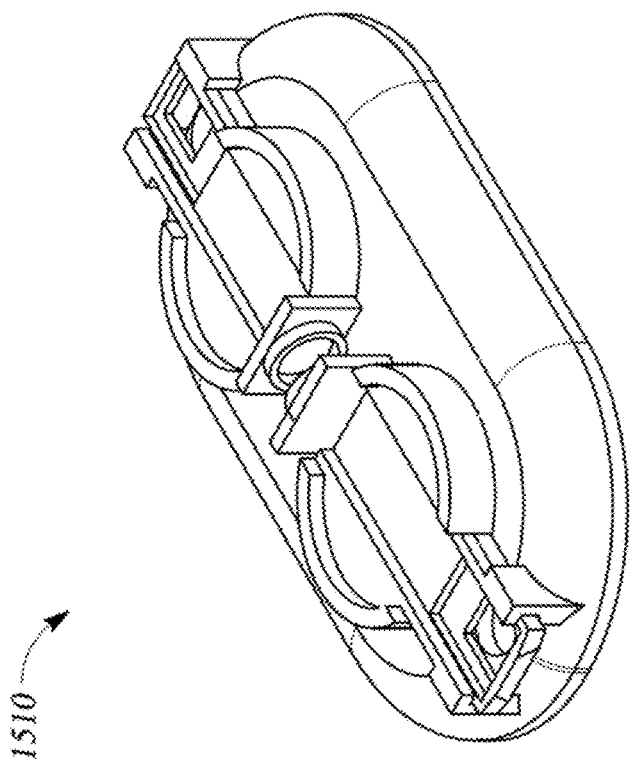
Figures 18, 21F:
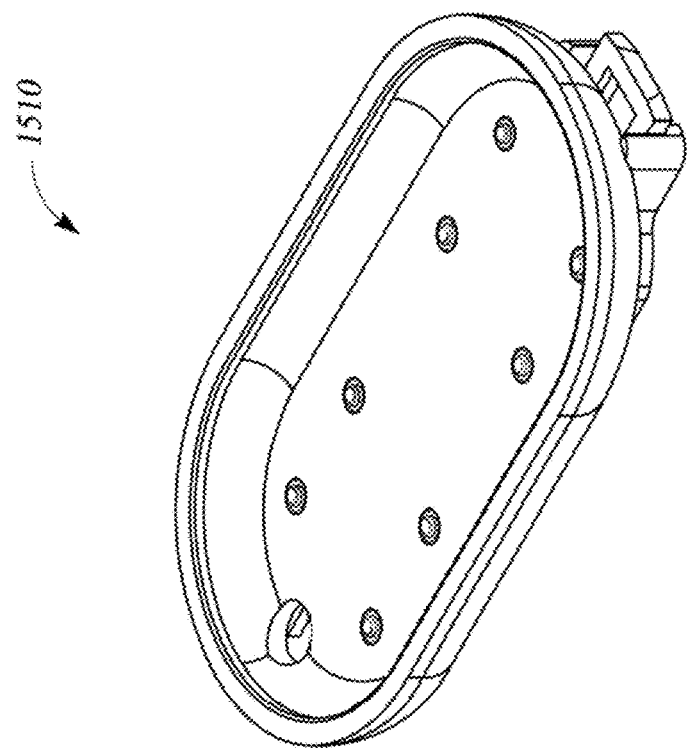
Figures 17, 21F:
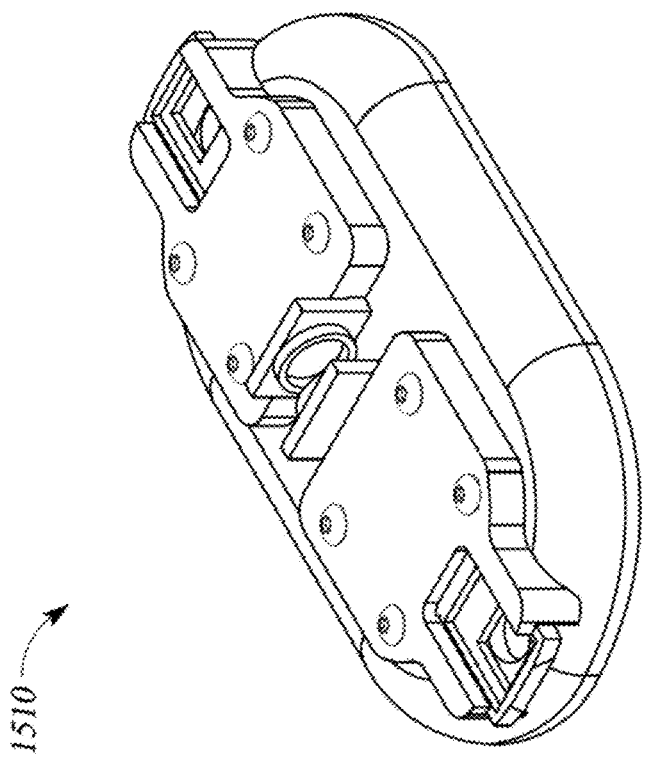

The air bubble removal can be designed to include membrane or holes, such as shown in FIG. 17. In some examples, a membrane can be configured to be disposed onto a portion of a cannula where insulin or other drug passes through, such as a bend in a cannula, so that air can be removed from the cannula through the micro membrane. In some examples, a cannula can include micro holes that may allow air bubbles to pass through prior to drug delivery of insulin or other drug in a cannula to a user.

F. EXAMPLE ALTERNATIVE GLUCOSE SENSOR SYSTEM

Figure 18B:
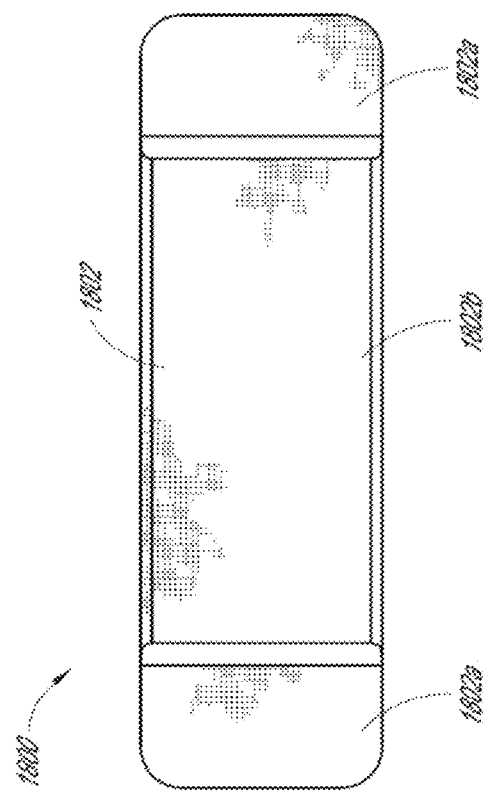
FIGS. 18A-18C illustrate various perspective views of a disease management system.
Figure 18A:
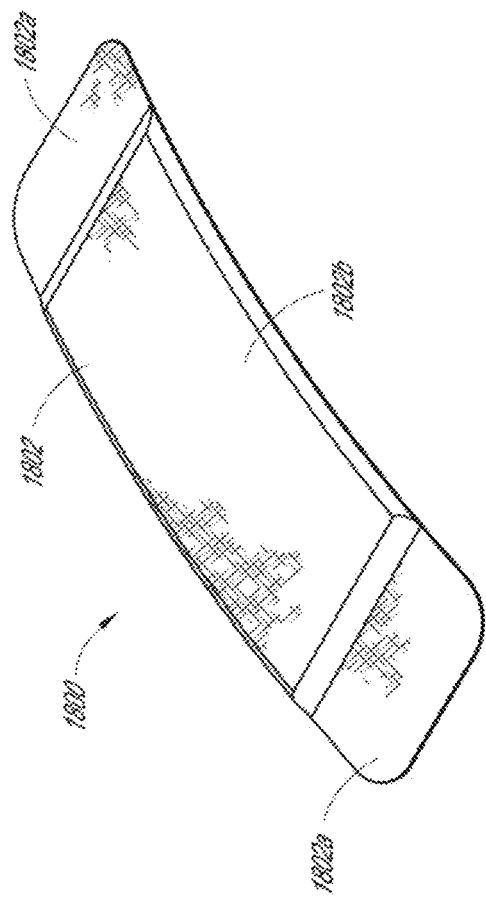
Figure 18D:
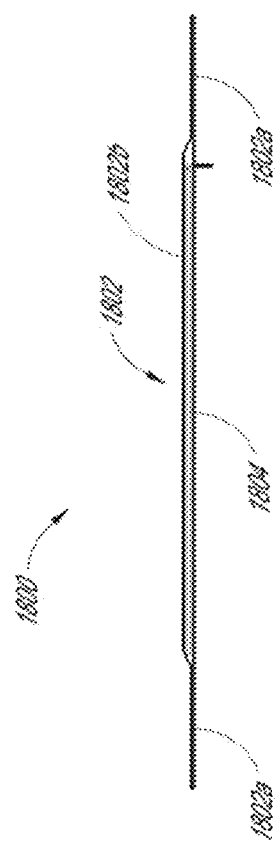
FIG. 18D illustrates a cross sectional view of the disease management system of FIGS. 18A-18C.
Figure 18C:
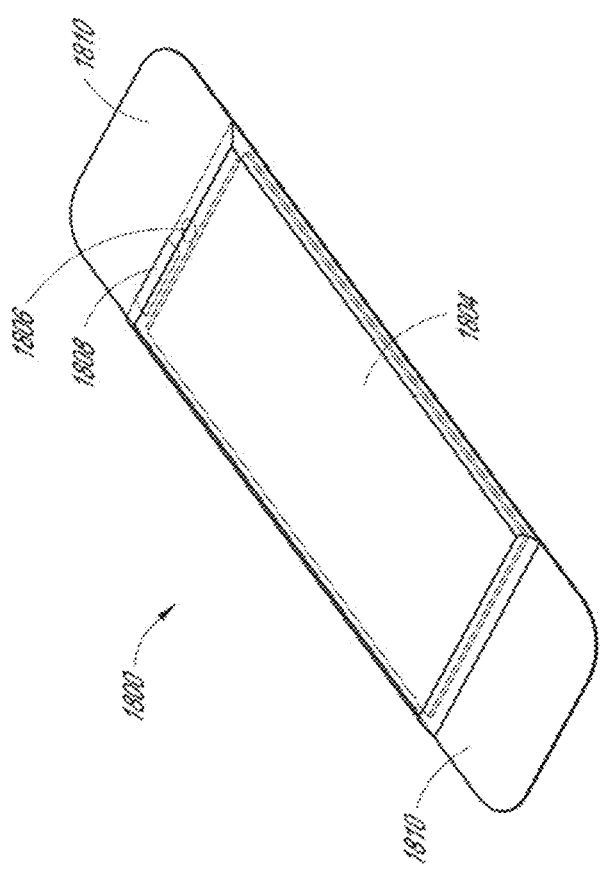
Figure 18E:
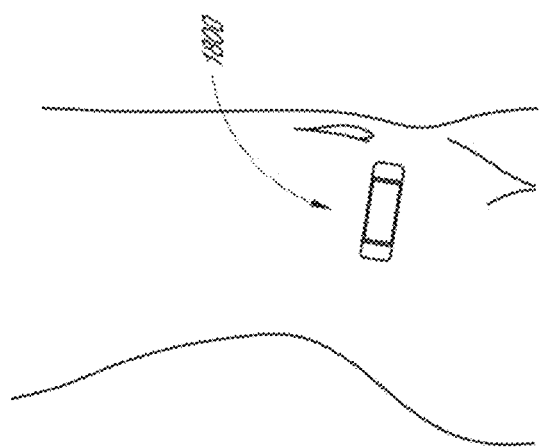
FIG. 18E illustrates a view of the disease management system 18A-18D applied to a patient.

FIG. 18A is a perspective view of the top side of an implementation of an alternative glucose sensor system 1800. FIG. 18B is a top down view of the glucose sensor system 1800. FIG. 18C is a perspective view of the bottom side of the glucose sensor system 1800. FIG. 18D is a cross sectional view of the glucose sensor system 1800. FIG. 18E is a view of the glucose sensor system 1800 while applied to the abdomen of a patient. The glucose sensor system 1800 includes a bandage 1802 which includes two side portions 1802A and a middle portion 1802B. The bandage 1802 may be made out of a pliable material such as fabric or a polymer. The side portions 1802A include adhesive bottoms 1810 which are capable of being adhered to a patient. Within the middle portion 1802B is included a battery 1804 and a module 1808. The module 1808 may include a computing device which includes a processor and memory which is connected to a glucose sensor. The computing device may further be connected to an antenna through which glucose measurements may be transmitted to other devices. The battery 1804 provides power to the module 1808 in order to power the glucose sensor and the computing device. A needle pass through 1806 allows a user to apply a needle through the bandage 1802 and into the patient when the glucose sensor system 1800 is applied to the patient. The needle implants a glucose probe into the patient which allows the glucose sensor to provide glucose measurements. The needle is removed once the glucose probe is installed. The module 1808 and battery 1804 may be overmolded within the bandage 1802. The battery 1804 may be a flexible battery in order to be more comfortable while the patient wears the glucose sensor system 1800.

1. Example Working Electrode of a Sensor System

An in-vivo, CGM sensor may be constructed with a working electrode (also referred to as a "WE" or cathode). The working electrode may include an alloy, such as for example, a platinum-iridium alloy ("Pt/Ir") wire onto which enzyme glucose oxidase (GOx) is deposited. A working electrode may be configured to work with a reference electrode (also referred to as an "RE" or anode). In one example, a wire working electrode may be inserted within a tubular electrode having a larger diameter than the wire working electrode that may be configured to serve as the reference electrode. The reference electrode may include a Silver chloride (or Ag/AgCl) electrode. The WE wire and tubular RE may be separated by an insular material, such as a thin insulating coating.

The enzyme GOx may be deposited and trapped onto the surface of the WE wire using some combination of electro-deposition, electro-polymerization, and physical adsorption of a polymer such as o-phenylenediamine, aniline, or other polymer. The inclusion of the polymer may have multiple purposes. For example, the polymerized mesh may physically trap the GOx enzyme and adsorb it to the WE surface. In another example, the polymer backbone may be electrically conductive and facilitate the transfer of electrons to the WE. Additionally or alternatively, other polymer layers constructed of, for example, Nafion, Cellulose acetate, the like or a combination thereof, deposited below or above the GOx deposition layer may normalize the levels of glucose and oxygen. These other polymer layers may help linearize a current response to physiologically relevant glucose concentrations. Additionally or alternatively, the other polymer layers, (such as cellulose acetate) may protect the activated WE metal surface (such as the Pt/Ir surface). This protection is beneficial because the activated surface of the WE is important in developing a sensitive glucose sensor because the reaction of the Pt/Ir surface with hydrogen peroxide is primarily responsible for the creation of the electrical signal which is measured by the electrical circuits of the system.

In another example, a sensor may be configured to remove or reduce the CGM's dependence on dissolved oxygen and help substitute the function of oxygen with the use of a small molecule, sometimes referred to as the "mediator". The mediator may function in a similar fashion to oxygen in the context of the sensor system to facilitate the transfer of electrons from the enzyme (GOx) catalytic center to the electrode. The mediator may be fabricated into the sensor head in a proportion that may enable this functionality. In some examples, the proportion may be empirically determined. The mediator may be constructed out of molecules that can accept electrons in a stable manner and/or give up the electrons in certain conditions, such as at the electrode surface. A mediator can include any number of materials, such as ferrocene, ferricyanide, Osmium based transition metal complexes or the like. In some examples, the enzyme (GOx), the mediator(s) and/or polymers may be covalently bound to the metal electrode to form the sensor for detecting glucose. In this sensor configuration, construction may also be encapsulated with multiple layers of polymers (such as Nafion). The layers of polymers may serve specific purposes. Additionally or alternatively, the polymers may limit the concentration of glucose at the enzyme to linearize the current response to various concentrations of glucose. In some examples, the addition of mediators may include additional steps to ensure biocompatibility of the mediator molecules along with the stability of the sensor fabrication to keep the molecules from leeching after invasive implantation. In some examples, an electrode that includes a mediator may be constructed using a of Gold (Au) or Pt/Ir electrode.

Advantageously, the selected polymer layers and GOx are biocompatible. Similarly, Pt/Ir, Au and Ag are noble metals with excellent biocompatibility.

Various methods of recording electrical signal may be used. For example, cyclic voltammometry, amperometry, voltammetry, or another method of recording electrical signal may be used A method may be selected based on parameters such as reproducibility and accuracy of glucose concentrations over the lifetime of the sensor.

A CGM sensor may detect and convert concentrations of glucose to a proportional electrical signal (current or potential) by a series of electron transfer steps between GOx, FAD, peroxide molecules and finally to the working electrode. However, this proportionality constant is sensitive to a range of physical and biochemical parameters. These parameters may be controlled and standardized during fabrication in order to help produce more consistent signal. For example, such parameters and example (but not exclusive) method(s) of standardizing these parameters for fabrication can include, but are not limited to: 1) geometry and size of the sensor head, which may be evaluated by cyclic voltammometry of a known and well-behaved redox compound like ferrocene or potassium ferrocyanide for consistency; 2) amount of glucose oxidase enzyme captured on the sensor head, which may be evaluated by electrical signal detected on the Pt/Ir electrode to known concentrations of peroxide and compared with the glucose response; 3) applied voltage between the working electrode and the reference electrode, wherein the working voltage can be determined by cycling through or probing of various voltages for a known concentration of glucose; 4) polymer coating(s) that may normalize the concentration of glucose and oxygen, which can be evaluated based on the linearization of electrical response to glucose concentration with various concentration of polymer coatings; 5) the surface "activation" and preservation of platinum electrode that oxidizes hydrogen peroxide, wherein the inclusion of cellulose acetate polymer coating of Pt/Ir electrode may protect the surface "activation" in a functioning glucose sensor for the purposes of standardization and consistency; 6) the polymer coating that filters out interfering species such as ascorbic acid, urea, acetaminophen, wherein a Nafion polymer coating may be utilized to reduce interference in electrical measurements; 7) the conducting polymer that provides an efficient "pathway" for the electrons to reach the platinum electrode, some polymers such as PANI, PoPD and other polymers that may include conducting polymers may be used for this purpose; 8) the local diffusion behavior of glucose and oxygen near the sensor, wherein the diffusion behavior can be characterized by comparing the electrical response of the constructed sensor to standard equations of electrochemistry; 9) leeching or degradation of polymer layers, mediators and glucose oxidase enzyme, wherein the binding strength of the components of the sensor will be characterized by following the "leakage" of these components during long-term usage and incubation of the sensor in in-vitro buffer or blood/plasma. UV/Vis spectroscopy, chemical determination, Raman spectroscopy and atomic force microscopy are some of the biophysical methods that can be used to characterize this phenomenon; 10) the drift/stability of the reference electrode (Ag/AgCl), wherein the Ag/AgCl reference electrode is constructed with any number of methods and wherein the electrodes may be calibrated against industry leading, low-noise and long-term stable commercial Ag/AgCl electrodes; 11) temperature and pH of the measurement location, which can be accounted for in testing in an electrochemical cell to test for the temperature and pH consistent with the human body (pH 7.4 and 37° C.); 12) depth of penetration of the sensor into the ISF. Ideally, the depth of insertion of the sensor head should be fairly precisely controlled using the applicator. This depth will partially determine the lag time of glucose values between blood and ISF. Location of the CGM (abdomen vs arm) is another factor that determines lag. This can be tested using a bio-simulator and/or animal testing.

To address the comfort of a user having to use a sensor device, the reduction in size (diameter) of sensor electrodes is important, as is the durability of the probe design to withstand the rigors of a physically active patient and importance of repeatable accuracy and economical production of these probes to keep CGM unit costs reasonable for typical patients. Systems and methods described herein help address the above concerns.

When constructing the electrochemical probe, the use of specific metals and electrode surface platting may be used to achieve a desired signal return. Some metals that may be used for this purpose include but are not limited to Platinum, Gold, Silver, and Silver-Chloride. Other combinations of metals and surface platting may also be possible. Other iterations could include other materials, such as electrodes made of carbon nanotubes, graphene electrodes, gold nanoparticles deposited on other metallic surfaces, glassy carbon, Zinc Oxide nanorods, indium tin oxide, the like or a combination thereof.

Once the probe is constructed of the correct combination of metal electrodes, many probe designs also require the application of chemical agents and buffers to either exaggerate or manage the gain of the electro-chemical reaction to target the desired molecule; in this case Glucose. FIGS. 19A-19D depict example iterations of an electrode system configured to perform electrochemical measurements. It is of note that the illustrated geometries can be extended to include additional electrode surfaces to meet the needs of the analytes being measured.

FIG. 19A illustrates example configurations 3300 of a metalized core structure for an example electrode system. For example, the illustrated configurations can include placement of wires 3304 with circular or partially circular cross sections on the sides of different support structures 3302. For example, a first configuration 3300A can include a cross shaped or square shaped with triangular cutouts core and partially circular wires. In a second configuration 3300B can include a square shaped core and partially circular wires. In a third configuration 3300C can include a square shaped core with circular cutouts and circular wires. In a fourth configurations 3300d can include a different configuration of a square shaped core with circular cutouts and circular wires. In a fifth configurations 3300e can include a triangular shaped core with partially circular wires. Additionally or alternatively, drawn wires with an enhanced cross-sectional profile may be used. A support structure can have a cross sectional shape having any number of sides to support more or less wires. The wires can include any combination of metals. The support structure may be made of a bio-compatible electrical insulating material. In some examples, wires may be adhered to the core.

FIG. 19B illustrates example configurations of an insulating core structure with flat wires applied to the core for an example electrode system. For example, the illustrated configurations can include placement of wires 3308 that have a flattened cross sectional profile, and would therefore have potential to increase an electrode surface area over a circular support structure 3306. A support structure can have a cross sectional shape of any number of sides to support more or fewer wires. For example, in a first configurations, a support structure can include a triangular core structure 3301A or a square core structure 3301A. Wires can be any combination of metals. A support structure may be made of a bio-compatible electrical insulating material. In some examples, wires may be adhered to the core.

Figure 19D:
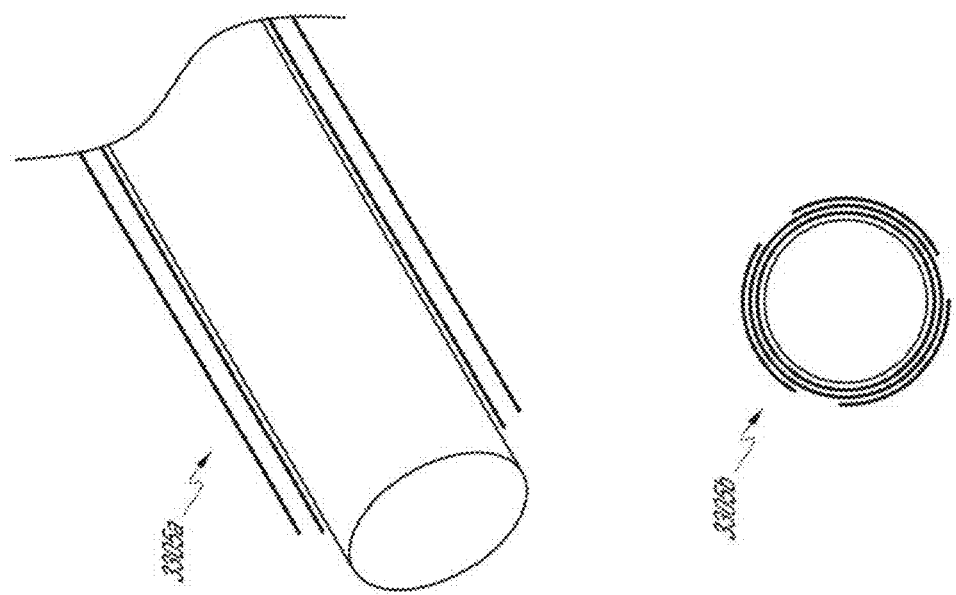
Figure 19C:
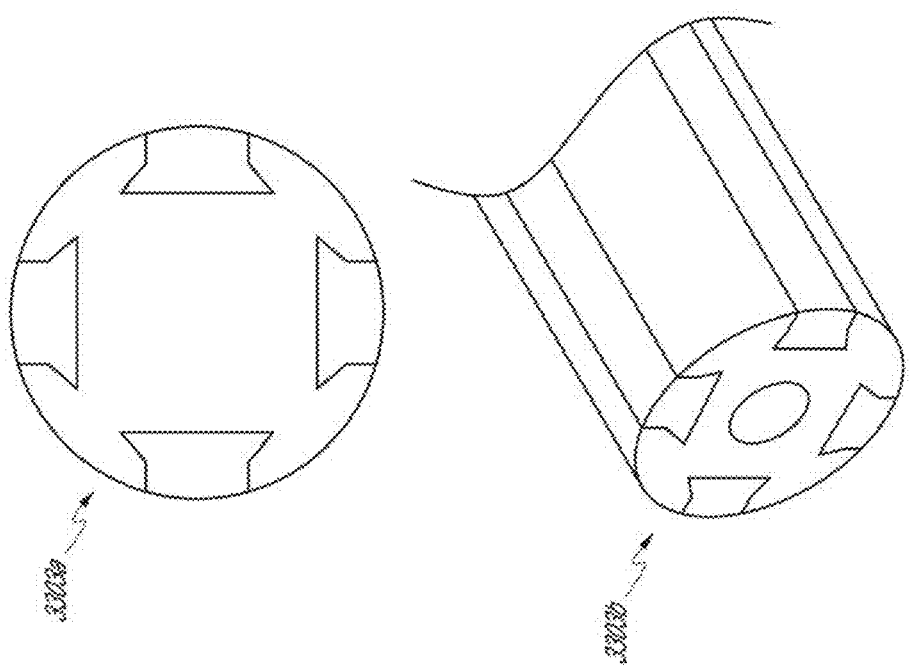

FIG. 19C illustrates example configurations 3303A, 3303B of an example electrode system with extrusion of a core with formed wires. For example, a method of manufacture for generating the illustrated configurations may include the placement of wires that are drawn with a profile that supports molding the electrodes in a continuous extrusion process. In an example extrusion process, the electrodes may be exposed on the entire or nearly entire length, creating the ability to cut to length sizing during manufacture. A support structure can have a cross sectional shape of any number of sides to support more or fewer wires. Wires can be any combination of metals. A support structure may be made of a bio-compatible electrical insulating material. In some examples, wires may be adhered to the core.

FIG. 19D illustrates example configurations of an example electrode system with a metalized core structure. For example, a method of manufacture for generating the illustrated configurations may include metalizing the surface of an insulating core structure having a circular or multi-sided cross sectional profile. In a first example step 3305A, an entire core may metalize an entire or nearly an entire core and then insulate the metalized core (with, for example, polyamide). In a second example step 3305B, metalized stripes may be added down the length of a structure, such as a core generated in the first example step.

2. Example Sensor Calibration

Glucose estimation in a sensor system may be determined based off one or more physical measurements. In some examples, one or more parallel engines may recombine multiple analyte or glucose estimates once a physical measurement has been acquired. The sensor system may include a plurality of hardware elements. The plurality of hardware elements may include: a 3-electrode system (reference, counter, and working) and one or more temperature sensors, such as one or more thermistors.

In some examples, a sensor system may include a single thermistor. The thermistor may be applied to a user at the same or similar depth fat the tissue site as the working electrode so as to measure internal skin temperature. In some examples, a sensor system may include two thermistors. For example, a first thermistor may measure a skin surface temperature and a second thermistor may measure an ambient temperature. The sensor system may then determine or extrapolate an estimate of temperature into the tissue at the depth of a working electrode. The selection of a single thermistor or dual thermistor system may be based on empirical testing, such as animal testing.

In some examples, an electrochemical signal from the interface of the working electrode may be quantified on an ADC. The sensor system may then temperature correct the raw digital signal and/or may utilize a calibration curve to linearize the CGM response with respect to glucose. In some examples, the calibration curve may be based on one or more empirical characterizations of one or more electrodes of the sensor system. For example, each unique electrode may have an empirical characterization. In another example, unique electrode characterization may be avoided and a generalized calibration curve may be used. In some examples, individual sensor calibration may not be needed or used.

The sensor system may determine a confidence parameter associated with one or more hardware components or a combination thereof of the system. In some examples, the confidence parameter may be based on one or more parameters associated with the sensor system, such as some combination of: sensor manufacture date, ship date, current date, insertion date, skin and/or ambient temperatures during use, high frequency electrical noise, insertion site consideration, observed sensitivity level, the present glucose prediction as compared to a voluntary SMBG or glucose insulin meal models, insulin considerations, and/or the like.

In some examples, the sensor system may make retrospective adjustments to the sensor calibration. For example, the sensor system may make adjustments with respect to a glucose trend, glucose insulin meal model, or other calculated value to account for interstitial lag. Advantageously, the adjustment may improve the analysis and display of historical data. In some examples, an actual glucose prediction presented at the time of prediction for every time point may also be stored.

In some examples, a device may coordinate one or more glucose estimates with a Kalman filter or weighted average to give an improved accuracy, precision, and resilience over traditional CGM systems.

G. EXAMPLE APPLICATOR FOR A DISEASE MANAGEMENT SYSTEM

A treatment system may include an applicator to provide a disease management system, such as an insulin administration device, to a tissue site of a user or patient. In some examples, an applicator may be reusable or one time use. In some examples, an applicator may include one or more measures to reduce anxiety of application and/or pain associated with application of a disease management system. In some examples, an insulin cannula may be retractable by an applicator once insulin reservoir is emptied. Advantageously, the retraction may allow wound healing to begin.

An applicator may be configured to insert both CGM and insulin pump needles simultaneously. An applicator may be configured to hide one or more needles from view at various stages of insertion, including, but not limited to opening sterile pack, loading any springs, insertion, applicator removal, and applicator disposal. The applicator may be usable with a single hand. An applicator may be usable with either a user's left or right hand. An applicator may have one or more features which releases a safety mechanism. An applicator may fire through a simple mechanism once a safety is released. In some examples, a safety mechanism may not be accessible from outside the sterile packaging. Advantageously, such a limit to accessibility may help prevent accidental firing while peeling off a sterile wrapper top, in shipment or in storage. An applicator may be intuitive and require minimal effort to apply. An applicator may have a rapid anesthetic injector to prevent feeling insertion pain. An applicator may limit the pieces of disposable items, such as merely a sterile container and/or applicator (if disposable). In some examples, an applicator may not have tape adhesive trash because a sterile unit may include adhesive protectant. In some examples, a size of the applicator may be larger than a disease management system being applied, such as twice the volume of a disease management system.

Figure 20A:
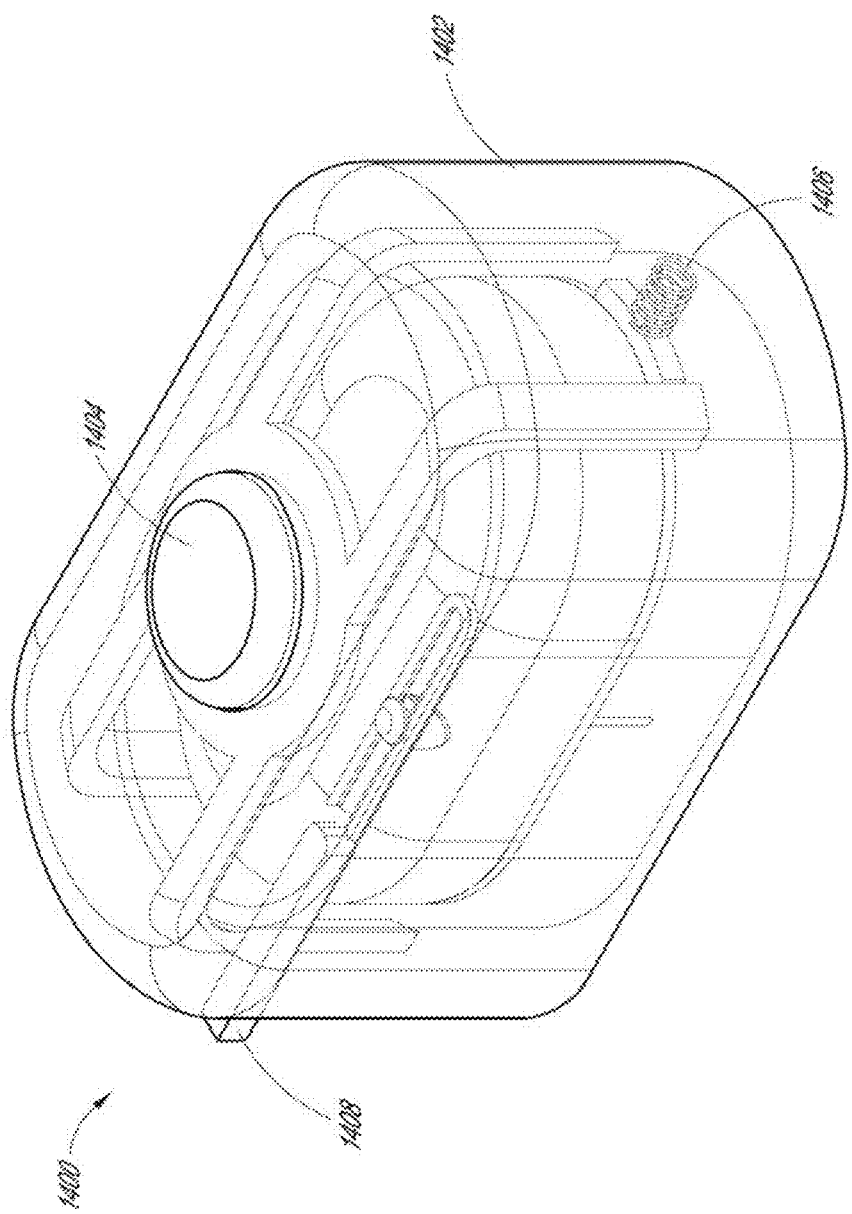
FIG. 20A illustrates a perspective view of an applicator for applying a disease management system to a patient.

FIG. 20A illustrates a perspective view of an applicator 1400 for applying a disease management system to a patient. The disease management system may be any implementation of a disease management system, such as a disease management system 100 of FIGS. 3A and 3B. FIG. 20B-20d illustrates various cross sectional views of the applicator 1400 of FIG. 20A. The applicator 1400 includes a housing 1402 which is adapted to carry a disease management system 1410 and one or more needles 1412. The disease management system 1410 may include one or more cannulas 1416 and the needles 1412 may go through the one or more cannulas 1416. The cannulas 1416 are adapted to be implanted within the patient while the needles 1412 are adapted to exit the patient after puncturing the patient. The needles 1412 go through the disease management system 1410 and extend out the bottom of the disease management system 1410. The housing 1402 is tall enough such that when the disease management system 1410 is docked within the housing 1402 with the needles 1412 extending through the disease management system, the needles 1412 do not extend out the bottom of the housing 1402. When the housing 1402 is placed onto the patient, the needles 1412 do not contact the patient.

A spring loaded holding mechanism 1406 is capable of securely holding the disease management system 1410 within the housing 1402. A button 1404 is located on the top of the housing 1402 which is connected to a force mechanism 1404A which is in contact with the disease management system 1410 with the needles 1412. When the button 1404 is pressed, the force mechanism 1404A is activated such that the spring loaded holding mechanism 1406 is released and the disease management system 1410 with the needles 1416 is propelled downwards towards the patient. After the disease management system 1410 is applied to the patient, the needles 1416 are retracted by needle holding mechanisms 1414 while the cannulas 1416 stay within the patient. Thus the disease management system 1410 is able to access the patient's interstitial fluid or blood.

The needle holding mechanisms 1414 attached to the needles 1416 are ejected by pushing another button 1408. While the button 1408 is located on the side and the button 1404 is located on top, in other implementations, the buttons may be located on other portions of the housing 1402.

Further, by ejecting the needles 1416, the applicator 1400 may be loaded with a fresh set of needles 1416 and another disease management system 1410 and thus be reusable. In some implementations, the applicator 1400 may be one time use with the needles 1416 being disposed of with the applicator 1400 thus making the applicator 1400 disposable.

FIG. 21A illustrates a perspective view of an applicator 1500 for applying a disease management system to a patient. The disease management system may be any implementation of a disease management system described herein, such as a disease management system 100 of FIGS. 3A and 3B. FIGS. 21B-21F-4 illustrates various cross sectional views at various stages of use of the applicator 1500 in applying the disease management system to the patient. The disease management system includes a housing 1502 which is capable of accommodating a disease management system 1510 and one or more needles 1512. The disease management system 1510 may include one or more cannulas and one or more glucose monitoring probes. The needles 1512 may be used to implant the one or more cannulas and one or more glucose monitoring probes onto the patient. The housing 1502 may include an outer portion 1502A and an inner portion 1502B. The needles 1512 can go through the disease management system 1510 and extend out the bottom of the disease management system 1510. The housing 1502 is tall enough such that when the disease management system 1510 is docked within the housing 1502 with the needles 1512 extending through the disease management system 1510, the needles 1512 do not extend out the bottom of the housing 1502. Below the housing 1502, an adhesive 1516 is used to attach the housing 1502 to the patient during application of the administration system 1510. The needles 1512 may be above the adhesive 1516 however do not contact the patient when the housing 1502 is placed onto the patient.

Figure 24E:
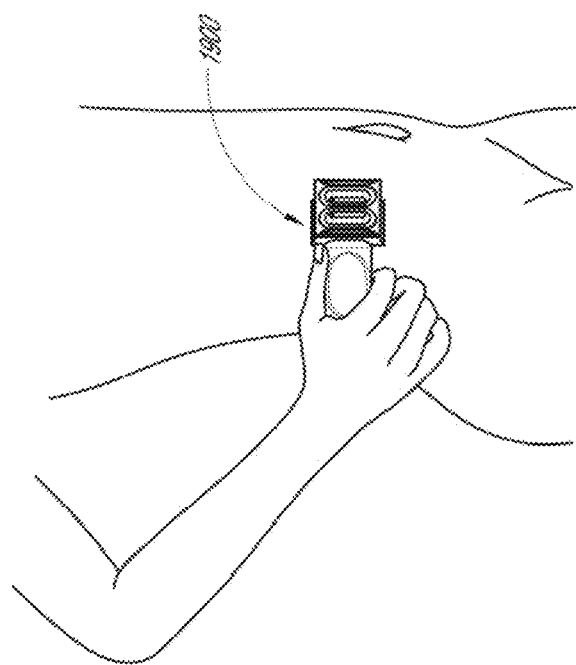
FIG. 24E illustrates a view of the applicator of FIGS. 24A-24D during application of disease management systems to a patient.
Figure 24D:
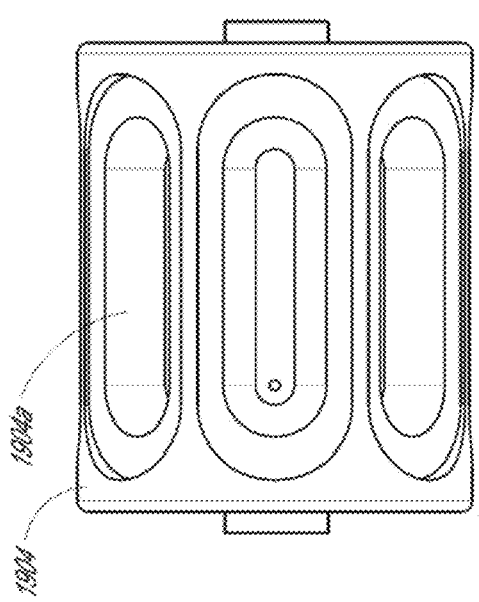

One or more clamping mechanisms 1506 is capable of securely holding the disease management system 1510 within the housing 1502. One or more force mechanisms 1504 are connected to the outer portion 1502A of the housing 1502. When the outer portion 1502A is pressed down into the inner portion 1502B, the clamping mechanisms 1506 releases the disease management system 1510 and the forcing mechanisms 1504 propel the disease management system 1510 with the needles 1512 downwards toward the patient. After the disease management system 1510 is applied to the patient, the needles 1512 are retracted by needle holding mechanisms 1514 which may be forced upwards by springs 1518. FIGS. 24B-1, 24B-2, and 24C illustrates the applicator 1500 with the outer portion 1502A and inner portion 1502B of the housing separated. FIG. 24D illustrate the applicator 1500 with pressure 1518 applied to the outer portion 1502A of the housing 1502 and the inner portion 1502B pressed against the patient. The outer portion 1502A presses vertically into the inner portion 1502B. As illustrated in FIG. 24E, after the outer portion 1502A of the housing 1502 and the inner portion 1502B are pressed into each other, the claiming mechanisms 1506 release outwards and the forcing mechanisms 1504 propel the disease management unit 1510 with the needles 1512 downwards toward the patient such that the needles 1512 penetrate the patient. As illustrated in FIG. 21F-1, after the disease management unit 1510 has been applied to the patient, the needles 1512 which are connected to needle holding mechanisms 1514 are retracted using springs 1518. As illustrated in FIGS. 21F-2-21F-3, the disease management system 1510 can include a glucose probe 1510A which is connected to a glucose sensor and a cannula 1510B which is connected to an insulin pump. The needles 1512 are used to implant the glucose probe 1510A and the cannula 1510B. When the needles 1512 are retracted, the glucose probe 1510A and the cannula 1510B remain implanted within the patient.

Figures 21, 21F:
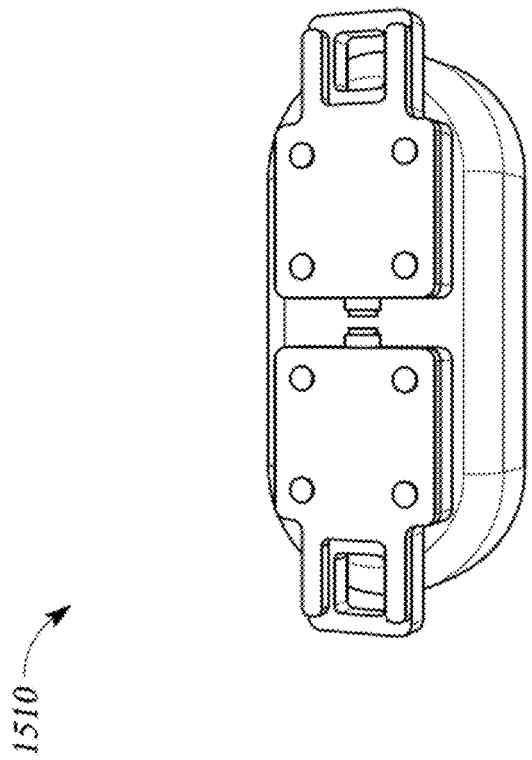
Figures 20, 21F:
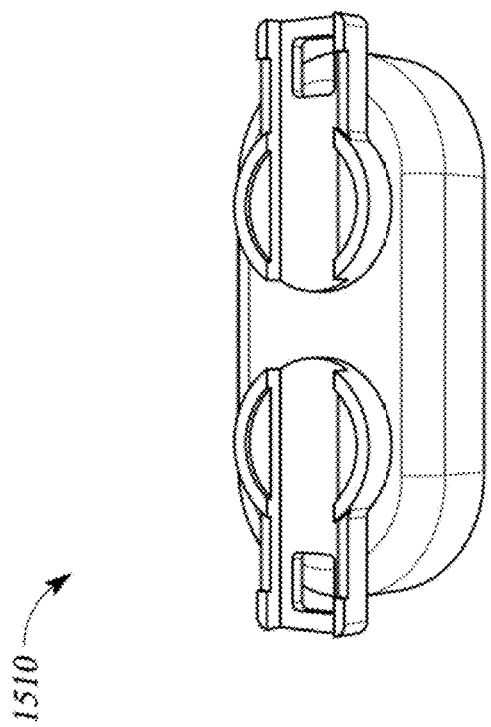
Figures 21, 21F:
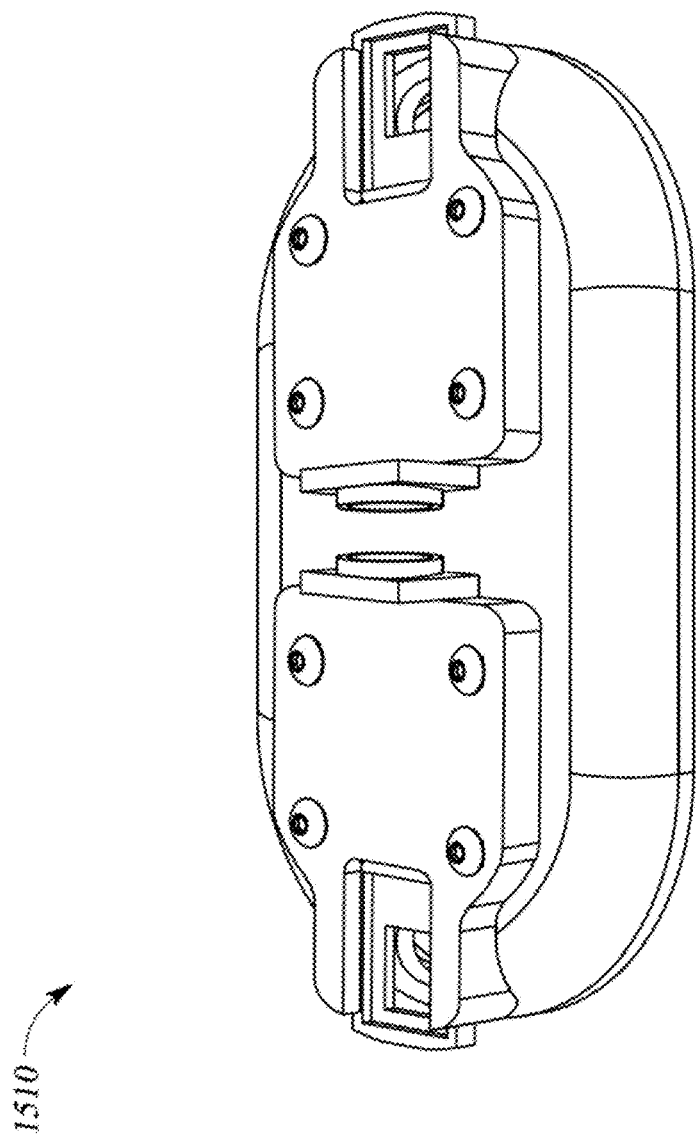
Figure 224:
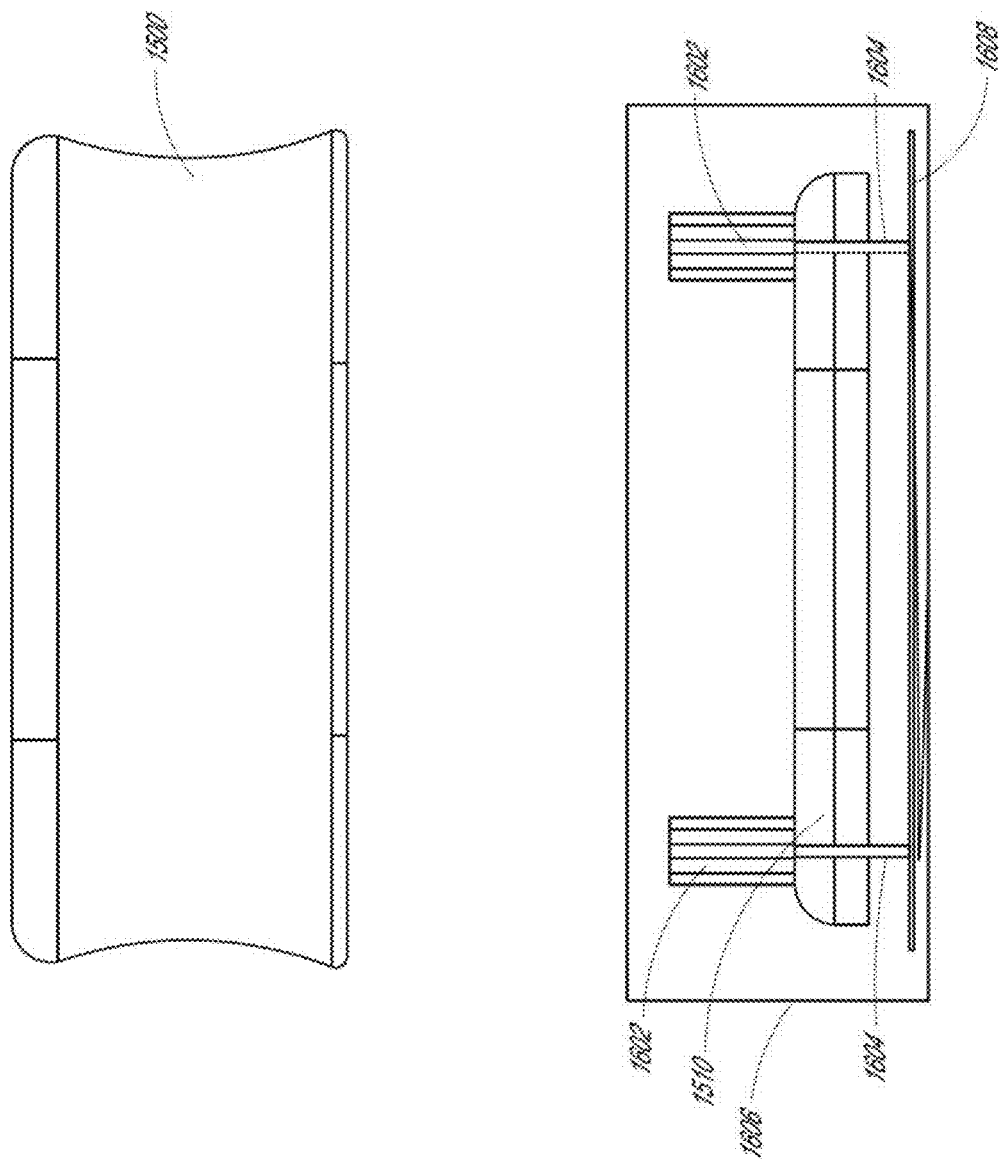
Figure 221:
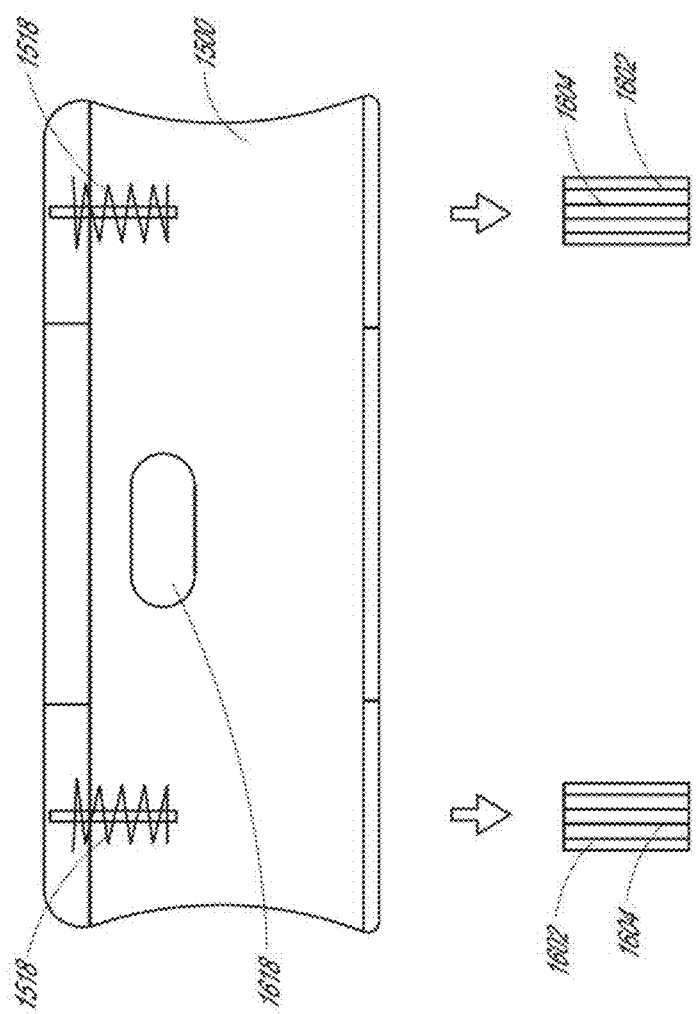

In some implementations, portions of the applicator 1500 may be disposable while other portions may be reusable. For example, as shown in FIG. 21F-4, the applicator 1500 can include at least two components. The at least two components can be an outer component 1500A and an inner component 1500B. The outer component 1500A can be reusable and able to apply multiple disease management systems 1510. The inner component 1500B can be disposable such that the inner component 1500B can be disposed of after applying a single disease management system 1510. The disease management system 1510 may also be disposable. Various views of these components 1500A, 1500B and systems 1510 are shown in FIGS. 21F-5-21F-21. In some configurations, the inner and outer components 1500A, 1500B of the applicator 1500 may both be reusable or disposable.

Figure 25B:
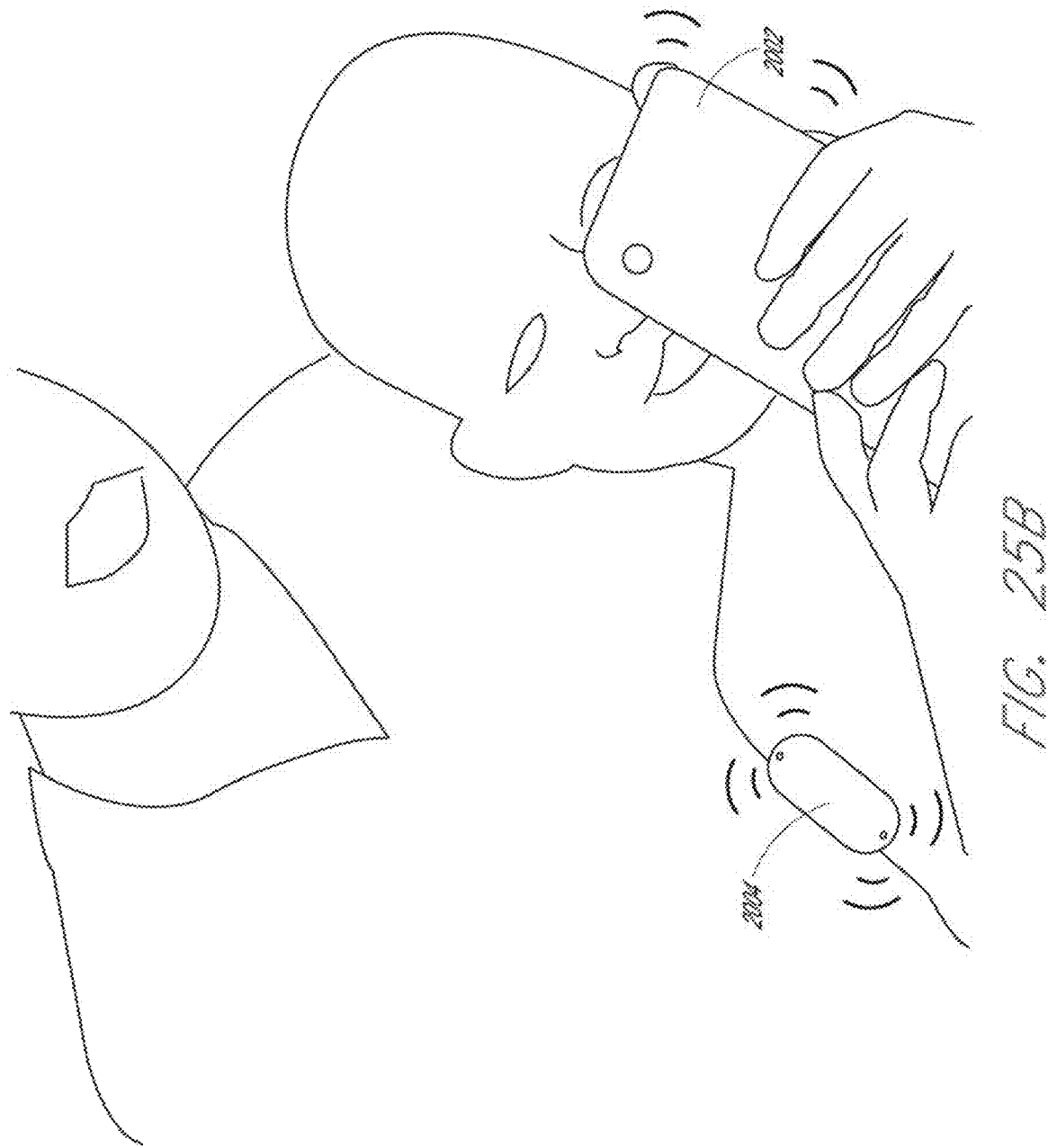

In some implementations, the applicator 1500 and the disease management system 1510 are presented to the patient as a packaged unit with the disease management system 1510 docked within the applicator 1500. The needles 1512 and the needle holding mechanisms 1514 may be disposed of with the applicator 1500 after application of the disease management system 1510. FIGS. 22A-22I illustrate various views of an implementation where the applicator is reusable and able to apply multiple disease management units. FIG. 22A illustrates an applicator 1500 and a disease management system 1510. The disease management system 1510 is within packaging 1606 and the disease management system 1510 is preloaded with needles 1604 which are connected to lancet backings 1602. The needles may be loaded onto an adhesive 1608. FIG. 25B illustrates the top 1606A of the packaging 1606 being removed to expose the top of the disease management system 1510. The needles 1604 will remain hidden facing towards the bottom of the packaging 1606. FIG. 25C illustrates the disease management system 1510 docked within the applicator 1500. A user is able to press the applicator 1500 into the packaging 1606 where the disease management system 1510 will dock into the applicator 1500. FIG. 16d illustrates the applicator 1500 being lifted from the packaging 1606 with the disease management system 1510. Further, the adhesive 1608 may include a liner 1608A. The liner 1608A may be adhered to the bottom of the packaging 1606 such that when the applicator 1500 is lifted from the packaging 1606, the liner 1608A is removed and the adhesive 1606 is ready to be applied to the patient.

FIG. 22E illustrates the applicator 1500 where the adhesive 1608 is adhered to the patient. The applicator 1500 may be equipped with a button 1610 which is configured to launch the disease management system 1510 into the patient. As described in FIG. 21A-21F, the applicator 1500 may not have a button 1610 but instead may have an outer housing 1502A and an inner housing 1502B and the outer housing 1502A compresses into the inner housing 1502B which launches the disease management system 1510.

FIG. 22F illustrates a view of the applicator 1500 after launching the disease management system 1510 into the patient. The adhesive 1608 attaches the applicator to the patient and when a user presses the button 1610 the disease management system 1510 is launched toward the patient with the needles 1604. The needles 1604 puncture through the adhesive 1608 and into the patient. FIG. 22G illustrates a view of the applicator 1500 after the springs 1518 withdraw the needles 1604 out of the patient. After puncturing the patient, the needles 1604 are withdrawn by the springs 1518 into the lancets 1602. The needles 1604 may be used to implant a cannula 1614 attached to an insulin pump and a glucose probe 1616 which is attached to a glucose sensor into the patient.

FIG. 22H illustrates a view of the applicator 1500 being lifted off the patient. Within the applicator 1500, the lancets 1602 with the needles 1604 are also lifted off the patient leaving the disease management system 1510 which is adhered to the patient by the adhesive 1608. FIG. 16i illustrates a view of the applicator 1500 during disposal of the needles 1604. After the applicator 1500 has been lifted off the patient, the user may press a side button 1618 located on the applicator 1500 which ejects the needles 1604 within the lancets 1602. The lancets 1602 safely store the needles 1604 such that the sharp end of the needles 1604 do not cause unintentional harm during disposal. Also, after puncturing the patient, the needles 1604 are contaminated with the patient's bodily fluids and the lancets 1602 keep the bodily fluid contained during disposal.

Figures 1, 22J:
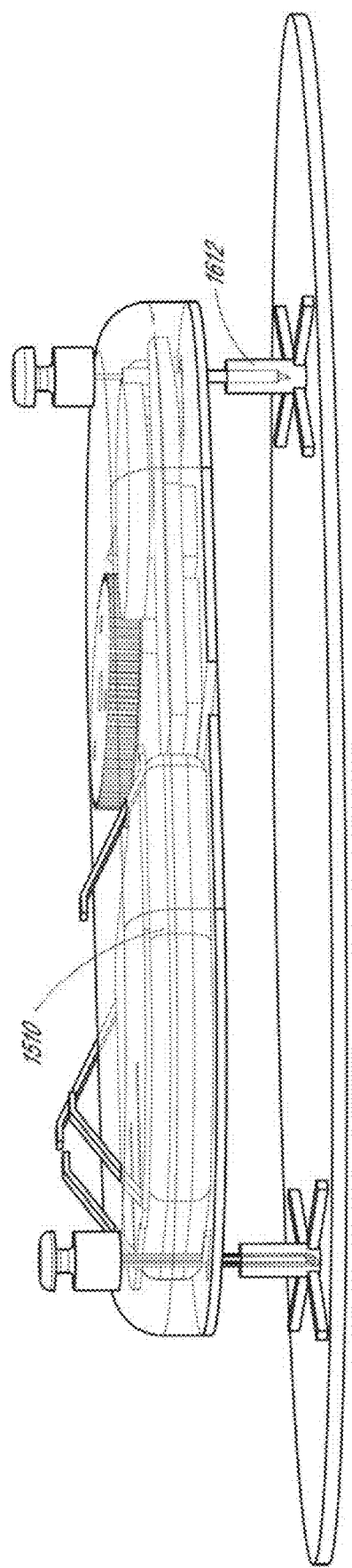
Figures 2, 22J:
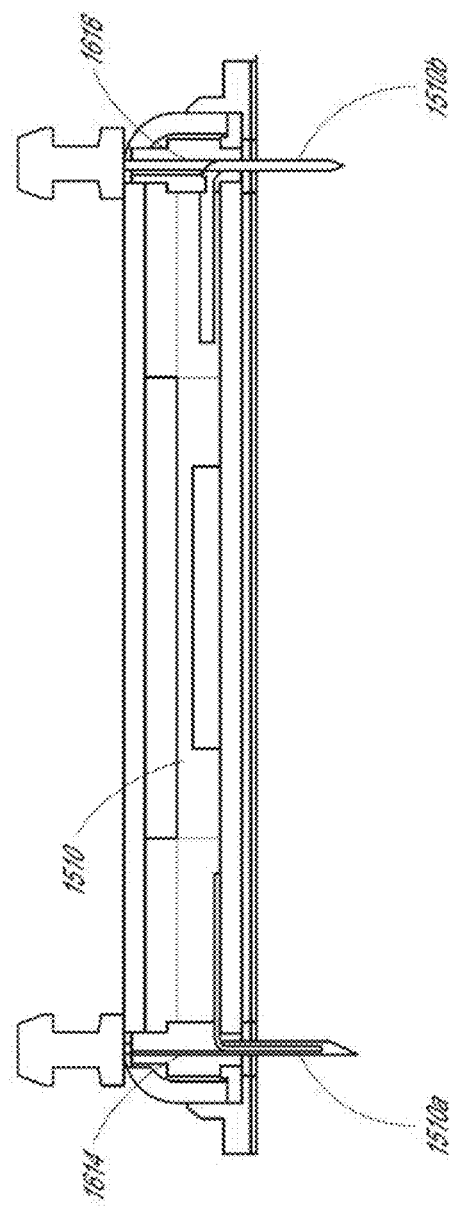

FIG. 22J-1 illustrates an implementation of the disease management system 1510 integrated with needles 1604. In this implementation, the needles 1604 pass through guide tubes 1612. The guide tubes 1612 such that when the applicator 1500 launches the disease management system 1510, the needles 1604 pass into the patient straight. Further, the guide tubes 1612 allow for easy storage of the needles on the adhesive 1608 while the disease management system 1510 is stored within the packaging 1606. For example, if the device is double in height of the needles, the needles may be retracted entirely into the device. Additionally or alternatively, needles may be retracted in their entirety from the device or back into the applicator.

FIG. 22J-2 illustrates an implementation of the disease management system 1510 integrated with needles 1614, 1616. The disease management system 1510 includes both a glucose probe 1510A and a cannula 1510B. A first needle 1614 is used to implant the glucose probe 1510A whereas a second needle 1616 is used to implant the cannula 1510B. The first needle 1614 may be a hollow needle such that the glucose probe 1510A fits within the hollow needle. The first needle may be a U-shaped needle. The second needle 1616 may be a solid needle capable of fitting into the middle of the cannula 1510B which is a hollow tube. In some implementations, the second needle 1616 may also be a U-shaped needle with a hollow center and the cannula 1510B may have a smaller diameter than the hollow center of the U-shaped needle which allows the cannula 1510B to fit within the U-shaped needle. When the second needle 1616 is a solid needle which fits within the hollow portion of the cannula 1510B, the solid needle may kink the cannula 1510B when retracting out of the patient because of the friction between the solid needle and the cannula 1510B. Advantageously, the U-shaped needle that goes around the cannula 1510B may produce less friction and thus not kink the cannula 1510B during retraction.

FIG. 22J-3 illustrate perspective views of an implementation of a disease management system 1510 that may be applied with an applicator described with reference to FIGS. 20A-22J-2.

Figure 23B:
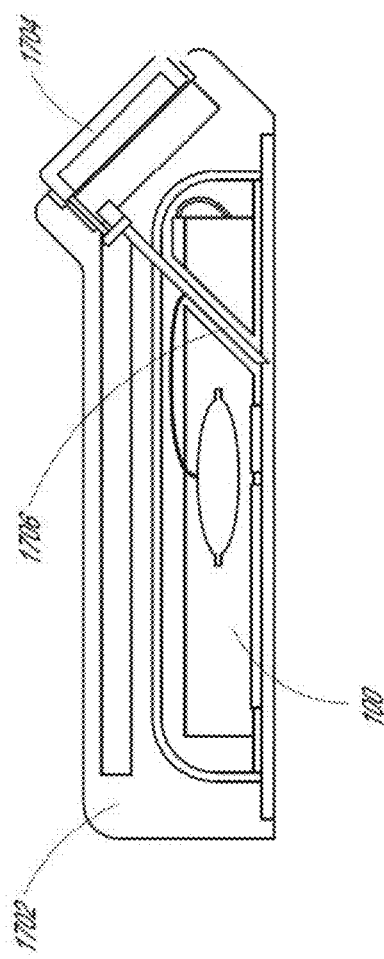
FIG. 23B illustrates a cross sectional view of the applicator of FIG. 23A installed on the disease management system.
Figure 23A:
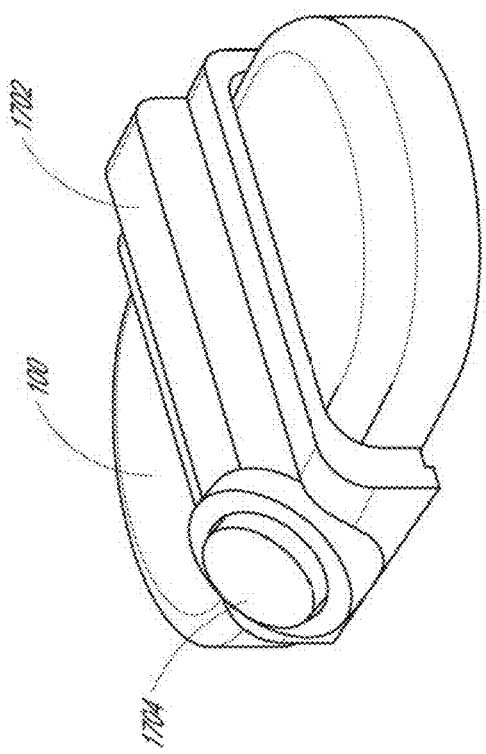
FIG. 23A illustrates a perspective view of an applicator for applying a disease management system.

FIG. 23A is a perspective view of an implementation of an applicator 1702 for applying a disease management system to a patient. FIG. 23B is a cross sectional view of the applicator 1702 and the disease management system 100. In this implementation, the applicator 1702 does not encase the entire disease management system 100 but merely grasps a portion of the disease management system 100. The applicator 1702 includes a button 1704 which is connected to a needle 1706 which sits within the disease management system 100. When a user presses the button 1704 the needle 1706 is inserted into the patient's skin. The needle may implant a cannula connected to an insulin pump into the patient. The needle may also implant a glucose probe which is connected to a glucose sensor into the patient. When the button 1704 is depressed, the needle 1706 may come back up out of the patient. As illustrated, the needle may be implanted at an angle to the patient's skin rather than perpendicularly. The angle may be 20°-70° with respect to the patient's skin. In some implementations, the angle may be 450 with respect to the patient's skin. Further, there may be two buttons to insert two separate needles into the patient to implant the cannula and the glucose probe into the patient. In some implementations the applicator 1702 may be made out of a plastic and may be textured in order to aid in user handling.

1. Example Applicator Wheel

FIG. 24A is a perspective view of an applicator 1900 which is configured to apply the disease management system, the insulin pump system 200A of FIGS. 4A and 4B, or the sensor system 200B of FIGS. 4A and 4B. FIG. 24B is a top down view of the applicator 1900. FIG. 24C is a side view of the applicator 1900. FIG. 24D is a top down view of an applicator wheel 1904 of the applicator 1900. FIG. 24E is a view of the applicator 1900 while applying one or more units to a patient. The applicator 1900 includes a handle portion 1902 and an applicator wheel 1904. The applicator wheel 1904 may be cylindrically shaped and includes one or more holes 1904A which are capable of storing one or more units. The units may be disease management systems 100, insulin pump systems 200A, and/or disease management systems 200B. A user grips the handle and rolls the applicator wheel 1904 over the patient with the applicator wheel 1904 physically contacting the patient. The applicator wheel 1904 may rotate when rolled across the patient such that when one of the disease management systems 100, insulin pump systems 200A, or disease management systems 200B contacts the patient, the system is applied to the patient such that when the applicator 1900 is removed from the patient, the system remains.

2. Example Distraction During System Application

Application of treatment systems may result in anticipated pain in certain users. Anticipatory pain can be high in, for example, new users who have needle phobia and can be a hindrance for children or their parents applying a treatment system to their children. Systems and methods described herein may help reduce anticipatory pain.

In one embodiment, a system may reduce anticipatory pain by distracting the patient during application of a treatment system. In some examples, the system may utilize companion software, such as an application on a user's mobile device or other graphical user interface or platform. In some examples, the companion software may communicate with one or more aspects of the treatment system, such as an applicator tool. The applicator tool may provide status of the placement of one or more aspects of the treatment system, such as a CGM sensor. The applicator tool may communicate with the mobile device running the companion software directly or indirectly, with wires or wirelessly, such as through Bluetooth and/or NFC communication.

The companion software may gamify the application process. A goal of the game is to distract the attention of the patient with visuals, audio, and tactile feedback. The game may be themed according to the interests and tastes of the user, maturity level of the user, familiarity with treatment system. The companion software may communicate stimuli based on a position of the applicator tool or other component of the treatment system and stimuli based associated with the process of the un-packing and application steps from preparing site to injecting needles to finally securing the device. The positioning may be captured by the CGM/pump device's accelerometer, gyroscope, and/or RFID tags within packing or based on the user's acknowledgment of steps through the entertainment game. A climax of the distraction stimuli can be timed with or just after the true injection action into the skin which will help to reduce the anticipatory pain.

FIG. 25A is a view of a step in a method of distracting a patient during application of a disease management system 2004. The disease management system 2004 includes one or more needles which may create anxiety based on the anticipation of pain for the patient. Specifically when the patient is a child, anticipation of pain may hinder application of the disease management system 2004. In this method of distracting the patient, the disease management system 2004 interacts with a distraction device 2002 which may be used to distract the patient during application of the disease management system 2004. The distraction device 2002 is configured to create a distracting event such that the distraction device 2002 times the distracting event with application of the disease management system 2004. The distraction device 2002 may be a user device such as a smartphone or another disease management system which is capable of vibrating. When the distraction device 2002 is a user device, such as mobile device or another device with a display, the user device may allow the patient to play a game, watch a movie, or read a story before and during application of the disease management system. The application of the disease management system 2004 may be timed with the climax of the game, the movie, or the story. The disease management system 2004 may be equipped with an indicator such as a vibration feature or a light in order to indicate to the person applying the disease management system 2004 to the patient that it is an optimal time to apply the disease management system 2004.

FIG. 25B is a view of another step in the method of distracting the patient during application of the disease management system 2004. The disease management system 2004 may be equipped with a feedback features such as a vibration feature. After application of the disease management system 2004, the disease management system 2004 may feedback so as to distract the patient from the pain or past anxiety.

3. Example Reduced Pain Application Systems

In addition or in the alternative to distraction systems for anticipatory pain, residual pan and actual pain can be reduced by one or more application systems.

Figure 26B:
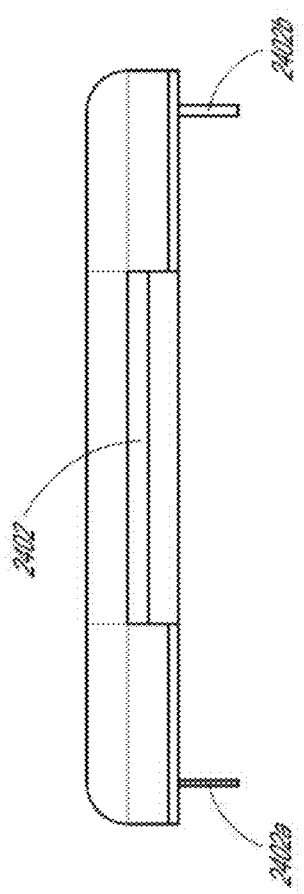
FIGS. 26A and 26B illustrate an exemplary method of implanting a disease management system on a patient.
Figure 26A:
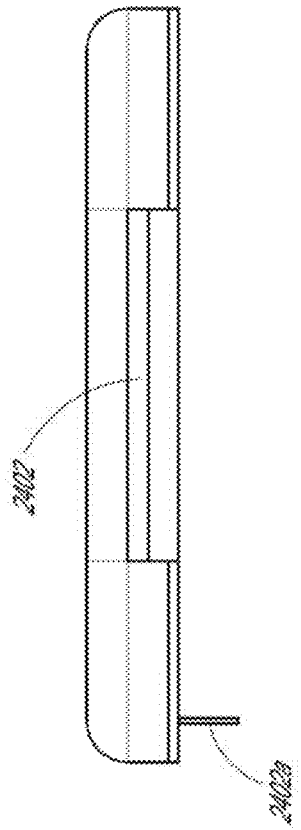

For example, FIGS. 26A and 26B illustrate an exemplary method of implanting a disease management system 2402 on a patient. FIG. 26A illustrates a first step which includes implanting a glucose probe 2402A of the disease management system 2402 into the patient. FIG. 26B illustrate a second step which includes implanting a cannula 2402B of the disease management system 2402 into the patient. While FIGS. 26A and 26B illustrate the glucose probe 2402A first, implanting the cannula 2402B may be performed first followed by the glucose probe 2402A as well. As discussed above, implanting the glucose probe 2402A and/or the cannula 2402B involves needles which can involve a great deal of pain. When implanting the glucose probe 2402A and cannula 2402B simultaneously, overall pain is much larger than the process of implanting just one of the glucose probe 2402A or the cannula 2402B. Thus, implanting them one at a time as opposed to simultaneously can reduce the overall amount of discomfort to the patient.

In some implementations, the less painful of the glucose probe 2402A or the cannula 2402B may be implanted first. With the implantation of one of the glucose probe 2402A or the cannula 2402B, an analgesic may be administered to the patient which may numb the patient before the implantation of the other of the glucose probe 2402A or the cannula 2402B. Thus, when the other of the glucose probe 2402A or the cannula 2402B is implanted, the patient may experience less discomfort.

In some examples, residual pain can also be reduced with hard needles that transition to become the soft cannula itself or dissolve away. Traditional insertion needles are hard needles are made of metal or hard plastic that may result in residual pain for a patient. Systems and methods described herein may allow for reduced residual pain.

Figures 2, 27A:
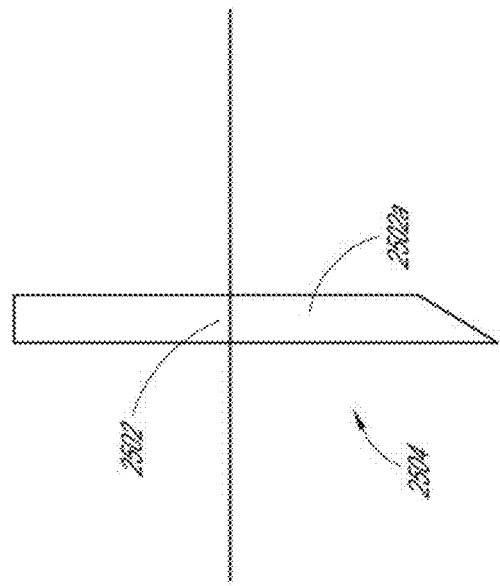
Figures 1, 27A:
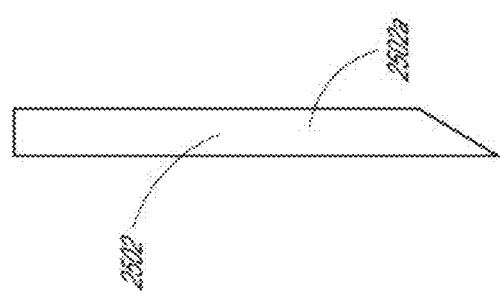

FIGS. 27A-1 and 27A-2 illustrate an exemplary implementation of a solid needle 2502. FIG. 27A-1 illustrates the solid needle 2502 out of the patient, for example, before implantation or after being removed from the patient. FIG. 27A-2 illustrates the solid needle 2502 after implantation into a patient 2504. Below the solid line represents the inner portion of the patient 2504. As illustrated, a bottom portion 2502A of the solid needle 2502 remains straight and stiff after implantation. In some implementations, the solid needle 2502 may be made out of metal or hard plastic.

In one embodiment for reducing residual pain, a treatment system may use a dehydrated-hydrated needle (DHN) to reduce residual pain. The DHN may be made of one or more materials, such as collagen or hydrogel or other materials that have following properties: soft at wet state (hydrated) and hard at dry state (dehydrated). The DHN may be constructed by dehydrated-hydrate materials by itself or with plastic support.

Figures 2, 27B:
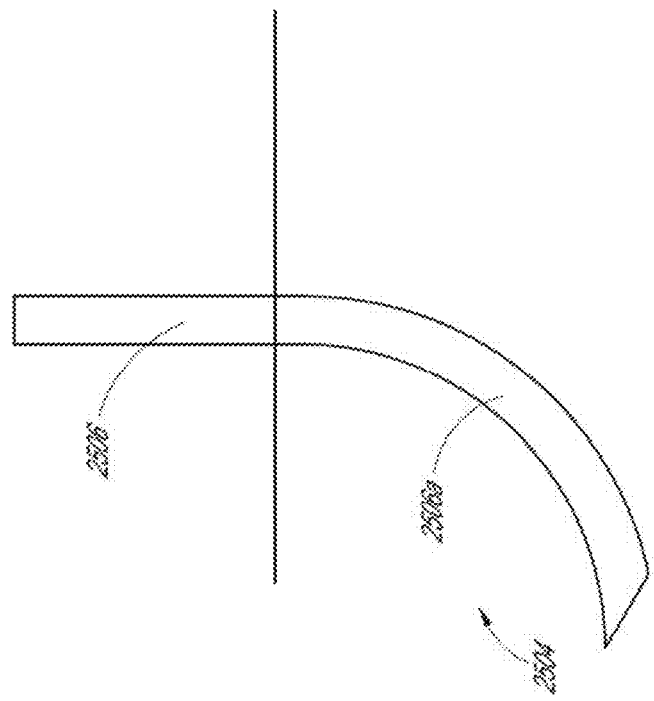
Figures 1, 27B:
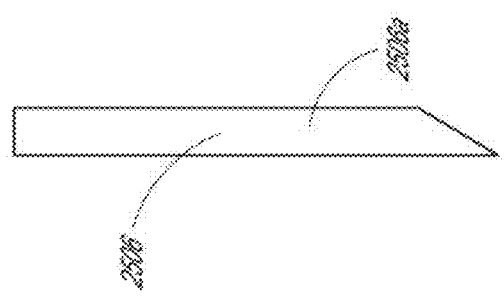
Figures 3, 27B:
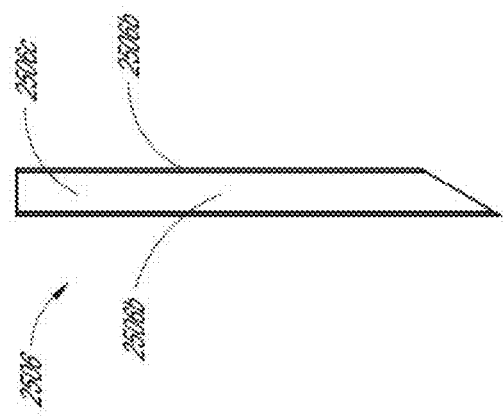

FIGS. 27B-1 and 27B-2 illustrate of another exemplary implementation of a solid needle 2506. FIG. 27B-1 illustrates the solid needle 2506 out of the patient, for example, before implantation or after being removed from the patient. As illustrated, the bottom portion 2506A of the solid needle 2506 remains straight and stiff while out of the patient. Advantageously, a straight and stiff bottom portion 2506A allows the solid needle 2506 to be properly implanted into the patient. FIG. 27B-2 illustrates the solid needle 2506 while implanted within the patient. In contrast to the solid needle 2502 described in connection with FIG. 27A-2, the bottom portion 2506A of the solid needle 2506 shown in FIG. 27B-2 becomes flexible while implanted within the patient. Below the solid line represents the inner portion of the patient 2504. In some implementations, the solid needle 2506 is made out of a material that is hard or stiff when dry or dehydrated. The solid needle 2506 then turns soft or pliable when wet or hydrated. The inner portion of the patient 2504 contains water and thus will turn the bottom portion 2506A of the solid needle 2506 soft or pliable when the solid needle 2506 is implanted within the patient. Advantageously, when the bottom portion 2506A becomes soft or pliable while implanted within the patient 2504, it may cause less discomfort to the patient. This also means that a separate needle and needle recovery system is not needed.

In some implementations, the solid needle 2506 may be made out of a collagen or hydrogel. FIG. 27B-3 illustrate an exemplary implementation of a solid needle 2506 including an inner layer 2506C and an outer layer 2506B. The outer layer 2506B surrounds the inner layer 2506B. The inner layer 2506C or the outer layer 2506B may be made out of a support layer such as plastic or metal. The other of the inner layer 2506C or the outer layer 2506B may be made out of a material that becomes soft or pliable when wet or hydrated such as hydrogel or collagen. In one implementation, the inner layer may be made out of plastic or metal and the outer layer may be made out of hydrogel or collagen.

Figures 2, 27C:
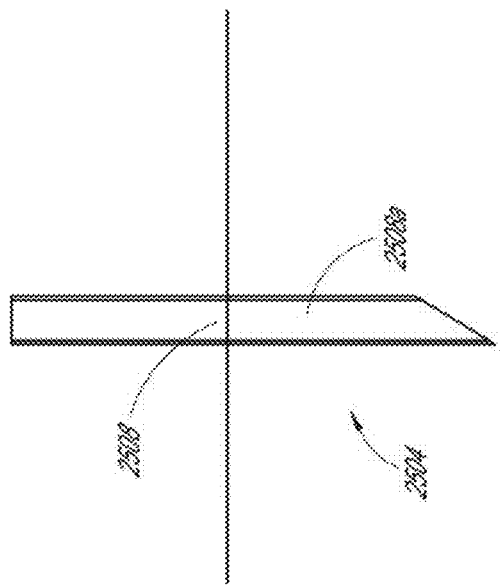
Figures 1, 27C:
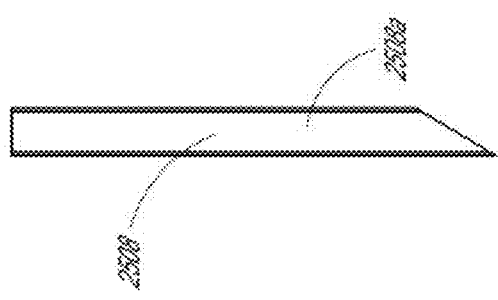

FIGS. 27C-1 and 27C-2 illustrate an exemplary implementation of a hollow needle 2508. FIG. 27C-1 illustrates the hollow needle 2508 out of the patient, for example, before implantation or after being removed from the patient. FIG. 27C-2 illustrates the hollow needled 2508 after implantation into a patient 2504. Below the solid line represents the inner portion of the patient 2504. As illustrated, a bottom portion 2508A of the hollow needle 2508 remains straight and stiff after implantation. In some implementations, the hollow needle 2508 may be made out of metal or hard plastic.

FIGS. 27D-1 and 27D-2 illustrate an exemplary implementation of a hollow needle 2510. FIG. 27D-1 illustrates the hollow needle 2510 out of the patient, for example, before implantation or after being removed from the patient. As illustrated, the bottom portion 2510A of the hollow needle 2510 remains straight and stiff while out of the patient. Advantageously, a straight and stiff bottom portion 2510A allows for the hollow needle 2510 to be properly implanted within the patient. FIG. 27D-2 illustrates the hollow needle 2510 while implanted within the patient. In contrast to the hollow needle 2508 described in connection with FIG. 27D-1, the bottom portion 2510A of the hollow needle 2510 becomes soft or pliable when wet or hydrated. The inner portion of the patient 2504 contains water and thus will turn the bottom portion 2510A of the hollow needle 2510 becomes soft or pliable when the hollow needle 2510 is implanted within the patient. Advantageously, when the bottom portion 2510A becomes soft or pliable while implanted within the patient 2504, it may cause less discomfort to the patient. In some implementations, the hollow needle 2510 may be made out of a collagen or hydrogel. Similar to the solid needle 2506 of FIG. 27B-3, the hollow needle 2510 may include an inner layer and an outer layer that are made out of different materials. The inner layer or outer layer may include a support material such as plastic or metal. The other of the inner layer or outer layer may be made out of a material that becomes soft or pliable when wet or hydrated such as hydrogel or collagen. In one implementation, the inner layer may be made out of plastic or metal while the outer layer is made out of hydrogel or collagen.

In another embodiment, a needle of the treatment system can be made by segments and which then can control hard or soft through muscle wires. When current is applied through the muscle wire, the wire may shorten to hold all segments straight (inserted state). Without the current, wires may be loose and the segments movable (relaxed state).

Figures 2, 27E:
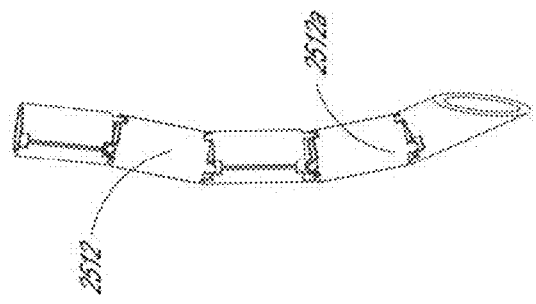
Figures 1, 27E:
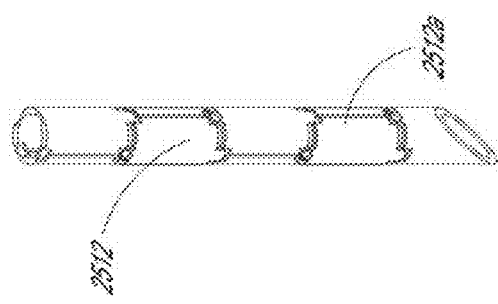

FIGS. 27E-1 and 27E-2 illustrate an exemplary implementation of a hollow needle 2512. The hollow needle 2512 may be made of a material that is stiff when inserted into the patient and then has the ability to a relaxed or limp state when the hollow needle 2512 has been implanted within the patient. As described previously, after the needle is implanted within the patient, it is advantageous for the needle to be soft or pliable in order to cause less discomfort to the patient. In some implementations the hollow needle 2512 may be made out of muscle wire which may be turned on making the hollow needle 2512 stiff and rigid when inserted into the patient and then turned off after inserted into the patient making the hollow needle 2512 soft and pliable and thus more comfortable to the patient after insertion. In some implementations, only the bottom portion 2512A of the hollow needle 2512 or the portion that resides within the patient may be made out of muscle wire. When a current is applied through the muscle wire, the wires within the muscle wire may be shorter to hold all the segments of the hollow needle 2512 straight and thus the hollow needle 2512 may be stiff and straight. When a current is not applied through the muscle wire, all the wires within the muscle wire may be loose and then the segments in the hollow needle 2512 may be moveable or flexible thus creating a relaxed state. While a hollow needle is illustrated, it is understood that the same or similar concepts may be applied to a solid needle.

In some implementations, at least a portion of the needle may be made out of a material which is soft when a radiation source such as ultra-violet (UV) light is applied to the material and rigid or hard when the radiation source is not applied to the material. In some implementations, at least a portion of the needle may be made out of a material which is hard or rigid when a radiation source such as UV light is applied to the material and soft or pliable when the radiation source is not applied to the material.

In another method, the needle can be a bioresorptable material that never needs to be removed and therefore also never needs an applicator to remove it. In this instance, the total height of a built-into-device applicator can also advantageously be reduced as much as 5 [mm], for example, because no retrieval springs or like methods need to be incorporated into the insertion mechanism. Additionally, as it is a bioresorptable material, the body may seal the wound and wound healing may be promoted to be faster than normal at the site. Additionally, there may also be better water-proofing and more resistance to external infection. Such materials can also have additional medicinal value with adsorbed, absorbed, or chemically altered material properties as they resorb into the body.

In some implementations, at least a portion of the needle may be made a material which degrades when exposed to the inside of the patient. The material which degrades may be a bioresorbable material. Advantageously, using a material which degrades when exposed to the inside of the patient allows for the needle not to be retracted after it is implanted within the patient. Thus, the applicator may not include springs for retracting the needles. For example, the springs 1518 of the applicator 1500 which are described in connection with FIGS. 21A through 21F-2 may not be included which may make the applicator 1500 less complicated and more compact. Additionally, a material which degrades when exposed to the inside of the patient allows the body of the patient to better seal the wound created by the needle and thus wound healing may be quicker. Further, not retracting the needles out of the patient may provide better water-proofing of the wound and more resistance to external infection. The material may have additional medicinal value with absorbed or chemically alerted material properties as they resorb into the body.

Additionally or alternatively, pain relief or analgesic may be administered to reduce both actual and residual pain. For example, analgesic can be incorporated into an adhesive layer of a CGM device or sensor. In one embodiment, a device would first attach to the user with the adhesive layer before launching needles. Before launching needles, the analgesic in the adhesive could diffuse over a period of time (for example, 15 minutes) in order to numb the site prior to needle insertion. Once numb, a built-into-device, re-usable, or disposable applicator can be fired to less painfully insert the device into the body.

In another example, pain relief can be administered in a time series based method. For example, first, a less painful needle could be inserted into the user at the insertion site that would sub-dermally deliver analgesic. Then after a period of time, the Cannula could be inserted in a manner that may less painfully (in terms of both physical and apprehensive pain) insert the device into the body.

In another example, analgesic can be administered by a pressurized jet that may be capable of delivering numbness in a relatively short period of time (for example, seconds). Once completed, a built-into-device, re-usable, or disposable applicator can be fired to less painfully (in terms of both physical and apprehensive pain) insert the device into the body.

H. EXAMPLE DISEASE MANAGEMENT SYSTEM APPLICATION

Figure 28:
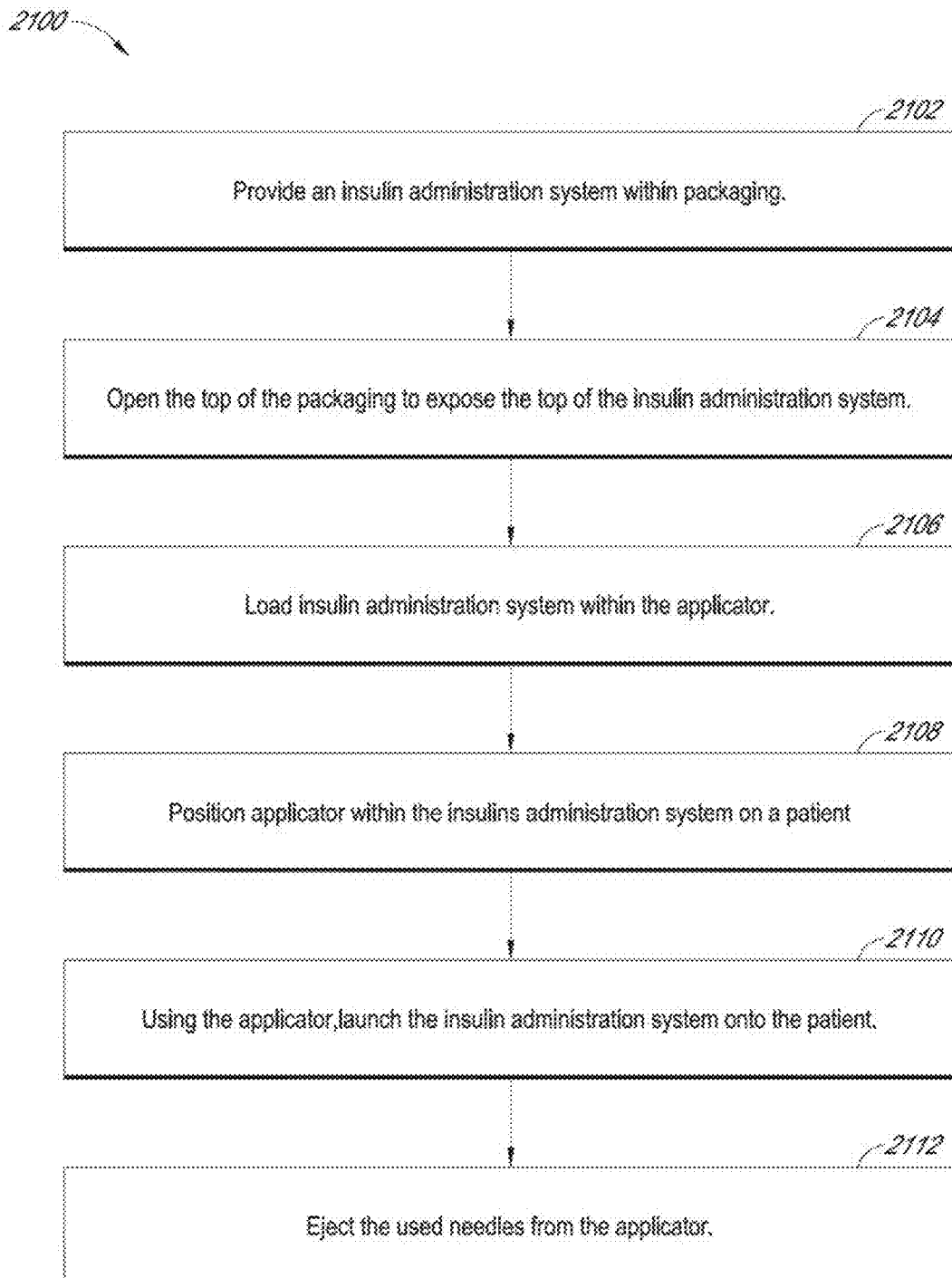
FIG. 28 is a flowchart illustrating a method for using an applicator to apply a disease management system.

FIG. 28 is a flowchart which illustrates a method 2100 for applying a disease management system to a patient. At block 2102, a disease management system is provided within packaging. The disease management system may be the disease management system 100 of FIGS. 3A and 3B or either of the sensor system 200B or the insulin pump unit 200A of FIGS. 4A-4C or any other implementation of disease management system described herein. At block 2104, a user can open the top of the packaging to expose the top of the disease management system. The disease management system may be stored within the packaging with the needles installed on the disease management system. The sharp portions of the needles may downwards and therefore when the user opens the top of the packaging, the needles are not exposed to the user.

At block 2106, the user loads the disease management system within the applicator. The user may load the disease management system by putting the applicator on the insulin dosage unit and pushing the applicator on the disease management system such that the applicator grasps the disease management system. At block 2108, while disease management system is loaded within the applicator, the applicator is positioned on the patient. An adhesive may be used to hold the applicator onto the patient.

At block 2110, the applicator launches the disease management system onto the patient. The applicator may include a button which is capable of releasing the applicator's grasp on the disease management system and therefore launching the disease management system onto the patient. Alternatively, the applicator may include an outer portion and an inner portion such as the applicator 1500 of FIGS. 24A-24F. In this instance, the applicator may release its grasp on the disease management system when the outer portion presses into the inner portion. The needles within the disease management system puncture the patient while the disease management system is applied to the patient. The needles further may implant a cannula attached to an insulin pump and a glucose probe attached to a glucose sensor. After the cannula and/or the glucose probe are implanted, the applicator withdraws needles from the patient. The applicator may be spring loaded such as to withdraw the needles or there may a button or lever which withdraws the needles.

After the applicator is removed from the patient, at block 2112, the applicator ejects the used needles and is thus ready to apply another disease management system and thus the applicator may be removable. The user may eject the needles by pressing a button or pulling a level. Alternatively, the applicator may be one time use and thus could be disposed of with the needles and thus the applicator may be disposable.

Figure 29B:
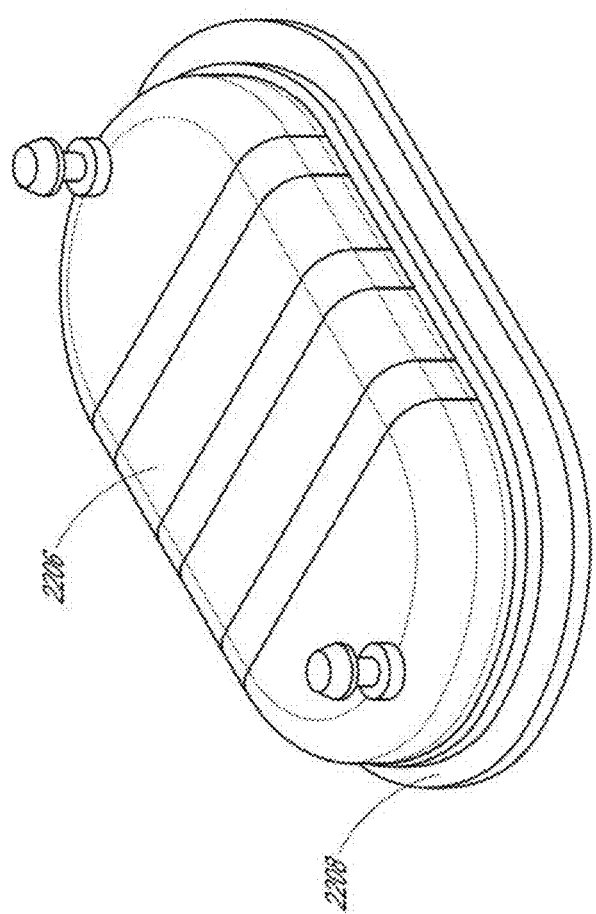
FIG. 29B is a perspective view of an exemplary implementation of a disease management system.
Figure 29A:
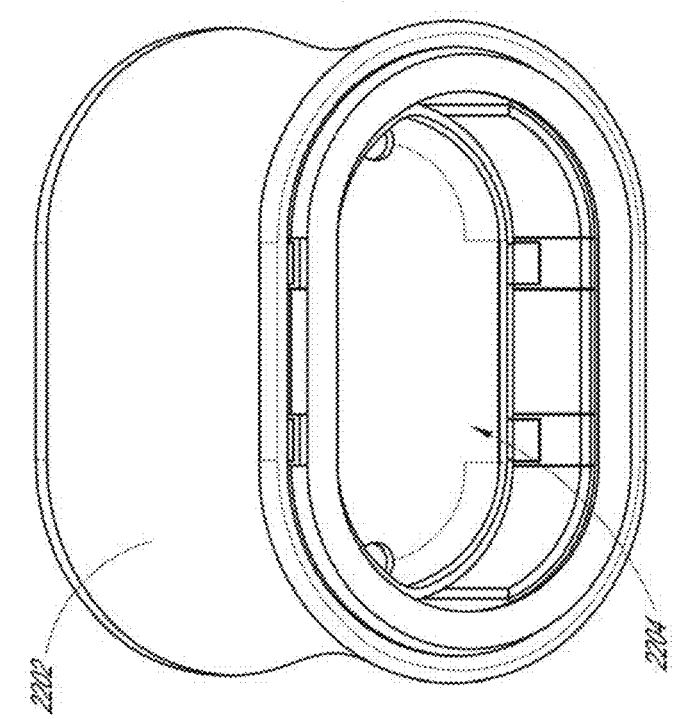
FIG. 29A is a perspective view of a bottom of an exemplary applicator for a disease management system.
Figure 29C:
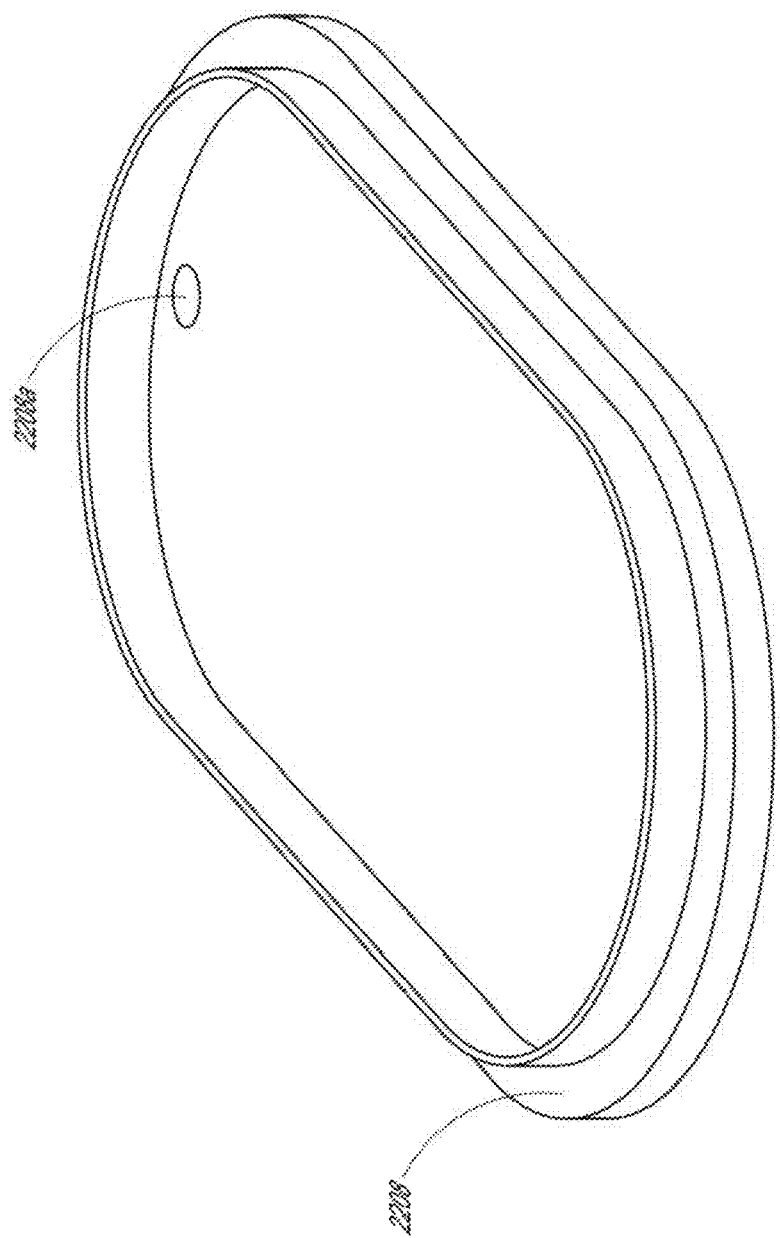
FIG. 29C is a perspective view of an exemplary implementation of an adhesive pad.
Figure 29D:
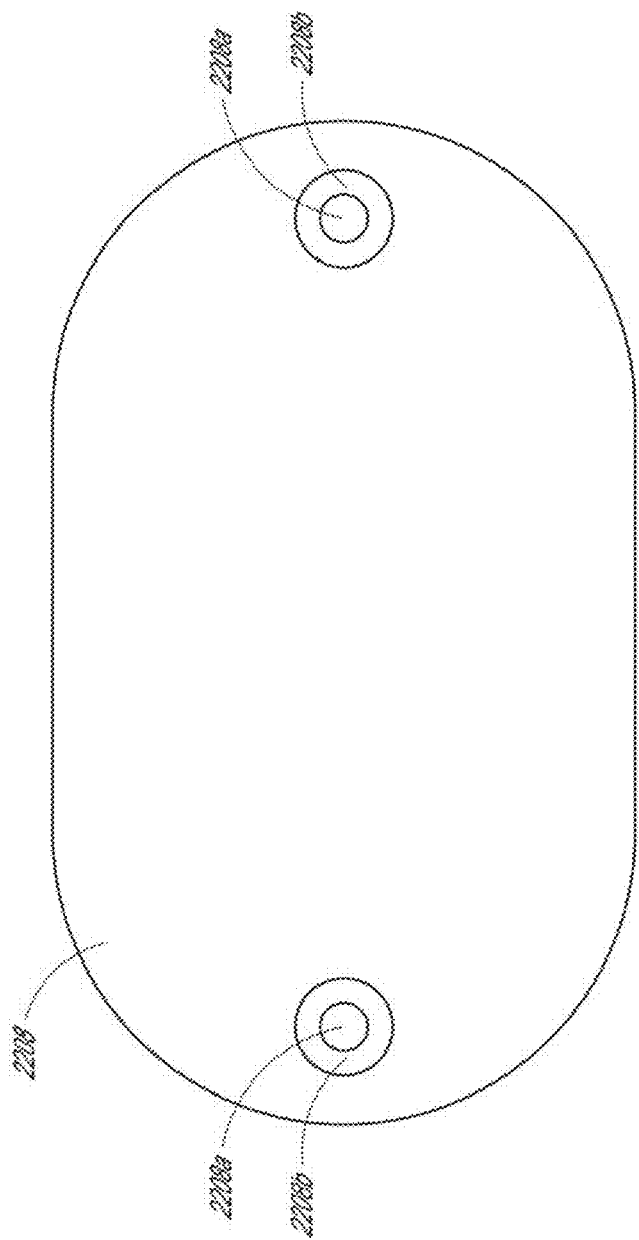
FIG. 29D is a bottom view of an exemplary implementation of an adhesive pad.

FIG. 29A is a perspective view of the bottom of an implementation of an applicator 2202. The applicator includes a cavity 2204 which is configured to hold a disease management system. FIG. 29B is a perspective view of a disease management system 2206 which is attached to an adhesive pad 2208. FIG. 29C is a perspective view of the adhesive pad 2208 which may be attached to the disease management system 2206 as illustrated in FIG. 29B. The adhesive pad 2208 may include one or more holes 2208A where a glucose probe and/or a cannula may pass through from the disease management system 2206 to the patient. FIG. 29D is a bottom side view of an implementation of the adhesive pad 2208. In this implementation of the adhesive pad 2208, each of the holes 2208A includes a ring of analgesic 2208B. When implanting the disease management system 2206 on the patient, the needles puncture the skin of the patient while implanting the glucose sensor and/or the cannula which may cause discomfort and/or pain. The analgesic 2208B may numb the patient at the position where the needles will puncture the skin in order to alleviate the discomfort and/or pain.

Figure 29E:
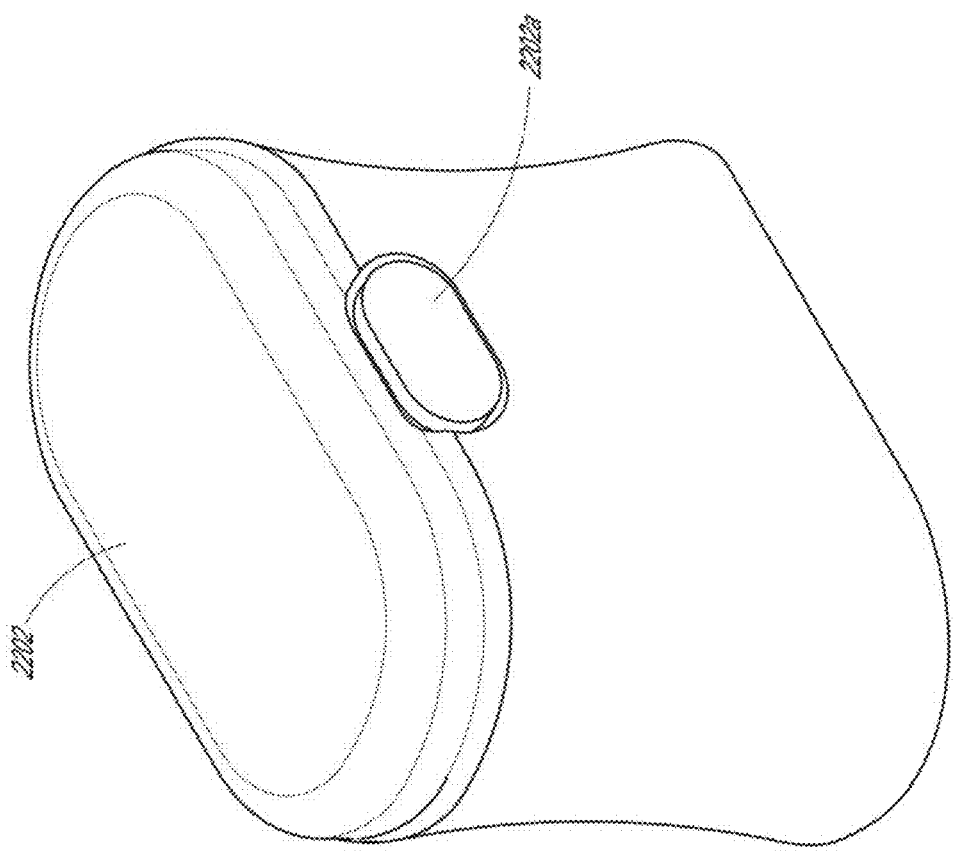
FIG. 29E is a perspective view of an exemplary implementation of an applicator for a disease management system.

FIG. 29E is a perspective view of an implementation of the applicator 2202. The applicator 2202 may include a safety button 2202A. While illustrated on the side of the applicator 2202, the safety button 2202A may be located at any position on the applicator 2202. The safety button 2202A prevents the launch of the applicator 2202 while the safety button 2202A is not activated. Thus, the applicator 2202 may not be launched while the safety button 2202A is not activated. The safety button 2202A is illustrated as a button and thus may be pressed to be activated. Alternatively, the safety button 2202A may be a mechanism which may be activated through a gesture, tapping, and/or swiping.

Figure 29F:
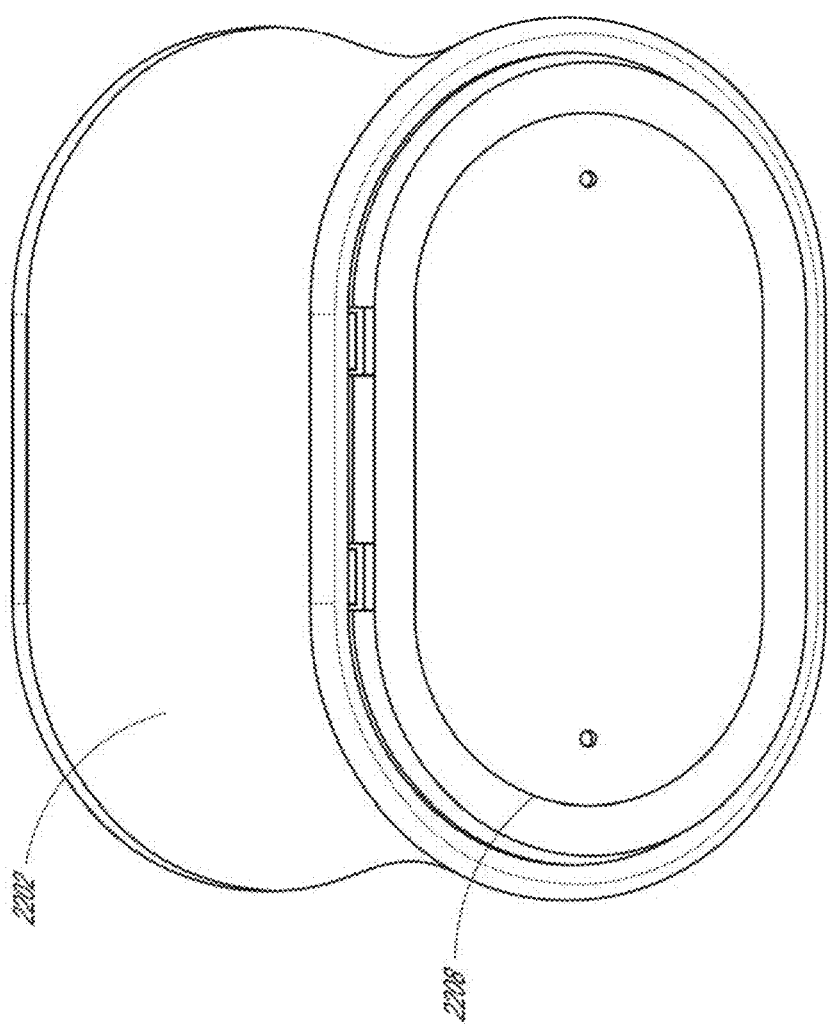
FIG. 29F is a perspective view of an exemplary implementation of a disease management system docked within an applicator.

FIG. 29F is a perspective view of the bottom of an implementation of the applicator 2202 which is loaded with a disease management system 2206. The disease management system 2206 is mounted on an adhesive pad 2208. During application, the applicator is placed on the patient such that the adhesive pad 2208 adheres to the patient.

FIG. 30A is a perspective view of an implementation of a disease management system 2302. FIG. 30B is a side view of the implementation of the disease management system 2302 of FIG. 30A. The disease management system 2302 includes two or more flex points 2302A. The flex points 2302A make the disease management system 2302 flexible and thus capable of better contouring to the curved surfaces of a patient's body when installed. When the disease management system 2303 better contours to a patient's body, the disease management system 2302 may be more stable while installed on the patient and also be more comfortable. The number of flex points 2302A may be optimized in order to provide adequate curvature of the disease management system 2303 to match the curves of the patient while also providing adequate stability for the components within the disease management system 2302 which may be flat. An adhesive pad 2304 is mounted on the disease management system 2302 in order to adhere the disease management system 2302 to a patient. The adhesive pad 2304 may include flex points which correspond to the flex points 2302A of the disease management system 2302

Figure 30C:
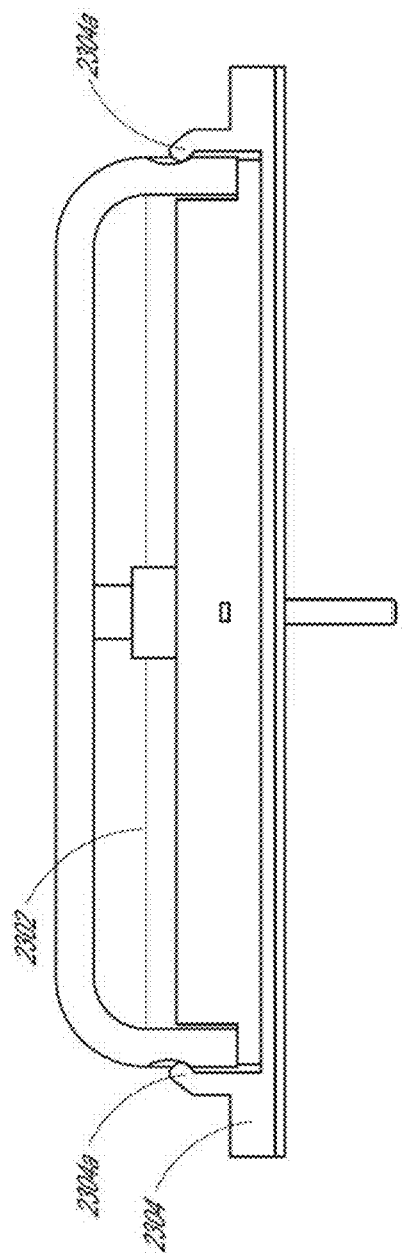

FIG. 30C is a side view of the implementation of the disease management system 2302 of FIGS. 33A and 33B. An adhesive pad 2304 is physically attached to the disease management system 2302 with side tabs 2304A at the side of the adhesive pad 2304. The side tabs 2304A create a hard interlock between the adhesive pad 2304 and the disease management system 2302. In some implementations, the adhesive pad 2304 may be attached to the disease management system 2302 through other methods such as adhesive, tape, and/or magnetic force. The disease management system 2302 may be separate from the adhesive pad 2304 through methods such as prying or lifting.

I. EXAMPLE CONNECTIVITY OF A DISEASE MANAGEMENT SYSTEM

Figure 31A:
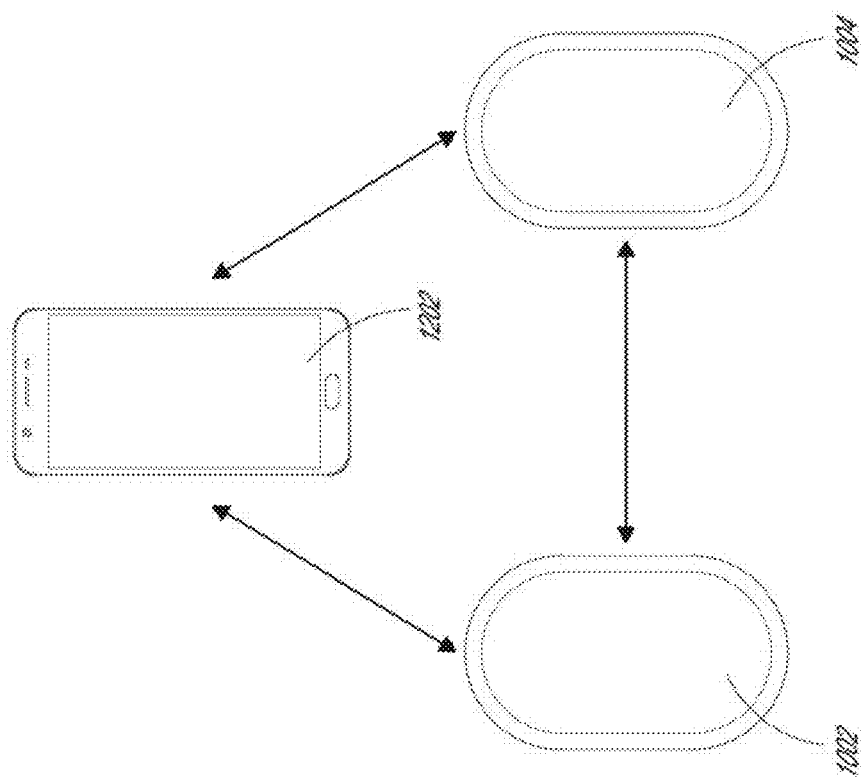
FIGS. 31A-31C illustrate various systems connecting two disease management systems to a user device.
Figure 31B:
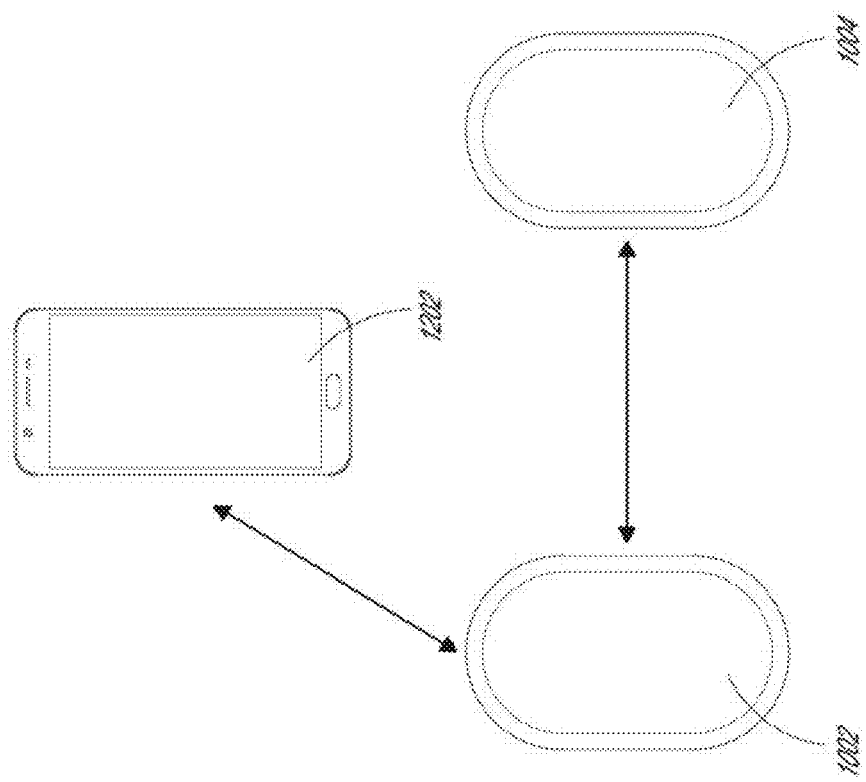
Figure 31C:
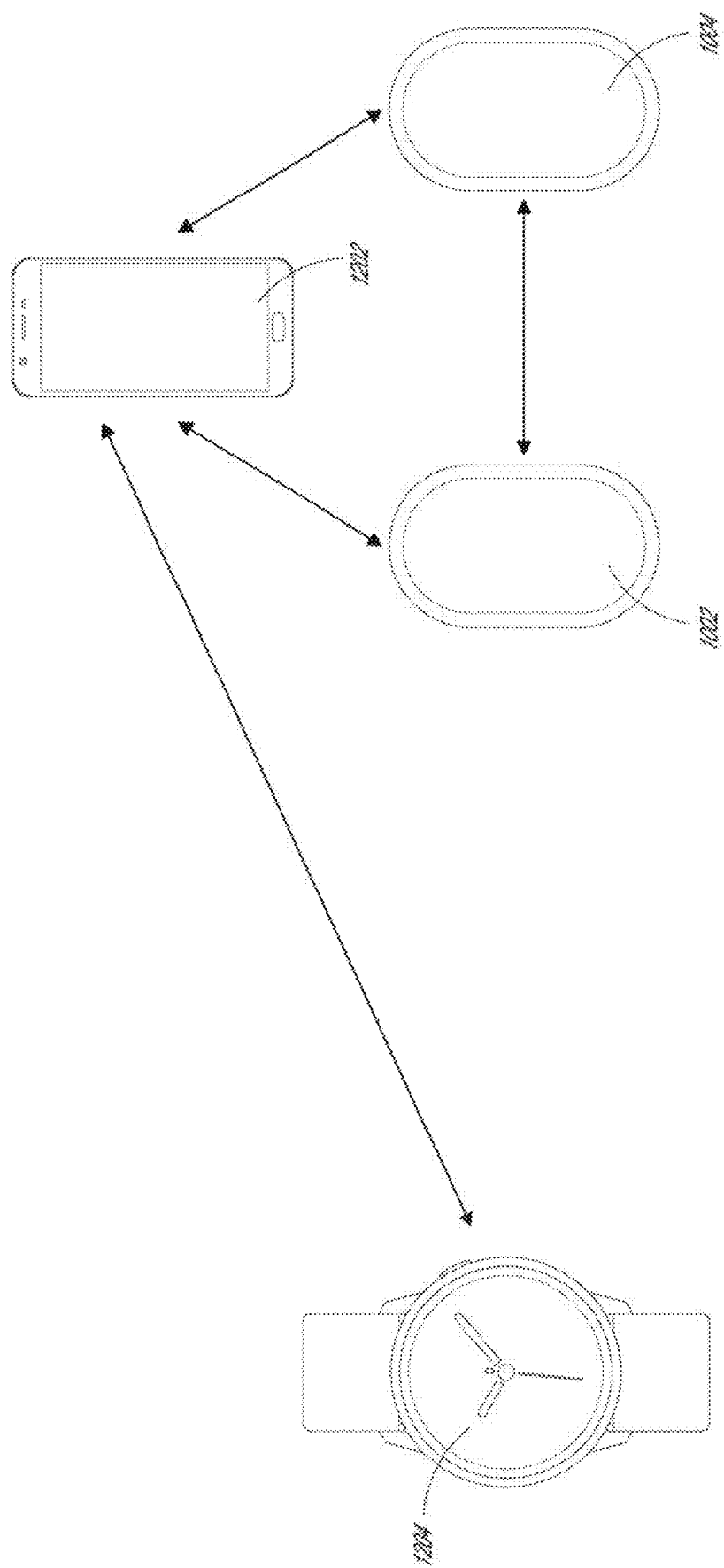

FIGS. 31A, 31B and 31C illustrate various systems connecting a first disease management system 1002 and a second disease management system 1004 to a user device 1202 such as a smartphone. In FIG. 31A, the first disease management system 1002 and the second disease management system 1004 are connected to each other and both of these are connected to the user device 1202. In FIG. 31B, the first disease management system 1002 and the second disease management system 1004 are connected to each other and only the first disease management system 1002 is connected to the user device 1202. The user device 1202 may communicate with the second disease management system 1004 through the first disease management system 1002. In some implementations, the first disease management system 1002 and the second disease management system 1004 are connected to each other and only the second disease management system 1004 is connected to the user device 1202. The user device may communicate with the first disease management system 1002 through the second administration system 1004. In FIG. 31C, the user device 1202 is further connected to a smartwatch 1204. In some implementations, the smartwatch 1204 may connect directly with one or both of the first disease management system 1002 or the second disease management system 1004.

The user device 1202 or the smartwatch 1204 may be used to display a variety of data or settings such as: glucose measurement data; insulin dosage settings; glucose dosage system status including status of individual disease management systems; glucose sensor life remaining within each disease management system; insulin remaining within each individual disease management system including estimated time the insulin within the individual disease management systems will be exhausted; time left until glucose expires or spoils within each individual disease management system; current or most recent patient glucose measurements; current or most recent patient insulin delivery amounts; graphs and charts depicting historical glucose measurements; comparisons between historical glucose measurements and current glucose measurements; graphs and charts depicting historical insulin administrations; comparisons between recent insulin administrations and historic insulin administrations; graphs and charts depicting historic basal insulin levels; graphs and charts depicting historic and recent dosage times; graphs and charts depicting historic patient carbohydrate consumption; estimated average patient glucose levels; estimated patient hemoglobin levels (for example, hemoglobin A1C levels); time the patient is within normal glucose range; time the patient is hypoglycemic; time the patient is hyperglycemic.

The smart device 1202 or the smartwatch 1204 may be configured to receive authentication credentials, such as a passcode, to actuate a party of the treatment system. In some examples, input of false authentication credentials may result in a cool down period, such as a 1 minute period before the system may accept more authentication credentials. In some examples, the smart device 1202 or the smartwatch 1204 may be configured to allow a user to manually bolus variable amounts of insulin, manually notify companion application of variable amounts of carbohydrate load with variable amounts of absorption time, manually notify the application of impending adverse pre-programmed event types (such as stress, exercise, food, and presentation mode), validate a heuristic guess from the application of possible upcoming adverse event or off-use insulin, or perform other actions. In some examples, the smart device 1202 or the smartwatch 1204 may be configured to present notifications associated with the treatment system or the user.

The smart device 1202 or the smartwatch 1204 may receive and respond to notifications, alarms, and/or alerts. Examples of user devices include, but are not limited to smartphones and tablets. The smart device 1202 or the smartwatch 1204 may be configured to manually send a command to one or more disease management systems to administer a dosage of insulin to the patient.

The smart device 1202 or the smartwatch 1204 may be configured to allow for the following inputs:
The selection from predetermined basal insulin programs
The selection of a target range of glucose levels, such as a doctor approved customized glucose target range from a default range
The selection of a custom basal insulin level
The selection of an action dependent basal insulin level (may be based on various activities such as exercise or resting)
The selection of patient sensitivities to specific insulin types
The selection of patient sensitivities to carbohydrates
The selection of a threshold suspend (for example, a patient glucose measurement threshold that stops insulin delivery when the patient glucose measurement falls below a threshold level)
The selection of maximum insulin delivery limits.
Logging of food intake (for example, carbohydrate intake) or liquid intake (for example, water intake)
Logging of patient external input application (for example, insulin inhaler usage)
Logging of patient medication application
Logging of various activities (for example, exercise or sleep)
Logging of a patient external glucose measurement (for example, a finger stick glucose measurement)
Logging of a patient's physical characteristics (for example, weight, height, gender, blood type, body mass index)

The logging of food intake or liquid intake may be performed manually, automatically, and/or artificial intelligence assisted. The smart device 1202 or smartwatch 1204 may be configured to react to an input by recommending temporary or permanent insulin dosage corrections adjustments. The insulin dosage corrections or adjustments may be gradual. The insulin dosage corrections or adjustments may correct a patient's basal insulin levels based on the input. The smart device 1202 or smartwatch 1204 may trigger the disease management system including one or more disease management systems to change the insulin dosage plan based on a patient's input. The smart device 1202 or smartwatch 1204 may require authentication of a user in order to receive the above mentioned inputs and/or make changes to the patient's insulin dosage plan. Authentication of the user may be facial identification, fingerprint identification, pin code identification, and/or password identification.

Different users may be allowed different levels of access to a patient's settings. For example, a caregiver or parent or the patient may be allowed to input whereas certain third parties may be allowed only to view a patient's settings. There may be intermediate levels of access allowed to some third party users which may allow the third party users to only access certain settings. Further certain third party users may be allowed access to manually administer a dosage to the patient. For example, emergency response personnel may be allowed access to manually administer a dosage to the patient in an emergency situation. Further, the patient's information may be accessible by third parties via electronic heath record or electronic medical record connectivity. The patient information may be accessed obscuring the patient's identity in order to provide access to third parties to perform statistical analysis. Also, for example, the patient information may be accessed by emergency response personnel to respond to an emergency situation. The smart device 1202 or smartwatch 1204 may provide access to instructional videos, instructional guides, and various health and wellness education. The access to the videos, guides, and education may be based on the patient's settings and inputs. A smartwatch 1204 may have different interface and displayed detail when compared to a smart device 1202. For example, the displayed controls or settings may be limited on a smartwatch 1204 when compared to a larger smart device 1202.

The smart device 1202 or the smartwatch 1204 may be used to input a variety of data or settings such as aggressiveness of insulin dosage, and/or meal data. The smart device 1202 or the smart watch 1204 may display information to the user such as a reminder to replace a disease management system, a reminder to fill a prescription, a reminder to eat a meal, a reminder to drink. The smart device 1202 or the smart watch 1204 may display warnings or alerts such as warnings of potential malfunctions of a disease management unit or warnings based on spikes in glucose.

Advantageously, the system described herein may facilitate changing of applied devices, such as an insulin pump and CGM sensor. Traditional insulin pumps must be changed every three days to refresh their insulin and each changing time may require the user to go through a multi-step process (14 steps or more and take up to 30 minutes) to connect their pump with a user device or a Personal Diabetes Manager (PDM). As the market moves towards a closed Loop system with two units (a CGM and a Pump), these types of connectivity steps could increase mental burden and introduce confusion, mistakes, and/or take too much time. Systems and methods described herein may reduce the effort and time of a first use and more importantly for repeating users from having to spend time setting up a new pump or closed loop device every three days. By simply scanning the closed loop CGM/Insulin pump device with their user device, a user device may communicate with the CGM/insulin pump device, open a complimentary application on the user device and/or automatically setup the Bluetooth connection between the devices. The application may then give the user feedback that the CGM/Pump device is correctly inserted, communicating, and functioning.

In some examples, a closed loop CGM/pump system (Device) may have communication electronics, such as a Near Field Communication (NFC) tag and an antenna. The communication electronics may be configured to interact and provide a trigger when a host device with a NFC reader and antenna comes near (such as within a few centimeters of) a device antenna. Once the contents of the NFC tag are read by the host device, the host device may open a companion application. Additionally, or alternatively, if no application is installed, the host device may open facilitate download of the companion application (such as by opening an application store link or application). Once the user's user device has the application open, the appropriate screen for new device setup may appear and communicate setup information.

In some examples, when a user brings their smart device within close proximity of their first body installed disease management system, an NFC tag of the disease management system may create a successful Bluetooth communication with the host device and a compendium application can launch (or if no app is installed, then a link to the app store would open to download the app). Once the app is launched, the appropriate screen sequence may load that walks the user through any necessary steps to successful engaged their disease management system to start monitoring and delivering insulin or other medication based on default settings and user adjusted settings that were selected in setup or through other means. These settings could be delivered in a manner to allow the user to think of the first device as a standard CGM and only prompt settings based on CGM features, which a user may be more familiar with. These settings may include, but are not limited to, glucose standard target ranges, glucose activity and food profile ranges.

When a second placed device is being placed for the first time, a user may be prompted to set up insulin pump based features, such as but not limited to insulin sensitivity, suspend thresholds, max basal rates, max bolus amounts, carb ratios, the like or a combination thereof. This secondary device placement may also be done by an applicator with NFC that initiates a cannula insertion on the disease management system when one is already being identified as the CGM the other would activate and insert a insulin cannula.

In another embodiment, all setup screen prompts could come during application of the first device or all during application of the second applied device for the first time. In an additional embodiment, the entire setup process could occur before the device is applied to the body.

In either method of first time use the next time of applying a replacement unit the user would bring the host device close to the new sensor and a Bluetooth connection would be established and the compendium app would launch a single confirmation of previous settings and then be done with setup. If either of the disease management systems the user is wearing reach end of life (for example, is out of or expired insulin) the user can be notified within the application using a feedback message to assure the user that all the insulin in that device was used before they are requested to take it off.

In some embodiments, a parent or other user may be given permission to use their own smart device to make changes to the dosing with an NFC close proximity wave of their child's or other patient's disease management system if that patient is too low to respond or unconscious or otherwise incapacitated.

If multiple disease management systems are used, the companion application on the smart device will also setup the communication between disease management systems to allow standalone operation without the use of a smart device.

FIG. 32A illustrates a system for connecting a user device 1202 with a disease management system 1304. The disease management system 1304 includes a near field communication (NFC) tag 1304A which is associated with a computing device 1304B controlling the disease management system 1304. When the user device 1302 gets into close proximity to the disease management system 1304, the user device 1302 broadcasts a signal which activates the NFC tag 1304A. Once activated, the NFC tag 1304A can broadcast a signal back to the user device 1302. The NFC tag 1304A is a passive device that receives power from the user device 1302. The signal broadcast by the NFC tag 1304A is unique to the particular disease management system 1304 thus allowing the user device 1302 to identify and pair with the disease management system 1304 through the computing device 1304B. The computing device may be a system on chip (SOC) which includes a processor and memory with instructions capable of operating the disease management system 1304. The user device 1302 may pair with a disease management system 1304 and also may alert the disease management system of the another disease management system and allow these two systems to recognize each other. By communicating with each other, the disease management system and another administration system may be run in the redundant fashion described in connection with FIGS. 1A, 1B, and 2A-e.

Figure 32B:
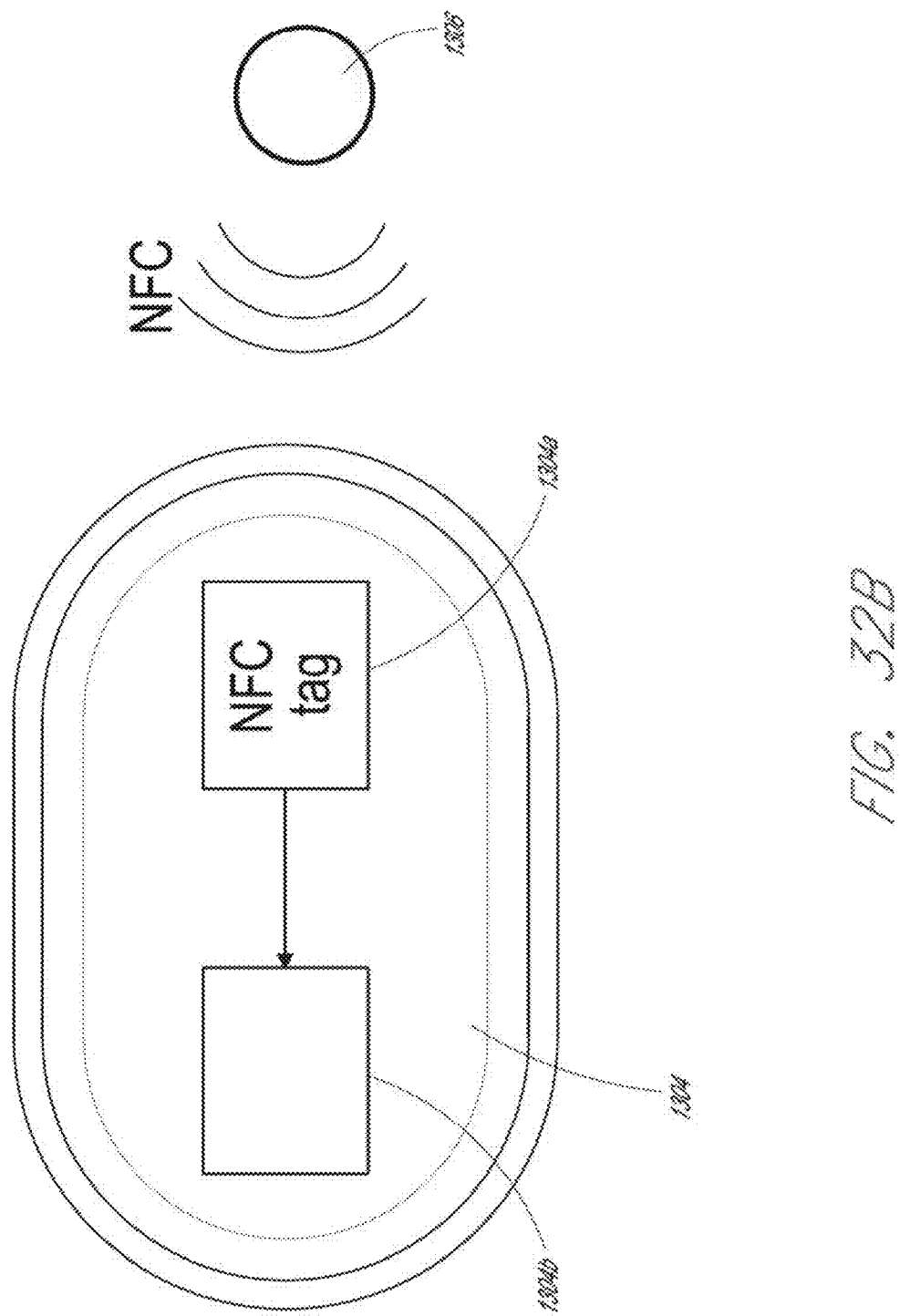
FIG. 32B illustrates a system for manually triggering a disease management system to administer an insulin dosage.

FIG. 32B illustrates a system for manually triggering a disease management system 1304 to administer an insulin dosage. The disease management system 1304 includes an NFC tag 1304A which may communicate wirelessly with an NFC device 1306. The NFC device 1306 may be configured such that the NFC device 1306 communicates wirelessly with the NFC tag 1304A when the NFC device 1306 is in close proximity with the NFC tag 1304A. The NFC device 1306 may be uniquely programmed such that a certain NFC device 1306 is provided to certain users such as a caretaker or a parent of a child or an elderly individual, or a physician of a patient. When the certain NFC device 1306 is brought in proximity with the NFC tag 1304A, the disease management system 1304 may be programmed to manually administer a dosage of insulin to the patient even when the disease management system 1304 is not scheduled to deliver a dosage to the patient at that time. However, the disease management system 1304 may be programmed such that certain restrictions may prevent or provide access to manually administer insulin to the patient. For example, the disease management system 1304 may restrict manually administering a dosage of insulin to around meal times. The NFC device 1306 may be mounted on a wearable device such as a bracelet, watch, necklace, and/or ring.

Figure 32C:
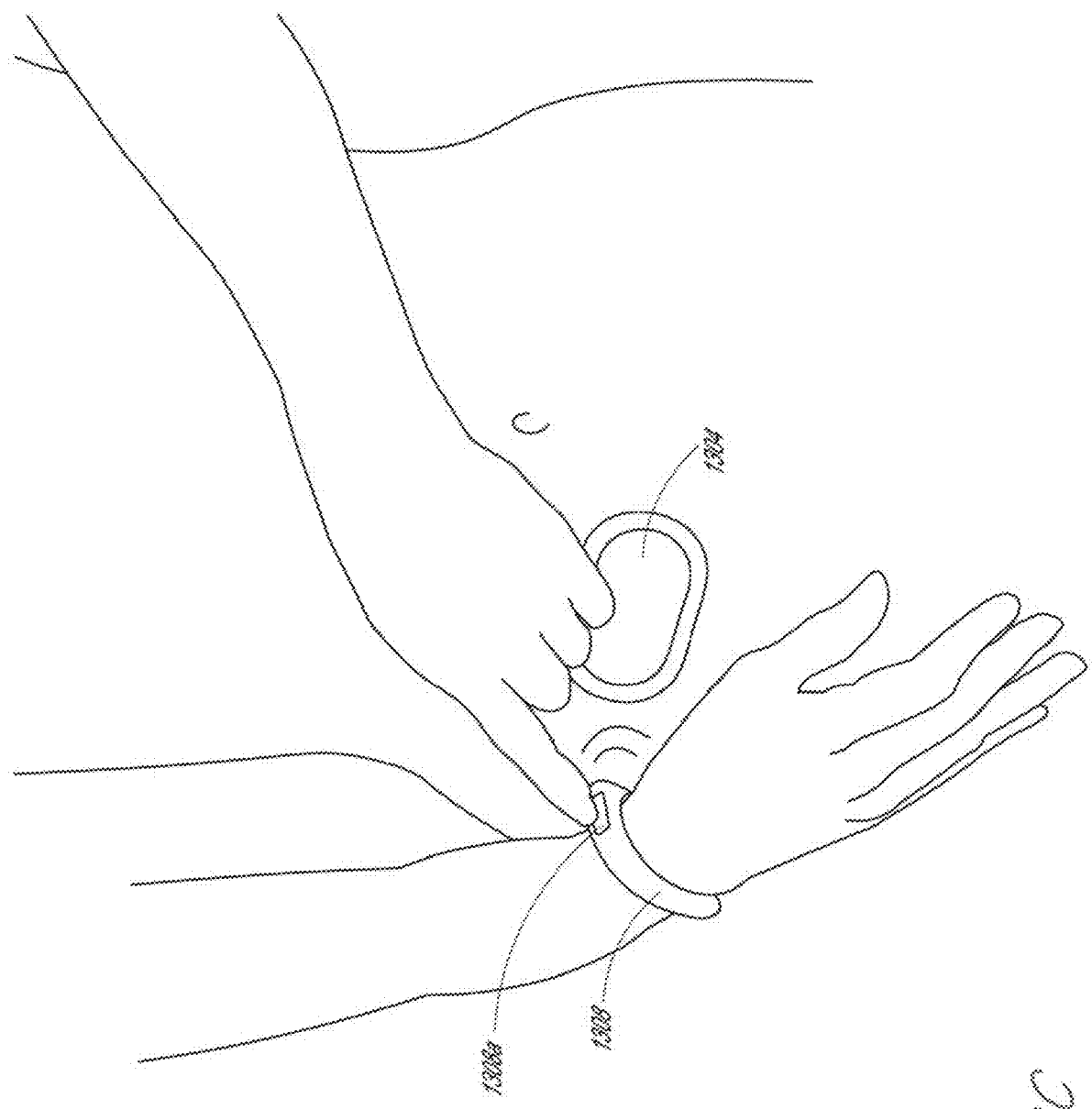
FIG. 32C illustrates a system for manually triggering a disease management system to administer an insulin dosage.

FIG. 32C illustrates another system for manually triggering a disease management system 1304. The disease management system 1304 may include an NFC tag which may communicate wirelessly with a wearable device 1308. While the wearable device 1308 is illustrated as a wrist worn device such as a bracelet or a watch, it is also envisioned that the wearable device 1308 may be a finger worn device such as a ring or a device worn around the neck such as a necklace. The wearable device 1308 is capable of interacting with the disease management system 1304 in order to manually trigger the disease management system 1304 to administer a dosage of insulin to the patient. The wearable device 1308 may include a safety device 1308A such as a button or gesture sensor. The safety device 1308A may be activated by pressing, squeezing, or tapping in order to enable the wearable device 1308 to interact with the disease management system 1304. Thus, the wearable device 1308 may only trigger the disease management system 1304 when the wearable device 1308 is in close proximity with the disease management system 1304 and the safety device 1308A is activated.

Different wearable devices 1308 may be coded differently to trigger the disease management system 1304 to administer different dosages. For instance, a parent may be provided with a wearable device 1308 that may trigger the disease management system 1304 to administer a larger dosage to the patient than a wearable device 1308 given to the patient when the patient is a child. Further, different rules can be applied to each of the wearable devices 1308. One wearable device 1308 may be allowed to manually trigger the disease management system 1304 at any time whereas another wearable device 1308 may be coded to only manually trigger the disease management system 1304 at certain times such as meal times. Further, wearable device 1308 given to different individuals may be separately color coded to enable individuals to differentiate the different wearable devices 1308. Advantageously, the wearable device 1308 may trigger the disease management system 1304 when an individual's user device is out of reach or is depleted of power.

While the wearable devices 1308 may be self-powered without an embedded battery, the wearable device 1308 may also be more robust and include a screen where a user may set specific details on the manual dosage to trigger the disease management system to apply to the patient. The specific details on the dosage may include suspend amounts or timing of the dosage such as how quickly to administer the dosage to the patient. In some implementations, the wearable device 1308 may include the capability of providing the electrocardiogram (EKG) signal of the patient's heart when the wearable device 1308 is worn by the patient and communicate this EKG signal with the disease management system 1304. The EKG signal could be used as a physiological check of the patient before receiving a dosage of insulin.

J. EXAMPLE SOFTWARE OPERATION

A disease management system may be configured to communicate with, be operated by, or in conjunction with one or more companion applications. The one or more companion applications may be configured to run in whole or in part on a user's computing device, such as a mobile phone device or wearable device. In some examples, a device may have native software configured to run the device.

A user interface of example companion application or native software may remain simple and intuitive to use for a patient or user. The application may facilitate easy setup of a disease management system through, for example, NFC, Bluetooth connectivity, application download/open, or device enumeration (such as ID, lot number, manufacturing date, shelf life expiry date.

An application may require authentication to configure critical insulin parameters, such as a passcode, password, face lock, or fingerprint in order to change insulin sensitivity, administer manual insulin bolus, external insulin types. If on a smart watch, critical insulin parameters may be implemented in a configurable manner. A companion application may include two factors of authentication to log into a companion application. The authentication may include one or more of a: password, google authenticator, text message, face lock, or email. A face lock may utilize an additional form of engagement such as pressing of a phone side-button or a sliding button gesture to verify that the user really did want their face to provide authentication for the system.

An application may utilize an NFC connection in order to deliver a remote insulin bolus. A companion application may utilize NFC to setup up Bluetooth connections with CGM or CAM devices, and/or Emergency glucagon systems (EGS). A companion application may interface with a device to identify remaining insulin life, CGM life, battery life. A device may utilize a mobile device to interface to a device to facilitate start, setup, or removal. However, the device may be able to operate independently during the rest of its lifetime without communicating with a mobile device when not in setup of a new device. A companion application may be able to synchronize with the cloud through a mobile device to a disease management system. This can include access of multiple days of data, for example, 6 days of secure data storage and personal configuration(s) at different domains (embedded, phone, and cloud). If a cloud connection is unavailable, data storage and configuration(s) may be stored securely on a mobile device and/or embedded on a disease management system. Once a cloud connection is restored, a mobile application and/or device may upload stored data to the cloud.

A companion application may allow a user to select their own insulin sensitivity for a pre-filled insulin brand. As this brand is used, the device may make recommendations in a configuration menu of a graphical user interface. In some examples, an application may notify a user what insulin sensitivity will work best for the pre-filled or other brand. A companion application may allow user to input and handle insulin intake from an external source (i.e. Inhaled insulin etc.) through a graphical user interface in a companion application on a mobile device. In some examples, a user may be able to use their own suggested insulin sensitivity to a brand of insulin. A companion application may allow user to input and handle alternative therapies (medications) from an external source (i.e. GLP-1 etc.) through a graphical user interface on a mobile device.

A companion application may be able to provide notifications or recommendations for helping a user handle hypoglycemic or other events. For example, an application may provide a personalized rescue candy notification for lows and simplified input thereof for pre-defined quantities. A companion application may engage a user if a user is dealing with a hypoglycemic event to prevent sleep until a user has recovered. In some examples, a companion application may facilitate tracking which caregivers participate in hypoglycemic events. A companion application may prevent manual boluses when a user is in a hypoglycemic or tending towards a hypoglycemic state. A companion application may allow user to configure a network of caregivers to be automatically notified in the event of hypoglycemia, hyperglycemia, disconnected cloud connection, empty insulin (across both devices), only single CAM or CGM active, no CAM or CGM active.

A companion application may be able to offer a bolus recommendation based on the meal input (and other states) and subsequently administer the insulin request after user confirmation. A companion application may display CAM or CGM Sensor Confidence Feedback (SIQ) (embedded algorithm may use the signal confidence to titrate therapy). A companion application may display insulin delivery confidence based on occlusion detection, insulin absorptivity, or other parameter.

A companion application may use Augmented Reality for information delivery to user through a graphical user interface or in AR glasses. A companion application may use Augmented Reality to retrieve information from a user's environment to predict patterns in food consumption and exercise. The application may enable AR food quantification and timing. AR detects unusual insulin actions. For example, a system may recognize picking up an insulin syringe to use when glucose is low or insulin on board is high.

A companion application may allow a user to select the site location of device placement. In some examples, an algorithm configured to create personal historical insulin absorptivity values may use this information. A companion application may allow meal and insulin entry from a smart watch command, verbal command, or other input.

A companion application may allow NFC active reading and/or background reading when it becomes available to setup up new disease management systems. In some examples, a graphical user interface of a companion application may allow viewing of absolute glucose/insulin/insulin on board and trending values. A companion application may allow meal entry with time, quantity, and type or other meal related parameters. In some examples, a user may be able to customize base basal rates, insulin sensitivity, and carbohydrate ratio through the mobile application. A companion application may include one or more control modes, such as full closed-loop mode or manual mode (with recommendations). In some examples, a starter or CGM only device may disable application features such as closed loop mode and manual boluses. A companion application may allow a user to synchronize or manually enter their weight. A companion application may allow a user to manually enter or otherwise determine a user's gender, height or age. A companion application may check that a user's weight falls within expected statistics correlated to age, gender and height. This check may be used as a determining factor in insulin dosing via a control algorithm, such as MPC or PID algorithms. A companion application may verify user weight with user and/or caregivers after 3 months of use without a user updating weight. The application may be able to allow user to utilize and configure their off-use insulin (for example, insulin not basal or bolused from insulin pump) by type (for example, ultra-long, long, medium, fast, ultra-fast) and vendor (for example, Novolog, Humalog). A companion application may provide a configuration to allow behavioral prediction of a user's off-use insulin dose and notify the user preemptively for easy entry.

In some examples, a graphical user interface of an application may display a graph with historical and predictive confidence intervals of glucose values. The application may display a graph with historical and predictive confidence intervals of insulin values. The application may display a graph with historical and predictive confidence intervals of meal values. The application may display a graph with historical and predictive values of exercise. The companion application may display an intuitive status of: overall system function (Green, yellow, or red) (Good to go, warnings (such as low battery or insulin supply), or errors). The companion application may display a status of expiring device near 6 day mark in a configurable way. The companion application may display a status of device maintenance every time insulin is empty in a configurable way. The companion application may display a status of CGM warmup time (for example, if only 1 device is active). The application may display a status of CGM stabilization time (for example, if only 1 device is active). The application may display a status and notify caregivers of user configurable alarms, such as current thresholds and predictive thresholds. The application may display a status what insulin sensitivity will work best for the user and bring them to the configuration menu. The notification may also share with the user the expected benefit of following a recommendation. The application may display a status to the user that they are not presently contained within the GIMM or GLIMM envelope. This may suggest that the CGM or CAM is out of calibration or that the user did not enter a meal/insulin/activity. The user may be able to configure display of statuses, such as alarms, notifications, or event history to have control over severity annoyance. Additional options should be possible for caregiver notification severities. A companion application may allow user to silence the most critical alarms of hypoglycemia for a period of time, such as up to 15 minutes. A companion application may request or detect what intervention was taken to silence the alarm. The application may be configurable to allow alarms on a wearable device, such as a smart watch. The application may display a status of low device battery on the mobile device. The application may display a status of device life. The application may display a status of abnormal user body model states (for example, insulin on board, lipids). The application should show how the face, body and mind will look in 5, 10, 20 and 50 years based on recent habit and measures tied to historical data. The application may display a status of out of norm user metadata activity (for example, GPS, activity, pulse rate, spO2, pressure sensor). A companion application may utilize a distraction game to prevent anticipation pain. The application may include an API that enables OAUTH sharing of measurements, user decisions, and model states outbound to other apps such as a companion application, emergency glucagon systems (EGS), external EMRs, or telehealth, such as DocTella. A companion application may provide educational content related to disease management, significance of other measurements, device management, application management, cloud management, or other aspect of the treatment system. The application may enable manual or automated logging, education, and charting of ketones, cholesterol, triglycerides, blood pressure, sleep, and exercise. The application may provide positive reinforcement and warnings when a user makes a lifestyle change that is beneficial and new or not.

In some examples, a backend system or cloud based system (sometimes herein referred to as cloud) may be in communication with a disease management system or mobile device. A cloud based system may send notifications to registered caregiver devices in the event of one or more occurrences, such as hypoglycemia, hyperglycemia, empty insulin (across both devices), only single CAM or CGM active, no CAM or CGM active, if enabled. Cloud may allow storage of all historical data from the user, provided that the cloud has been given adequate time to synchronize with the device and mobile device. A cloud system may provide cross regional cloud architecture, where customer traffic is load balanced across multiple regions, and data is kept eventually in sync using a distributed cross-regional NoSQL database. A cloud system may analyze stored data to provide personalized coefficients to the mobile device and device. A cloud system may enable electronic health record (EHR) connections to allow easy data sharing. A cloud system may enable a user to allow full record allowance with other entities, such as a hospital. A cloud system may enable a user to retrieve CGM data, such as in a spreadsheet format. A cloud system may enable a user to request identifiable data not be tracked or used. A cloud system may provide functionality to record caregiver/coaches decisions/suggestions on behalf/towards the patient when provided. A cloud system may enable a user to request all their data be deleted from device associated databases. A cloud system may allow users to access their historical data and analysis of that data from a web browser.

A cloud system may allow device users and caregivers to make management decisions and observations for the closed loop system. A cloud system may allow device users who are of consenting ability to add caregivers as solely observers or managers of their closed loop system. A cloud system may allow parents of type one diabetes patients who cannot give consent to both own and manage closed loop systems of device users. Cloud based managers of closed loop systems may be able to configure and lock configurations in an application if the device user is unable to consent. Cloud managers of closed loop systems may not be able to insulin bolus a user from the cloud. A cloud system may allow healthcare providers a mechanism to override unsafe configurations and generally provide a method of safe operation ranges a user or caregiver should be personally constrained to for parameters such as carbohydrate ratio or insulin sensitivity. Cloud system may produce a healthcare provider, caregiver and user reports related to user weekly and monthly progress in glycemic control.

A cloud system may provide backup services. A cloud system may provide data aggregation to a coach's dashboard. A cloud system may provide ability for a coach to look into and respond via email, mobile device, or text to chronic and episodic type one diabetes events. A cloud system may contain chatbot to assist with technical support knowledge questions, FAQs, or symptom and side effects. A cloud system may enable troubleshooting of malfunctioning devices for technology support agents. A cloud system may provide payers population management reports. A cloud system may run an MPC control algorithm that is personalized to user. If instability is detected the cloud system controller may move to personal fallback configuration. If instability is still detected controller may move to safe mode configuration. A cloud system may determine a maximum and minimum theoretical limit for the system given current user inputs (for example, meal, insulin, activity, sleep). A connection between mobile device and cloud system may be secured, such as by TLS 1.2 or newer.

In some examples, a companion application may be configured to provide one or more recommendations for managing a user's disease based on one or more inputs. For example, a companion application may be configured to recommend updates to insulin sensitivity, carbohydrate ratio, bolus prediction amounts and timing, or other parameter based on collected user data. In some examples, a companion application may determine a recommendation once a sufficient amount of user data is collected to provide a recommendation over a threshold confidence value. User data may include an amount of insulin administered, glucose values, meal information or other data.

In some examples, a companion application may determine a recommendation through communication with a backend system. For example, a companion application may upload data to a backend system through a network. The backend system may determine a recommendation and communicate that recommendation to the companion application. In some examples, a companion application may determine a recommendation locally, such as through one or more processers associated with a user device, such as a mobile phone or smart watch. In some examples, one or more local processors and a backend system may both perform aspects of a recommendation algorithm. For example, one or more local processors may pre-process data for analysis by a backend system and a backend system may analyze the data to determine a recommendation.

The companion application may be configured to then transmit the one or more recommendations to one or more disease management systems. In other examples, one or more disease management systems may directly communicate with a backend system to transmit user data and/or receive one or more recommendations.

In some examples, a companion application may be configured to utilize a mobile device camera to provide an augmented reality experience. In other examples, a companion application may be configured to interact with an augmented reality device or application to provide an augmented reality experience. An augmented reality experience related to system notifications can include providing virtual content associated with system information, including but not limited to button names, LED light feedback, insulin remaining, section views of a product, failure drawings, active and working renderings or other content, within a user's real world view as perceived through the mobile device or augmented reality device camera. In some examples, an augmented reality experience can include gamification of application of a disease management system (such as the distraction system described herein). In some examples, an augmented reality experience can include using augmented reality tools to communicate food consumption estimations, carbs, food or macronutrient volume, calories, or other food related values through virtual content displayed within a user's real world view as perceived through the mobile device or augmented reality device camera.

A companion application may be configured to allow a user to configure one or more aspects of the treatment system, such as one or more closed loop aspects, one or more notifications settings, one or more connections settings, or other settings. For example, a closed loop configuration can include a closed loop toggle, a carbohydrate ratio, an insulin sensitivity, a suspend threshold, basal ranges, bolus confirmations, or other setting. In some examples, notifications settings can include settings related to notifications regarding predicted plasma or interstitial glucose hypoglycemic events, predicted plasma or interstitial glucose hyperglycemic events, current plasma or interstitial glucose hypoglycemic events, current plasma or interstitial glucose hyperglycemic events, insulin related status, pump related status, CGM related status, heuristic lifestyle related status (such as off-use insulin guesses, meal guesses, adverse event guesses, the like or a combination thereof), disease management system status (or device health), or caregiver notification of patient status. In some examples, connections settings can include configurations related to a primary disease management system, a secondary disease management system, Apple Healthkit™, or 3rd party connections. In some examples, other settings may include audio or haptic settings, airplane mode, serial number, certifications, copyrights, patents, user guides, the like or a combination thereof.

A companion application or other aspect of a treatment system may be configured to display one more notifications associated with a disease management system, companion application, or other aspect of a treatment system. For example, a companion application may have one or more system status icons or states. The status icons or states may include a color based indicator, such as a green, yellow, or red indicator. In some examples, a disease management system may have a light indicator, such as an LED light configured to display one or more colors, such as yellow, red, or green. In some examples, a green color in an icon or light indicator may indicate a control algorithm status, such as an activation of closed loop mode. In some examples, a yellow color in an icon or light indicator may indicate a warning status, such as Bluetooth connection failure, low insulin, or low battery. In some examples, a red color in an icon or light indicator may indicate a caution status, such as where an action by a user is required or a dangerous condition is detected. For example, a caution status can include a system replacement required, such as insulin out, cannula error, sensor error, the like or a combination thereof. In some examples, a system may contact or cause a companion application or backend system to contact a caregiver if an action to address the caution status is not taken in a threshold period of time. In some examples, a blinking indicator or status icon may indicate a different status from a non-blinking indicator or status indicator. For example, a blinking green light may indicate that all systems are functioning as expected.

Other notifications are also possible. For example, a system may notify a user via audio, graphics, text, or haptic feedback of one or more parameters or statuses of the system. In some examples, a most recent glucose level (such as within the last 5 minutes) may be displayed to a user, optionally in conjunction with a time the measurement was obtained. In some examples, an insulin remaining within one or more of the disease management systems may be displayed, such as a total insulin remaining across two interleaved disease management systems. In some examples an active insulin value may be displayed. In some examples, a sensor life remaining, such as some combination of battery life, CGM duration and insulin, may be displayed. In some examples, device warm up progress and/or stabilization may be displayed. In some examples, a history log may be displayed. In some examples, one or more graphs associated with system data may be displayed over a default or selected period of time. A default period of time can include 6 hours, 1 day, or other amount of time. In some examples, the system data can include glucose target range, observed and predicted glucose with confidence interval (CI if cloud connectivity is available) and event (such as insulin, exercise, food, and other events) markers visible and interactable by the user. In some examples, the system may display an insulin graph, an insulin basal and/or bolus graph that may include suspend descriptions, a meal digestion graph, the like or a combination thereof.

In some examples, a system may notify a user of glucose related states of a user, such as hypoglycemic state, near hypoglycemic state (such as within 30 minutes or other period of time), hyperglycemic state, near hyperglycemic state (such as within 30 minutes or other period of time), glucose trending high out of target range, or glucose trending low out of target range, or the like. In some examples, a system may notify a user of insulin status, such as a warning associated with bolus administration, a changing basal notification, an adverse event insulin detected, or the like. In some examples, a system may notify a user when a periodic report, such as described above, is available for review.

In some examples, a treatment system may be configured to determine a hypoglycemic event or a near hypoglycemic event based on collected user data. A hypoglycemic event can be relative to a recent eating or exercise time, time of day, or other values. Symptoms of hypoglycemia can include, but are not limited to clumsiness, trouble talking, confusion, loss of consciousness, seizures, and death. In some examples, symptoms can include hunger, sweating, shakiness, and/or weakness. Impaired awareness of hypoglycemia (IAH) may afflict up to 28 percent of type one diabetics. Thus, tools for assessing IAH can be useful in helping users avoid dangerous hypoglycemic events. Advantageously, a treatment system may identify a hypoglycemic event or improve user awareness of hypoglycemia through the tracking and analysis of biometric parameters, such as heart rate variability (HRV), ECG (such as QT intervals from ECG), heart rate, BMI (which can be a high risk factor for insulin resistance and diabetes), race (which can be a factor in incidence and mortality of diabetes), body or skin temperature and sweat (body temperature may lower when in a hypoglycemic state and sweat may have an inverse relationship with hypoglycemia), seasonal variations in parameters, years diagnosed, age (which can be more important to understand years diagnosed), type 1 or type 2 diabetes type, other parameters, or a combination thereof.

QT intervals from ECG may be used as a marker in type 1 and type 2 diabetics. For example, many diabetics have a prolonged QT interval (for example, greater than 440 ms). Diabetics with a prolonged QT interval may be associated with an increased mortality compared with diabetics with a normal QT normal. Thus, tracking a QT interval can be used to identify a user's increased risk of mortality.

In some examples, a treatment system may provide recommendations, notifications, or reports based on detection of hypoglycemic events or near hypoglycemic events. In some examples, a treatment system may classify one or more users as having Impaired awareness of hypoglycemia or not. The treatment system may provide short and/or long term predictions based on detected parameters for both non-IAH and IAH classified users. For example, if a non-IAH type 1 diabetic user has a heart rate and QT interval increase followed 5-10 minutes later by a wrist or abdomen sweat increase, they may be approaching a hypoglycemic event in 5 to 10 minutes. A treatment system may then notify the patient or user of a predicted hypoglycemic event. In another example, if a pattern of declining heart rate pattern with 10 beats per minute fluctuation 70 minutes prior and optionally a slight increase in sweat 70 minutes prior, the system may predict a longer term risk of predicted hypoglycemic event and notify the patient or user of a predicted hypoglycemic event. A notification may include an audible alarm, graphical alarm, or haptic feedback, such as buzzing on a user's mobile device to capture to attention of the user. In some examples, a treatment system may communicate with a wearable device to notify a user, such as a smart watch or other wearable device that may audibly or vibrationally alert the user to a predicted hypoglycemic event. In some examples, a treatment system may provide one or more notifications based on an identified pattern or risk of hypoglycemia, hyperglycemia, glucose variability, and/or testing deficiencies.

K. EXAMPLE PERIODIC IMPACT REPORTS

In some examples, a companion application may be configured to provide periodic reports on one or more parameters, such as but not limited to time in proactive closed loop, time in reactive closed loop, time in manual mode, time in range for different modes, estimated average glucose, calculated HbA1C, exercise impact on glucose, sleep impact on glucose, and food impact on glucose. Reports may be daily, weekly, monthly, or cover another time frame. In some examples, a companion application may be configured to provide a current on instant report on one or more parameters, such as estimated average glucose, exercise impact on glucose, sleep impact on glucose, and food impact on glucose.

Advantageously, periodic reports described herein may help a user better track and/or manage their disease. In contrast, while current systems for Continuous Glucose Monitoring provide a life changing awareness of near real time glucose levels and trends, these systems often fall short of offering a user with feedback as to the impact or damage caused by severe hypoglycemic or hyperglycemic events, lifestyle, food, time of day or cycles at which their body processes glucose and insulin differently or if any patterns in sleep, carbs, diurnal or nocturnal activities affect their glucose levels. For example, a type 1 diabetic with a good HbA1C can still suffer high mortality from previous or future glycemic related events1. Advantageously, the periodic reports described herein may help address this issue by facilitating better data tracking and helping a user make sense of the subtleties of what effects their body's glycemic swings by providing a summary of findings and facilitating or providing recommended opportunities to improve disease management.

In some examples, a companion application may include a graphical user interface with a dashboard component. The dashboard component may include a graphical or textual overview or icon of the user's status, such as an index percentage number and/or graphical representation of user data. The overview may be interactive. For example, in the case of the companion application running on a touch screen device, the overview that can be tapped or otherwise selected. The selection may be to open an aspect of a graphical user interface of the companion application that is configured to display a periodic report.

In some examples, a periodic report may include a glucose impact report. The glucose impact report may include one or more metrics based on some combination of calculations that may be beneficial to a user in understanding lifetime management of diabetes, a Personal Glycemic State Index (PGS) or other index which may be based on some combination of time, frequency, or severity out of and in range, glycemic variability, and mean glucose, other tracked details including, but not limited to: weight to height ratio, waist to height ratio, pulse rate, pulse rate variability, sweat (measured, for example, via skin conductance), ECG QR interval, active minutes or steps, exercise, food and/or carbohydrates, medications, sleep, weather, temperature, and humidity (determined, for example, from GPS location).

In some examples, a metric can include a combination of factors that work together to provide a better assessment of an individual's state of glycemic management. The individual could work to maintain the index above a specific level but can also drill down into details, such as understanding how specific amounts of sleep affect them (such as 6 hours compared to 8 hours of sleep) and understanding how and if certain locations or times of day can correlate with different glucose patterns. In addition or in the alternative to these metrics and/or parameters, a report may delineate how many hypoglycemic events may have been felt by a user if they are becoming hypoglycemic unaware, how humidity and temperature from weather may impact their biometric parameters, such as glucose values, and how activity may contribute or prevent severe hypoglycemic events.

In some examples, a report may be determined by a companion application. In some examples, a report may be determined by a backend system. In some examples, a report may be determined based on historical user data. In some examples, a report may be determined based on population data, such as de-identified user data, by machine learning. In some examples, a machine learning algorithm may analyze population data in order to find trends across populations of users and make predictions or recommend self-corrective actions to improve a user's report values. Self-corrective actions may include, for example, self-adjusting insulin levels and timing, food changes, sleep or changes, or other lifestyle changes.

L. EXAMPLE CLOSED LOOP CONTROL ALGORITHMS

Current classes of closed loop control often fall in two categories: reactive closed loop and hybrid closed loop. Reactive closed loop can be defined as a control system that only changes its stimuli based on observation of analytes. A hybrid closed loop system utilizes user supplied information such as notification of meal or insulin information. To date the best models have utilized hybrid closed loop models. However, these models generally are still highly insufficient to reach normalcy. Closed loop control remains a challenging problem involving the integration of algorithms, optimization, embedded systems, cloud support, mobile apps, 3rd party hardware, and potentially complex user interactions. Systems and methods described herein may uniquely addresses the above overlapping issues with a first goal of being as safe as possible and a second goal of being as simple as possible.

In terms of a control aspect of a closed loop system, the tools available to a medical device can be disadvantaged to the natural control algorithm that exists in a normal (non-diabetic) body. In a natural control system, glucose may is nearly directly measured by the pancreas, liver, and other cells throughout the body. In a medical device control system glucose may be measured less directly, such as interstitially and with delay (for example, approximately a 15 minute delay). In the natural control system, insulin is dispensed by the pancreas almost directly into blood. In a medical device control system, insulin may be dispensed interstitially and with delay (for example, approximately a 15 minute delay). However, a good model of the body may enable forward accounting of these delays.

In some examples, a treatment system may utilize a multi-tiered algorithm to facilitate improved glycemic control for a user given different levels of connectivity of system devices to a network and/or each other. In some examples, a multi-tiered algorithm may include 3 tiers. In a first tier, a user may have connectivity between a disease management system, such as an insulin administration and/or CGM device, a mobile device, such as a smart mobile device, and a cloud or network. In a second tier, a user may have connectivity between a disease management system, such as an insulin administration and/or CGM device, and a mobile device, such as a smart mobile device, but may not have connectivity to a cloud or network. In a third tier, a user may lack connectivity between a disease management system, such as an insulin administration and/or CGM device, a mobile device, such as a smart mobile device, and a cloud or network. Advantageously, a multi-tiered system may reduce computational strain on local devices, such as a mobile device or disease management system by performing more complex processing to an external backend system so that local devices may devote their processing power to more basic processes.

Connectivity between one or more devices and/or the cloud or network may be through any number of wireless or wired connections. For example, a disease management system may wirelessly connect to a mobile device through an NFC connection or Bluetooth. In another example, a mobile device may have connectivity to the cloud or a network via Wi-Fi or a cellular network. It should be noted that a mobile device may not be a permanent communication line and may not be required by the system to keep a user in tight glycemic control.

In the first tier, a user may have connectivity between the disease management system, mobile device, and cloud. Since there is virtually unlimited processing and memory in the cloud, more computationally expensive algorithms, such as MPC (Model Predictive Control), can be performed in the cloud or a backend system connected to a network that the mobile device or disease management system is also connected to. In some examples, an MPC can include a control algorithm configured to utilize a physiological model of the user to predict future glucose values and determine the optimal sequence of stimuli necessary to achieve a desired outcome, such as a desired glucose value. A cloud algorithm may take past and present observations to generate a model that simulates glucose and insulin transfer between different organs or compartments of the body. Thus, the cloud algorithm can foresee the effect of meal intake and insulin injection on the plasma and interstitial fluid glucose at future points in time. In this way, the algorithm can recommend a set of insulin doses in the present and future to compensate for glucose excursions due to meals and other effects. A backend system running the cloud algorithm may then communicate those recommendations to the mobile device through the network and the mobile device may then communicate with the disease management system based on the recommendations to facilitate insulin treatment and/or analyte measurements. In some examples, the backend system may directly communicate recommendations with the disease management system.

In the second tier, a user may have connectivity between the disease management system, and the mobile device, but may have no or limited connectivity with the cloud and/or network. In some examples, a mobile device may not be configured to run computationally expensive or a proprietary algorithm code because the code running on the mobile device cannot be ensured to be secure. In a second tier, an algorithm may still allow a user to interact with a disease management system with a mobile device by, for example, allowing user input to specify when a meal will occur with the number of carbohydrates or other nutritional information. Thus, an algorithm may correctly bolus an amount of insulin to counteract the effect of carbohydrates and/or keep the user in a target range of blood glucose. In some examples, the algorithm may allow a user to set user may also set temporary basal effects in anticipation of future exercise, sleep, stress, caffeine, etc., which will affect the user's insulin sensitivity and requirements.

In the third tier, a user may have no or limited connectivity between a disease management system and a mobile device and/or a network or cloud. In the third tier, an algorithm may deliver insulin reactively to recent glucose measurements to keep the user in the target range. In some examples, a third tier algorithm may also supply a prediction and planned stimuli of how a user may respond given only first tier or second tier algorithmic control.

It should be understood that a user may not be continuously in a single tier (such as a first tier, a second tier, or a third tier). For example, as connectivity changes, the algorithm chosen to dose insulin safely for that time period may dynamically change. As an example, a user may have just received a 30 minute time prediction from the third tier algorithm. This prediction and planned stimuli looking forward in time may be saved for access by the disease management system, such as in embedded software of the device. At a next time step, connectivity may cease to both the cloud and the user's mobile device. The disease management system may choose to hybridize its first tier basal closed loop algorithm with the high confidence 30 minute extrapolation of the third tier algorithm over the next few measurements. This hybridized result would be valid so long as the device is not notified of any new environmental stimuli such as an insulin bolus or the disease management system continues to see the CGM outputs course be very similar to the third tier's 30 minute extrapolation. Should the device see a deviation from the third tier extrapolation it may resume entirely to first tier algorithmic control and comparisons to the prediction and planned stimuli therein. Should the device see a deviation from the first tier extrapolation it may suspend all insulin dosing and even raise an alarm.

As another example, a user may have just received the 30 minute time prediction from the third tier algorithm. This prediction and planned stimuli looking forward in time may be saved for access by the disease management system, such as in the embedded software of the device. At the next time step, connectivity may cease to the cloud. The disease management system may choose to hybridize its second tier hybrid closed loop algorithm with the high confidence 30 minute extrapolation of the third tier algorithm over the next few measurements. This hybridized result would be valid so long as the device is not notified of any new environmental stimuli such as an insulin bolus, food bolus, or the device continues to see the CGM outputs course be very similar to the third tiers 30 minute extrapolation. Should the device see a deviation from the third tier's extrapolation, it may resume to second tier algorithmic control and comparisons to the prediction and planned stimuli therein. Should the device see a deviation from the second tier extrapolation it may suspend all insulin dosing and even raise an alarm. Other hybridizations of the multi-tier algorithm process may also be possible.

In some examples, a treatment system may facilitate different access levels to user information and/or device control. For example, should any user have insufficient mental capacity or education where they could make life threatening choices, a need exists to utilize increasingly higher levels of user authority that have the final judgement on behavior available and that may limit system operations. In some examples, it may be preferable and/or highly dependent on the situation at hand whether the user should have access to features relevant to control of the closed loop system at subsystems, such as the three major subsystems of the one or more disease management systems, the user's mobile device, or the cloud.

Figure 33:
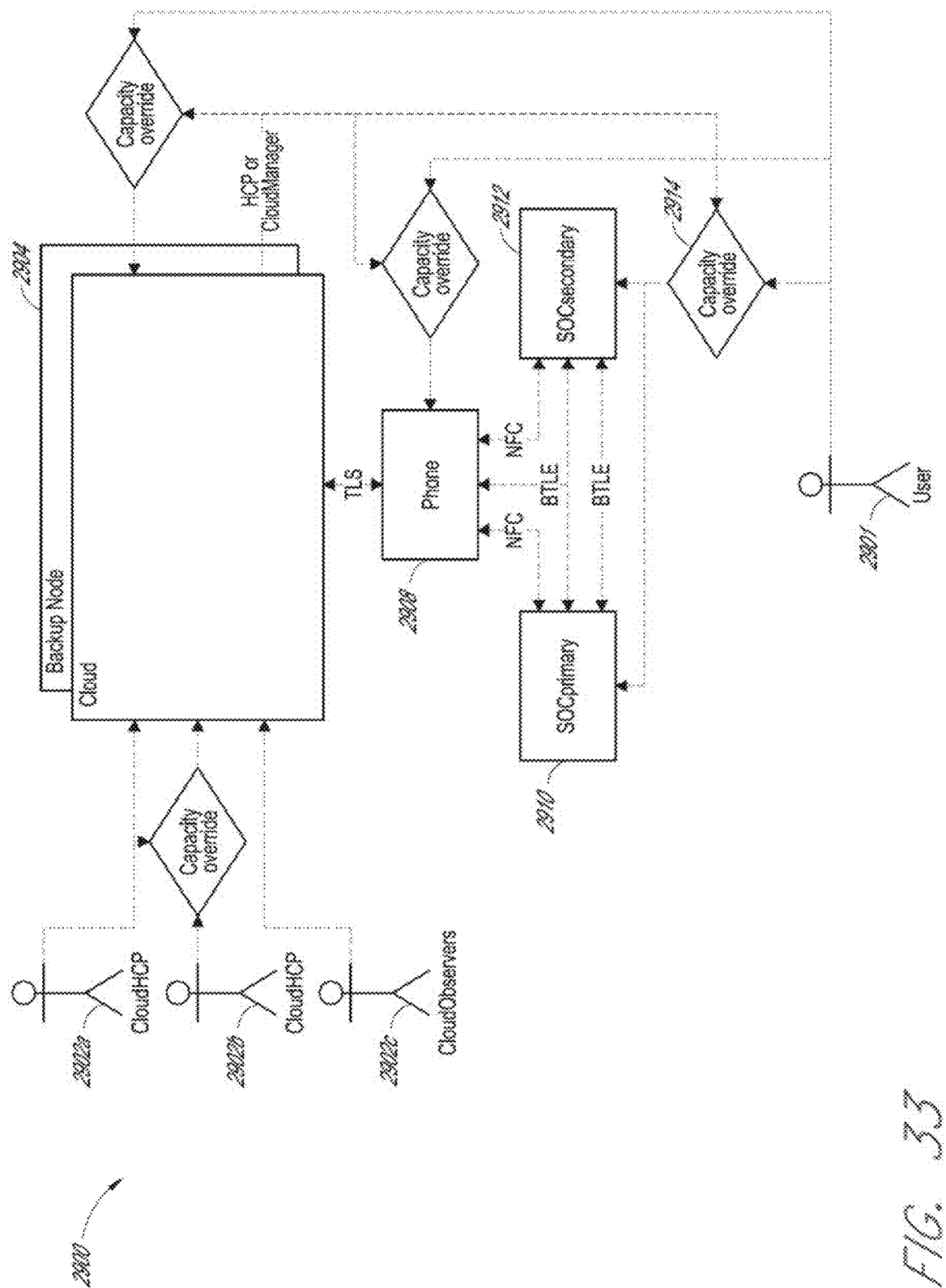
FIG. 33 illustrates an example authentication environment that may be associated with a treatment system.

FIG. 33 illustrates an example authentication environment 2900 that may be associated with a treatment system. For example, an authentication environment 2900 may include one or more users 2902A, 2902B, 2902C other than the patient user 2901. The users may have different access or authentication levels for accessing user data that may be stored on a backend system 2904 or in the cloud. For example, a healthcare provider user 2902A and manager 2902B may have override permissions. Override permissions may include the ability to interact with a user's primary device 2910 and/or secondary device 2912 by communicating instructions to a backend system 2904 that may in turn communicate instructions to a user's mobile device 2908 or directly to the devices 2910, 2912. The mobile device 2908 of a user 2901 may then communicate instructions to the primary device 2910 and/or secondary device 2912 that may be applied to a user 2901. In other examples, an observer user 2902C may have observer only permissions that do not enable communication of instructions or override to a user's devices. In some examples, a user 2901 may have either override or observer only permissions. A user 2901 may be granted override or observer only permissions based on factors, such as user age. For example, a child user may be given observer only permissions and an adult user may be given override permissions. Permissions may be assigned by a manager user 2902B, user 2901, healthcare provider user 2902A, or automatically based on determined factors.

An algorithm may be able to recognize patterns in individuals' physiology and reaction to stimuli as well as user behavior and insulin response to provide a better control algorithm. This may cover user observations (individual and population) (long-term) and model based (short-term). Time in range (TIR) may be greater than 70% and closed loop remains on without being forced into manual mode by a probe-off greater than 90% of the time while having a cloud connection. TIR may be greater than 60% and closed loop remains on without being forced into manual mode by a probe-off greater than 90% of the time while having only an app connection but no cloud connection. TIR may be greater than 50% and closed loop remains on without being forced into manual mode by a probe-off greater than 90% of the time while only using embedded device.

The algorithm may suspend insulin on low detected absolute or derivative CGM glucose or model prediction value configurable thresholds and may notify app. An algorithm may have a glucose set point or target range mode based on user context. These set points or target range modes made be temporary in nature and detected. There may exist at least one embedded closed loop control algorithm that can function independent of an application or cloud. There may exist at least one embedded closed loop control algorithm that may function independent of cloud but utilize the app for dosing verification and meal entry. There may exist an arbitrator algorithm that determines the best insulin dose based off of some combination of conditions or algorithms, such as embedded only, embedded and mobile device, embed and mobile device and cloud algorithms, meta information, and heuristic information of user.

In some examples, a TIR performance and user safety may be improved by cloud connection. An algorithm may configurably incorporate external insulin injections by, for example: syringe (muscle or ISF), patch, and inhaled from various vendors. A user's personal insulin sensitivity may be assessed after OGTT-like meals are consumed and logged. Records of the insulin type used may be retained for possible future calibrations with that insulin type.

In some examples, an algorithm may utilize EHR records to improve personalization around sparse variables of interest such as: HbA1C, fasting glucose test, existing disease progression, or other blood works considered gold standards. In some examples, an algorithm may utilize lipid information to make meal time corrections. In some examples, an algorithm may utilize lipid information to make meal time confidences. In some examples, an algorithm may dynamically re-estimate quantity of meal quantities based on CAM measurements. In some examples, an algorithm may use rate of appearance and food quantity to retrospectively modify a foods particle size in order to properly account for large CGM oscillations (30 minute time periods). In some examples, an algorithm may use fine sampling rates (1 minute measurements) to assess the personal delay time of users pyloris when CGM short oscillations occur (5 minute time frame) due to high nutrient levels. Additionally or alternatively, an algorithm may assess the trigger threshold for opening and closing the pyloris. In some examples, user body temperature may be measured to provide alarms related to whether the user is having a fever or not. In some examples, an algorithm may determine body orientation of each device, such as if a user is on back, belly, or butt and allowed a user-engaged calibration. In some examples, an algorithm may use users described body placement to historically and personally analyze insulin absorptivity rate. In some examples an algorithm may have an SIQ system that takes into account electrical instability, and/or known sensor-body responses. In some examples, an algorithm in cloud may monitor its confidence that it is likely in full-use (User is supplying all required information such as 3 meals, insulin injections, and activity). In some examples, an algorithm may monitor that CGM or CAM output(s) stay contained in at least one state of a glucose prediction model, such as a glucose-insulin-lipid meal model (GLIMM). If a user deviates from a predication or target, an algorithm may communicate a notification to an application. An algorithm may monitor internal model (such as MPC) states with simple thresholds to prevent erroneous dosing. An algorithm may monitor outbound insulin dosing with simple rules to act as a sanity check. Insulin on board may be monitored with simple rules to prevent overdosing from the app. An algorithm may monitor personalized insulin dosing based on heuristic dosing of user and compare it with current dosing to prevent overdosing from the app or cloud. An algorithm may determine physical activity and/or physical activity confidence value(s) via one or more sensors, such as an accelerometer, gyroscope, pulse rate, spo2, or a GPS. In some examples, an algorithm may determine time of day and other parameters associated with whole body model states.

An algorithm may alarm on oxygen lows that may indicate hypoglycemic or compression related low events or independently bad events such as opioid overdoes with the SpO2 and/or use an SpO2 monitor to detect sleep apnea. An algorithm may monitor diffuse reflectance SpO2 to estimate insulin metabolism at one or more measurement sites to assess oxygen consumption by a sensor, such as a GOx sensor.

An algorithm and/or disease management system(s) may include one or more safe mode configurations. In some examples, an algorithm may maintain a historically safe personalized user configuration.

An algorithm may build cloud-based confidence in expected patterns for insulin bolus, based on one or more user parameters, such as exercise behavior, food bolus, mobile device GPS location, time of day, sleep status, pulse rate, or SpO2.

An algorithm may predict at what time an insulin reservoir will approach zero. A threshold may be used to determine the time at which a new device should to be put on the body in order to ensure adequate insulin supply. This time, threshold, or alarm may be communicated to a companion application.

An algorithm may predict the effectiveness of insulin based on temperatures and time and dose accordingly for primary and secondary devices insulin reservoirs. This prediction may be separate and/or operate in parallel or in conjunction with a control algorithm to correct an insulin dose.

An algorithm may detect when user is moving towards hypo or hyperglycemia and may test into the future, such as a few hours from a current time.

M. SELF-CALIBRATION OF CGM SENSORS USING EIS

Amperometric CGMs can measure electrical current produced by enzymatic oxidation of glucose at a constant electrode potential and translate the measured current value into a glucose concentration using a predefined value for sensitivity. Drift in this sensitivity can present a major challenge in long-term accuracy of CGMs. This drift could have multiple causes. For example, the drift can be caused by a change in the polymer films on the electrode, a change in the electrode surface properties that affect the charge transfer kinetics at the electrode surface, and/or a change in the enzyme (e.g., GOx) activity. Since the only output in amperometry is a single current value at each time point, amperometry alone is unable to detect drift in sensitivity and its possible causes.

A possible method for detecting sensitivity drifts in a CGM sensor is electrochemical impedance spectroscopy (EIS). Unlike amperometry, EIS can simultaneously reveal multiple parameters that represent different physical and chemical properties of the sensor. By correlating the value of each parameter found using EIS with the amperometric sensitivity of the CGM, periodic EIS scans can help diagnose and correct for changes in sensitivity in order to improve the long-term accuracy of the CGM. For example, slow and long-term detachment of a polymer film from the sensor results in certain changes in a specific parameter output of EIS. If the correlation between that specific parameter output and amperometric sensitivity is known, the sensitivity can be adjusted accordingly during the operation of the sensor by periodic EIS scanning.

When testing for major issues such as improper initial insertion that represent a binary test (e.g., proper or improper insertion), impedance measurements at a single or a few frequencies may be enough to diagnose the problem. In contrast, in EIS scans an entire range of frequencies may need to be scanned to give quantitative estimates of specific physical and chemical parameters of the sensor. Therefore, the range and number of frequencies used for electrochemical impedance measurements can largely vary based on the desired test.

Figure 34A:
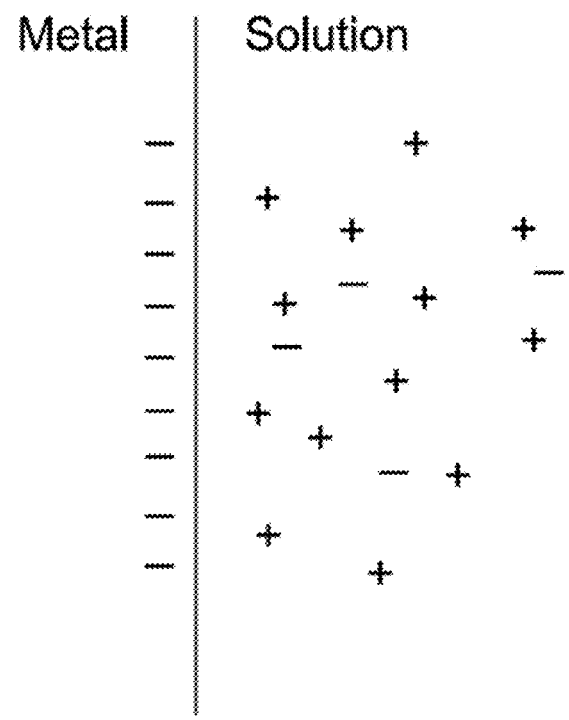
FIG. 34A illustrates an example electrode-solution interface that can act as a capacitor.
Figure 34B:
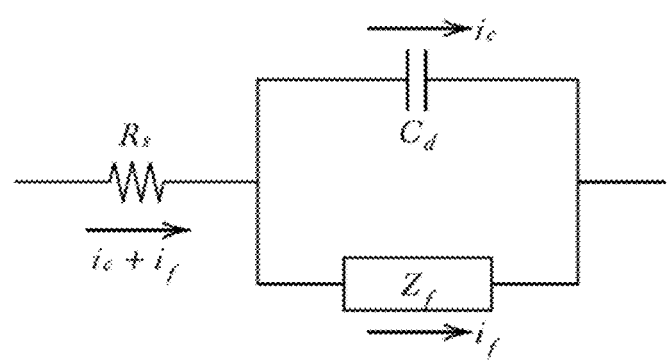
FIG. 34B illustrates an example circuit model.
Figure 34C:
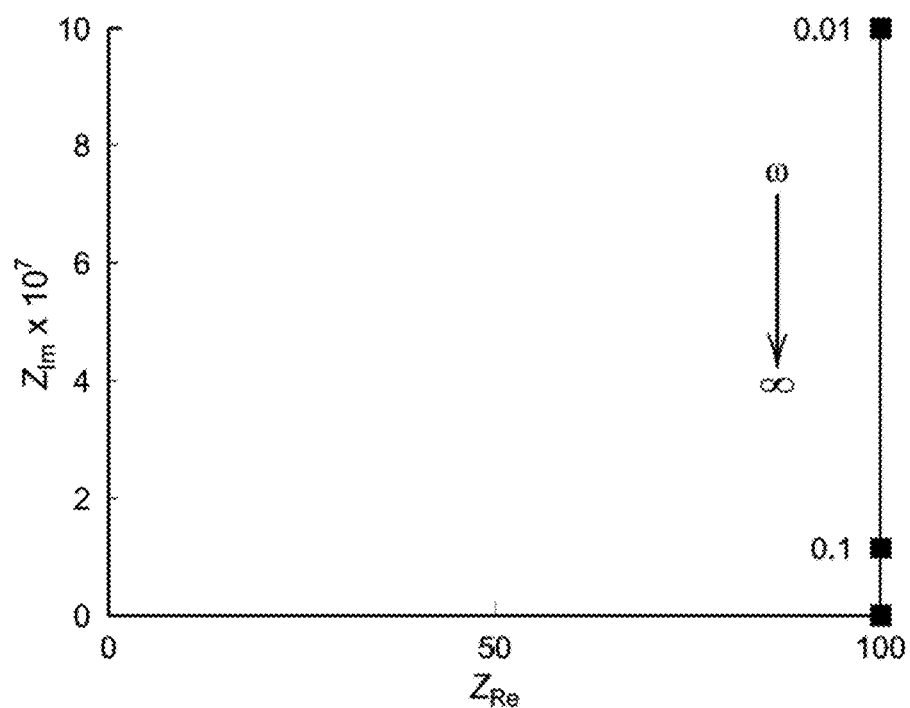
FIG. 34C illustrates a Nyquist plot for a series RC equivalent circuit.
Figure 34D:
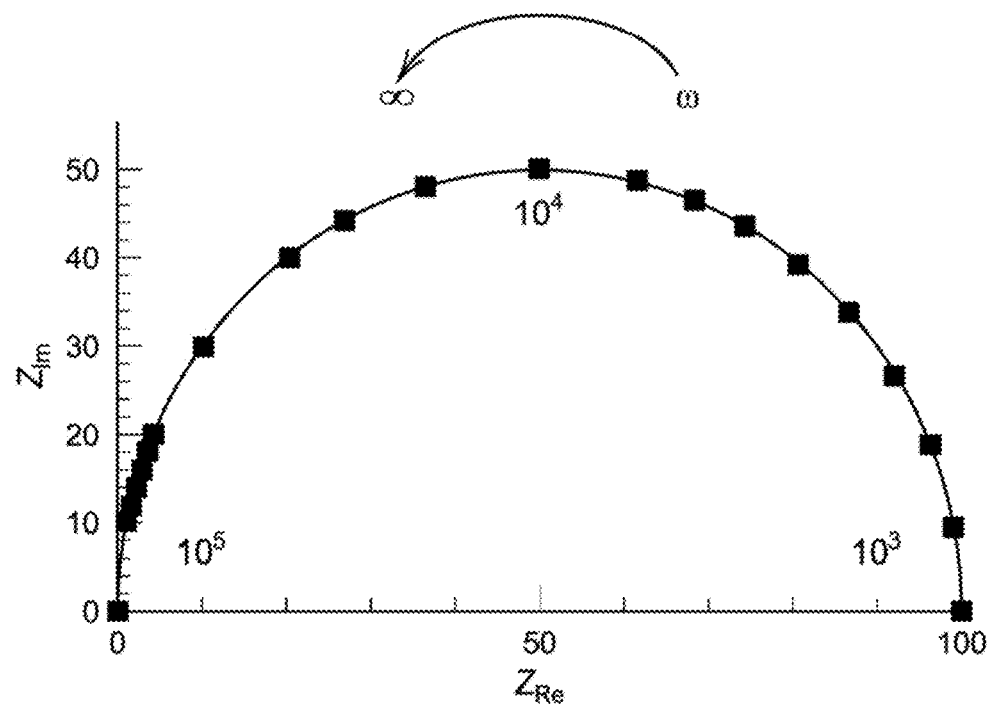
FIG. 34D illustrates a Nyquist plot for a parallel RC equivalent circuit.

In EIS, a sinewave AC potential is applied on the working electrode of an electrochemical system, the AC current produced as a result of this potential is measured, and an impedance value is calculated. This procedure is then performed at a range of frequencies to give impedance as a function of frequency. Multiple electrochemical processes contribute to this impedance. For example, as shown in FIG. 34, one electrochemical process is electrode-solution interface capacitance with electrons in the electrode (e.g., metal) and ions in the solution forming a capacitor at the electrode surface. Another electrochemical process is charge transfer resistance, which involves transfer of electrons across the electrode-solution interface. A third electrochemical process is solution resistance, which arises from electrical conduction in the bulk solution due to presence of electrolytes. Other phenomena such as diffusion of molecules within the sensor structure can also play a role in the impedance. Each of these components can be modeled as an electrical circuit element with a unique dependence of impedance on frequency. The overall system can then be represented by an equivalent circuit model composed of the combination of these individual elements. For example, FIG. 34B illustrates an EIS equivalent circuit model, which includes a solution resistance $R_\Omega$ in series with a capacitor $C_d$ and a charge transfer resistance $Z_f$ in parallel. Data from EIS scans can be fit with the expected impedance-frequency behavior of an equivalent circuit model to extract the value of each circuit element. One way of visualizing the impedance-frequency data from EIS is via Nyquist plots (imaginary vs. real impedance). FIGS. 34C and 34D shows examples of Nyquist plots for series (FIG. 34C) and parallel RC circuits (FIG. 34D). For the series RC circuit, the relationship can be represented by the following equation:

$Z = R - j/\omega C$

For the parallel RC circuit, the relationship can be represented by the following equation:

$$\frac{1}{Z} = \frac{1}{R} + j\omega C$$

Figure 34E:
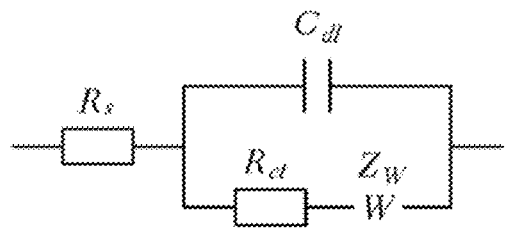
FIG. 34E illustrates an example circuit model with a Warbug element.
Figure 34F:
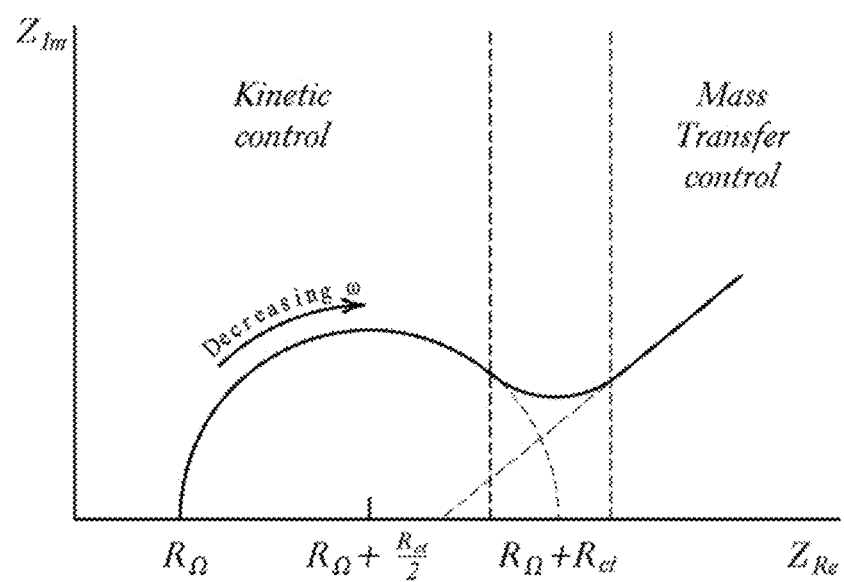
FIG. 34F illustrates an example Nyquist plot for the example circuit model shown in FIG. 34E.

FIG. 34E shows a common EIS equivalent circuit model that includes a Warburg element $Z_w$ and FIG. 34F shows its theoretical Nyquist plot. The Warburg element $Z_w$ represents the diffusion of molecules in the system (e.g., toward the electrode). As shown in FIG. 34F, the charge transfer resistance $R_{ct}$ plays a larger role in the left part of the plot (e.g., the semi-circle) while the Warburg element $Z_w$ is more prominent on the right part of the plot (e.g., the linear regime).

To understand the relationship between EIS circuit elements and the amperometric sensitivity of a CGM, a number of sensors can be studied in vitro by performing both periodic EIS and sensitivity measurements using known glucose concentrations. The correlation between EIS circuit element values and CGM sensitivity can then be extracted from this dataset. This correlation can then be incorporated into the CGM online during operation. During in vivo use, the CGM can automatically perform EIS, extract the circuit elements, find the expected drift in sensitivity using the pre-defined correlation, and adjust the sensitivity to improve the sensor accuracy.

Figure 34G:
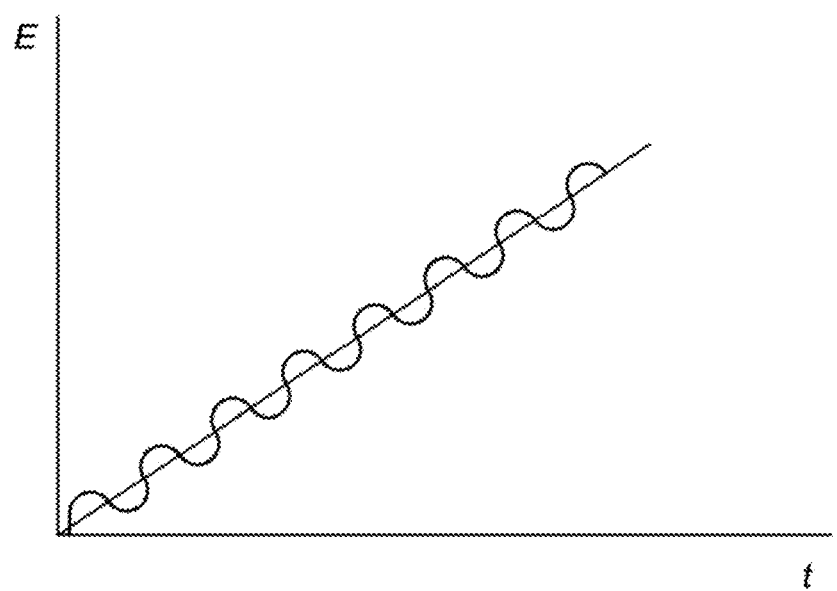
FIG. 34G illustrates a schematic of an electrode potential as a function of time in AC voltammetry.

The periodic EIS can be performed at various DC potentials. Typically, EIS is performed at the open circuit potential (i.e., while no DC potential is applied to the electrode). However, it is possible to perform EIS even at a non-zero applied DC potential. For example, one possibility is to perform EIS at the same DC potential as the amperometry potential (e.g. +0.6 V). In that case, the amperometry does not need to be stopped during the EIS scan because the same constant DC potential is applied and the DC current is still measured. This method has the advantage that the DC potential is not turned on and off, which avoids creating any transient currents due to potential being turned on/off. Another modification of the EIS technique involves performing EIS during a potential sweep (i.e., superimposing an AC potential on a slowly and linearly varying potential (FIG. 34G). This method is usually referred to as AC voltammetry, and can potentially reveal additional information about the electrochemical system.

Other than AC voltammetry, there are multiple modifications of the EIS method that can be used for self-calibration. A first example involved modifying the equivalent circuit model used to extract circuit elements. Many different models exist, and depending on the sensor structure, a unique model may result in better correlations between extracted circuit elements and sensitivity. A second example involves modifying the range of frequencies scanned in EIS. A third example involves modifying the number of points scanned in an EIS scan. A fourth example involved adjusting the timing and interval of the periodic EIS scans based on the need for self-calibration of the sensor.

N. SENSOR DIAGNOSTICS USING IMPEDANCE MEASUREMENTS

Electrochemical impedance measurements can indicate potential issues in the sensor. Most importantly, if a sensor does not have proper contact with liquid (e.g., interstitial fluid) upon the initial insertion, the impedance will be vastly different than if the sensor is inserted properly and is in contact with bodily fluids. Therefore, impedance measurements in general, and EIS in particular, can allow detection of erroneous insertion of the CGM sensor.

Electrochemical impedance can be measured at a single or a few different frequencies shortly after the insertion of the sensor in the body. The impedance value can be compared with a range of pre-defined acceptable impedance values. If the measured impedance lies within this range, the sensor is considered "properly inserted". If not, the device can alert the user that the sensor is not inserted properly and corrective action must be taken. The measured impedance value can also inform about the initiation state of the sensor and whether the sensor is hydrated enough to begin making glucose measurements.

A similar method can be used to detect any significant damage to sensor, loss of contact with bodily fluids, or other major issues. Single-frequency impedance can be measured periodically to diagnose these major problems with a binary answer (e.g., the sensor is working or the sensor has undergone significant change and needs to be replaced).

There are multiple modifications of the impedance-based diagnostic method that can be implemented. A first example is modifying the frequency at which impedance is measured. A second example is measuring impedance at multiple specific frequencies and using a combination of these values to make a decision about whether the sensor is damaged or improperly inserted. A third example is adjusting the timing and interval of the periodic impedance measurements based on the need for self-diagnosis in the sensor.

O. EXAMPLE ELECTROACTIVE NON-KINKING CANNULAS

Insulin infusion may fail for many reasons including catheter failure, pain at the infusion site, pull out, adhesive failure, and infection. For example, a catheter may fail due to kinking of the catheter and/or a patient's immune response. Additionally, when kinking occurs an unexpected and unquantified additional dose of insulin can occur. Thus, an impedance measurement with a measuring element inside a cannula can be used to address insulin infusion failure due to a catheter failure (for example, due to kinking and the patient's immune response). Moreover, by using the catheter as described herein, the system can estimate an amount of the unexpected additional dose of insulin to be sent back to a close loop algorithm to fine tune control. The use of an impedance measurement can also be used when the cannula is straight to quantify the amount of aggregated insulin on the helical spring element and/or the amount of encapsulation outside of the cannula.

Figure 35D:
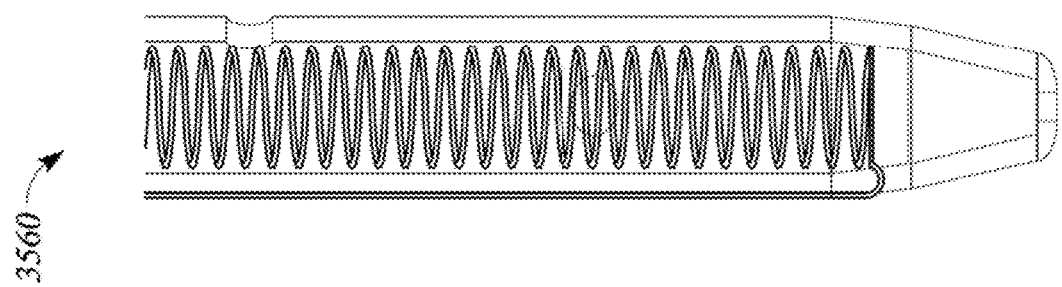

FIGS. 35A-35D illustrate different configurations of a non-kinking cannula. The different configurations can include a single helix cannula 3500 (FIG. 35A), a double helix cannula 3520 (FIG. 35B), a straight helix cannula 3540 (FIG. 35C), and a c-straight helix cannula 3560 (FIG. 35D). The single helix cannula 3500 can, for example, make an impedance measurement if the cannula 3500 and the insulators along the cannula 3500 is conductive on at least one surface and connected along the tip. The straight helix cannula 3540 can be more sensitive to interstitial fluid (ISF) relative to the other configurations of the non-kinking cannula. Advantageously, this sensitivity can be used to observe a change in conductance of the ISF and detecting a kink or expiring medication (e.g., insulin or glucagon). Additionally, each of these cannulas 3500, 3520, 3540, 3560 can include a helical spring that can have a filtration effect when the spring is located near the exit flow holes of the cannula 3500, 3520, 3540, 3560. The helical spring can trap insulin protein or other medication such that protein, which would otherwise produce an immune response in the patient, aggregates in the cannula. Advantageously, this can increase the usable span of time the cannula 3500, 3520, 3540, 3560 can function.

The cannulas 3500, 3520, 3540, 3560 can be configured to detect kinking in the cannula 3500, 3520, 3540, 3560. For example, the double helix cannula 3520 and the c-straight helix cannula 3560 can be configured to detect kinking by detecting a change in resistance. These configurations 3520, 3560 can include first and second wires. The first wire can be configured to separate resistance changes in series. The second wire may or may not be configured to have resistance in series. When the cannula 3520, 3560 is straight the circuit can be modeled by Ohms law, as represented by the following equation:

$$R_T = \Sigma R_j$$

If a kink occurs in the cannula 3520, 3560, then the circuit can become a parallel measurement, as represented by the following equation:

$$R_T = \frac{1}{\frac{1}{\sum R_i} + \frac{1}{\sum R_j}}$$

Therefore, a change in resistance can be expected when a kink occurs in the cannula 3520, 3560. If there multiple kinks in the cannula 3520, 3560, then more parallel elements can occur, as represented by the following equation:

$$R_T = \frac{1}{\frac{1}{\sum R_i} + \frac{1}{\sum R_j} + \ldots + \frac{1}{\sum R_k}}$$

In order to identify the location of the kink, the resistance must be varied along at least one of the first and second wires. If the resistance remains the same, it will be unclear whether the kink is in the top half or the bottom half of the cannula 3520, 3560. The resistance can be continuously or discretely varied down the first wire and/or the second wire. Thus, the parallel resistance can be unique as the kinking occurs differently at two different symmetric locations, as represented by the following equations:

$$R_{T1} = \frac{1}{\frac{1}{\sum R_i + \sum R_j} + \frac{1}{\sum R_k}}$$

$$R_{T2} = \frac{1}{\frac{1}{\sum R_i} + \frac{1}{\sum R_k + \sum R_j}}$$

Where RT1 is equal to RT2 (i.e., $R_{T1}=R_{T2}$) when Ri, Rj, and Rk are equal (i.e., $R_i=R_j=R_k$). When $R_i<R_j<R_k$, then $R_{T2}<R_{T1}$. When there are multiple kinks, more resistances in parallel can be added, as shown in the following equation:

$$R_{T,multi} = \cfrac{1}{\cfrac{1}{\sum R_i} + \cfrac{1}{\sum R_k + \sum R_j} + \cfrac{1}{\sum R_g} \cdots}$$

Based on the total measured resistance, the location(s) of the kink(s) in the cannula 3520, 3560 can have a regressable or classifiable variable. These cannulas 3520, 3560 can also be configured to conduct impedance analysis, as the cannulas 3520, 3560 can naturally have some impedance and capacitance, which can improve the ability to determine the location(s) of the kink(s) in the cannula 3520, 3560.

The cannulas 3500, 3520, 3540, 3560 can be configured to estimate of an amount of the unexpected additional dose of a drug (e.g., insulin) that can occur with kinking in the cannula 3500, 3520, 3540, 3560. For example, the location of the kinking can be used in conjunction with the location of flow holes in the cannula 3500, 3520, 3540, 3560 and respective size of the flow holes to estimate the amount of the unexpected additional dose of insulin. With a known kink location, a diameter of the cannula 3500, 3520, 3540, 3560, and a length of the cannula 3500, 3520, 3540, 3560, the displaced insulin upon bending or kinking can be estimated. This estimation can be based on an empirical estimation, an analytical estimation via Bernoulli equations and/or simple kinetic diffusion approximations at steady state, or by a priori fluid flow models (e.g., Navier-Stokes simulations) stored and utilized upon various kink locations observations.

The viscosity of insulin (e.g., U100 vs U200) and ISF viscosity can be utilized to improve the estimation of the displaced insulin. For example, excipients for a medication (e.g., insulin or glucagon) may be advantageously chosen such that the ionic character of the solvent or solutes can allow a larger dynamic range of signals to be observed. The larger dynamic range of signals can occur due to diffusion changing the concentrations of the ionic character of the solvent or solutes in or around the cannula 3500, 3520, 3540, 3560. Moreover, the changing concentrations of the ionic character of the solvent or solutes can cause a change in impedance in or around the cannula 3500, 3520, 3540, 3560. Additionally, diffusion can be determined over time via a model to discern when insulin may have been fractionally displaced via diffusion through the infusion holes even if a bend or kink occurs. Under this circumstance, it will be known that despite the kink no medication volume was displaced, only diffused ISF or a fractional amount of ISF and medication.

Impedance characteristics can be used to determine a diffusion coefficient of the filtration effect of the helical spring on insulin over the use life of the cannula 3500, 3520, 3540, 3560. Additionally, impedance characteristics can be used to determine the clogging or encapsulation state of the cannula 3500, 3520, 3540, 3560. These measurements can be taken when the cannula 3500, 3520, 3540, 3560 is not kinked or bent. Additionally, all of these measurements together can be used to estimate how much longer the cannula 3500, 3520, 3540, 3560 can remain in the body before there is complete biofouling or encapsulation of the cannula 3500, 3520, 3540, 3560.

In some configurations, any of the resistive elements of the cannulas 3500, 3520, 3540, 3560 discussed herein may comprise one or more temperature sensitive elements, which can be naturally resistive. The temperature sensitive elements can measure a temperature under the patient's skin, which can be used, for example, in a closed loop system. In some configurations, a plurality of temperature sensitive elements can be used to predict the patient's core body temperature. For example, the plurality of temperature sensitive elements can generate a temperature gradient of the location of the cannula 3500, 3520, 3540, 3560 in use (e.g., under the patient's skin).

Haptic motion can also be induced in a cannula or outside of a cannula. The choice of haptic frequency and power can be chosen such that a resonant force can appear near infusion holes to maximize the dislodging affect. Other modes of haptic motion may be utilized that optimally dislodge blockage or kinking in the cannula or surrounding tissue space with a travelling wave. This wave can move debris away from infusing holes. Multiple failure modes can potentially be addressed by such motion, such as failure due to aggregated insulin, which can be dislodged to allow clearance of an infusion hole, failure due to fibrin encapsulated sensors, which can be shaken free allowing a pathway out of the to allow clearance of an infusion hole, and/or failure due to kinks in the infusion cannula, which can be straightened by haptic motion if lodged in a compromising fashion.

P. ADDITIONAL EXAMPLES

Disclosed herein are additional examples of a disease management system. Any of the examples disclosed herein may be combined in whole or in part.

Example 1: A disease management system comprising:
a first disease management system comprising:
a first glucose sensor; and
a first insulin pump;
a second disease management system comprising:
a second glucose sensor; and a second insulin pump;
wherein the first disease management system and second disease management system are configured to simultaneously attach to a patient and communicate with each other, and
wherein while the first glucose sensor is in a settling period, the second glucose sensor is configured to provide patient glucose information to at least one of the first disease management system or the second disease management system.

Example 2: The disease management system of Claim 1, wherein the settling period comprises a warmup period or a stabilization period.

Example 3: The disease management system of Claim 1, wherein at least one of the first disease management system or the second disease management system is configured to calculate a proper dosage of insulin based on patient glucose information from at least one of the first glucose sensor or the second glucose sensor.

Example 4: The disease management system of Claim 3, wherein calculating the proper dosage of insulin is further based on patient entered data.

Example 5: The disease management system of Claim 4, wherein the patient entered data comprises age, height, weight, or weight.

Example 6: The disease management system of Claim 3, wherein calculating the proper dosage of insulin is further based on a customized glucose metabolization rating for the patient.

Example 7: The disease management system of Claim 6, wherein the customized glucose metabolization rating is based on the patient's weight, age, digestion rate, or insulin sensitivity.

Example 8: The disease management system of Claim 1, wherein at least one of the first disease management system or the second disease management system is configured to communicate with a smart device or a smartwatch.

Example 9: The disease management system of Claim 8, wherein the first disease management system or the second disease management system is configured to communicate with the smartphone or the smartwatch through Bluetooth or RF signal.

Example 10: The disease management system of Claim 8, wherein the at least one of the first disease management system or the second disease management system is configured to communicate with the smart device and wherein the smart device is configured to communicate with the smartwatch.

Example 11: The disease management system of Claim 1, wherein the first disease management system further comprises a first insulin storage container fluidly connected to the first insulin pump.

Example 12: The disease management system of Claim 11, wherein the first insulin pump is fluidly connected to a needle which is capable of being inserted into a cannula that is implanted into a patient.

Example 13: The disease management system of Claim 11, wherein the first insulin storage container comprises a flexible insulin pouch and the first disease management system further comprises a spring configured to apply pressure to the flexible insulin pouch.

Example 14: The disease management system of Claim 13, wherein the flexible insulin pouch is prefilled with insulin.

Example 15: The disease management system of Claim 13, wherein the first insulin pump comprises a valve that is controlled in order administer a specific dosage of insulin to the patient.

Example 16: The disease management system of Claim 15, wherein the valve comprises 3 or more piezoelectric crystal valves.

Example 17: The disease management system of Claim 15, wherein the valve comprises 3 or more voice coil valves.

Example 18: The disease management system of Claim 15, wherein the valve comprises 3 or more piezoelectric stack valves.

Example 19: The disease management system of Claim 15, wherein the first insulin pump further comprises a filter connected between the valve and the needle.

Example 20: The disease management system of Claim 13, wherein the valve comprises a beginning valve, an end valve, and one or more intermediate valves located between the beginning valve and the end valve, the intermediate valves individually controllable in order to administer the specific dosage of insulin.

Example 21: The disease management system of Claim 11, wherein the first insulin pump comprises a peristaltic pump.

Example 22: The disease management system of Claim 21, wherein the peristaltic pump comprises:
  a circular gear;
  a circular portion attached to the circular gear such that when the circular gear rotates the circular portion rotates at the same rotational speed, the circular portion located below the circular gear;
  two or more rollers located radially outward from the circular portion and in physical contact with the circular portion such that the roller rotate as the circular portion rotates;
  a casing which wraps around the circumference of the rollers and the circular portion such that the casing and the rollers cooperate to form a circular channel, wherein the rollers are located at an inside portion of the circular channel and the casing is located on the outside of the circular channel; and
  a tubing located within the circular channel such that the tubing physically contacts both the casing and the rollers,
  wherein when the circular gear is rotated, the circular portion drives the two or more rollers which apply pressure to the tubing such that liquid within the tubing is driven from an inlet of the tubing to an outlet of the tubing.

Example 23: The disease management system of Claim 22, wherein the peristaltic pump is a ratcheting peristaltic pump comprising a ratcheting driving mechanism in physical contact with the circular gear, wherein the ratcheting driving mechanism is capable of ratcheting teeth within the circular gear at one tooth at a time.

Example 24: The disease management system of Claim 21, wherein the peristaltic pump comprises:
  a circular gear with a circular hollow center;
  two or more rollers located within the circular hollow center and in physical contact with an inner wall of the circular gear such that the rollers rotate when the circular gear rotates;
  a stationary inner portion which is fixed, the stationary inner portion and the roller cooperate to form a circular channel, wherein the rollers are located at an outside portion of the circular channel and the stationary inner portion is located at the inner portion of the channel; and
  a tubing located within the circular channel such that the tubing physical contacts both the stationary inner portion and the rollers,
  wherein when the circular gear is rotated, the two or more rollers rotate which applies pressure to the tubing such that liquid within the tubing is driven from an inlet of the tubing to an outlet of the tubing.

Example 25: The disease management system of Claim 24, wherein the peristaltic pump is a ratcheting peristaltic pump comprising a ratcheting driving mechanism in physical contact with the circular gear, wherein the ratcheting driving mechanism is capable of ratcheting teeth within the circular gear at one tooth at a time.

Example 26: The disease management system of Claim 1, wherein the first disease management system comprises:
  a case;
  a computing device capable of controlling the first insulin pump and receiving measurements from the first glucose sensor;
  a battery configured to power the first glucose sensor, the first insulin pump; and the computing device; and
  an antenna connected to the computing device, wherein the computer device is configured to broadcast information through the antenna,
  wherein at least one of the computing device, battery, first glucose sensor or the first insulin pump are housed within the case, and
  wherein the antenna is located outside of the case.

Example 27: The disease management system of Claim 26, wherein the case includes one or more needle insertion holes capable of having a needle inserted.

Example 28: The disease management system of Claim 26, wherein the first disease management system is mounted to a patient through an adhesive which connects to the case.

Example 29: The disease management system of Claim 26, wherein the first disease management system further comprises at least one of a light source, a photodiode, a vibration device, a tissue impedance measurement device, an insulin cannula impedance measurement device, an accelerometer, or a gyroscope.

Example 30: The disease management system of Claim 26, wherein the first disease management system further comprises one or more flexion points which allows the first disease management system to flex.

Example 31: The disease management system of Claim 30, wherein the one or more flexion points comprises two flexion points.

Example 32: The disease management system of Claim 1, wherein the first disease management system comprises:
 a first case housing the first insulin pump, a first computing device, an antenna, and a first battery; and
 a second case housing the first glucose sensor, a second computing device, an antenna, and a second battery.

Example 33: The disease management system of Claim 32, wherein at least one of the first case or the second case further houses at least one of a light source, a photodiode, a vibration device, an accelerometer, or a gyroscope.

Example 34: A peristaltic pump comprising:
 a circular gear;
 a circular portion attached to the circular gear such that when the circular gear rotates the circular portion rotates at the same rotational speed, the circular portion located below the circular gear;
 two or more rollers located radially outward from the circular portion and in physical contact with the circular portion such that the roller rotate as the circular portion rotates;
 a casing which wraps around the circumference of the rollers and the circular portion such as to cooperate to form a circular channel, wherein the rollers are located at an inside portion of the circular channel and the casing is located on the outside of the circular channel; and
 a tubing located within the circular channel such that the tubing physically contacts both the casing and the rollers,
 wherein when the circular gear is rotated, the circular portion drives the two or more rollers which apply pressure to the tubing such that liquid within the tubing is driven from an inlet of the tubing to an outlet of the tubing.

Example 35: A peristaltic pump comprising:
 a circular gear with a circular hollow center;
 two or more rollers located within the circular hollow center and in physical contact with an inner wall of the circular gear such that the rollers rotate when the circular gear rotates;
 a stationary inner portion which is fixed, the stationary inner portion and the roller cooperate to form a circular channel, wherein the roller are located at an outside portion of the circular channel and the stationary inner portion is located at the inner portion of the channel; and
 a tubing located within the circular channel such that the tubing physical contacts both the stationary inner portion and the rollers,
 wherein when the circular gear is rotated, the two or more rollers rotate which applies pressure to the tubing such that liquid within the tubing is driven from an inlet of the tubing to an outlet of the tubing.

Example 36: A ratcheting peristaltic pump comprising:
 the peristaltic pump of any one of Claims 34 or 35;
 a ratcheting driving mechanism in physical contact with the circular gear, wherein the ratcheting driving mechanism is capable of ratcheting teeth within the circular gear at one tooth at a time.

Example 37: The ratcheting peristaltic pump of Claim 36, wherein the ratcheting driving mechanism comprises a solenoid, muscle wire, a ratchet motor, or a direct current motor.

Example 38: A method of priming a peristaltic pump, the method comprising:
 providing the peristaltic pump of any one of Claims 34-36;
 connecting the inlet of the tubing an insulin source;
 running the peristaltic pump to pump insulin from the insulin source from the inlet to the outlet until insulin exits the outlet;
 connecting the outlet of the tubing to a buffered solution source;
 running the peristaltic pump to pump buffered solution from the buffered solution source until the buffered solution enters all of the tubing contacting each of the rollers.

Example 39: A primed peristaltic pump comprising:
 the peristaltic pump of any one of Claims 30-32,
 wherein the input of the tubing is connected to an insulin source,
 wherein the portion of the tubing from the closest roller to the input of the tubing all the way to the output of the tubing is filled with a buffered solution, and
 wherein the portion of the tubing starting where the buffered solution is located all the way to the input of the tubing connected to the insulin source is filled with insulin.

Example 40: A method of using a primed peristaltic pump comprising: providing the primed peristaltic pump of Claim 34;
 connecting the outlet of the tubing to a patient;
 monitoring the patient's glucose level;
 determining the patient's glucose level is at a safe range to accept a small dosage of insulin;
 operating the primed peristaltic pump until all of the buffered solution has exited the tubing; and
 verifying that the patient's glucose level has not changed.

Example 41: A method of operating redundant glucose sensors, the method comprising:
 operating a first glucose sensor on a patient;
 operating a second glucose sensor on the patient;
 wherein at least one of the first glucose sensor or second glucose sensor is not in a warmup period, a stabilization period, or an end of life period;
 operating an insulin pump based on the measurements of the first glucose sensor or second glucose sensor not operating during a warmup period, a stabilization period, or an end of life period.

Example 42: The method of Claim 41, wherein the first glucose sensor or the second glucose sensor and the insulin pump are housed in one unit.

Example 43: The method of Claim 41, wherein the insulin pump and at least one of the first glucose sensor or second glucose sensor operating during a warmup period, a stabilization period, or an end of life period are housed in one unit.

Example 44: The method of Claim 43, wherein the first glucose sensor or second glucose sensor not operating during a warmup period, a stabilization period, or an end of life period and another insulin pump are housed in another unit.

Example 45: The method of Claim 44, further comprising operating the another insulin pump based on the measurements of the first glucose sensor or second glucose sensor not operating during a warmup period when the insulin pump is not operating.

Example 46: The method of Claim 45, wherein the one unit comprises a first insulin source storing insulin and wherein the another unit comprises a second insulin source storing insulin, and wherein the insulin pump and another insulin pump deliver insulin from the first insulin source and the second insulin source such that the insulin in the first insulin source and the second insulin source is emptied before the insulin in the first insulin source and the second insulin source expires.

Example 47: The method of Claim 46, further comprising notifying the patient when it is time to replace the one unit or the another unit.

Example 48: The method of Claim 47, wherein notifying the patient comprises sending a message through the patient's smart device or enabling the one unit or the another unit to vibrate.

Example 49: The method of Claim 41, wherein the first glucose sensor, the second glucose sensor, and the insulin pump are all housed in separate units.

Example 50: The method of Claim 41, wherein the first glucose sensor or the second glucose sensor and the insulin pump are housed in one unit.

Example 51: The method of Claim 41, wherein the first glucose sensor or the second glucose sensor and another insulin pump are housed in one unit, and wherein the insulin pump is housed in another system.

Example 52: The method of Claim 41, further comprising replacing the first glucose sensor or the second glucose sensor with a third glucose sensor when the not replaced first glucose sensor or second glucose sensor is not operating in a warmup period, a stabilization period, or an end of life period, wherein the not replaced first glucose sensor or second glucose sensor will not be operating in an end of life period when the third glucose sensor is running in a warmup period or a stabilization period.

Example 53: A method of using an applicator for applying a disease management system, the method comprising:
  providing the disease management system within packaging;
  opening the top of the packaging to expose the top of the disease management system, wherein the disease management system is preloaded with needles, the needles including tips which face towards the bottom of the packaging;
  grasping the disease management system within the applicator;
  positioning the applicator with the disease management system on a patient;
  launching the disease management system onto the patient such that the needles puncture the patient's skin, wherein the applicator comprises a retracting mechanism which retracts the needles after they puncture the patient's skin; and
  ejecting the used needles from the applicator such that the applicator is ready to apply another disease management system.

Example 54: The method of Claim 53, wherein the needles are housed within guidance tubes before launching the insulin dosage unit onto the patient.

Example 55: The method of Claim 53, wherein, when in the packaging, the disease management system is preloaded with lancet backings, wherein when the needles are retracted, the needles retract into the lancet backings, and wherein ejecting the used needles comprises ejecting the used needles within the lancet backings.

Example 56: The method of Claim 55, further comprising removing the applicator after launching the disease management system onto the patient, wherein removing the applicator comprises leaving the applicator on the patient while removing the needles within the lancet backings.

Example 57: A disease management system comprising:
  a case;
  a glucose sensor;
  an insulin storage chamber;
  an insulin pump in fluid connection with the insulin storage chamber;
  a battery;
  a computing device configured to receive measurements from the glucose sensor and control the insulin pump provide dosages of insulin to a patient based on measurements from the glucose sensor; and
  an antenna connected to the computing device,
  wherein the computing device is further configured to send measurements from the glucose sensor to other disease management units, a smart device, or a smartwatch through the antenna, receive glucose measurements from other disease management units, a smart device, or a smartwatch, and send dosage instructions through the antenna to other disease management units, and
  wherein the case houses the glucose sensor, the insulin storage chamber, the insulin pump, the battery, and the computer device.

Example 58: The disease management system of Claim 57, further comprising a near field communication (NFC) device including a unique ID tag associated with the disease management system, wherein a smart device is capable of causing the NFC device to send the unique ID tag to the smart device which allows the smart device to identify the disease management unit and pair with the disease management system.

Example 59: The disease management system of Claim 58, wherein the NFC device is configured to communicate with the smart device to trigger the disease management system to manually administer a dosage of insulin to the patient.

Example 60: The disease management system of Claim 58, wherein the NFC device is configured to communicate with a wearable NFC device to trigger the disease management system to manually administer a dosage of insulin to the patient.

Example 61: The disease management system of Claim 60, wherein the wearable NFC device comprises a safety mechanism to prevent the wearable NFC device from triggering the disease management system from manually administering a dosage of insulin to the patient unless the safety mechanism is enabled.

Example 62: The disease management system of Claim 61, wherein the safety mechanism comprises a switch, toggle, button, or knob.

Example 63: The disease management system of Claim 60, wherein the wearable NFC device is mounted on a bracelet, watch, necklace, or belt.

Example 64: The disease management system of Claim 60, wherein the NFC device is configured to differentiate between different wearable NFC devices such that one of the wearable NFC devices communicates with the NFC device to trigger the disease management system to manually administer a different dosage of insulin to the patient than another of the wearable NFC devices.

Example 65: The disease management system of Claim 60, wherein the computing device is configured to block a manual administration of a dosage from the wearable NFC device at least during a portion of the time.

Example 66: The disease management system of Claim 57, wherein the case comprises a manual dosage mechanism which is capable of triggering the disease management system to manually administer a dosage of insulin to the patient.

Example 67: The disease management system of Claim 66, wherein the case is segmented such that the portion of the case with the manual dosage mechanism is removable and replaceable.

Example 68: The disease management system of Claim 57, wherein the computing device is configured to communicate with an additional manual dosage device which is configured to be physically connected with the case, the additional manual dosage device is configured to trigger the disease management system to manually administer a dosage of insulin to the patient.

Example 69: The disease management system of Claim 57, wherein the antenna embedded within the case or on the outside of the case.

Example 70: A disease management system comprising:
 a first disease management system comprising:
  a first glucose sensor;
  a first insulin pump;
  a first computing device configured to receive measurements from the first glucose sensor and control the first insulin pump provide dosages of insulin to a patient based on measurements from the first glucose sensor;
  a first antenna connected to the first computing device;
  a first near field communication (NFC) device including a first unique ID tag associated with the first disease management unit, wherein a smart device is capable of causing the first NFC device to send the first unique ID tag to the smart device which allows the smart device to identify the disease management unit and pair with the disease management unit.
 a second disease management system comprising:
  a second glucose sensor;
  a second insulin pump;
  a second computing device configured to receive measurements from the second glucose sensor and control the second insulin pump provide dosages of insulin to a patient based on measurements from the second glucose sensor;
  a second antenna connected to the second computing device;
  a second near field communication (NFC) device including a second unique ID tag associated with the second disease management unit, wherein the smart device is capable of causing the second NFC device to send the second unique ID tag to the smart device which allows the smart device to identify the second disease management unit, and
 wherein the first disease management system is configured to pair to the second disease management system through request of the smart device.

Example 71: The disease management system of Claim 70, wherein the second disease management system is configured to pair with the smart device.

Example 72: The disease management system of Claim 70, wherein the smart device comprises a smartphone or tablet.

Example 73: A flexible disease management system comprising:
 a glucose sensor;
 a computer device;
 an antenna, wherein the computing device is configured to transmit glucose data received from the glucose sensor through the antenna;
 a flexible battery configured to power the computer device and the glucose sensor; and
 a flexible bandage configured to adhere the flexible battery, computer device, and the glucose sensor to the patient.

Example 74: An applicator for a disease management system comprising:
 a cylindrical applicator wheel capable of storing one or more patient treatment units;
 a handle attached to the applicator wheel at the center of two opposing sides of the applicator wheel,
 wherein the applicator wheel is configured to physically contact a patient and roll on a patient and, when rolling, apply at least one of the one or more patient treatment units to a patient.

Example 75: The applicator of Claim 74, wherein the one or more disease management systems comprises one or more glucose sensor units, one or more insulin pump systems, or one or more combined glucose sensor and insulin pump units.

Example 76: A method of distracting a patient during application of a disease management system, the method comprising:
 providing the disease management system for application to the patient, wherein the disease management system comprises one or more needles;
 applying the disease management system to the patient; and
 using a distraction device to distract the patient during application of the disease management system to the patient, wherein the distraction device interacts with the disease management system such that the distraction device times a distracting event with application of the disease management system.

Example 77: The method of Claim 76, wherein the distraction device comprises a smart device or another disease management system including a vibration device.

Example 78: The method of Claim 77, wherein the distraction device comprises the smart device which allows a patient to play a game, watch a movie, or read a story before and during application of the disease management system, and wherein the distracting event comprises the climax of the game, movie, or story.

Example 79: The method of Claim 77, wherein the distraction device comprises the another disease management system including the vibration device, and wherein the distracting event comprises vibration of the vibration device just before and during application of the disease management system.

Example 80: The method of Claim 76, further comprising operating a vibration device within the patient treatment unit after application of the disease management system to the patient.

Example 81: The method of Claim 76, wherein the disease management system comprises a indicator which indicates when a distracting event is occurring in order to indicate that the timing is optimal to apply the disease management system to the patient.

Example 82: The method of Claim 81, wherein the indicator comprises a light emitter or a vibrating module.

Example 83: A needle for implanting a glucose sensor or cannula comprising a top portion and a bottom portion, wherein the bottom portion is rigid at some times and flexible at some times.

Example 84: The needle of Claim 83, wherein the bottom portion comprises a material which is flexible when exposed to water and rigid when not exposed to water.

Example 85: The needle of Claim 84, wherein the bottom portion comprises hydrogel or collagen Example 86: The needle of Claim 84, wherein the bottom portion comprises an inner layer and an outer layer, wherein the inner layer and outer layer are made out of different materials.

Example 87: The needle of Claim 86, wherein one of the inner layer or the outer layer comprises hydrogel or collagen and the other of the inner layer or the outer layer comprises metal or plastic.

Example 88: The needle of Claim 83, wherein the bottom portion is rigid when not exposed to ultra-violet light and flexible when exposed to ultra-violet light.

Example 89: The needle of Claim 83, wherein the bottom portion comprises a bioresorbable material.

Example 90: The needle of Claim 83, wherein the needle is a hollow needle.

Example 91: The needle of Claim 83, wherein the needle is a solid needle.

Example 92: A disease management system comprising:
at least one analyte sensor;
a medication administration system; and
a housing for the at least one analyte sensor and medication administration pump, the housing comprising:
a top portion configured to bend, the top portion comprising rigid portions and flexible portions; and
a bottom portion configured to adhere to skin of a patient.

Example 93: The disease management system of Claim 92 wherein the bottom portion comprises an adhesive layer.

Example 94: The disease management system of Claim 93, wherein the bottom portion comprises an adhesive layer locking mechanism configured to join the adhesive layer to at least a second portion of the bottom portion of the housing.

Example 95: The disease management system of Claim 92, wherein the bottom portion comprises a metal plate configured to provide support for components of the disease management system.

Example 96: The disease management system of Claim 92, wherein the at least one analyte sensor and a cannula of the medication administration system are offset from each other in relation to a center line of the glucose administration system.

Example 97: The disease management system of Claim 92, wherein the at least one analyte sensor comprises an invasive sensor applied using a needle configured to retract from the skin after application.

Example 98: The disease management system of Claim 92, wherein the medication administration system comprises a medication pouch, pump, and cannula configured to be administered to the patient using a needle configured to retract from the skin after application.

Example 99: The disease management system of Claim 98, wherein the pouch is prefilled with medication.

Example 100: The disease management system of Claim 99, wherein the medication is insulin.

Example 101: The disease management system of Claim 99, wherein the pouch is sealed with a stopper configured to accept a needle for access to the medication.

Example 102: The disease management system of Claim 92, wherein the medication administration system comprises a pressure relief valve configured to release pressure from a fluid line in the medication administration system in the event of excess pressure.

Example 103: The disease management system of Claim 102, wherein the event of excess pressure comprises collapse of at least a portion of the disease management system due to a crushing force.

Example 104: The disease management system of Claim 92 further comprising at least one non-invasive sensor.

Example 105: The disease management system of Claim 104, wherein the non-invasive sensor comprises a pulse rate sensor.

Example 106: The disease management system of Claim 104, wherein the non-invasive sensor comprises a temperature sensor.

Example 107: The disease management system of Claim 92 comprising a buzzer configured to output audible feedback to the patient associated with the disease management system.

Example 108: The disease management system of Claim 92, comprising a haptic motor configured to output haptic feedback associated with the disease management system.

Example 109: The disease management system of Claim 92, comprising at least one battery configured to power components of the disease management system for a prolonged period.

Example 110: The disease management system of Claim 109, wherein the prolonged period comprises greater than 3 days.

Example 111: The disease management system of Claim 111, wherein the prolonged period comprises 6 days.

Example 112: The disease management system of Claim 92, comprising at least one communication component.

Example 113: The disease management system of Claim 112, wherein the at least one communication component comprises a Bluetooth antenna.

Example 114: The disease management system of Claim 112, wherein the at least one communication component comprises an NFC antenna.

Example 115: The disease management system of Claim 112, wherein the disease management system is configured to communicate with a user device.

Example 116: The disease management system of Claim 115, wherein the disease management system is configured to receive bolus instructions for administration of medication to the patient through the at least one communication component.

Example 117: The disease management system of Claim 115, wherein the glucose administration system is configured to communicate one or more physiological parameters to the user device.

Example 118: The disease management system of Claim 115, wherein the glucose administration system is configured to update a status of the device based on a connection status with the user device.

Example 119: The disease management system of Claim 92, wherein a pump of the medication administration system comprises a peristaltic pump.

Example 120: The disease management system of Claim 92, wherein a pump of the medication administration system comprises a valve pump.

Example 121: The disease management system of Claim 92, wherein a pump of the medication administration system comprises a plunger pump.

Example 122: The disease management system of Claim 121, wherein the plunger pump comprises: at least one plunger and at least one actuation component configured to cause the at least one plunger to apply pressure to a tube of fluid containing medication so that medication is transferred from a medication reservoir to a cannula inserted into the patient.

Example 123: The disease management system of Claim 122, wherein the at least one actuation component comprises at least one solenoid and spring assembly.

Example 124: The disease management system of Claim 122, wherein the at least one actuation component comprises at least one muscle wire and spring assembly.

Example 125: The disease management system of Claim 124, wherein the at least one actuation component comprises a plurality of rollers configured to allow the muscle wire to move the plungers when activated.

Example 126: The disease management system of Claim 122, wherein the at least one actuation component comprises an actuator and gear configured to engage the at least one plunger.

Example 127: The disease management system of Claim 126, wherein the gear comprises a plurality of humps and wherein the at least one plunger comprises an engagement portion configured to move in response to the position of a hump.

Example 128: The disease management system of Claim 127, wherein a hump of the plurality of humps comprises a thirty degree slope.

Example 129: The disease management system of Claim 126, wherein the actuator comprises a solenoid actuator configured to move a cleat, wherein the cleat is configured to engage the gear.

Example 130: The disease management system of Claim 128, wherein the pump comprises a lock configured to prevent unintended rotation of the gear.

Example 131: The disease management system of Claim 122, wherein the at least one plunger comprises a flat portion configured to contact the tubing of the medication administration system.

Example 132: The disease management system of Claim 122, wherein the at least one plunger comprises a cylindrical portion configured to contact the tubing of the medication administration system.

Example 133: The disease management system of Claim 122, wherein the at least one actuation component comprises a gear and an engagement portion configured to engage one or more plungers to move in an approximately radial direction from the gear.

Example 134: The disease management system of Claim 133 wherein the one or more plungers are configured to apply pressure to tubing between the gear and the one or more plungers.

Example 135: The disease management system of Claim 92, wherein a pump of the medication administration system comprises a piston pump.

Example 136: The disease management system of Claim 135, wherein the piston pump comprises a piston driven by a muscle wire spring and standard spring.

Example 137: The disease management system of Claim 136 wherein the piston is configured to engage a valve assembly in fluid communication with a medication pouch and medication cannula configured to be inserted into the patient.

Example 138: The disease management system of Claim 137 wherein fluid is moved through the valve assembly to the medication cannula as a result of the piston engaging a valve in the valve assembly.

Example 139: The disease management system of Claim 92, wherein the medication administration system comprises an electroactive cannula.

Example 140: The disease management system of Claim 139, wherein the electroactive cannula comprises a helical spring in an inside portion of the cannula.

Example 141: The disease management system of Claim 140, wherein the helical spring is configured to trap medication aggregated in the cannula.

Example 142: The disease management system of Claim 139, wherein the electroactive cannula is configured to detect a change in fluid conductance.

Example 143: The disease management system of Claim 142 wherein the change in fluid conductance is a result of a kink in the cannula or expiring or expired medication.

Example 144: The disease management system of Claim 139, wherein measurements of the electroactive cannula are used to estimate lifetime remaining for the cannula.

Example 145: The disease management system of Claim 144, wherein a lifetime is associated with a usable life of the cannula before there is biofouling or encapsulation.

Example 146: The disease management system of Claim 92, wherein the medication administration system comprises a haptic motion mechanism to aid in dislodging blockages in a cannula of the medication administration system.

Q. TERMINOLOGY

Conditional language used herein, such as, among others, "can," "could," "might," "may," "e.g.," and the like, unless specifically stated otherwise, or otherwise understood within the context as used, is generally intended to convey that certain, certain features, elements and/or steps are optional. Thus, such conditional language is not generally intended to imply that features, elements and/or steps are in any way required or that one or more implementations necessarily include logic for deciding, with or without other input or prompting, whether these features, elements and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other users.

Depending on the implementation, certain acts, events, or functions of any of the processes or algorithms described herein can be performed in a different sequence, can be added, merged, or left out altogether (for example, not all described operations or events are necessary for the practice of the algorithm). Moreover, in certain implementations, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the disclosure herein can be implemented as electronic hardware (for example, ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the disclosure herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. A processor device can include an FPGA or other programmable device that performs logic operations without processing computer-executable instructions. A processor device can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the disclosure herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A method of operating redundant disease management systems, each comprising a glucose sensor and an insulin pump, the method comprising:
    during a first period comprising at least the warm-up and stabilization period for the first disease management system glucose sensor:
        operating a first disease management system on a patient in a primary mode, and operating a second disease management system on the patient in a secondary mode;

during a second period comprising at least the end of life period of the first disease management system glucose sensor:

operating the first disease management system in the secondary mode, and operating the second disease management system in the primary mode; wherein the disease management system operating in the primary mode delivers insulin to the patient; and the disease management system operating in the secondary mode Provides only glucose sensor data.

2. The method of claim 1, wherein the first disease management system insulin pump and at least one of the first or second disease management system glucose sensor are housed in a first unit.

3. The method of claim 2, wherein the first or second disease management system glucose sensor is housed in a second unit.

4. The method of claim 3, further comprising operating a second disease management system insulin pump based on the measurements of the first or second disease management system glucose sensor when the first disease management system is operating in the secondary mode.

5. The method of claim 4, wherein the first unit comprises a first insulin source storing insulin and wherein the second unit comprises a second insulin source storing insulin, and wherein the first disease management system insulin pump and the second-disease management system insulin pump deliver insulin from the first insulin source or the second insulin source such that the insulin in the first insulin source and the second insulin source is emptied before the insulin in the first insulin source and the second insulin source expires.

6. The method of claim 5, further comprising notifying the patient when it is time to replace the first unit or the second unit.

7. The method of claim 1, wherein the first disease management system glucose sensor, the second disease management system glucose sensor, and the first disease management system insulin pump are all housed in separate units.

8. The method of claim 1, wherein the first disease management system glucose sensor or the second disease management system glucose sensor and the first disease management system insulin pump are housed in one unit.

9. The method of claim 1, further comprising outputting a notification to replace the first disease management system glucose sensor or the second disease management system glucose sensor with a third glucose sensor when the not replaced first disease management system glucose sensor or not replaced second disease management system glucose sensor is not operating in the warmup period, the stabilization period, or the end of life period, wherein the not replaced first disease management system glucose sensor or second disease management system glucose sensor will not be operating in the end of life period when the third glucose sensor is operating in a warmup period or a stabilization period.

* * * * *